(12) United States Patent
Holt et al.

(10) Patent No.: US 11,730,827 B2
(45) Date of Patent: Aug. 22, 2023

(54) MATERIALS AND METHODS FOR DELIVERING NUCLEIC ACIDS TO COCHLEAR AND VESTIBULAR CELLS

(71) Applicant: CHILDREN'S MEDICAL CENTER CORPORATION, Boston, MA (US)

(72) Inventors: Jeffrey Holt, Boston, MA (US); Gwenaelle Geleoc, Boston, MA (US); Yukako Asai, Boston, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 483 days.

(21) Appl. No.: 16/483,668

(22) PCT Filed: Feb. 6, 2018

(86) PCT No.: PCT/US2018/017104
§ 371 (c)(1),
(2) Date: Aug. 5, 2019

(87) PCT Pub. No.: WO2018/145111
PCT Pub. Date: Aug. 9, 2018

(65) Prior Publication Data
US 2019/0351072 A1     Nov. 21, 2019

Related U.S. Application Data

(60) Provisional application No. 62/455,197, filed on Feb. 6, 2017.

(51) Int. Cl.
| A61K 48/00 | (2006.01) |
| C12N 15/86 | (2006.01) |
| C07H 21/04 | (2006.01) |
| A61P 27/16 | (2006.01) |
| C07K 14/47 | (2006.01) |
| C07K 14/705 | (2006.01) |

(52) U.S. Cl.
CPC .......... *A61K 48/0058* (2013.01); *A61P 27/16* (2018.01); *C07K 14/4716* (2013.01); *C07K 14/705* (2013.01); *C12N 15/86* (2013.01); *C07H 21/04* (2013.01)

(58) Field of Classification Search
CPC .. A61K 48/005; A61K 48/0058; C12N 15/86; C12N 2750/14143; C07H 21/04
See application file for complete search history.

(56) References Cited

U.S. PATENT DOCUMENTS

| 2005/0287127 A1 | 12/2005 | Li et al. |
| 2013/0095071 A1 | 4/2013 | Bance et al. |

FOREIGN PATENT DOCUMENTS

| JP | 2016536011 A | 11/2016 |
| JP | 2018536420 A | 12/2018 |
| WO | 2006026570 A2 | 3/2006 |
| WO | 2011075838 A1 | 6/2011 |
| WO | WO 2011/075838 A1 * | 6/2011 |
| WO | 2015089462 A1 | 6/2015 |
| WO | 2015054653 A2 | 4/2016 |
| WO | 2017100791 A1 | 6/2017 |
| WO | 20170136764 A1 | 8/2017 |
| WO | 2018017834 A1 | 1/2018 |

OTHER PUBLICATIONS

Kotterman et al., 2014, Nature Reviews, vol. 15, p. 445-451.*
Shim et al., 2017, Current Gene Therapy, vol. 17, No. 5, p. 1-18.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Durymanov et al., 2018, Frontiers in Pharmacology, vol. 9, Article 971, p. 1-15.*
Medlineplus, 2022, Usher Syndrome, National Institute of Health/ National Library of Medicine, p. 1-8.*
Arnold et al., "Novel Slow- and Fast-Type Drug Release Round-Window Microimplants for Local Drug Application to the Cochlea: An Experimental Study in Guinea Pigs," Audiology and Neuro-Otology, 2005, vol. 10, pp. 53-63.
Grimm et al., "Helper Virus-Free, Optically Controllable, and Two-Plasmid-Based Production of Adeno-associated Virus Vectors of Serotypes 1 to 6," Molecular Therapy, Jun. 2003, vol. 7, No. 6, pp. 839-850.
Kawashima et al., "Mechanotransduction in mouse inner ear hair cells requires transmembrane channel-like genes," The Journal of Clinical Investigation, 2011, vol. 121, No. 12, pp. 4796-4809.
Maison et al., "Muscarinic Signaling in the Cochlea: Presynaptic and Postsynaptic Effects on Efferent Feedback and Afferent Excitability," The Journal of Neuroscience, May 12, 2010, vol. 30, No. 19, pp. 6751-6762.
Mathur et al., "Usher syndrome: Hearing loss, retinal degeneration and associated abnormalities," Biochimica et Biophysica Acta, Mar. 2015, vol. 1852, No. 3, pp. 406-420.
Parker et al., "Genetic investigations in childhood deafness," Archives of Disease in Childhood, 2015, vol. 100, No. 3, pp. 271-278.
Office Action dated Oct. 29, 2021 in corresponding Japanese Patent Application No. 2019-542464 (7 pages).

(Continued)

*Primary Examiner* — Shin Lin Chen
(74) *Attorney, Agent, or Firm* — Melissa Hunter-Ensor; Evelyn Kwon; Greenberg Traurig, LLP

(57) ABSTRACT

Provided herein are materials and methods for efficiently delivering nucleic acids to cochlear and vestibular cells, and methods of treating sensory transduction disorders associated with a genetic defect. Some embodiments are directed to a synthetic inner ear hair cell targeting adeno-associated virus (AAV) vector, a cell comprising the synthetic inner ear hair cell targeting AAV vector, and method of treating Usher Syndrome in a subject using the synthetic inner ear hair cell targeting AAV vector.

9 Claims, 27 Drawing Sheets

Specification includes a Sequence Listing.

(56) References Cited

OTHER PUBLICATIONS

English translation of the Office Action dated Oct. 29, 2021 in corresponding Japanese Patent Application No. 2019-542464 (7 pages).
Office Action dated Nov. 11, 2021 in corresponding Chinese Patent Application No. 201880022337.9 (6 pages).
English translation of the Office Action dated Nov. 11, 2021 in corresponding Chinese Patent Application No. 201880022337.9 (5 pages).
Askew et al., "Tmc gene therapy restores auditory function in deaf mice," Science Translational Medicine, Jan. 1, 2015, pp. 295ra108-295ra108.
Géléoc et al., "35 Gene Therapy Restores Auditory and Vestibular Function in a Mouse Model of Usher Syndrome, Type 1C," Symposium—New horizons in hearing rehabilitation, Abstract Book, Inner Ear Biology 2016, Montpellier, Sep. 18, 2016.
Landegger et al., "269. Novel Synthetic AAV Efficiently Transduces Neurosensory Hair Cells in the Cochlea," Molecular Therapy, May 1, 2016, vol. 24, Suppl. 1, p. S107.
Landegger et al., "A synthetic AAV vector enables safe and efficient gene transfer to the mammalian inner ear," Nature Biotechnology, Feb. 6, 2017, vol. 35, No. 3, pp. 280-284.
Pan et al., "Gene therapy restores auditory and vestibular function in a mouse model of Usher syndrome type 1c," Nature Biotechnology, Feb. 6, 2017, vol. 35, No. 3, pp. 264-272.
Extended European Search Report in corresponding European Patent Application No. 18747407.7, dated Aug. 19, 2020 (11 pages).
György, et al., "Rescue of Hearing by Gene Delivery to Inner-Ear Hair Cells Using Exosome-Associated AAV," Molecular Therapy, Jan. 9, 2017, vol. 25, No. 2, pp. 379-391.
Shu, et al., "Identification of Adeno-Associated Viral Vectors That Target Neonatal and Adult Mammalian Inner Ear Cell Subtypes," Human Gene Therapy, Sep. 1, 2016), vol. 27, Issue 9, pp. 687-699.
International Search Report and Written Opinion for corresponding PCT Patent Application No. PCT/US2018/017104, dated May 10, 2018 (8 pages).
GenBank Accession No. AKU89595.1.
Examination Report dated Aug. 19, 2022 in corresponding Australian Patent Application No. 2018215785 (6 pages).
Office Action dated Sep. 1, 2022 in corresponding Japanese Patent Application No. 2019-542464 (4 pages).
English translation of the Office Action dated Sep. 1, 2022 in corresponding Japanese Patent Application No. 2019-542464 (4 pages).
Office Action and Search Report dated Oct. 11, 2022 in corresponding Chinese Patent Application No. 201880022337.9 (10 pages).
English translation of the Office Action and Search Report dated Oct. 11, 2022 in corresponding Chinese Patent Application No. 201880022337 9 (11 pages).
Office Action dated Feb. 2, 2023 in corresponding Chinese Patent Application No. 201880022337.9 (11 pages).
English translation of the Office Action dated Feb. 2, 2023 in corresponding Chinese Patent Application No. 201880022337.9 (17 pages).

* cited by examiner

SEQUENCE LISTING

<160> NUMBER OF SEQ ID NOS: 34

<210> SEQ ID NO 1
<211> LENGTH: 736
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (168)..(168)
<223> OTHER INFORMATION: Lys or Arg
<220> FEATURE:
<221> NAME/KEY: MOD_RES
<222> LOCATION: (204)..(204)
<223> OTHER INFORMATION: Ala or Ser
<220> FEATURE:
<221> NAME/KEY: MOD_RES
<222> LOCATION: (266)..(266)
<223> OTHER INFORMATION: Ala or Gly
<220> FEATURE:
<221> NAME/KEY: MOD_RES
<222> LOCATION: (311)..(311)
<223> OTHER INFORMATION: Arg or Lys
<220> FEATURE:
<221> NAME/KEY: MOD_RES
<222> LOCATION: (411)..(411)
<223> OTHER INFORMATION: Glu or Gln
<220> FEATURE:
<221> NAME/KEY: MOD_RES
<222> LOCATION: (460)..(460)
<223> OTHER INFORMATION: Thr or Glu
<220> FEATURE:
<221> NAME/KEY: MOD_RES
<222> LOCATION: (493)..(493)
<223> OTHER INFORMATION: Ala or Thr
<220> FEATURE:
<221> NAME/KEY: MOD_RES
<222> LOCATION: (562)..(562)
<223> OTHER INFORMATION: Ser or Asn
<220> FEATURE:
<221> NAME/KEY: MOD_RES
<222> LOCATION: (576)..(576)
<223> OTHER INFORMATION: Gln or Glu
<220> FEATURE:
<221> NAME/KEY: MOD_RES
<222> LOCATION: (587)..(587)
<223> OTHER INFORMATION: Ser or Ala
<220> FEATURE:
<221> NAME/KEY: MOD_RES
<222> LOCATION: (609)..(609)
<223> OTHER INFORMATION: Asn or Asp

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro

```
                50                  55                  60
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Gly Ile Gly
145                 150                 155                 160

Lys Lys Gly Gln Gln Pro Ala Xaa Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Xaa Ala Gly Gly Gly
        195                 200                 205

Ala Pro Met Ala Asp Asn Asn Glu Gly Ala Asp Gly Val Gly Asn Ala
        210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Xaa Ser Thr Asn Asp Asn Thr
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
        290                 295                 300

Trp Gly Phe Arg Pro Lys Xaa Leu Asn Phe Lys Leu Phe Asn Ile Gln
305                 310                 315                 320

Val Lys Glu Val Thr Thr Asn Asp Gly Thr Thr Ile Ala Asn Asn
                325                 330                 335

Leu Thr Ser Thr Val Gln Val Phe Thr Asp Ser Glu Tyr Gln Leu Pro
        340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Xaa Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Xaa Leu Gln Phe Ser
    450                 455                 460

Gln Ala Gly Pro Ser Ser Met Ala Asn Gln Ala Lys Asn Trp Leu Pro
465                 470                 475                 480
```

Gly Pro Cys Tyr Arg Gln Gln Arg Val Ser Lys Thr Xaa Asn Gln Asn
                    485                 490                 495

Asn Asn Ser Asn Phe Ala Trp Thr Gly Ala Thr Lys Tyr His Leu Asn
                500                 505                 510

Gly Arg Asp Ser Leu Val Asn Pro Gly Pro Ala Met Ala Thr His Lys
            515                 520                 525

Asp Asp Glu Asp Lys Phe Phe Pro Met Ser Gly Val Leu Ile Phe Gly
        530                 535                 540

Lys Gln Gly Ala Gly Asn Ser Asn Val Asp Leu Asp Asn Val Met Ile
545                 550                 555                 560

Thr Xaa Glu Glu Glu Ile Lys Thr Thr Asn Pro Val Ala Thr Glu Xaa
                565                 570                 575

Tyr Gly Thr Val Ala Thr Asn Leu Gln Ser Xaa Asn Thr Ala Pro Ala
                580                 585                 590

Thr Gly Thr Val Asn Ser Gln Gly Ala Leu Pro Gly Met Val Trp Gln
            595                 600                 605

Xaa Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 2
<211> LENGTH: 736
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly

-continued

```
                100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
        130                 135                 140
Pro Val Glu Gln Ser Pro Gln Glu Pro Asp Ser Ser Ser Gly Ile Gly
145                 150                 155                 160
Lys Lys Gly Gln Gln Pro Ala Arg Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Ala Pro Ser Gly Val Gly Ser Asn Thr Met Ala Ala Gly Gly Gly
        195                 200                 205
Ala Pro Met Ala Asp Asn Asn Glu Gly Ala Asp Gly Val Gly Asn Ala
210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Gly Ser Thr Asn Asp Asn Thr
            260                 265                 270
Tyr Phe Gly Tyr Ser Thr Pro Trp Gly Tyr Phe Asp Phe Asn Arg Phe
        275                 280                 285
His Cys His Phe Ser Pro Arg Asp Trp Gln Arg Leu Ile Asn Asn Asn
    290                 295                 300
Trp Gly Phe Arg Pro Lys Lys Leu Asn Phe Lys Leu Phe Asn Ile Gln
305                 310                 315                 320
Val Lys Glu Val Thr Thr Asn Asp Gly Thr Thr Thr Ile Ala Asn Asn
                325                 330                 335
Leu Thr Ser Thr Val Gln Val Phe Thr Asp Ser Glu Tyr Gln Leu Pro
            340                 345                 350
Tyr Val Leu Gly Ser Ala His Gln Gly Cys Leu Pro Pro Phe Pro Ala
        355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Gln Phe Ser Tyr Thr Phe
                405                 410                 415
Glu Asp Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Ser Arg
        435                 440                 445
Thr Gln Thr Thr Ser Gly Thr Ala Gly Asn Arg Thr Leu Gln Phe Ser
    450                 455                 460
Gln Ala Gly Pro Ser Ser Met Ala Asn Gln Ala Lys Asn Trp Leu Pro
465                 470                 475                 480
Gly Pro Cys Tyr Arg Gln Gln Arg Val Ser Lys Thr Thr Asn Gln Asn
                485                 490                 495
Asn Asn Ser Asn Phe Ala Trp Thr Gly Ala Thr Lys Tyr His Leu Asn
            500                 505                 510
Gly Arg Asp Ser Leu Val Asn Pro Gly Pro Ala Met Ala Thr His Lys
        515                 520                 525
```

Asp Asp Glu Asp Lys Phe Phe Pro Met Ser Gly Val Leu Ile Phe Gly
          530                 535                 540

Lys Gln Gly Ala Gly Asn Ser Asn Val Asp Leu Asp Asn Val Met Ile
545                 550                 555                 560

Thr Asn Glu Glu Glu Ile Lys Thr Thr Asn Pro Val Ala Thr Glu Glu
                565                 570                 575

Tyr Gly Thr Val Ala Thr Asn Leu Gln Ser Ala Asn Thr Ala Pro Ala
                580                 585                 590

Thr Gly Thr Val Asn Ser Gln Gly Ala Leu Pro Gly Met Val Trp Gln
            595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Asn Lys Ser Thr Asn Val Asp Phe Ala Val Asp Thr Asn Gly Val
                705                 710                 715                 720

Tyr Ser Glu Pro Arg Pro Ile Gly Thr Arg Tyr Leu Thr Arg Asn Leu
            725                 730                 735

<210> SEQ ID NO 3
<211> LENGTH: 7064
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaagctagc tagttattaa tagtaatcaa ttacggggtc    240
attagttcat agcccatata tggagttccg cgttacataa cttacggtaa atggcccgcc    300
tggctgaccg cccaacgacc cccgcccatt gacgtcaata atgacgtatg ttcccatagt    360
aacgccaata gggactttcc attgacgtca atgggtggag tatttacggt aaactgccca    420
cttggcagta catcaagtgt atcatatgcc aagtacgccc cctattgacg tcaatgacgg    480
taaatggccc gcctggcatt atgcccagta catgacctta tgggactttc ctacttggca    540
gtacatctac gtattagtca tcgctattac catggtgatg cggttttggc agtacatcaa    600
tgggcgtgga tagcggtttg actcacgggg atttccaagt ctccacccca ttgacgtcaa    660
tgggagtttg ttttggcacc aaaatcaacg ggactttcca aaatgtcgta caactccgc    720 cccattgacg caaatgggcg gtaggcgtgt acggtgggag gtctatataa gcagagctgg    780
tttagtgaac cgtcagatcc tgcagaagtt ggtcgtgagg cactgggcag gtaagtatca    840

-continued

```
aggttacaag acaggtttaa ggagaccaat agaaactggg cttgtcgaga cagagaagac    900
tcttgcgttt ctgataggca cctattggtc ttactgacat ccactttgcc tttctctcca    960
caggtgtcca ggcggccgcg gatgccaccc aaaaaagtgc aaatccaagt ggaggagaaa   1020
gaagaggata cagaggaaag ctcaagtgaa gaagaagaag ataagctacc cagaagagag   1080
agcttgagac caaagaggaa acggaccaga gatgtcatca atgaggatga cccagaaccg   1140
gagccggagg atgaagaaac aagaaaggca agagaaaaag aaaggcggag gaggctgcgg   1200
agaggagcgg aagaagaaga agaaattgat gaagaggaat tagaacggtt aaaagcactg   1260
ctcgatgaga atagacaaat gatcgctact gtcaaatgta aaccttggaa atggagaag    1320
aaaattgaag ttctcaagga agcaaagaaa tttgtgagtg agaatgaagg cgctcttggg   1380
aaaggaaagg gaagaagtg gtttgcattt aagatgatga tggccaagaa atgggcaaaa   1440
ttcctccgag attttgagaa cttcaaagcg gcttgcgtcc catgggaaaa caaaatcaag   1500
gcaattgaaa gtcagtttgg ttcctcagtg gcctcgtact tcctgttcct caggtggatg   1560
tacggcgtca acatggttct ctttgtgttg accttcagcc tcatcatgtt accggagtac   1620
ctctggggtt taccgtacgg cagcttacct aggaaaacag tcccaagagc tgaagaagca   1680
tctgcagcca actttggtgt gttgtatgac ttcaatggcc tggcgcagta ctctgtcctc   1740
ttttatggct attacgacaa taaacgcacg atcggatggc tgaatttccg gctacctctt   1800
tcctacttcc tggtggggat tatgtgcatt ggatacagct cctggttgt cctcaaagcg    1860
atgaccaaaa atattggtga cgatggtggt ggcgatgaca acactttcaa cttcagctgg   1920
aaggtgttct gtagctggga ctatctgatt ggtaaccctg aaacagccga caacaagttt   1980
aactctatca cgatgaactt taaggaagcc atcatagaag agagagccgc acaggtggag   2040
gagaacatcc acctcatcag atttctgagg tttctcgcta acttcttcgt gttcctcaca   2100
cttggtgcaa gtggatacct catcttttgg gctgtgaagc gatcccagga gttcgcccag   2160
caagatcctg acacccttgg gtggtgggaa aaaaatgaaa tgaacatggt aatgtccctc   2220
ctggggatgt tctgtcccac cctgtttgac ttatttgctg aactggaaga ttaccatcct   2280
ctcattgctc tgaagtggct cctggggcgc atttttgctc ttcttctagg caacttgtat   2340
gtattcattc tcgccttgat ggatgagatt aacaacaaga ttgaagagga gaagcttgtg   2400
aaggccaata ttaccctgtg ggaagccaac atgattaagg cttacaatga atctctctct   2460
gggctctctg gaacaccac aggagcaccc tttttcgttc atcctgcaga tgtccctcgc    2520
ggtccctgct gggaaacaat ggtggggcag gaattcgtgc gtctcaccgt ttctgacgtc   2580
ctgaccactt acgtcacgat cctcattggc gacttcctca gagcatgttt cgtgaggttc   2640
tgcaattact gctggtgctg ggacttagaa tatggatatc cttcatacac agaattcgac   2700
atcagtggca acgtcctcgc tctgatcttc aaccaaggca tgatctggat gggctccttc   2760
ttcgctccta gcctcccggg catcaacatc ctccgtctcc acacatccat gtatttccag   2820
tgctgggctg tgatgtgctg caatgttccc gaggccaggg tgttcaaagc ttccagatcc   2880
aacaacttct acctcggcat gctgctactc atcctcttcc tgtccaccat gccggtcctg   2940
tacatgatcg tctccctccc gccatctttt gattgtgggc ccttcagtgg taaaaacagg   3000
atgtttgaag tcatcggtga caccctggaa catgacttcc caagctggat ggcgaagatc   3060
ctgaggcagc tttctaaccc cggccttgtc attgctgtca ttctggtgat ggttctgacc   3120
atctattatc tcaatgctac tgccaagggc cagaaagcag cgaatctgga cctcaaaaag   3180
aagatgaaac agcaagcttt ggagaacaaa atgcgaaaca agaaaatggc agcggctcga   3240
```

```
gcagctgcag ctgctggtgg ccagtaagga tccaatcaac ctctggatta caaaatttgt    3300
gaaagattga ctggtattct taactatgtt gctccttta cgctatgtgg atacgctgct    3360
ttaatgcctt tgtatcatgc tattgcttcc cgtatggctt tcattttctc ctccttgtat    3420
aaatcctggt tgctgtctct ttatgaggag ttgtggcccg ttgtcaggca acgtggcgtg    3480
gtgtgcactg tgtttgctga cgcaaccccc actggttggg gcattgccac cacctgtcag    3540
ctcctttccg ggactttcgc tttccccctc cctattgcca cggcggaact catcgccgcc    3600
tgccttgccc gctgctggac aggggctcgg ctgttgggca ctgacaattc cgtggtgttg    3660
tcggggaaat catcgtcctt ccttggctg ctcgcctgtg ttgccacctg gattctgcgc    3720
gggacgtcct tctgctacgt cccttcggcc ctcaatccag cggaccttcc ttcccgcggc    3780
ctgctgccgg ctctgcggcc tcttccgcgt cttcgagatc tgcctcgact gtgccttcta    3840
gttgccagcc atctgttgtt tgcccctccc ccgtgccttc cttgaccctg aaggtgcca    3900 ctcccactgt cctttcctaa taaaatgagg aaattgcatc gcattgtctg agtaggtgtc    3960
attctattct ggggggtggg gtggggcagg acagcaaggg ggaggattgg aagacaata    4020 gcaggcatgc tggggactcg agttaagggc gaattcccga taaggatctt cctagagcat    4080
ggctacgtag ataagtagca tggcgggtta atcattaact acaaggaacc cctagtgatg    4140
gagttggcca ctccctctct gcgcgctcgc tcgctcactg aggccgggcg accaaaggtc    4200
gcccgacgcc cgggctttgc ccgggcggcc tcagtgagcg agcgagcgcg cagccttaat    4260
taacctaatt cactggccgt cgttttacaa cgtcgtgact gggaaaaccc tggcgttacc    4320
caacttaatc gccttgcagc acatccccct tcgccagct ggcgtaatag cgaagaggcc    4380
cgcaccgatc gcccttccca cagttgcgc agcctgaatg gcgaatggga cgcgccctgt    4440
agcggcgcat taagcgcggc gggtgtggtg gttacgcgca gcgtgaccgc tacacttgcc    4500
agcgccctag cgcccgctcc tttcgcttc ttccttcct ttctcgccac gttcgccggc    4560
tttccccgtc aagctctaaa tcgggggctc cctttagggt tccgatttag tgctttacgg    4620
cacctcgacc ccaaaaaact tgattagggt gatggttcac gtagtgggcc atcgccctga    4680
tagacggttt ttcgcccttt gacgttggag tccacgttct ttaatagtgg actcttgttc    4740
caaactggaa caacactcaa ccctatctcg gtctattctt ttgatttata agggattttg    4800
ccgatttcgg cctattggtt aaaaatgag ctgatttaac aaaaatttaa cgcgaatttt    4860
aacaaaatat taacgtttat aatttcaggt ggcatcttc ggggaaatgt gcgcggaacc    4920
cctatttgtt tatttttcta aatacattca aatatgtatc cgctcatgag acaataaccc    4980
tgataaatgc ttcaataata ttgaaaaagg aagagtatga gtattcaaca tttccgtgtc    5040
gcccttattc ccttttttgc ggcatttgc cttcctgttt ttgctcaccc agaaacgctg    5100
gtgaaagtaa aagatgctga agatcagttg ggtgcacgag tgggttacat cgaactggat    5160
ctcaatagtg gtaagatcct tgagagtttt cgccccgaag aacgttttcc aatgatgagc    5220
acttttaaag ttctgctatg tggcgcggta ttatcccgta ttgacgccgg caagagcaa    5280 ctcggtcgcc gcatacacta ttctcagaat gacttggttg agtactcacc agtcacagaa    5340
aagcatctta cggatggcat gacagtaaga gaattatgca gtgctgccat aaccatgagt    5400
gataacactg cggccaactt acttctgaca acgatcggag gaccgaagga gctaaccgct    5460 ttttgcaca acatgggga tcatgtaact cgccttgatc gttgggaacc ggagctgaat    5520
gaagccatac caaacgacga gcgtgacacc acgatgcctg tagtaatggt aacaacgttg    5580
```

```
cgcaaactat taactggcga actacttact ctagcttccc ggcaacaatt aatagactgg    5640
atggaggcgg ataaagttgc aggaccactt ctgcgctcgg cccttccggc tggctggttt    5700
attgctgata aatctggagc cggtgagcgt gggtctcgcg gtatcattgc agcactgggg    5760
ccagatggta agccctcccg tatcgtagtt atctacacga cggggagtca ggcaactatg    5820
gatgaacgaa atagacagat cgctgagata ggtgcctcac tgattaagca ttggtaactg    5880
tcagaccaag tttactcata tatactttag attgatttaa aacttcattt ttaatttaaa    5940
aggatctagg tgaagatcct ttttgataat ctcatgacca aaatccctta acgtgagttt    6000
tcgttccact gagcgtcaga ccccgtagaa aagatcaaag gatcttcttg agatcctttt    6060
tttctgcgcg taatctgctg cttgcaaaca aaaaaaccac cgctaccagc ggtggtttgt    6120
ttgccggatc aagagctacc aactctttt ccgaaggtaa ctggcttcag cagagcgcag    6180
ataccaaata ctgtccttct agtgtagccg tagttaggcc accacttcaa gaactctgta    6240
gcaccgccta catacctcgc tctgctaatc ctgttaccag tggctgctgc cagtggcgat    6300
aagtcgtgtc ttaccgggtt ggactcaaga cgatagttac cggataaggc gcagcggtcg    6360
ggctgaacgg ggggttcgtg cacacagccc agcttggagc gaacgaccta caccgaactg    6420
agatacctac agcgtgagct atgagaaagc gccacgcttc ccgaagggag aaaggcggac    6480
aggtatccgg taagcggcag ggtcggaaca ggagagcgca cgagggagct tccaggggga    6540
aacgcctggt atctttatag tcctgtcggg tttcgccacc tctgacttga gcgtcgattt    6600
ttgtgatgct cgtcaggggg gcggagccta tggaaaaacg ccagcaacgc ggccttttta    6660
cggttcctgg ccttttgctg gccttttgct cacatgttct ttcctgcgtt atcccctgat    6720
tctgtggata accgtattac cgcctttgag tgagctgata ccgctcgccg cagccgaacg    6780
accgagcgca gcgagtcagt gagcgaggaa gcggaagagc gcccaatacg caaaccgcct    6840
ctccccgcgc gttggccgat tcattaatgc agctggcacg acaggtttcc cgactggaaa    6900
gcgggcagtg agcgcaacgc aattaatgtg agttagctca ctcattaggc accccaggct    6960
ttacacttta tgcttccggc tcgtatgttg tgtggaattg tgagcggata acaatttcac    7020
acaggaaaca gctatgacca tgattacgcc agatttaatt aagg                   7064
```

<210> SEQ ID NO 4
<211> LENGTH: 7052
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaagctagc tagttattaa tagtaatcaa ttacggggtc    240
attagttcat agcccatata tggagttccg cgttacataa cttacggtaa atggcccgcc    300
tggctgaccg cccaacgacc cccgcccatt gacgtcaata atgacgtatg ttcccatagt    360
aacgccaata gggactttcc attgacgtca atgggtggag tatttacggt aaactgccca    420
cttggcagta catcaagtgt atcatatgcc aagtacgccc cctattgacg tcaatgacgg    480
taaatggccc gcctggcatt atgcccagta catgacctta tgggactttc ctacttggca    540
```

-continued

| | | | | | |
|---|---|---|---|---|---|
| gtacatctac | gtattagtca | tcgctattac | catggtgatg | cggttttggc | agtacatcaa | 600 |
| tgggcgtgga | tagcggtttg | actcacgggg | atttccaagt | ctccacccca | ttgacgtcaa | 660 |
| tgggagtttg | ttttggcacc | aaaatcaacg | ggactttcca | aaatgtcgta | acaactccgc | 720 |
| cccattgacg | caaatgggcg | gtaggcgtgt | acggtgggag | gtctatataa | gcagagctgg | 780 |
| tttagtgaac | cgtcagatcc | tgcagaagtt | ggtcgtgagg | cactgggcag | gtaagtatca | 840 |
| aggttacaag | acaggtttaa | ggagaccaat | agaaactggg | cttgtcgaga | cagagaagac | 900 |
| tcttgcgttt | ctgataggca | cctattggtc | ttactgacat | ccactttgcc | tttctctcca | 960 |
| caggtgtcca | ggcggccgcg | gatgttgcaa | atccaagtgg | aggagaaaga | agaggataca | 1020 |
| gaggaaagct | caagtgaaga | agaagaagat | aagctaccca | gaagagagag | cttgagacca | 1080 |
| aagaggaaac | ggaccagaga | tgtcatcaat | gaggatgacc | cagaaccgga | gccggaggat | 1140 |
| gaagaaacaa | gaaaggcaag | agaaaaagaa | aggcggagga | ggctgcggag | aggagcggaa | 1200 |
| gaagaagaag | aaattgatga | agaggaatta | gaacggttaa | aagcactgct | cgatgagaat | 1260 |
| agacaaatga | tcgctactgt | caaatgtaaa | ccttggaaaa | tggagaagaa | aattgaagtt | 1320 |
| ctcaaggaag | caaagaaatt | tgtgagtgag | aatgaaggcg | ctcttgggaa | aggaaaggga | 1380 |
| aagaagtggt | ttgcatttaa | gatgatgatg | gccaagaaat | gggcaaaatt | cctccgagat | 1440 |
| tttgagaact | tcaaagcggc | ttgcgtccca | tgggaaaaca | aaatcaaggc | aattgaaagt | 1500 |
| cagtttggtt | cctcagtggc | ctcgtacttc | ctgttcctca | ggtggatgta | cggcgtcaac | 1560 |
| atggttctct | tgtgttgac | cttcagcctc | atcatgttac | cggagtacct | ctggggttta | 1620 |
| ccgtacggca | gcttacctag | gaaaacagtc | ccaagagctg | aagaagcatc | tgcagccaac | 1680 |
| tttggtgtgt | tgtatgactt | caatggcctg | gcgcagtact | ctgtcctctt | ttatggctat | 1740 |
| tacgacaata | aacgcacgat | cggatggctg | aatttccggc | tacctctttc | ctacttcctg | 1800 |
| gtggggatta | tgtgcattgg | atacagcttc | ctggttgtcc | tcaaagcgat | gaccaaaaat | 1860 |
| attggtgacg | atggtggtgg | cgatgacaac | actttcaact | tcagctggaa | ggtgttctgt | 1920 |
| agctgggact | atctgattgg | taaccctgaa | acagccgaca | caagtttaa | ctctatcacg | 1980 |
| atgaacttta | aggaagccat | catagaagag | agagccgcac | aggtggagga | gaacatccac | 2040 |
| ctcatcagat | ttctgaggtt | tctcgctaac | ttcttcgtgt | tcctcacact | tggtgcaagt | 2100 |
| ggatacctca | tcttttgggc | tgtgaagcga | tcccaggagt | tcgcccagca | agatcctgac | 2160 |
| acccttgggt | ggtgggaaaa | aaatgaaatg | aacatggtaa | tgtccctcct | ggggatgttc | 2220 |
| tgtcccaccc | tgtttgactt | atttgctgaa | ctggaagatt | accatcctct | cattgctctg | 2280 |
| aagtggctcc | tggggcgcat | ttttgctctt | cttctaggca | acttgtatgt | attcattctc | 2340 |
| gccttgatgg | atgagattaa | caacaagatt | gaagaggaga | agcttgtgaa | ggccaatatt | 2400 |
| accctgtggg | aagccaacat | gattaaggct | tacaatgaat | ctctctctgg | gctctctggg | 2460 |
| aacaccacag | gagcacccctt | tttcgttcat | cctgcagatg | tccctcgcgg | tccctgctgg | 2520 |
| gaaacaatgg | tggggcagga | attcgtgcgt | ctcaccgttt | ctgacgtcct | gaccacttac | 2580 |
| gtcacgatcc | tcattggcga | cttcctcaga | gcatgtttcg | tgaggttctg | caattactgc | 2640 |
| tggtgctggg | acttagaata | tggatatcct | tcatacacag | aattcgacat | cagtggcaac | 2700 |
| gtcctcgctc | tgatcttcaa | ccaaggcatg | atctggatgg | gctccttctt | cgctcctagc | 2760 |
| ctcccgggca | tcaacatcct | ccgtctccac | acatccatgt | atttccagtg | ctgggctgtg | 2820 |
| atgtgctgca | atgttcccga | ggccagggtg | ttcaaagctt | ccagatccaa | caacttctac | 2880 |
| ctcggcatgc | tgctactcat | cctcttcctg | tccaccatgc | cggtcctgta | catgatcgtc | 2940 |

```
tccctcccgc catcttttga ttgtgggccc ttcagtggta aaaacaggat gtttgaagtc    3000
atcggtgaga ccctggaaca tgacttccca agctggatgg cgaagatcct gaggcagctt    3060
tctaaccccg gccttgtcat tgctgtcatt ctggtgatgg ttctgaccat ctattatctc    3120
aatgctactg ccaagggcca gaaagcagcg aatctggacc tcaaaaagaa gatgaaacag    3180
caagctttgg agaacaaaat gcgaaacaag aaaatggcag cggctcgagc agctgcagct    3240
gctggtggcc agtaaggatc caatcaacct ctggattaca aaatttgtga agattgact    3300 ggtattctta actatgttgc tccttttacg ctatgtggat acgctgcttt aatgcctttg    3360
tatcatgcta ttgcttcccg tatggctttc attttctcct ccttgtataa atcctggttg    3420
ctgtctcttt atgaggagtt gtggcccgtt gtcaggcaac gtggcgtggt gtgcactgtg    3480
tttgctgacg caaccccac tggttggggc attgccacca cctgtcagct cctttccggg     3540
actttcgctt tccccctccc tattgccacg gcggaactca tcgccgcctg ccttgcccgc    3600
tgctggacag gggctcggct gttgggcact gacaattccg tggtgttgtc ggggaaatca    3660
tcgtcctttc cttggctgct cgcctgtgtt gccacctgga ttctgcgcgg gacgtccttc    3720
tgctacgtcc cttcggccct caatccagcg gaccttcctt cccgcggcct gctgccggct    3780
ctgcggcctc ttccgcgtct tcgagatctg cctcgactgt gccttctagt tgccagccat    3840
ctgttgtttg cccctccccc gtgccttcct gacccctgga aggtgccact cccactgtcc    3900
tttcctaata aaatgaggaa attgcatcgc attgtctgag taggtgtcat tctattctgg    3960
ggggtggggt gggcaggac agcaagggg aggattggga agacaatagc aggcatgctg      4020
gggactcgag ttaagggcga attcccgata aggatcttcc tagagcatgg ctacgtagat    4080
aagtagcatg gcgggttaat cattaactac aaggaacccc tagtgatgga gttggccact    4140
ccctctctgc gcgctcgctc gctcactgag gccgggcgac caaaggtcgc ccgacgcccg    4200
ggctttgccc gggcggcctc agtgagcgag cgagcgcgca gccttaatta acctaattca    4260
ctggccgtcg ttttacaacg tcgtgactgg gaaaaccctg gcgttaccca acttaatcgc    4320
cttgcagcac atcccccttt cgccagctgg cgtaatagcg aagaggcccg caccgatcgc    4380
ccttcccaac agttgcgcag cctgaatggc gaatgggacg cgccctgtag cggcgcatta    4440
agcgcggcgg gtgtggtggt tacgcgcagc gtgaccgcta cacttgccag cgccctagcg    4500
cccgctcctt tcgctttctt cccttccttt ctcgccacgt tcgccggctt tccccgtcaa    4560
gctctaaatc gggggctccc tttagggttc cgatttagtg ctttacggca cctcgacccc    4620
aaaaaacttg attagggtga tggttcacgt agtgggccat cgccctgata gacggttttt    4680
cgccctttga cgttggagtc cacgttcttt aatagtggac tcttgttcca actggaaca    4740 acactcaacc ctatctcggt ctattctttt gatttataag ggattttgcc gatttcggcc    4800
tattggttaa aaaatgagct gatttaacaa aaatttaacg cgaattttaa caaaatatta    4860
acgtttataa tttcaggtgg catctttcgg ggaaatgtgc gcggaacccc tatttgttta    4920
tttttctaaa tacattcaaa tatgtatccg ctcatgagac aataaccctg ataaatgctt    4980
caataatatt gaaaaaggaa gagtatgagt attcaacatt tccgtgtcgc ccttattccc    5040
ttttttgcgg cattttgcct tcctgttttt gctcacccag aaacgctggt gaaagtaaaa    5100
gatgctgaag atcagttggg tgcacgagtg ggttacatcg aactggatct caatagtggt    5160
aagatccttg agagttttcg ccccgaagaa cgttttccaa tgatgagcac ttttaaagtt    5220
ctgctatgtg gcgcggtatt atcccgtatt gacgccgggc aagagcaact cggtcgccgc    5280
```

| | | | | |
|---|---|---|---|---|
| atacactatt | ctcagaatga | cttggttgag | tactcaccag | tcacagaaaa gcatcttacg | 5340 |
| gatggcatga | cagtaagaga | attatgcagt | gctgccataa | ccatgagtga taacactgcg | 5400 |
| gccaacttac | ttctgacaac | gatcggagga | ccgaaggagc | taaccgcttt tttgcacaac | 5460 |
| atggggatc | atgtaactcg | ccttgatcgt | tgggaaccgg | agctgaatga agccatacca | 5520 |
| aacgacgagc | gtgacaccac | gatgcctgta | gtaatggtaa | caacgttgcg caaactatta | 5580 |
| actggcgaac | tacttactct | agcttcccgg | caacaattaa | tagactggat ggaggcggat | 5640 |
| aaagttgcag | gaccacttct | gcgctcggcc | cttccggctg | gctggtttat tgctgataaa | 5700 |
| tctggagccg | gtgagcgtgg | gtctcgcggt | atcattgcag | cactgggcc agatggtaag | 5760 |
| ccctcccgta | tcgtagttat | ctacacgacg | gggagtcagg | caactatgga tgaacgaaat | 5820 |
| agacagatcg | ctgagatagg | tgcctcactg | attaagcatt | ggtaactgtc agaccaagtt | 5880 |
| tactcatata | tactttagat | tgatttaaaa | cttcattttt | aatttaaaag gatctaggtg | 5940 |
| aagatccttt | ttgataatct | catgaccaaa | atcccttaac | gtgagttttc gttccactga | 6000 |
| gcgtcagacc | ccgtagaaaa | gatcaaagga | tcttcttgag | atcctttttt tctgcgcgta | 6060 |
| atctgctgct | tgcaaacaaa | aaaaccaccg | ctaccagcgg | tggtttgttt gccggatcaa | 6120 |
| gagctaccaa | ctcttttttcc | gaaggtaact | ggcttcagca | gagcgcagat accaaatact | 6180 |
| gtccttctag | tgtagccgta | gttaggccac | cacttcaaga | actctgtagc accgcctaca | 6240 |
| tacctcgctc | tgctaatcct | gttaccagtg | gctgctgcca | gtggcgataa gtcgtgtctt | 6300 |
| accgggttgg | actcaagacg | atagttaccg | gataaggcgc | agcggtcggg ctgaacgggg | 6360 |
| ggttcgtgca | cacagcccag | cttggagcga | acgacctaca | ccgaactgag atacctacag | 6420 |
| cgtgagctat | gagaaagcgc | cacgcttccc | gaagggagaa | aggcggacag gtatccggta | 6480 |
| agcggcaggg | tcggaacagg | agagcgcacg | agggagcttc | caggggaaa cgcctggtat | 6540 |
| ctttatagtc | ctgtcgggtt | tcgccacctc | tgacttgagc | gtcgatttt gtgatgctcg | 6600 |
| tcagggggc | ggagcctatg | gaaaaacgcc | agcaacgcgg | cctttttacg gttcctggcc | 6660 |
| ttttgctgcg | gttttgctca | catgttcttt | cctgcgttat | cccctgattc tgtggataac | 6720 |
| cgtattaccg | cctttgagtg | agctgatacc | gctcgccgca | gccgaacgac cgagcgcagc | 6780 |
| gagtcagtga | gcgaggaagc | ggaagagcgc | ccaatacgca | aaccgcctct ccccgcgcgt | 6840 |
| tggccgattc | attaatgcag | ctggcacgac | aggtttcccg | actggaaagc gggcagtgag | 6900 |
| cgcaacgcaa | ttaatgtgag | ttagctcact | cattaggcac | cccaggcttt acactttatg | 6960 |
| cttccggctc | gtatgttgtg | tggaattgtg | agcggataac | aatttcacac aggaaacagc | 7020 |
| tatgaccatg | attacgccag | atttaattaa | gg | | 7052 |

<210> SEQ ID NO 5
<211> LENGTH: 7451
<212> TYPE: DNA
<213> ORGANISM: Artificial Sequence
<220> FEATURE:
<223> OTHER INFORMATION: Description of Artificial Sequence: Synthetic
  polynucleotide

<400> SEQUENCE: 5

| | | | | |
|---|---|---|---|---|
| ctgcgcgctc | gctcgctcac | tgaggccgcc | cgggcaaagc | ccgggcgtcg ggcgaccttt | 60 |
| ggtcgcccgg | cctcagtgag | cgagcgagcg | cgcagagagg | gagtggccaa ctccatcact | 120 |
| aggggttcct | tgtagttaat | gattaacccg | ccatgctact | tatctacgta gccatgctct | 180 |
| aggaagatcg | gaattcgccc | ttaagctagc | tagttattaa | tagtaatcaa ttacggggtc | 240 |

```
attagttcat agcccatata tggagttccg cgttacataa cttacggtaa atggcccgcc      300
tggctgaccg cccaacgacc cccgcccatt gacgtcaata atgacgtatg ttcccatagt      360
aacgccaata gggactttcc attgacgtca atgggtggag tatttacggt aaactgccca      420
cttggcagta catcaagtgt atcatatgcc aagtacgccc cctattgacg tcaatgacgg      480
taaatggccc gcctggcatt atgcccagta catgacctta tgggactttc ctacttggca      540
gtacatctac gtattagtca tcgctattac catggtgatg cggttttggc agtacatcaa      600
tgggcgtgga tagcggtttg actcacgggg atttccaagt ctccacccca ttgacgtcaa      660
tgggagtttg ttttggcacc aaaatcaacg ggactttcca aaatgtcgta acaactccgc      720
cccattgacg caaatgggcg gtaggcgtgt acggtgggag gtctatataa gcagagctgg      780
tttagtgaac cgtcagatcc tgcagaagtt ggtcgtgagg cactgggcag gtaagtatca      840
aggttacaag acaggtttaa ggagaccaat agaaactggg cttgtcgaga cagagaagac      900
tcttgcgttt ctgataggca cctattggtc ttactgacat ccactttgcc tttctctcca      960
caggtgtcca ggcggccgcc atgagccccc agttaaagag cttggacgag aaggtgaca     1020 agtcagcaag aagacccaca aggaaacaaa cctccagagc tgcatgtccc caagacgggc     1080
accgagccca atctagccgg aaggatcctg ctaagggtag cccaagacca gggtcttccc     1140
ggaagaaaca gatggaacat ggaagctatc acaaggggtt gcaggacag aaaccacgaa     1200 aggtggagag gtctctacaa gggaggaaga aggatcggaa aacttccctt aaggagcaga     1260
gagcatctcc aaagaaggag agggaggctc tgaggaagga ggcaggcaag cagctgagaa     1320
aacccaggtc cacttccttg ggctccagtg tctctactgg agactccctg tctgaggagg     1380
agctggctca gatcctggaa caggtagaag aaaaaaagaa gctcatcact accgtgagga     1440
acaaaccctg gccatggca aagaagctga gggaactcag ggaagcccaa gcctttgtgg     1500
agaagtatga aggagccttg gggaaaggca agggcaaaca cctctacgcc tacaggatga     1560
tgatggctaa gaaatgggtc aagtttaaga gggactttga taatttcaag actcaatgta     1620
ttccctggga aatgaagatc aaggacattg aaagtcactt cggttcttct gtggcatctt     1680
acttcatctt tctccgatgg atgtatggag ttaaccttgt ccttttggc ttaatatttg     1740 gtctagtcat catcccagag gtgctgatgg gcatgcccta tggaagtata cccagaaaga     1800
cggtgcctcg ggctgaggaa gagcgagcca tggacttctc tgtccttggg gattttgagg     1860
gctacatcaa atattctgct ctcttctatg ctactacaa caaccagcgg accattggat     1920
ggctgaggta caggctgccc atggcttact ttatggtggg ggtcagcgtg tttggctaca     1980
gcttgatgat cgtcattagg tcgatggcca gcaatacccca gggtagcacc agtgaggggg     2040
acagtgacag cttcacgttc agcttcaaga tgttcaccag ctgggactac ctcatcggga     2100
attcagagac agcagacaac aaatatgtct ccatcactac cagcttcaag gagtctatag     2160
tggacgaaca agagagtaac aaagaaggga atatccacct gacaagattc ctccgcgtcc     2220
tggccaactt tctcattctc tgctgtctgt gtggaagcgg gtacctcatt tactttgtgg     2280
tgaaacggtc ccaggagttc tccaaaatgc aaaatgtcag ctggtatgaa aggaatgagg     2340
tggagatcgt gatgtctctg ctagggatgt tttgtccccc tctgtttgaa accatcgctg     2400
ccttggagaa ttatcaccca cgaactgggc tgaagtggca gctgggccgc atctttgccc     2460
ttttcctggg aaacctctac acgtttctcc tggcctcat ggacgatgtc caccttaagc     2520
tttctaatga ggaaaaaatc aagaacatca ctcactggac cctgtttaac tattacaatt     2580
cctcaggtgg gaatgagagt gtgcccggc caccaccaca ccctgcagat gtgcccagag     2640
```

```
gttcttgctg ggagacagct gtgggcattg agtttatgag gctcaccgtg tctgacatgc    2700
tggtaacata cctcaccatc ttggtcggag atttcctccg agcttgtttt gtccggttca    2760
tgaatcactg ctggtgttgg gacctcgagg ctggttttcc ctcatatgcc gagtttgata    2820
ttagtggaaa tgtgttgggt ttgatcttca accaaggaat gatctggatg ggctccttct    2880
atgctccagg actggtgggc atcaatgtcc tgcgcctgtt gacctccatg tacttccagt    2940
gctgggcagt gatgagcagc aacgttcccc atgagcgtgt gtttaaagcc tcccgatcca    3000
acaacttcta catgggcctg ctgctgttgg tgctcttcct cagcctcctg cctgtggcct    3060
acactgtcat gtctctccca ccctcgtttg actgtggccc cttcagtggg aaaaacagaa    3120
tgtacgatgt cctccatgag accatcgaga cgatttccc taagttcctg ggcaagatct    3180
ttgcgttcct tgccaaccca ggcctgatca ttccagccat cctgctaatg tttctggcca    3240
tttactacct gaactcagtt tcaaaaagtc tttccagagc taatgcccag ctgcgaaaga    3300
agatccaagc gctccgtgaa gttgagaaga accataaatc catcaaggga aaagccatag    3360
tcacatattc agaggacaca atcaagaaca gctccaaaaa tgccacccag atacatctta    3420
ctaaagaaga gccacatctc actcttcca gccaaatcca gaccctggac aagaaagcgc    3480
agggccccca cacctccagt actgagggtg gggcctcgcc gtctacctcc tggcaccatg    3540
ttgggtctca accaccgaga ggcagacgag attctggcca accccagtct cagacttata    3600
caggcaggtc accttctgga aagagaaccc agaggcctca caactgataa gcttggatcc    3660
aatcaacctc tggattacaa aatttgtgaa agattgactg gtattcttaa ctatgttgct    3720
ccttttacgc tatgtggata cgctgcttta atgcctttgt atcatgctat tgcttcccgt    3780
atggctttca ttttctcctc cttgtataaa tcctggttgc tgtctcttta tgaggagttg    3840
tggcccgttg tcaggcaacg tggcgtggtg tgcactgtgt ttgctgacgc aacccccact    3900 ggttgggca ttgccaccac ctgtcagctc ctttccggga cttttgctttt cccctccct     3960 attgccacgg cggaactcat cgccgcctgc cttgcccgct gctggacagg ggctcggctg    4020 ttggcactg acaattccgt ggtgttgtcg gggaaatcat cgtcctttcc ttggctgctc    4080
gcctgtgttg ccacctggat tctgcgcggg acgtccttct gctacgtccc ttcggccctc    4140
aatccagcgg accttccttc ccgcggcctg ctgccggctc tgcggcctct tccgcgtctt    4200
cgagatctgc ctcgactgtg ccttctagtt gccagccatc tgttgtttgc ccctcccccg    4260
tgccttcctt gaccctggaa ggtgccactc ccactgtcct ttcctaataa aatgaggaaa    4320
ttgcatcgca ttgtctgagt aggtgtcatt ctattctggg gggtggggtg gggcaggaca    4380
gcaaggggga ggattgggaa gacaatagca ggcatgctgg ggactcgagt taagggcgaa    4440
ttcccgataa ggatcttcct agagcatggc tacgtagata gtagcatgg cgggttaatc     4500 attaactaca aggaacccct agtgatggag ttggccactc cctctctgcg cgctcgctcg    4560
ctcactgagg ccgggcgacc aaaggtcgcc cgacgcccgg ctttgcccg gcggcctca     4620 gtgagcgagc gagcgcgcag ccttaattaa cctaattcac tggccgtcgt tttacaacgt    4680
cgtgactggg aaaaccctgg cgttacccaa cttaatcgcc ttgcagcaca tccccctttc    4740
gccagctggc gtaatagcga agaggcccgc accgatcgcc cttcccaaca gttgcgcagc    4800
ctgaatggcg aatgggacgc gccctgtagc ggcgcattaa gcgcggcggg tgtggtggtt    4860
acgcgcagcg tgaccgctac acttgccagc gccctagcgc ccgctccttt cgctttcttc    4920
ccttcctttc tcgccacgtt cgccggcttt ccccgtcaag ctctaaatcg ggggctccct    4980
```

```
ttagggttcc gatttagtgc tttacggcac ctcgaccccca aaaaacttga ttagggtgat    5040
ggttcacgta gtgggccatc gccctgatag acggtttttc gcccttttgac gttggagtcc    5100
acgttctttta atagtggact cttgttccaa actggaacaa cactcaaccc tatctcggtc    5160
tattcttttg atttataagg gattttgccg atttcggcct attggttaaa aaatgagctg    5220
atttaacaaa aatttaacgc gaattttaac aaaatattaa cgtttataat ttcaggtggc    5280
atctttcggg gaaatgtgcg cggaacccct atttgtttat ttttctaaat acattcaaat    5340
atgtatccgc tcatgagaca ataaccctga taaatgcttc aataatattg aaaaggaag    5400
agtatgagta ttcaacattt ccgtgtcgcc cttattccct tttttgcggc attttgcctt    5460
cctgtttttg ctcacccaga aacgctggtg aaagtaaaag atgctgaaga tcagttgggt    5520
gcacgagtgg gttacatcga actggatctc aatagtggta agatccttga gagttttcgc    5580
cccgaagaac gttttccaat gatgagcact tttaaagttc tgctatgtgg cgcggtatta    5640
tcccgtattg acgccgggca agagcaactc ggtcgccgca tacactattc tcagaatgac    5700
ttggttgagt actcaccagt cacagaaaag catcttacgg atggcatgac agtaagagaa    5760
ttatgcagtg ctgccataac catgagtgat aacactgcgg ccaacttact tctgacaacg    5820
atcggaggac cgaaggagct aaccgctttt ttgcacaaca tgggggatca tgtaactcgc    5880
cttgatcgtt gggaaccgga gctgaatgaa gccataccaa acgacgagcg tgacaccacg    5940
atgcctgtag taatggtaac aacgttgcgc aaactattaa ctggcgaact acttactcta    6000
gcttcccggc aacaattaat agactggatg gaggcggata agttgcagg accacttctg    6060
cgctcggccc ttccggctgg ctggtttatt gctgataaat ctggagccgg tgagcgtggg    6120
tctcgcggta tcattgcagc actggggcca gatggtaagc cctcccgtat cgtagttatc    6180
tacacgacgg ggagtcaggc aactatggat gaacgaaata gacagatcgc tgagataggt    6240
gcctcactga ttaagcattg gtaactgtca gaccaagttt actcatatat actttagatt    6300
gatttaaaac ttcatttta atttaaaagg atctaggtga agatcctttt tgataatctc    6360
atgaccaaaa tcccttaacg tgagttttcg ttccactgag cgtcagaccc cgtagaaaag    6420
atcaaaggat cttcttgaga tccttttttt ctgcgcgtaa tctgctgctt gcaaacaaaa    6480
aaaccaccgc taccagcggt ggtttgtttg ccggatcaag agctaccaac tctttttccg    6540
aaggtaactg gcttcagcag agcgcagata ccaaatactg tccttctagt gtagccgtag    6600
ttaggccacc acttcaagaa ctctgtagca ccgcctacat acctcgctct gctaatcctg    6660
ttaccagtgg ctgctgccag tggcgataag tcgtgtctta ccgggttgga ctcaagacga    6720
tagttaccgg ataaggcgca gcggtcgggc tgaacggggg gttcgtgcac acagcccagc    6780
ttggagcgaa cgacctacac cgaactgaga tacctacagc gtgagctatg agaaagcgcc    6840
acgcttcccg aagggagaaa ggcggacagg tatccggtaa gcggcagggt cggaacagga    6900
gagcgcacga gggagcttcc agggggaaac gcctggtatc tttatagtcc tgtcgggttt    6960
cgccacctct gacttgagcg tcgatttttg tgatgctcgt cagggggcg gagcctatgg    7020
aaaaacgcca gcaacgcggc cttttacgg ttcctggcct tttgctgcgg ttttgctcac    7080
atgttctttc ctgcgttatc ccctgattct gtggataacc gtattaccgc ctttgagtga    7140
gctgataccg ctcgccgcag ccgaacgacc gagcgcagcg agtcagtgag cgaggaagcg    7200
gaagagcgcc caatacgcaa accgcctctc cccgcgcgtt ggccgattca ttaatgcagc    7260
tggcacgaca ggtttcccga ctggaaagcg ggcagtgagc gcaacgcaat taatgtgagt    7320
tagctcactc attaggcacc ccaggcttta cactttatgc ttccggctcg tatgttgtgt    7380
```

```
ggaattgtga gcggataaca atttcacaca ggaaacagct atgaccatga ttacgccaga    7440
tttaattaag g                                                          7451

<210> SEQ ID NO 6
<211> LENGTH: 6999
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgcaag aaccctcact ggctgaacta     180
tcttgccagc cccttatttt gttttcatat taacctcttt tttctagtaa aggagatgtt     240
tgctctcaaa tttgcatagg aatgtaatat ttaatttaaa aagatgaccc acatatgacc     300
ttataaggac agtaaaatta acaaccgga aagataaagc gggccagttg gctcagttct     360
ataaaaccag cccacaagga ttgtcactat tcttaggctt gcgcgggcta catgatgagt     420
tccaggactg cctggttaca gaccgagact ctctcaagag tccagataaa caacaacaaa     480
gggggcgagg tggaaataca ggggctgtaa gaagtaaata tgatatctgc atgggaggct     540
agccagagaa gaaaaaattt tcttccgtgg ttcaatcctc aagggctga caggaagtt      600 gacgcaggca ggtgaggagc acgagcctag atgggctgcg gtgccaccct taatccccac     660
aagcgagttc ctccgcaatt cgcctgtccc actctcaact tttcttcaac tgactctttg     720
ctgtggtccc tcgctgtggc agtggaaaca actaccactg cgaggtaggg aatgtcatga     780
ggggctacct gcagcccttg gcttgcaggg atgcagggat gcggtcggaa cctgaggccc     840
cgcccttctc ttgccccacg ccattaggcc acgcccctac ccagcactcc ttcaaccacc     900
cccttccccg gcgcctcatg aggtcccgcc cctctcaacc ctagctcttg aggcctcccc     960
ttcacagccg ccccggcgtt ccttgacttg aggccacgtc cctctgctcc ttcattccca    1020
agaccctacg cttttgcgagt cctccctgtc ctgctgccta ggaccccgcc cctctcagcc    1080
cttctgcccc aagaccccgc cccttaggct gttcccgccc actggccaat gaagacccgc    1140
cctttcttta gccgccccgc cccggtccca caaaatcccg cctccggccc cgcctcccgc    1200
cccccttggg cgctccgtagc agtgacgtgc gcaggctggg cactctgcag ggctctctgg    1260
ccggcgggtg gagaccgatc cgggatctgt cccagcagga agcgtatccc ggccgccgtc    1320
gtgctgtcgt ctccggtgct cgctctcggc gcggtgtcg cgcttgccct tcgcgcccgc    1380
agcccggcag cctctcgagc tcaagcttcg aattcgtcga caggatgcca cccaaaaaag    1440
tgcaaatcca gtggaggag aaagaagagg atacagagga aagctcaagt gaagaagaag     1500
aagataagct acccagaaga gagagcttga gaccaaagag gaaacggacc agagatgtca    1560
tcaatgagga tgacccagaa ccggagccgg aggatgaaga acaagaaag gcaagagaaa    1620 aagaaaggcg gaggaggctg cggagaggag cggaagaaga agaagaaatt gatgaagagg    1680
aattagaacg gttaaaagca ctgctcgatg agaatagaca aatgatcgct actgtcaaat    1740
gtaaaccttg gaaaatggag aagaaaattg aagttctcaa ggaagcaaag aaatttgtga    1800
gtgagaatga aggcgctctt gggaaaggaa agggaaagaa gtggtttgca tttaagatga    1860
tgatggccaa gaaatgggca aaattcctcc gagattttga gaacttcaaa gcggcttgcg    1920
```

-continued

| | |
|---|---|
| tcccatggga aaacaaaatc aaggcaattg aaagtcagtt tggttcctca gtggcctcgt | 1980 |
| acttcctgtt cctcaggtgg atgtacggcg tcaacatggt tctctttgtg ttgaccttca | 2040 |
| gcctcatcat gttaccggag tacctctggg gtttaccgta cggcagctta cctaggaaaa | 2100 |
| cagtcccaag agctgaagaa gcatctgcag ccaactttgg tgtgttgtat gacttcaatg | 2160 |
| gcctggcgca gtactctgtc ctcttttatg gctattacga caataaacgc acgatcggat | 2220 |
| ggctgaattt ccggctacct ctttcctact tcctggtggg gattatgtgc attggataca | 2280 |
| gcttcctggt tgtcctcaaa gcgatgacca aaaatattgg tgacgatggt ggtggcgatg | 2340 |
| acaacacttt caacttcagc tggaaggtgt tctgtagctg ggactatctg attggtaacc | 2400 |
| ctgaaacagc cgacaacaag tttaactcta tcacgatgaa ctttaaggaa gccatcatag | 2460 |
| aagagagagc cgcacaggtg gaggagaaca tccacctcat cagatttctg aggtttctcg | 2520 |
| ctaacttctt cgtgttcctc acacttggtg caagtggata cctcatcttt tgggctgtga | 2580 |
| agcgatccca ggagttcgcc cagcaagatc ctgacaccct tggtggtgg gaaaaaaatg | 2640 |
| aaatgaacat ggtaatgtcc ctcctgggga tgttctgtcc caccctgttt gacttatttg | 2700 |
| ctgaactgga agattaccat cctctcattg ctctgaagtg gctcctgggg cgcattttg | 2760 |
| ctcttcttct aggcaacttg tatgtattca ttctcgcctt gatggatgag attaacaaca | 2820 |
| agattgaaga ggagaagctt gtgaaggcca atattaccct gtgggaagcc aacatgatta | 2880 |
| aggcttacaa tgaatctctc tctgggctct ctgggaacac cacaggagca cccttttttcg | 2940 |
| ttcatcctgc agatgtccct cgcggtccct gctgggaaac aatggtgggg caggaattcg | 3000 |
| tgcgtctcac cgtttctgac gtcctgacca cttacgtcac gatcctcatt ggcgacttcc | 3060 |
| tcagagcatg tttcgtgagg ttctgcaatt actgctggtg ctgggactta gaatatggat | 3120 |
| atccttcata cacagaattc gacatcagtg gcaacgtcct cgctctgatc ttcaaccaag | 3180 |
| gcatgatctg gatgggctcc ttcttcgctc ctagcctccc gggcatcaac atcctccgtc | 3240 |
| tccacacatc catgtatttc cagtgctggg ctgtgatgtg ctgcaatgtt cccgaggcca | 3300 |
| gggtgttcaa agcttccaga tccaacaact tctacctcgg catgctgcta ctcatcctct | 3360 |
| tcctgtccac catgccggtc ctgtacatga tcgtctccct cccgccatct tttgattgtg | 3420 |
| ggcccttcag tggtaaaaac aggatgtttg aagtcatcgg tgagaccctg aacatgact | 3480 |
| tcccaagctg gatggcgaag atcctgaggc agctttctaa ccccggcctt gtcattgctg | 3540 |
| tcattctggt gatggttctg accatctatt atctcaatgc tactgccaag ggccagaaag | 3600 |
| cagcgaatct ggacctcaaa aagaagatga acagcaagc tttggagaac aaaatgcgaa | 3660 |
| acaagaaaat ggcagcggct cgagcagctg cagctgctgg tggccagtaa gcggccgctc | 3720 |
| gagcctaagc ttctagaaga tctacggtgt gcatccctgt gacccctccc cagtgcctct | 3780 |
| cctggccctg gaagttgcca ctccagtgcc caccagcctt gtcctaataa aattaagttg | 3840 |
| catcattttg tctgactagg tgtccttcta taatattatg gggtggaggg gggtggtatg | 3900 |
| gagcaagggg caagttggga agacaacctg tagggcctgc ggggtctatt gggaaccaag | 3960 |
| ctggagtgca gtggcacaat cttggctcac tgcaatctcc gcctcctggg ttcaagcgat | 4020 |
| tctcctgcct cagcctcccg agttgttggg attccaggca tgcatgacca ggctcagcta | 4080 |
| attttttgttt ttttggtaga cggggtttt caccatattg gccaggctgg tctccaactc | 4140 |
| ctaatctcag gtgatctacc cacccttgcc tcccaaattg ctgggattac aggcgtgaac | 4200 |
| cactgctccc ttccctgtcc ttctgatttt gtaggtaacc acgtgcggac cgagcggccg | 4260 |

-continued

```
caggaacccc tagtgatgga gttggccact ccctctctgc gcgctcgctc gctcactgag    4320
gccgggcgac caaaggtcgc ccgacgcccg ggctttgccc gggcggcctc agtgagcgag    4380
cgagcgcgca gctgcctgca ggggcgcctg atgcggtatt ttctccttac gcatctgtgc    4440
ggtatttcac accgcatacg tcaaagcaac catagtacgc gccctgtagc ggcgcattaa    4500
gcgcggcggg tgtggtggtt acgcgcagcg tgaccgctac acttgccagc gccctagcgc    4560
ccgctccttt cgctttcttc ccttcctttc tcgccacgtt cgccggcttt ccccgtcaag    4620
ctctaaatcg ggggctccct ttagggttcc gatttagtgc tttacggcac ctcgacccca    4680
aaaaacttga tttgggtgat ggttcacgta gtgggccatc gccctgatag acggtttttc    4740
gccctttgac gttggagtcc acgttcttta atagtggact cttgttccaa actggaacaa    4800
cactcaaccc tatctcgggc tattcttttg atttataagg gattttgccg atttcggcct    4860
attggttaaa aaatgagctg atttaacaaa aatttaacgc gaattttaac aaaatattaa    4920
cgtttacaat tttatggtgc actctcagta caatctgctc tgatgccgca tagttaagcc    4980
agccccgaca cccgccaaca cccgctgacg cgccctgacg ggcttgtctg ctcccggcat    5040
ccgcttacag acaagctgtg accgtctccg ggagctgcat gtgtcagagg ttttcaccgt    5100
catcaccgaa acgcgcgaga cgaaagggcc tcgtgatacg cctattttta taggttaatg    5160
tcatgataat aatggtttct tagacgtcag gtggcacttt tcggggaaat gtgcgcggaa    5220
cccctatttg tttatttttc taaatacatt caaatatgta tccgctcatg agacaataac    5280
cctgataaat gcttcaataa tattgaaaaa ggaagagtat gagtattcaa catttccgtg    5340
tcgcccttat tcccttttt gcggcatttt gccttcctgt ttttgctcac ccagaaacgc    5400
tggtgaaagt aaaagatgct gaagatcagt tgggtgcacg agtgggttac atcgaactgg    5460
atctcaacag cggtaagatc cttgagagtt ttcgccccga agaacgtttt ccaatgatga    5520
gcacttttaa agttctgcta tgtggcgcgg tattatcccg tattgacgcc gggcaagagc    5580
aactcggtcg ccgcatacac tattctcaga atgacttggt tgagtactca ccagtcacag    5640
aaaagcatct tacggatggc atgacagtaa gagaattatg cagtgctgcc ataaccatga    5700
gtgataacac tgcggccaac ttacttctga caacgatcgg aggaccgaag gagctaaccg    5760
cttttttgca caacatgggg gatcatgtaa ctcgccttga tcgttgggaa ccggagctga    5820
atgaagccat accaaacgac gagcgtgaca ccacgatgcc tgtagcaatg gcaacaacgt    5880
tgcgcaaact attaactggc gaactactta ctctagcttc ccggcaacaa ttaatagact    5940
ggatggaggc ggataaagtt gcaggaccac ttctgcgctc ggcccttccg gctggctggt    6000
ttattgctga taaatctgga gccggtgagc gtgggtctcg cggtatcatt gcagcactgg    6060
ggccagatgg taagccctcc cgtatcgtag ttatctacac gacggggagt caggcaacta    6120
tggatgaacg aaatagacag atcgctgaga taggtgcctc actgattaag cattggtaac    6180
tgtcagacca gtttactca tatatacttt agattgattt aaaacttcat ttttaattta    6240
aaaggatcta ggtgaagatc ctttttgata atctcatgac caaaatccct taacgtgagt    6300
tttcgttcca ctgagcgtca gaccccgtag aaaagatcaa aggatcttct tgagatcctt    6360
tttttctgcg cgtaatctgc tgcttgcaaa caaaaaaacc accgctacca gcggtggttt    6420
gtttgccgga tcaagagcta ccaactcttt ttccgaaggt aactggcttc agcagagcgc    6480
agataccaaa tactgtcctt ctagtgtagc cgtagttagg ccaccacttc aagaactctg    6540
tagcaccgcc tacatacctc gctctgctaa tcctgttacc agtggctgct gccagtggcg    6600
ataagtcgtg tcttaccggg ttggactcaa gacgatagtt accggataag cgcagcggt    6660
```

```
cgggctgaac gggggggttcg tgcacacagc ccagcttgga gcgaacgacc tacaccgaac    6720
tgagatacct acagcgtgag ctatgagaaa gcgccacgct tcccgaaggg agaaaggcgg    6780
acaggtatcc ggtaagcggc agggtcggaa caggagagcg cacgagggag cttccagggg    6840
gaaacgcctg gtatctttat agtcctgtcg ggtttcgcca cctctgactt gagcgtcgat    6900
ttttgtgatg ctcgtcaggg gggcggagcc tatggaaaaa cgccagcaac gcggcctttt    6960
tacggttcct ggccttttgc tggccttttg ctcacatgt                            6999

<210> SEQ ID NO 7
<211> LENGTH: 7728
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgcaag aaccctcact ggctgaacta     180
tcttgccagc cccttatttt gttttcatat taacctcttt tttctagtaa aggagatgtt     240
tgctctcaaa tttgcatagg aatgtaatat ttaatttaaa aagatgaccc acatatgacc     300
ttataaggac agtaaaatta acaaccgga aagataaagc gggccagttg gctcagttct     360
ataaaaccag cccacaagga ttgtcactat tcttaggctt gcgcgggcta catgatgagt     420
tccaggactg cctggttaca gaccgagact ctctcaagag tccagataaa caacaacaaa     480
gggggcgagg tggaaataca ggggctgtaa gaagtaaata tgatatctgc atgggaggct     540
agccagagaa gaaaaaattt tcttccgtgg ttcaatcctc caagggctga acaggaagtt     600
gacgcaggca ggtgaggagc acgagcctag atgggctgcg gtgccaccct taatccccac     660
aagcgagttc ctccgcaatt cgcctgtccc actctcaact tttcttcaac tgactctttg     720
ctgtggtccc tcgctgtggc agtggaaaca actaccactg cgaggtaggg aatgtcatga     780
ggggctacct gcagcccttg gcttgcaggg atgcagggat gcggtcggaa cctgaggccc     840
cgcccttctc ttgccccacg ccattaggcc acgcccctac ccagcactcc ttcaaccacc     900
cccttccccg gcgcctcatg aggtcccgcc cctctcaacc ctagctcttg aggcctcccc     960
ttcacagccg ccccggcgtt ccttgacttg aggccacgtc cctctgctcc ttcattccca    1020
agaccctacg ctttgcgagt cctccctgtc ctgctgccta ggaccccgcc cctctcagcc    1080
cttctgcccc aagaccccgc cccttaggct gttcccgccc actggccaat gaagacccgc    1140
cctttcttta gccgccccgc cccggtccca caaaatcccg cctccggccc cgcctcccgc    1200
cccccttggg cgctccgtag cagtgacgtg caggctggg cactctgcag gctctctgg     1260 ccggcgggtg gagaccgatc cgggatctgt cccagcagga agcgtatccc ggccgccgtc    1320
gtgctgtcgt ctccggtgct cgctctcggc cgcggtgtcg cgcttgccct tcgcgcccgc    1380
agcccggcag cctctcgagc tcaagcttcg aattcgtcga caggatgttg caaatccaag    1440
tggaggagaa agaagaggat acagaggaaa gctcaagtga agaagaagaa gataagctac    1500
ccagaagaga gagcttgaga ccaaagagga aacggaccag agatgtcatc aatgaggatg    1560
acccagaacc ggagccggag gatgaagaaa caagaaaggc aagagaaaaa gaaaggcgga    1620
ggaggctgcg gagaggagcg gaagaagaag aagaaattga tgaagaggaa ttagaacggt    1680
```

```
taaaagcact gctcgatgag aatagacaaa tgatcgctac tgtcaaatgt aaaccttgga    1740
aaatggagaa gaaaattgaa gttctcaagg aagcaaagaa atttgtgagt gagaatgaag    1800
gcgctcttgg gaaaggaaag ggaaagaagt ggtttgcatt taagatgatg atggccaaga    1860
aatgggcaaa attcctccga gattttgaga acttcaaagc ggcttgcgtc ccatgggaaa    1920
acaaaatcaa ggcaattgaa agtcagtttg gttcctcagt ggcctcgtac ttcctgttcc    1980
tcaggtggat gtacggcgtc aacatggttc tctttgtgtt gaccttcagc ctcatcatgt    2040
taccggagta cctctggggt ttaccgtacg gcagcttacc taggaaaaca gtcccaagag    2100
ctgaagaagc atctgcagcc aactttggtg tgttgtatga cttcaatggc ctggcgcagt    2160
actctgtcct cttttatggc tattacgaca ataaacgcac gatcggatgg ctgaatttcc    2220
ggctacctct ttcctacttc ctggtgggga ttatgtgcat tggatacagc ttcctggttg    2280
tcctcaaagc gatgaccaaa aatattggtg acgatggtgg tggcgatgac aacactttca    2340
acttcagctg gaaggtgttc tgtagctggg actatctgat tggtaaccct gaaacagccg    2400
acaacaagtt taactctatc acgatgaact ttaaggaagc catcatagaa gagagagccg    2460
cacaggtgga ggagaacatc cacctcatca gatttctgag gtttctcgct aacttcttcg    2520
tgttcctcac acttggtgca agtggatacc tcatcttttg ggctgtgaag cgatcccagg    2580
agttcgccca gcaagatcct gacacccttg ggtggtggga aaaaaatgaa atgaacatgg    2640
taatgtccct cctggggatg ttctgtccca ccctgtttga cttatttgct gaactggaag    2700
attaccatcc tctcattgct ctgaagtggc tcctggggcg catttttgct cttcttctag    2760
gcaacttgta tgtattcatt ctcgccttga tggatgagat taacaacaag attgaagagg    2820
agaagcttgt gaaggccaat attaccctgt gggaagccaa catgattaag gcttacaatg    2880
aatctctctc tgggctctct gggaacacca caggagcacc cttttcgtt catcctgcag    2940 atgtccctcg cggtcctgc tgggaaacaa tggtggggca ggaattcgtg cgtctcaccg    3000
tttctgacgt cctgaccact tacgtcacga tcctcattgg cgacttcctc agagcatgtt    3060
tcgtgaggtt ctgcaattac tgctggtgct gggacttaga atatggatat ccttcataca    3120
cagaattcga catcagtggc aacgtcctcg ctctgatctt caaccaaggc atgatctgga    3180
tgggctcctt cttcgctcct agcctcccgg catcaacat cctccgtctc cacacatcca    3240
tgtatttcca gtgctgggct gtgatgtgct gcaatgttcc cgaggccagg gtgttcaaag    3300
cttccagatc caacaacttc tacctcggca tgctgctact catcctcttc ctgtccacca    3360
tgccggtcct gtacatgatc gtctccctcc cgccatcttt tgattgtggg cccttcagtg    3420
gtaaaaacag gatgtttgaa gtcatcggtg agaccctgga acatgacttc ccaagctgga    3480
tggcgaagat cctgaggcag ctttctaacc ccggccttgt cattgctgtc attctggtga    3540
tggttctgac catctattat ctcaatgcta ctgccaaggg ccagaaagca gcgaatctgg    3600
acctcaaaaa gaagatgaaa cagcaagctt ggagaacaa atgcgaaac aagaaaatgg    3660 cagcggctcg agcagctgca gctgctggtg gccagtggat ccaccggccg gtcgccacca    3720
tggtgagcaa gggcgaggag ctgttcaccg gggtggtgcc catcctggtc gagctggacg    3780
gcgacgtaaa cggccacaag ttcagcgtgt ccggcgaggg cgaggcgat gccacctacg    3840 gcaagctgac cctgaagttc atctgcacca ccggcaagct gcccgtgccc tggcccaccc    3900
tcgtgaccac cctgacctac ggcgtgcagt gcttcagccg ctaccccgac cacatgaagc    3960
agcacgactt cttcaagtcc gccatgcccg aaggctacgt ccaggagcgc accatcttct    4020
```

```
tcaaggacga cggcaactac aagacccgcg ccgaggtgaa gttcgagggc gacaccctgg    4080
tgaaccgcat cgagctgaag ggcatcgact caaggagga cggcaacatc ctggggcaca    4140
agctggagta caactacaac agccacaacg tctatatcat ggccgacaag cagaagaacg    4200
gcatcaaggt gaacttcaag atccgccaca acatcgagga cggcagcgtg cagctcgccg    4260
accactacca gcagaacacc cccatcggcg acggccccgt gctgctgccc gacaaccact    4320
acctgagcac ccagtccgcc ctgagcaaag accccaacga aaagcgcgat cacatggtcc    4380
tgctggagtt cgtgaccgcc gccgggatca ctctcggcat ggacgagctg tacaagtaag    4440
cggccgctcg agcctaagct tctagaagat ctacgggtgg catccctgtg accctccccc    4500
agtgcctctc ctggccctgg aagttgccac tccagtgccc accagccttg tcctaataaa    4560
attaagttgc atcattttgt ctgactaggt gtccttctat aatattatgg ggtggagggg    4620
ggtggtatgg agcaaggggc aagttgggaa gacaacctgt agggcctgcg ggtctattg    4680 ggaaccaagc tggagtgcag tggcacaatc ttggctcact gcaatctccg cctcctgggt    4740
tcaagcgatt ctcctgcctc agcctcccga gttgttggga ttccaggcat gcatgaccag    4800
gctcagctaa ttttttgtttt tttggtagag acggggtttc accatattgg ccaggctggt    4860
ctccaactcc taatctcagg tgatctaccc accttggcct cccaaattgc tgggattaca    4920
ggcgtgaacc actgctccct tccctgtcct tctgattttg taggtaacca cgtgcggacc    4980
gagcggccgc aggaacccct agtgatggag ttggccactc cctctctgcg cgctcgctcg    5040
ctcactgagg ccgggcgacc aaaggtcgcc cgacgcccgg gctttgcccg gcggcctca    5100 gtgagcgagc gagcgcgcag ctgcctgcag gggcgcctga tgcggtattt tctccttacg    5160
catctgtgcg gtatttcaca ccgcatacgt caaagcaacc atagtacgcg ccctgtagcg    5220
gcgcattaag cgcggcgggt gtggtggtta cgcgcagcgt gaccgctaca cttgccagcg    5280
ccctagcgcc cgctcctttc gctttcttcc cttcctttct cgccacgttc gccggctttc    5340
cccgtcaagc tctaaatcgg gggctccctt tagggttccg atttagtgct ttacggcacc    5400
tcgaccccaa aaaacttgat ttgggtgatg gttcacgtag tgggccatcg ccctgataga    5460 cggttttcg ccctttgacg ttggagtcca cgttctttaa tagtggactc ttgttccaaa    5520
ctggaacaac actcaaccct atctcgggct attcttttga tttataaggg attttgccga    5580
tttcggccta ttggttaaaa aatgagctga tttaacaaaa atttaacgcg aattttaaca    5640
aaatattaac gtttacaatt ttatggtgca ctctcagtac aatctgctct gatgccgcat    5700
agttaagcca gccccgacac ccgccaacac ccgctgacgc gccctgacgg gcttgtctgc    5760
tcccggcatc cgcttacaga caagctgtga ccgtctccgg gagctgcatg tgtcagaggt    5820
tttcaccgtc atcaccgaaa cgcgcgagac gaaagggcct cgtgatacgc ctatttttat    5880
aggttaatgt catgataata atggtttctt agacgtcagg tggcacttt cggggaaatg    5940 tgcgcggaac ccctatttgt ttatttttct aaatacattc aaatatgtat ccgctcatga    6000
gacaataacc ctgataaatg cttcaataat attgaaaaag gaagagtatg agtattcaac    6060
atttccgtgt cgcccttatt ccctttttttg cggcattttg ccttcctgtt tttgctcacc    6120
cagaaacgct ggtgaaagta aaagatgctg aagatcagtt gggtgcacga gtgggttaca    6180
tcgaactgga tctcaacagc ggtaagatcc ttgagagttt tcgccccgaa gaacgttttc    6240
caatgatgag cacttttaaa gttctgctat gtggcgcggt attatcccgt attgacgccg    6300
ggcaagagca actcggtcgc cgcatacact attctcagaa tgacttggtt gagtactcac    6360
cagtcacaga aaagcatctt acggatggca tgacagtaag agaattatgc agtgctgcca    6420
```

```
taaccatgag tgataacact gcggccaact tacttctgac aacgatcgga ggaccgaagg   6480
agctaaccgc ttttttgcac aacatggggg atcatgtaac tcgccttgat cgttgggaac   6540
cggagctgaa tgaagccata ccaaacgacg agcgtgacac cacgatgcct gtagcaatgg   6600
caacaacgtt gcgcaaacta ttaactggcg aactacttac tctagcttcc cggcaacaat   6660
taatagactg gatggaggcg gataaagttg caggaccact tctgcgctcg gcccttccgg   6720
ctggctggtt tattgctgat aaatctggag ccggtgagcg tgggtctcgc ggtatcattg   6780
cagcactggg gccagatggt aagccctccc gtatcgtagt tatctacacg acggggagtc   6840
aggcaactat ggatgaacga atagacaga tcgctgagat aggtgcctca ctgattaagc   6900
attggtaact gtcagaccaa gtttactcat atatacttta gattgattta aacttcatt   6960 tttaatttaa aaggatctag gtgaagatcc ttttgataa tctcatgacc aaaatccctt   7020
aacgtgagtt ttcgttccac tgagcgtcag accccgtaga aagatcaaa ggatcttctt   7080 gagatccttt ttttctgcgc gtaatctgct gcttgcaaac aaaaaaacca ccgctaccag   7140
cggtggtttg tttgccggat caagagctac caactctttt tccgaaggta actggcttca   7200
gcagagcgca gataccaaat actgtccttc tagtgtagcc gtagttaggc caccacttca   7260
agaactctgt agcaccgcct acatacctcg ctctgctaat cctgttacca gtggctgctg   7320
ccagtggcga taagtcgtgt cttaccgggt tggactcaag acgatagtta ccggataagg   7380
cgcagcggtc gggctgaacg gggggttcgt gcacacagcc cagcttggag cgaacgacct   7440
acaccgaact gagataccta cagcgtgagc tatgagaaag cgccacgctt cccgaaggga   7500
gaaaggcgga caggtatccg gtaagcggca gggtcggaac aggagagcgc acgagggagc   7560
ttccaggggg aaacgcctgg tatctttata gtcctgtcgg gtttcgccac ctctgacttg   7620
agcgtcgatt tttgtgatgc tcgtcagggg gcggagcct atggaaaaac gccagcaacg   7680
cggccttttt acggttcctg gccttttgct ggccttttgc tcacatgt   7728
```

<210> SEQ ID NO 8
<211> LENGTH: 7380
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac taggggttcc tgcggccgca cgcgtgcaag aaccctcact ggctgaacta   180
tcttgccagc cccttatttt gttttcatat taacctcttt tttctagtaa aggagatgtt   240
tgctctcaaa tttgcatagg aatgtaatat ttaatttaaa aagatgaccc acatatgacc   300
ttataaggac agtaaaatta aacaaccgga aagataaagc gggccagttg gctcagttct   360
ataaaaccag cccacaagga ttgtcactat tcttaggctt gcgcgggcta catgatgagt   420
tccaggactg cctggttaca gaccgagact ctctcaagag tccagataaa caacaacaaa   480
gggggcgagg tggaaataca ggggctgtaa gaagtaaata tgatatctgc atgggaggct   540
agccagagaa gaaaaaattt tcttccgtgg ttcaatcctc caagggctga acaggaagtt   600
gacgcaggca ggtgaggagc acgagcctag atgggctgcg gtgccaccct taatccccac   660
aagcgagttc ctccgcaatt cgcctgtccc actctcaact tttcttcaac tgactctttg   720
```

-continued

| | |
|---|---|
| ctgtggtccc tcgctgtggc agtggaaaca actaccactg cgaggtaggg aatgtcatga | 780 |
| ggggctacct gcagcccttg gcttgcaggg atgcagggat gcggtcggaa cctgaggccc | 840 |
| cgcccttctc ttgccccacg ccattaggcc acgcccctac ccagcactcc ttcaaccacc | 900 |
| cccttccccg gcgcctcatg aggtcccgcc cctctcaacc ctagctcttg aggcctccca | 960 |
| ttcacagccg ccccggcgtt ccttgacttg aggccacgtc cctctgctcc ttcattccca | 1020 |
| agaccctacg ctttgcgagt cctccctgtc ctgctgccta ggaccccgcc cctctcagcc | 1080 |
| cttctgcccc aagacccggc ccttaggct gttcccgccc actggccaat gaagacccgc | 1140 |
| cctttcttta gccgccccgc cccggtccca caaaatcccg cctccggccc cgcctcccgc | 1200 |
| ccccttgggc gctccgtagc agtgacgtgc gcaggctggg cactctgcag ggctctctgg | 1260 |
| ccggcgggtg gagaccgatc cgggatctgt cccagcagga agcgtatccc ggccgccgtc | 1320 |
| gtgctgtcgt ctccggtgct cgctctcggc cgcggtgtcg cgcttgccct tcgcgcccgc | 1380 |
| agcccggcag cctctcgagc tcaagcttcg aattcgtcga caggatgagc ccccagttaa | 1440 |
| agagcttgga cgaggaaggt gacaagtcag caagaagacc cacaaggaaa caaacctcca | 1500 |
| gagctgcatg tccccaagac gggcaccgag cccaatctag ccggaaggat cctgctaagg | 1560 |
| gtagcccaag accagggtct tcccggaaga acagatgga acatggaagc tatcacaagg | 1620 |
| ggttgcaggg acagaaacca cgaaaggtgg agaggtctct acaagggagg aagaaggatc | 1680 |
| ggagaacttc ccttaaggag cagagagcat ctccaaagaa ggagagggag gctctgagga | 1740 |
| aggaggcagg caagcagctg agaaaaccca ggtccacttc cttgggctcc agtgtctcta | 1800 |
| ctggagactc cctgtctgag gaggagctgg ctcagatcct ggaacaggta gaagaaaaaa | 1860 |
| agaagctcat cactaccgtg aggaacaaac cctggcccat ggcaaagaag ctgagggaac | 1920 |
| tcagggaagc ccaagccttt gtggagaagt atgaaggagc cttggggaaa ggcaagggca | 1980 |
| aacacctcta cgcctacagg atgatgatgg ctaagaaatg ggtcaagttt aagagggact | 2040 |
| tgataaattt caagactcaa tgtattccct gggaaatgaa gatcaaggac attgaaagtc | 2100 |
| acttcggttc ttctgtggca tcttacttca tctttctccg atggatgtat ggagttaacc | 2160 |
| ttgtcctttt tggcttaata tttggtctag tcatcatccc agaggtgctg atgggcatgc | 2220 |
| cctatggaag tacccagaa agacggtgc ctcgggctga ggaagagcga gccatggact | 2280 |
| tctctgtcct ttgggatttt gagggctaca tcaaatattc tgctctcttc tatggctact | 2340 |
| acaacaacca gcggaccatt ggatggctga ggtacaggct gcccatggct tactttatgg | 2400 |
| tgggggtcag cgtgtttggc tacagcttga tgatcgtcat taggtcgatg ccagcaata | 2460 |
| cccagggtag caccagtgag ggggacagtg acagcttcac gttcagcttc aagatgttca | 2520 |
| ccagctggga ctacctcatc gggaattcag agacagcaga caacaaatat gtctccatca | 2580 |
| ctaccagctt caaggagtct atagtggacg aacaagagag taacaaagaa gggaatatcc | 2640 |
| acctgacaag attcctccgc gtcctggcca actttctcat tctctgctgt ctgtgtggaa | 2700 |
| gcgggtacct catttacttt gtggtgaaac ggtcccagga gttctccaaa atgcaaaatg | 2760 |
| tcagctggta tgaaaggaat gaggtggaga tcgtgatgtc tctgctaggg atgttttgtc | 2820 |
| cccctctgtt tgaaaccatc gctgccttgg agaattatca cccacgaact gggctgaagt | 2880 |
| ggcagctggg ccgcatcttt gccctttcc tgggaaacct ctacacgttt ctcctggccc | 2940 |
| tcatggacga tgtccacctt aagctttcta atgaggaaaa atcaagaac atcactcact | 3000 |
| ggaccctgtt taactattac aattcctcag gtgggaatga gagtgtgccc cggccaccac | 3060 |

```
cacaccctgc agatgtgccc agaggttctt gctgggagac agctgtgggc attgagttta    3120
tgaggctcac cgtgtctgac atgctggtaa catacctcac catcttggtc ggagatttcc    3180
tccgagcttg ttttgtccgg ttcatgaatc actgctggtg ttgggacctc gaggctggtt    3240
ttccctcata tgccgagttt gatattagtg gaaatgtgtt gggtttgatc ttcaaccaag    3300
gaatgatctg gatgggctcc ttctatgctc caggactggt gggcatcaat gtcctgcgcc    3360
tgttgacctc catgtacttc cagtgctggg cagtgatgag cagcaacgtt ccccatgagc    3420
gtgtgtttaa agcctcccga tccaacaact tctacatggg cctgctgctg ttggtgctct    3480
tcctcagcct cctgcctgtg cctacactg tcatgtctct cccaccctcg tttgactgtg    3540
gccccttcag tgggaaaaac agaatgtacg atgtcctcca tgagaccatc gagaacgatt    3600
tccctaagtt cctgggcaag atctttgcgt tccttgccaa cccaggcctg atcattccag    3660
ccatcctgct aatgtttctg gccatttact acctgaactc agtttcaaaa agtctttcca    3720
gagctaatgc ccagctgcga aagaagatcc aagcgctccg tgaagttgag aagaaccata    3780
aatccatcaa gggaaaagcc atagtcacat attcagagga cacaatcaag aacagctcca    3840
aaaatgccac ccagatacat cttactaaag aagagcccac atctcactct tccagccaaa    3900
tccagaccct ggacaagaaa gcgcagggcc cccacacctc cagtactgag ggtggggcct    3960
cgccgtctac ctcctggcac catgttgggt ctcaaccacc gagaggcaga cgagattctg    4020
gccaacccca gtctcagact tatacaggca ggtcaccttc tggaaagaga cccagaggc    4080
ctcacaactg agcggccgct cgagcctaag cttctagaag atctacgggt ggcatccctg    4140
tgacccctcc ccagtgcctc tcctggccct ggaagttgcc actccagtgc ccaccagcct    4200
tgtcctaata aaattaagtt gcatcatttt gtctgactag gtgtccttct ataatattat    4260
ggggtggagg ggggtggtat ggagcaaggg gcaagttggg aagacaacct gtagggcctg    4320
cggggtctat tgggaaccaa gctggagtgc agtggcacaa tcttggctca ctgcaatctc    4380
cgcctcctgg gttcaagcga ttctcctgcc tcagcctccc gagttgttgg gattccaggc    4440
atgcatgacc aggctcagct aattttgtt ttttggtag agacggggtt tcaccatatt    4500
ggccaggctg gtctccaact cctaatctca ggtgatctac ccaccttggc ctcccaaatt    4560
gctgggatta caggcgtgaa ccactgctcc cttcctgtc cttctgattt tgtaggtaac    4620
cacgtgcgga ccgagcggcc gcaggaaccc ctagtgatgg agttggccac tccctctctg    4680
cgcgctcgct cgctcactga ggccgggcga ccaaggtcg cccgacgccc gggctttgcc    4740
cgggcggcct cagtgagcga gcgagcgcgc agctgcctgc aggggcgcct gatgcggtat    4800
tttctcctta cgcatctgtg cggtatttca caccgcatac gtcaaagcaa ccatagtacg    4860
cgccctgtag cggcgcatta gcgcggcgg gtgtggtggt tacgcgcagc gtgaccgcta    4920
cacttgccag cgccctagcg cccgctcctt tcgctttctt cccttccttt ctcgccacgt    4980
tcgccggctt tccccgtcaa gctctaaatc ggggggctccc tttagggttc cgatttagtg    5040
ctttacggca cctcgacccc aaaaaacttg atttgggtga tggttcacgt agtgggccat    5100
cgccctgata cggggtttt cgccctttga cgttggagtc cacgttcttt aatagtggac    5160
tcttgttcca aactggaaca cactcaacc ctatctcggg ctattctttt gatttataag    5220
ggattttgcc gatttcggcc tattggttaa aaaatgagct gatttaacaa aaatttaacg    5280
cgaattttaa caaaatatta cgtttacaa ttttatggtg cactctcagt acaatctgct    5340
ctgatgccgc atagttaagc cagccccgac acccgccaac acccgctgac gcgccctgac    5400
gggcttgtct gctcccggca tccgcttaca gacaagctgt gaccgtctcc gggagctgca    5460
```

-continued

```
tgtgtcagag gttttcaccg tcatcaccga aacgcgcgag acgaaagggc ctcgtgatac      5520
gcctattttt ataggttaat gtcatgataa taatggtttc ttagacgtca ggtggcactt      5580
ttcggggaaa tgtgcgcgga acccctattt gtttattttt ctaaatacat tcaaatatgt      5640
atccgctcat gagacaataa ccctgataaa tgcttcaata atattgaaaa aggaagagta      5700
tgagtattca acatttccgt gtcgcccatta ttccttttttt tgcggcattt tgccttcctg    5760
tttttgctca cccagaaacg ctggtgaaag taaaagatgc tgaagatcag ttgggtgcac      5820
gagtgggtta catcgaactg gatctcaaca gcggtaagat ccttgagagt tttcgccccg      5880
aagaacgttt tccaatgatg agcactttta aagttctgct atgtggcgcg gtattatccc      5940
gtattgacgc cgggcaagag caactcggtc gccgcataca ctattctcag aatgacttgg      6000
ttgagtactc accagtcaca gaaaagcatc ttacggatgg catgacagta agagaattat      6060
gcagtgctgc cataaccatg agtgataaca ctgcggccaa cttacttctg acaacgatcg      6120
gaggaccgaa ggagctaacc gcttttttgc acaacatggg ggatcatgta actcgccttg      6180
atcgttggga accggagctg aatgaagcca taccaaacga cgagcgtgac accacgatgc      6240
ctgtagcaat ggcaacaacg ttgcgcaaac tattaactgg cgaactactt actctagctt      6300
cccggcaaca attaatagac tggatggagg cggataaagt tgcaggacca cttctgcgct      6360
cggcccttcc ggctggctgg tttattgctg ataaatctgg agccggtgag cgtgggtctc      6420
gcggtatcat tgcagcactg gggccagatg gtaagccctc ccgtatcgta gttatctaca      6480
cgacggggag tcaggcaact atggatgaac gaaatagaca gatcgctgag ataggtgcct      6540
cactgattaa gcattggtaa ctgtcagacc aagtttactc atatatactt tagattgatt      6600
taaaacttca tttttaattt aaaaggatct aggtgaagat cctttttgat aatctcatga      6660
ccaaaatccc ttaacgtgag ttttcgttcc actgagcgtc agaccccgta gaaaagatca      6720
aaggatcttc ttgagatcct ttttttctgc gcgtaatctg ctgcttgcaa acaaaaaaac      6780
caccgctacc agcggtggtt tgtttgccgg atcaagagct accaactctt tttccgaagg      6840
taactggctt cagcagagcg cagataccaa atactgtcct tctagtgtag ccgtagttag      6900
gccaccactt caagaactct gtagcaccgc ctacatacct cgctctgcta atcctgttac      6960
cagtggctgc tgccagtggc gataagtcgt gtcttaccgg gttggactca agacgatagt      7020
taccggataa ggcgcagcgg tcgggctgaa cggggggttc gtgcacacag cccagcttgg      7080
agcgaacgac ctacaccgaa ctgagatacc tacagcgtga gctatgagaa agcgccacgc      7140
ttcccgaagg gagaaaggcg gacaggtatc cggtaagcgg cagggtcgga acaggagagc      7200
gcacgaggga gcttccaggg ggaaacgcct ggtatcttta tagtcctgtc gggtttcgcc      7260
acctctgact tgagcgtcga tttttgtgat gctcgtcagg gggcggagc  ctatggaaaa      7320 acgccagcaa cgcggccttt ttacggttcc tggccttttg ctggccttt gctcacatgt       7380
```

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
catctgcagc caactttggt gtgt                                              24

```
<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agaggtagcc ggaaattcag ccat                                              24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgagcgcaag tactctgtgt ggat                                              24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
actcatcgta ctcctgcttg ctga                                              24

<210> SEQ ID NO 13
<211> LENGTH: 734
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13
```

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

```
Lys Lys Gly Gln Gln Pro Ala Arg Lys Arg Leu Asn Phe Gly Gln Thr
            165                 170                 175
Gly Asp Ser Glu Ser Val Pro Asp Pro Gln Pro Leu Gly Glu Pro Pro
        180                 185                 190
Ala Ala Pro Ser Gly Val Gly Ser Asn Thr Met Ala Ala Gly Gly Gly
        195                 200                 205
Ala Pro Met Ala Asp Asn Asn Glu Gly Ala Asp Gly Val Gly Asn Ala
210                 215                 220
Ser Gly Asn Trp His Cys Asp Ser Thr Trp Leu Gly Asp Arg Val Ile
225                 230                 235                 240
Thr Thr Ser Thr Arg Thr Ala Leu Pro Thr Tyr Asn Asn His Leu Tyr
            245                 250                 255
Lys Gln Ile Ser Ser Gln Ser Gly Gly Ser Thr Asn Asp Asn Thr Tyr
            260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
        290                 295                 300
Gly Phe Arg Pro Lys Lys Leu Asn Phe Lys Leu Phe Asn Ile Gln Val
305                 310                 315                 320
Lys Glu Val Thr Thr Asn Asp Gly Thr Thr Thr Ile Ala Asn Asn Leu
            325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Ile Pro Gln Tyr Gly Tyr Leu Thr Leu Asn Asn Gly Ser
        370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Thr Phe Glu
            405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Gln Thr Thr Ser Gly Thr Ala Gly Asn Arg Thr Leu Gln Phe Ser Gln
        450                 455                 460
Ala Gly Pro Ser Ser Met Ala Asn Gln Ala Lys Asn Trp Leu Pro Gly
465                 470                 475                 480
Pro Cys Tyr Arg Gln Gln Arg Val Ser Lys Thr Thr Asn Gln Asn Asn
            485                 490                 495
Asn Ser Asn Phe Ala Trp Thr Gly Ala Thr Lys Tyr His Leu Asn Gly
        500                 505                 510
Arg Asp Ser Leu Val Asn Pro Gly Pro Ala Met Ala Thr His Lys Asp
        515                 520                 525
Asp Glu Asp Lys Phe Phe Pro Met Ser Gly Val Leu Ile Phe Gly Lys
    530                 535                 540
Gln Gly Ala Gly Asn Ser Asn Val Asp Leu Asp Asn Val Met Ile Thr
545                 550                 555                 560
Asn Glu Glu Glu Ile Lys Thr Thr Asn Pro Val Ala Thr Glu Glu Tyr
                565                 570                 575
Gly Thr Val Ala Thr Asn Leu Gln Ser Ala Asn Thr Ala Pro Ala Thr
```

```
                580               585               590
Gly Thr Val Asn Ser Gln Gly Ala Leu Pro Gly Met Val Trp Gln Asp
            595               600               605
Arg Asp Val Tyr Leu Gln Gly Pro Ile Trp Ala Lys Ile Pro His Thr
        610               615               620
Asp Gly His Phe His Pro Ser Pro Leu Met Gly Phe Gly Leu Lys
625               630               635               640
His Pro Pro Gln Ile Leu Ile Lys Asn Thr Pro Val Pro Ala Asn
                645               650               655
Pro Pro Thr Thr Phe Ser Pro Ala Lys Phe Ala Ser Phe Ile Thr Gln
            660               665               670
Tyr Ser Thr Gly Gln Val Ser Val Glu Ile Glu Glu Leu Gln Lys Glu
        675               680               685
Asn Ser Lys Arg Trp Asn Pro Glu Ile Gln Tyr Thr Ser Asn Tyr Asn
        690               695               700
Lys Ser Thr Asn Val Asp Phe Ala Val Asp Thr Asn Gly Val Tyr Ser
705               710               715               720
Glu Pro Arg Pro Ile Gly Thr Arg Tyr Leu Thr Arg Asn Leu
                725               730

<210> SEQ ID NO 14
<211> LENGTH: 760
<212> TYPE: PRT
<213> ORGANISM: Homo sapiens

<400> SEQUENCE: 14

Met Ser Pro Lys Lys Val Gln Ile Lys Val Glu Glu Lys Glu Asp Glu
1               5                   10                  15
Thr Glu Glu Ser Ser Ser Glu Glu Glu Glu Val Glu Asp Lys Leu
            20                  25                  30
Pro Arg Arg Glu Ser Leu Arg Pro Lys Arg Lys Arg Thr Arg Asp Val
        35                  40                  45
Ile Asn Glu Asp Asp Pro Glu Pro Glu Pro Glu Asp Glu Glu Thr Arg
    50                  55                  60
Lys Ala Arg Glu Lys Glu Arg Arg Arg Leu Lys Arg Gly Ala Glu
65                  70                  75                  80
Glu Glu Glu Ile Asp Glu Glu Leu Glu Arg Leu Lys Ala Glu Leu
                85                  90                  95
Asp Glu Lys Arg Gln Ile Ile Ala Thr Val Lys Cys Lys Pro Trp Lys
            100                 105                 110
Met Glu Lys Lys Ile Glu Val Leu Lys Glu Ala Lys Lys Phe Val Ser
        115                 120                 125
Glu Asn Glu Gly Ala Leu Gly Lys Gly Lys Arg Trp Phe Ala
    130                 135                 140
Phe Lys Met Met Met Ala Lys Lys Trp Ala Lys Phe Leu Arg Asp Phe
145                 150                 155                 160
Glu Asn Phe Lys Ala Ala Cys Val Pro Trp Glu Asn Lys Ile Lys Ala
                165                 170                 175
Ile Glu Ser Gln Phe Gly Ser Ser Val Ala Ser Tyr Phe Leu Phe Leu
            180                 185                 190
Arg Trp Met Tyr Gly Val Asn Met Val Leu Phe Ile Leu Thr Phe Ser
        195                 200                 205
Leu Ile Met Leu Pro Glu Tyr Leu Trp Gly Leu Pro Tyr Gly Ser Leu
    210                 215                 220
```

```
Pro Arg Lys Thr Val Pro Arg Ala Glu Glu Ala Ser Ala Ala Asn Phe
225                 230                 235                 240

Gly Val Leu Tyr Asp Phe Asn Gly Leu Ala Gln Tyr Ser Val Leu Phe
            245                 250                 255

Tyr Gly Tyr Tyr Asp Asn Lys Arg Thr Ile Gly Trp Met Asn Phe Arg
        260                 265                 270

Leu Pro Leu Ser Tyr Phe Leu Val Gly Ile Met Cys Ile Gly Tyr Ser
    275                 280                 285

Phe Leu Val Val Leu Lys Ala Met Thr Lys Asn Ile Gly Asp Asp Gly
    290                 295                 300

Gly Gly Asp Asp Asn Thr Phe Asn Phe Ser Trp Lys Val Phe Thr Ser
305                 310                 315                 320

Trp Asp Tyr Leu Ile Gly Asn Pro Glu Thr Ala Asp Asn Lys Phe Asn
            325                 330                 335

Ser Ile Thr Met Asn Phe Lys Glu Ala Ile Thr Glu Lys Ala Ala
        340                 345                 350

Gln Val Glu Glu Asn Val His Leu Ile Arg Phe Leu Arg Phe Leu Ala
        355                 360                 365

Asn Phe Phe Val Phe Leu Thr Leu Gly Gly Ser Gly Tyr Leu Ile Phe
370                 375                 380

Trp Ala Val Lys Arg Ser Gln Glu Phe Ala Gln Gln Asp Pro Asp Thr
385                 390                 395                 400

Leu Gly Trp Trp Glu Lys Asn Glu Met Asn Met Val Met Ser Leu Leu
            405                 410                 415

Gly Met Phe Cys Pro Thr Leu Phe Asp Leu Phe Ala Glu Leu Glu Asp
        420                 425                 430

Tyr His Pro Leu Ile Ala Leu Lys Trp Leu Leu Gly Arg Ile Phe Ala
        435                 440                 445

Leu Leu Leu Gly Asn Leu Tyr Val Phe Ile Leu Ala Leu Met Asp Glu
    450                 455                 460

Ile Asn Asn Lys Ile Glu Glu Lys Leu Val Lys Ala Asn Ile Thr
465                 470                 475                 480

Leu Trp Glu Ala Asn Met Ile Lys Ala Tyr Asn Ala Ser Phe Ser Glu
            485                 490                 495

Asn Ser Thr Gly Pro Pro Phe Phe Val His Pro Ala Asp Val Pro Arg
        500                 505                 510

Gly Pro Cys Trp Glu Thr Met Val Gly Gln Glu Phe Val Arg Leu Thr
        515                 520                 525

Val Ser Asp Val Leu Thr Thr Tyr Val Thr Ile Leu Ile Gly Asp Phe
    530                 535                 540

Leu Arg Ala Cys Phe Val Arg Phe Cys Asn Tyr Cys Trp Cys Trp Asp
545                 550                 555                 560

Leu Glu Tyr Gly Tyr Pro Ser Tyr Thr Glu Phe Asp Ile Ser Gly Asn
            565                 570                 575

Val Leu Ala Leu Ile Phe Asn Gln Gly Met Ile Trp Met Gly Ser Phe
        580                 585                 590

Phe Ala Pro Ser Leu Pro Gly Ile Asn Ile Leu Arg Leu His Thr Ser
        595                 600                 605

Met Tyr Phe Gln Cys Trp Ala Val Met Cys Cys Asn Val Pro Glu Ala
    610                 615                 620

Arg Val Phe Lys Ala Ser Arg Ser Asn Phe Tyr Leu Gly Met Leu
625                 630                 635                 640

Leu Leu Ile Leu Phe Leu Ser Thr Met Pro Val Leu Tyr Met Ile Val
```

|  | 645 |  |  |  | 650 |  |  |  | 655 |  |  |
|---|---|---|---|---|---|---|---|---|---|---|---|
| Ser | Leu | Pro | Pro | Ser | Phe | Asp | Cys | Gly | Pro | Phe | Ser | Gly | Lys | Asn | Arg |
|  |  |  | 660 |  |  |  |  | 665 |  |  |  |  | 670 |  |  |

Met Phe Glu Val Ile Gly Glu Thr Leu Glu His Asp Phe Pro Ser Trp
            675                 680                 685

Met Ala Lys Ile Leu Arg Gln Leu Ser Asn Pro Gly Leu Val Ile Ala
    690                 695                 700

Val Ile Leu Val Met Val Leu Ala Ile Tyr Tyr Leu Asn Ala Thr Ala
705                 710                 715                 720

Lys Gly Gln Lys Ala Ala Asn Leu Asp Leu Lys Lys Met Lys Met
                725                 730                 735

Gln Ala Leu Glu Asn Lys Met Arg Asn Lys Lys Met Ala Ala Ala Arg
        740                 745                 750

Ala Ala Ala Ala Ala Gly Arg Gln
        755                 760

<210> SEQ ID NO 15
<211> LENGTH: 3201
<212> TYPE: DNA
<213> ORGANISM: Homo sapiens

<400> SEQUENCE: 15

| cagaaactat gagggcagaa cccagcaatc tgtgctttct ttcacaagcc ctccaggagt | 60 |
|---|---|
| tgctgaaatt taggaatcat tgccccaaaa agtggccctc ataatgatgc agatgggat | 120 |
| cttactctgt tgcccaggct ggagtgcagt ggtgcgatct cggctctctg caacctccgc | 180 |
| ctcccaggtt caagtgattc tcctgcctcg gcctcctgag tagctgggat ttcaggccat | 240 |
| gaaagatcac tgttttagtc tgcgtggtgc agtggaacag atagacctcg gtttgaatct | 300 |
| cagctctact gtttactaga catgaaatgg ggaaatctaa aatgagatgc agaagcctc | 360 |
| aaaaatggaa acccccctgt gcttcacatc tgaaaatctc tgctggggc agcaactttg | 420 |
| agcctgtggg gaaggaactg tccacgtgga gtggtctggt gaatgcttaa ggagctgcag | 480 |
| aagggaagtc cctctccaaa ctagccagcc actgagacct tctgacagga cacccccagg | 540 |
| atgtcaccca aaaagtaca aatcaaagtg gaggaaaaag aagacgagac tgaggaaagc | 600 |
| tcaagtgaag aggaagagga ggtggaagat aagctacctc gaagagagag cttgagacca | 660 |
| aagaggaaac ggaccagaga tgttatcaat gaggatgacc cagaacctga accagaggat | 720 |
| gaagaaacaa ggaaggcaag agaaaaagag aggaggagga ggctaaagag aggagcagaa | 780 |
| gaagaagaaa ttgatgaaga ggaattggaa agattgaagg cagagttaga tgagaaaaga | 840 |
| caaataattg ctactgtcaa atgcaaacca tggaagatgg agaagaaaat tgaagttctc | 900 |
| aaggaggcaa aaaatttgt gagtgaaaat aaggggctc ttgggaaagg aaaaggaaaa | 960 |
| cggtggtttg catttaagat gatgatggcc aagaaatggg caaaattcct ccgtgatttt | 1020 |
| gagaacttca agctgcgtg tgtcccatgg gaaaataaaa tcaaggctat tgaaagtcag | 1080 |
| tttggctcct cagtggcctc atacttcctc ttcttgagat ggatgtatgg agtcaatatg | 1140 |
| gttctcttta tcctgacatt tagcctcatc atgttgccag agtacctctg ggtttgcca | 1200 |
| tatggcagtt tacctaggaa aaccgttccc agagccgaag aggcatcggc agcaaacttt | 1260 |
| ggtgtgttgt acgacttcaa tggtttggca caatattccg ttctctttta tggctattat | 1320 |
| gacaataaac gaacaattgg atggatgaat ttcaggttgc cgctctccta ttttctagtg | 1380 |
| gggattatgt gcattggata cagctttctg gttgtcctca aagcaatgac caaaaacatt | 1440 |

-continued

```
ggtgatgatg gaggtggaga tgacaacact ttcaatttca gctggaaggt ctttaccagc    1500
tgggactacc tgatcggcaa tcctgaaaca gcagacaaca aatttaattc tatcacaatg    1560
aactttaagg aagctatcac agaagaaaaa gcagcccaag tagaagaaaa cgtccacttg    1620
atcagattcc tgaggtttct ggctaacttc ttcgtgtttc taacacttgg agggagtgga    1680
tacctcatct tttgggctgt gaagcgatcc caggaatttg cacagcaaga tcctgacacc    1740
cttgggtggt gggaaaaaaa tgaaatgaac atggttatgt ccctcctagg gatgttctgt    1800
ccaacattgt ttgacttatt tgctgaatta gaagactacc atcctctcat cgctttgaaa    1860
tggctactgg gacgcatttt tgctcttctt ttaggcaatt tatacgtatt tattcttgca    1920
ttaatggatg agattaacaa caagattgaa gaggagaagc tagtaaaggc caatattacc    1980
ctttgggaag ccaatatgat caaggcctac aatgcatcat tctctgaaaa tagcactgga    2040
ccacccttt  ttgttcaccc tgcagatgta cctcgaggac cttgctggga aacaatggtg    2100
ggacaggagt ttgtgaggct gacagtctct gatgttctga ccacctacgt cacaatcctc    2160
attgggact  ttctaagggc atgttttgtg aggttttgca attattgctg gtgctgggac    2220
ttggagtatg gatatccttc atacaccgaa ttcgacatca gtggcaacgt cctcgctctg    2280
atcttcaacc aaggcatgat ctggatgggc tccttctttg ctcccagcct cccaggcatc    2340
aatatccttc gactccatac atccatgtac ttccagtgct gggccgttat gtgctgcaat    2400
gttcctgagg ccagggtctt caaagcttcc agatcaaata acttctacct gggcatgcta    2460
ctgctcatcc tcttcctgtc cacaatgcct gtcttgtaca tgatcgtgtc cctcccacca    2520
tctttttgatt gtggtccatt cagtggcaaa aatagaatgt ttgaagtcat ggagagacc    2580
ctggagcacg atttcccaag ctggatggcg aagatcttga cagctttc aaaccctggg    2640
ctggtcattg ctgtcatttt ggtgatggtt ttggccatct attatctcaa tgctactgcc    2700
aagggccaga aggcagcgaa tctggatctc aaaaagaaga tgaaaatgca agctttggag    2760
aacaaaatgc gaaacaagaa aatggcagct gcacgagcag ctgcagctgc tggtcgccag    2820
taataagtat cctgagagcc agaaaaggt  acactttgcc ttgctgttta aaagtaatgc    2880
aatatgtgaa cgcccagaga acaagcactg tggaactgct attttcctgt tctacccttg    2940
atggattttc aaggtcatgc tggccaatta aggcatcatc agtcctacct gagcaacaag    3000
aatctaaact ttattccaag tcagaaactg tttctgcaga gccactctct cccctgctcc    3060
atttcgtgac ttttttttt  tttttaacaa attgagttta gaagtgagtg taatccagca    3120
atacagttta ctggtttagt tggtgggtta attaaaaaaa atttgctcat atgaactttc    3180
attttatatg tttctttgc c                                               3201
```

<210> SEQ ID NO 16
<211> LENGTH: 906
<212> TYPE: PRT
<213> ORGANISM: Homo sapiens

<400> SEQUENCE: 16

Met Ser His Gln Val Lys Gly Leu Lys Glu Glu Ala Arg Gly Gly Val
1               5                   10                  15

Lys Gly Arg Val Lys Ser Gly Ser Pro His Thr Gly Asp Arg Leu Gly
            20                  25                  30

Arg Arg Ser Ser Ser Lys Arg Ala Leu Lys Ala Glu Gly Thr Pro Gly
        35                  40                  45

Arg Arg Gly Ala Gln Arg Ser Gln Lys Glu Arg Ala Gly Gly Ser Pro
    50                  55                  60

-continued

Ser Pro Gly Ser Pro Arg Arg Lys Gln Thr Gly Arg Arg His Arg
65                  70                  75                  80

Glu Glu Leu Gly Glu Gln Glu Arg Gly Glu Ala Glu Arg Thr Cys Glu
            85                  90                  95

Gly Arg Arg Lys Arg Asp Glu Arg Ala Ser Phe Gln Glu Arg Thr Ala
            100                 105                 110

Ala Pro Lys Arg Glu Lys Glu Ile Pro Arg Arg Glu Lys Ser Lys
            115                 120                 125

Arg Gln Lys Lys Pro Arg Ser Ser Leu Ala Ser Ser Ala Ser Gly
            130                 135                 140

Gly Glu Ser Leu Ser Glu Glu Leu Ala Gln Ile Leu Glu Gln Val
145                 150                 155                 160

Glu Glu Lys Lys Lys Leu Ile Ala Thr Met Arg Ser Lys Pro Trp Pro
            165                 170                 175

Met Ala Lys Lys Leu Thr Glu Leu Arg Glu Ala Gln Glu Phe Val Glu
            180                 185                 190

Lys Tyr Glu Gly Ala Leu Gly Lys Gly Lys Gly Lys Gln Leu Tyr Ala
            195                 200                 205

Tyr Lys Met Leu Met Ala Lys Lys Trp Val Lys Phe Lys Arg Asp Phe
            210                 215                 220

Asp Asn Phe Lys Thr Gln Cys Ile Pro Trp Glu Met Lys Ile Lys Asp
225                 230                 235                 240

Ile Glu Ser His Phe Gly Ser Ser Val Ala Ser Tyr Phe Ile Phe Leu
                245                 250                 255

Arg Trp Met Tyr Gly Val Asn Leu Val Leu Phe Gly Leu Ile Phe Gly
                260                 265                 270

Leu Val Ile Ile Pro Glu Val Leu Met Gly Met Pro Tyr Gly Ser Ile
                275                 280                 285

Pro Arg Lys Thr Val Pro Arg Ala Glu Glu Glu Lys Ala Met Asp Phe
            290                 295                 300

Ser Val Leu Trp Asp Phe Glu Gly Tyr Ile Lys Tyr Ser Ala Leu Phe
305                 310                 315                 320

Tyr Gly Tyr Tyr Asn Asn Gln Arg Thr Ile Gly Trp Leu Arg Tyr Arg
                325                 330                 335

Leu Pro Met Ala Tyr Phe Met Val Gly Val Ser Val Phe Gly Tyr Ser
                340                 345                 350

Leu Ile Ile Val Ile Arg Ser Met Ala Ser Asn Thr Gln Gly Ser Thr
                355                 360                 365

Gly Glu Gly Glu Ser Asp Asn Phe Thr Phe Ser Phe Lys Met Phe Thr
            370                 375                 380

Ser Trp Asp Tyr Leu Ile Gly Asn Ser Glu Thr Ala Asp Asn Lys Tyr
385                 390                 395                 400

Ala Ser Ile Thr Thr Ser Phe Lys Glu Ser Ile Val Asp Glu Gln Glu
                405                 410                 415

Ser Asn Lys Glu Glu Asn Ile His Leu Thr Arg Phe Leu Arg Val Leu
            420                 425                 430

Ala Asn Phe Leu Ile Ile Cys Cys Leu Cys Gly Ser Gly Tyr Leu Ile
            435                 440                 445

Tyr Phe Val Val Lys Arg Ser Gln Gln Phe Ser Lys Met Gln Asn Val
            450                 455                 460

Ser Trp Tyr Glu Arg Asn Glu Val Glu Ile Val Met Ser Leu Leu Gly
465                 470                 475                 480

```
Met Phe Cys Pro Pro Leu Phe Glu Thr Ile Ala Ala Leu Glu Asn Tyr
                485                 490                 495
His Pro Arg Thr Gly Leu Lys Trp Gln Leu Gly Arg Ile Phe Ala Leu
            500                 505                 510
Phe Leu Gly Asn Leu Tyr Thr Phe Leu Leu Ala Leu Met Asp Asp Val
            515                 520                 525
His Leu Lys Leu Ala Asn Glu Glu Thr Ile Lys Asn Ile Thr His Trp
        530                 535                 540
Thr Leu Phe Asn Tyr Tyr Asn Ser Ser Gly Trp Asn Glu Ser Val Pro
545                 550                 555                 560
Arg Pro Pro Leu His Pro Ala Asp Val Pro Arg Gly Ser Cys Trp Glu
                565                 570                 575
Thr Ala Val Gly Ile Glu Phe Met Arg Leu Thr Val Ser Asp Met Leu
            580                 585                 590
Val Thr Tyr Ile Thr Ile Leu Leu Gly Asp Phe Leu Arg Ala Cys Phe
            595                 600                 605
Val Arg Phe Met Asn Tyr Cys Trp Cys Trp Asp Leu Glu Ala Gly Phe
        610                 615                 620
Pro Ser Tyr Ala Glu Phe Asp Ile Ser Gly Asn Val Leu Gly Leu Ile
625                 630                 635                 640
Phe Asn Gln Gly Met Ile Trp Met Gly Ser Phe Tyr Ala Pro Gly Leu
                645                 650                 655
Val Gly Ile Asn Val Leu Arg Leu Leu Thr Ser Met Tyr Phe Gln Cys
            660                 665                 670
Trp Ala Val Met Ser Ser Asn Val Pro His Glu Arg Val Phe Lys Ala
            675                 680                 685
Ser Arg Ser Asn Asn Phe Tyr Met Gly Leu Leu Leu Val Leu Phe
        690                 695                 700
Leu Ser Leu Leu Pro Val Ala Tyr Thr Ile Met Ser Leu Pro Pro Ser
705                 710                 715                 720
Phe Asp Cys Gly Pro Phe Ser Gly Lys Asn Arg Met Tyr Asp Val Leu
                725                 730                 735
Gln Glu Thr Ile Glu Asn Asp Phe Pro Thr Phe Leu Gly Lys Ile Phe
            740                 745                 750
Ala Phe Leu Ala Asn Pro Gly Leu Ile Ile Pro Ala Ile Leu Leu Met
            755                 760                 765
Phe Leu Ala Ile Tyr Tyr Leu Asn Ser Val Ser Lys Ser Leu Ser Arg
        770                 775                 780
Ala Asn Ala Gln Leu Arg Lys Ile Gln Val Leu Arg Glu Val Glu
785                 790                 795                 800
Lys Ser His Lys Ser Val Lys Gly Lys Ala Thr Ala Arg Asp Ser Glu
                805                 810                 815
Asp Thr Pro Lys Ser Ser Lys Asn Ala Thr Gln Leu Gln Leu Thr
            820                 825                 830
Lys Glu Glu Thr Thr Pro Ser Ala Ser Gln Ser Gln Ala Met Asp
        835                 840                 845
Lys Lys Ala Gln Gly Pro Gly Thr Ser Asn Ser Ala Ser Arg Thr Thr
850                 855                 860
Leu Pro Ala Ser Gly His Leu Pro Ile Ser Arg Pro Pro Gly Ile Gly
865                 870                 875                 880
Pro Asp Ser Gly His Ala Pro Ser Gln Thr His Pro Trp Arg Ser Ala
                885                 890                 895
Ser Gly Lys Ser Ala Gln Arg Pro Pro His
```

<210> SEQ ID NO 17
<211> LENGTH: 552
<212> TYPE: PRT
<213> ORGANISM: Homo sapiens

<400> SEQUENCE: 17

```
Met Asp Arg Lys Val Ala Arg Glu Phe Arg His Lys Val Asp Phe Leu
1               5                   10                  15

Ile Glu Asn Asp Ala Glu Lys Asp Tyr Leu Tyr Asp Val Leu Arg Met
                20                  25                  30

Tyr His Gln Thr Met Asp Val Ala Val Leu Val Gly Asp Leu Lys Leu
            35                  40                  45

Val Ile Asn Glu Pro Ser Arg Leu Pro Leu Phe Asp Ala Ile Arg Pro
50                  55                  60

Leu Ile Pro Leu Lys His Gln Val Glu Tyr Asp Gln Leu Thr Pro Arg
65                  70                  75                  80

Arg Ser Arg Lys Leu Lys Glu Val Arg Leu Asp Arg Leu His Pro Glu
                85                  90                  95

Gly Leu Gly Leu Ser Val Arg Gly Gly Leu Glu Phe Gly Cys Gly Leu
            100                 105                 110

Phe Ile Ser His Leu Ile Lys Gly Gly Gln Ala Asp Ser Val Gly Leu
        115                 120                 125

Gln Val Gly Asp Glu Ile Val Arg Ile Asn Gly Tyr Ser Ile Ser Ser
130                 135                 140

Cys Thr His Glu Glu Val Ile Asn Leu Ile Arg Thr Lys Lys Thr Val
145                 150                 155                 160

Ser Ile Lys Val Arg His Ile Gly Leu Ile Pro Val Lys Ser Ser Pro
                165                 170                 175

Asp Glu Pro Leu Thr Trp Gln Tyr Val Asp Gln Phe Val Ser Glu Ser
            180                 185                 190

Gly Gly Val Arg Gly Ser Leu Gly Ser Pro Gly Asn Arg Glu Asn Lys
        195                 200                 205

Glu Lys Lys Val Phe Ile Ser Leu Val Gly Ser Arg Gly Leu Gly Cys
210                 215                 220

Ser Ile Ser Ser Gly Pro Ile Gln Lys Pro Gly Ile Phe Ile Ser His
225                 230                 235                 240

Val Lys Pro Gly Ser Leu Ser Ala Glu Val Gly Leu Glu Ile Gly Asp
                245                 250                 255

Gln Ile Val Glu Val Asn Gly Val Asp Phe Ser Asn Leu Asp His Lys
            260                 265                 270

Glu Ala Val Asn Val Leu Lys Ser Ser Arg Ser Leu Thr Ile Ser Ile
        275                 280                 285

Val Ala Ala Gly Arg Glu Leu Phe Met Thr Asp Arg Glu Arg Leu
290                 295                 300

Ala Glu Ala Arg Gln Arg Glu Leu Gln Arg Gln Glu Leu Leu Met Gln
305                 310                 315                 320

Lys Arg Leu Ala Met Glu Ser Asn Lys Ile Leu Gln Glu Gln Gln Glu
                325                 330                 335

Met Glu Arg Gln Arg Arg Lys Glu Ile Ala Gln Lys Ala Ala Glu Glu
            340                 345                 350

Asn Glu Arg Tyr Arg Lys Glu Met Glu Gln Ile Val Glu Glu Glu
        355                 360                 365
```

```
Lys Phe Lys Lys Gln Trp Glu Glu Asp Trp Gly Ser Lys Glu Gln Leu
    370                 375                 380

Leu Leu Pro Lys Thr Ile Thr Ala Glu Val His Pro Val Pro Leu Arg
385                 390                 395                 400

Lys Pro Lys Tyr Asp Gln Gly Val Glu Pro Glu Leu Glu Pro Ala Asp
                405                 410                 415

Asp Leu Asp Gly Gly Thr Glu Glu Gln Gly Glu Gln Asp Phe Arg Lys
            420                 425                 430

Tyr Glu Glu Gly Phe Asp Pro Tyr Ser Met Phe Thr Pro Glu Gln Ile
        435                 440                 445

Met Gly Lys Asp Val Arg Leu Leu Arg Ile Lys Lys Glu Gly Ser Leu
    450                 455                 460

Asp Leu Ala Leu Glu Gly Gly Val Asp Ser Pro Ile Gly Lys Val Val
465                 470                 475                 480

Val Ser Ala Val Tyr Glu Arg Gly Ala Ala Glu Arg His Gly Gly Ile
                485                 490                 495

Val Lys Gly Asp Glu Ile Met Ala Ile Asn Gly Lys Ile Val Thr Asp
            500                 505                 510

Tyr Thr Leu Ala Glu Ala Glu Ala Leu Gln Lys Ala Trp Asn Gln
        515                 520                 525

Gly Gly Asp Trp Ile Asp Leu Val Val Ala Val Cys Pro Pro Lys Glu
    530                 535                 540

Tyr Asp Asp Glu Leu Thr Phe Phe
545                 550

<210> SEQ ID NO 18
<211> LENGTH: 2237
<212> TYPE: DNA
<213> ORGANISM: Homo sapiens

<400> SEQUENCE: 18
agctccgagg gcggctggcc cggtcgcggt cgcggctctt ccagctcct ggcagccggg      60 cacccgaagg aacgggtcgt gcaacgacgc agctggacct ggcccagcca tggaccgaaa    120
agtggcccga gaattccggc ataaggtgga ttttctgatt gaaatgatg cagagaagga    180 ctatctctat gatgtgctgc gaatgtacca ccagaccatg acgtggccg tgctcgtggg    240 agacctgaag ctggtcatca tgaacccag ccgtctgcct ctgtttgatg ccattcggcc    300
gctgatccca ctgaagcacc aggtggaata tgatcagctg accccccggc gctccaggaa    360
gctgaaggag gtgcgtctgg accgtctgca ccccgaaggc ctcggcctga gtgtgcgtgg    420
tggcctggag tttggctgtg gctcttcat ctcccacctc atcaaaggcg gtcaggcaga    480
cagcgtcggg ctccaggtag gggacgagat cgtccggatc aatggatatt ccatctcctc    540
ctgtacccat gaggaggtca tcaacctcat tcgaaccaag aaaactgtgt ccatcaaagt    600
gagacacatc ggcctgatcc ccgtgaaaag ctctcctgat gagcccctca cttggcagta    660
tgtggatcag tttgtgtcgg aatctgggg cgtgcgaggc agcctgggct cccctggaaa    720
tcgggaaaac aaggagaaga aggtcttcat cagcctggta ggctcccgag gccttggctg    780
cagcatttcc agcggcccca tccagaagcc tggcatcttt atcagccatg tgaaacctgg    840 ctcccctgtct gctgaggtgg gattggagat aggggaccag attgtcgaag tcaatggcgt    900
cgacttctct aacctggatc acaaggaggc tgtaaatgtg ctgaagagta gccgcagcct    960
gaccatctcc attgtagctg cagctggccg ggagctgttc atgacagacc gggagcggct   1020
ggcagaggcg cggcagcgtg agctgcagcg gcaggagctt ctcatgcaga gcggctggc   1080
```

| | | | |
|---|---|---|---|
| gatggagtcc | aacaagatcc tccaggagca | gcaggagatg gagcggcaaa | ggagaaaaga 1140 |
| aattgcccag | aaggcagcag aggaaaatga | gagataccgg aaggagatgg | aacagattgt 1200 |
| agaggaggaa | gagaagttta agaagcaatg | ggaagaagac tggggctcaa | aggaacagct 1260 |
| actcttgcct | aaaaccatca ctgctgaggt | acacccagta ccccttcgca | agccaaagta 1320 |
| tgatcaggga | gtggaacctg agctcgagcc | cgcagatgac ctggatggag | gcacggagga 1380 |
| gcagggagag | caggatttcc ggaaatatga | ggaaggcttt gaccccctact | ctatgttcac 1440 |
| cccagagcag | atcatgggga aggatgtccg | gctcctacgc atcaagaagg | agggatcctt 1500 |
| agacctggcc | ctgaaggcg gtgtggactc | ccccattggg aaggtggtcg | tttctgctgt 1560 |
| gtatgagcgg | ggagctgctg agcggcatgg | tggcattgtg aaaggggacg | agatcatggc 1620 |
| aatcaacggc | aagattgtga cagactacac | cctggctgag gctgaggctg | ccctgcagaa 1680 |
| ggcctggaat | cagggcgggg actggatcga | ccttgtggtt gccgtctgcc | ccccaaagga 1740 |
| gtatgacgat | gagctgacct tcttctgaag | tccaaaaggg gaaaccaaat | tcaccgttag 1800 |
| gaaacagtga | gctccggccc cacctcgtga | acacaaagcc tcggatcagc | cttgagagag 1860 |
| gccacactac | acacaccaga tggcatcctt | gggacctgaa tctatcaccc | aggaatctca 1920 |
| aactcccttt | ggccctgaac cagggccaga | taaggaacag ctcgggccac | tcttctgaag 1980 |
| gccaacgtgg | aggaaaggga gcagccagcc | atttgggaga agatctcaag | gatccagact 2040 |
| ctcattcctt | tcctctggcc cagtgaattt | ggtctctccc agctctgggg | gactccttcc 2100 |
| ttgaacccta | ataagacccc actggagtct | ctctctctcc atccctctcc | tctgccctct 2160 |
| gctctaattg | ctgccaggat tgtcactcca | aaccttactc tgagctcatt | aataaaatag 2220 |
| atttattttc | cagctta | | 2237 |

<210> SEQ ID NO 19
<211> LENGTH: 2385
<212> TYPE: DNA
<213> ORGANISM: Homo sapiens

<400> SEQUENCE: 19

| | | | |
|---|---|---|---|
| agctccgagg | gcggctggcc cggtcgcggt | cgcggctctt tccagctcct | ggcagccggg 60 |
| cacccgaagg | aacgggtcgt gcaacgacgc | agctggacct ggcccagcca | tggaccgaaa 120 |
| agtggcccga | gaattccggc ataaggtgga | ttttctgatt gaaaatgatg | cagagaagga 180 |
| ctatctctat | gatgtgctgc gaatgtacca | ccagaccatg gacgtggccg | tgctcgtggg 240 |
| agacctgaag | ctggtcatca tgaacccag | ccgtctgcct ctgtttgatg | ccattcggcc 300 |
| gctgatccca | ctgaagcacc aggtggaata | tgatcagctg accccccggc | gctccaggaa 360 |
| gctgaaggag | gtgcgtctgg accgtctgca | ccccgaaggc ctcggcctga | gtgtgcgtgg 420 |
| tggcctggag | tttggctgtg ggctcttcat | ctcccacctc atcaaaggcg | gtcaggcaga 480 |
| cagcgtcggg | ctccaggtag gggacgagat | cgtccggatc aatggatatt | ccatctcctc 540 |
| ctgtacccat | gaggaggtca tcaacctcat | tcgaaccaag aaaactgtgt | ccatcaaagt 600 |
| gagacacatc | ggcctgatcc ccgtgaaaag | ctctcctgat gagcccctca | cttggcagta 660 |
| tgtggatcag | tttgtgtcgg aatctggggg | cgtgcgaggc agcctgggct | cccctggaaa 720 |
| tcgggaaaac | aaggagaaga aggtcttcat | cagcctggta ggctcccgag | gccttggctg 780 |
| cagcatttcc | agcggcccca tccagaagcc | tggcatcttt atcagccatg | tgaaacctgg 840 |
| ctcccctgtct | gctgaggtgg gattggagat | aggggaccag attgtcgaag | tcaatggcgt 900 |

-continued

```
cgacttctct aacctggatc acaaggaggc tgtaaatgtg ctgaagagta gccgcagcct    960
gaccatctcc attgtagctg cagctggccg ggagctgttc atgacagacc gggagcggct   1020
ggcagaggcg cggcagcgtg agctgcagcg gcaggagctt ctcatgcaga agcggctggc   1080
gatggagtcc aacaagatcc tccaggagca gcaggagatg gagcggcaaa ggagaaaaga   1140
aattgcccag aaggcagcag aggaaaatga gagataccgg aaggagatgg aacagattgt   1200
agaggaggaa gagaagtttta gaagcaatg ggaagaagac tggggctcaa ggaacagct   1260 actcttgcct aaaaccatca ctgctgaggt acacccagta cccctttcgca agccaaagta   1320 tgatcaggga gtggaacctg agctcgagcc cgcagatgac ctggatggag cacggagga   1380 gcagggagag cagaaaggaa aagataagaa gaaagccaag tatggcagcc tgcaggactt   1440
gagaaagaat aagaaagaac tggagtttga gcaaaagctt tacaaagaga agaggaaat   1500 gctggagaag gaaaagcagc taaagatcaa ccggctggcc caggaggatt tccggaaata   1560
tgaggaaggc tttgaccct actctatgtt caccccagag cagatcatgg ggaaggatgt   1620
ccggctccta cgcatcaaga aggagggatc cttagacctg ccctggaag gcggtgtgga   1680 ctcccccatt gggaaggtgg tcgtttctgc tgtgtatgag cggggagctg ctgagcggca   1740
tggtggcatt gtgaaagggg acgagatcat ggcaatcaac ggcaagattg tgacagacta   1800 cacccctggct gaggctgagg ctgccctgca gaaggcctgg aatcagggcg gggactggat   1860
cgaccttgtg gttgccgtct gccccccaaa ggagtatgac gatgagctga ccttcttctg   1920
aagtccaaaa ggggaaacca aattcaccgt taggaaacag tgagctccgg ccccacctcg   1980
tgaacacaaa gcctcggatc agccttgaga gaggccacac tacacacacc agatggcatc   2040
cttgggacct gaatctatca cccaggaatc tcaaactccc tttggccctg aaccagggcc   2100
agataaggaa cagctcgggc cactcttctg aaggccaacg tggaggaaag ggagcagcca   2160
gccatttggg agaagatctc aaggatccag actctcattc ctttcctctg gcccagtgaa   2220
tttggtctct cccagctctg ggggactcct tccttgaacc ctaataagac cccactggag   2280
tctctctctc tccatccctc tcctctgccc tctgctctaa ttgctgccag gattgtcact   2340
ccaaacctta ctctgagctc attaataaaa tagatttatt ttcca               2385
```

<210> SEQ ID NO 20
<211> LENGTH: 899
<212> TYPE: PRT
<213> ORGANISM: Homo sapiens

<400> SEQUENCE: 20

```
Met Asp Arg Lys Val Ala Arg Glu Phe Arg His Lys Val Asp Phe Leu
1               5                   10                  15

Ile Glu Asn Asp Ala Glu Lys Asp Tyr Leu Tyr Asp Val Leu Arg Met
            20                  25                  30

Tyr His Gln Thr Met Asp Val Ala Val Leu Val Gly Asp Leu Lys Leu
        35                  40                  45

Val Ile Asn Glu Pro Ser Arg Leu Pro Leu Phe Asp Ala Ile Arg Pro
    50                  55                  60

Leu Ile Pro Leu Lys His Gln Val Glu Tyr Asp Gln Leu Thr Pro Arg
65                  70                  75                  80

Arg Ser Arg Lys Leu Lys Glu Val Arg Leu Asp Arg Leu His Pro Glu
                85                  90                  95

Gly Leu Gly Leu Ser Val Arg Gly Gly Leu Glu Phe Gly Cys Gly Leu
            100                 105                 110
```

```
Phe Ile Ser His Leu Ile Lys Gly Gly Gln Ala Asp Ser Val Gly Leu
            115                 120                 125
Gln Val Gly Asp Glu Ile Val Arg Ile Asn Gly Tyr Ser Ile Ser Ser
        130                 135                 140
Cys Thr His Glu Glu Val Ile Asn Leu Ile Arg Thr Lys Lys Thr Val
145                 150                 155                 160
Ser Ile Lys Val Arg His Ile Gly Leu Ile Pro Val Lys Ser Ser Pro
                165                 170                 175
Asp Glu Pro Leu Thr Trp Gln Tyr Val Asp Gln Phe Val Ser Glu Ser
            180                 185                 190
Gly Gly Val Arg Gly Ser Leu Gly Ser Pro Gly Asn Arg Glu Asn Lys
        195                 200                 205
Glu Lys Lys Val Phe Ile Ser Leu Val Gly Ser Arg Gly Leu Gly Cys
    210                 215                 220
Ser Ile Ser Ser Gly Pro Ile Gln Lys Pro Gly Ile Phe Ile Ser His
225                 230                 235                 240
Val Lys Pro Gly Ser Leu Ser Ala Glu Val Gly Leu Glu Ile Gly Asp
                245                 250                 255
Gln Ile Val Glu Val Asn Gly Val Asp Phe Ser Asn Leu Asp His Lys
            260                 265                 270
Glu Ala Val Asn Val Leu Lys Ser Ser Arg Ser Leu Thr Ile Ser Ile
        275                 280                 285
Val Ala Ala Gly Arg Glu Leu Phe Met Thr Asp Arg Glu Arg Leu
    290                 295                 300
Ala Glu Ala Arg Gln Arg Glu Leu Gln Arg Gln Glu Leu Leu Met Gln
305                 310                 315                 320
Lys Arg Leu Ala Met Glu Ser Asn Lys Ile Leu Gln Glu Gln Gln Glu
                325                 330                 335
Met Glu Arg Gln Arg Arg Lys Glu Ile Ala Gln Lys Ala Ala Glu Glu
            340                 345                 350
Asn Glu Arg Tyr Arg Lys Glu Met Glu Gln Ile Val Glu Glu Glu
        355                 360                 365
Lys Phe Lys Lys Gln Trp Glu Glu Asp Trp Gly Ser Lys Glu Gln Leu
    370                 375                 380
Leu Leu Pro Lys Thr Ile Thr Ala Glu Val His Pro Val Pro Leu Arg
385                 390                 395                 400
Lys Pro Lys Ser Phe Gly Trp Phe Tyr Arg Tyr Asp Gly Lys Phe Pro
                405                 410                 415
Thr Ile Arg Lys Lys Gly Lys Asp Lys Lys Ala Lys Tyr Gly Ser
            420                 425                 430
Leu Gln Asp Leu Arg Lys Asn Lys Lys Glu Leu Glu Phe Glu Gln Lys
        435                 440                 445
Leu Tyr Lys Glu Lys Glu Met Leu Glu Lys Glu Lys Gln Leu Lys
    450                 455                 460
Ile Asn Arg Leu Ala Gln Glu Val Ser Glu Thr Glu Arg Glu Asp Leu
465                 470                 475                 480
Glu Glu Ser Glu Lys Ile Gln Tyr Trp Val Glu Arg Leu Cys Gln Thr
                485                 490                 495
Arg Leu Glu Gln Ile Ser Ser Ala Asp Asn Glu Ile Ser Glu Met Thr
            500                 505                 510
Thr Gly Pro Pro Pro Pro Pro Ser Val Ser Pro Leu Ala Pro Pro
        515                 520                 525
Leu Arg Arg Phe Ala Gly Gly Leu His Leu His Thr Thr Asp Leu Asp
```

```
            530                 535                 540
Asp Ile Pro Leu Asp Met Phe Tyr Tyr Pro Pro Lys Thr Pro Ser Ala
545                 550                 555                 560

Leu Pro Val Met Pro His Pro Pro Ser Asn Pro Pro His Lys Val
            565                 570                 575

Pro Ala Pro Pro Val Leu Pro Leu Ser Gly His Val Ser Ala Ser Ser
            580                 585                 590

Ser Pro Trp Val Gln Arg Thr Pro Pro Ile Pro Ile Pro Pro Pro
            595                 600                 605

Pro Ser Val Pro Thr Gln Asp Leu Thr Pro Thr Arg Pro Leu Pro Ser
            610                 615                 620

Ala Leu Glu Glu Ala Leu Ser Asn His Pro Phe Arg Thr Gly Asp Thr
625                 630                 635                 640

Gly Asn Pro Val Glu Asp Trp Glu Ala Lys Asn His Ser Gly Lys Pro
            645                 650                 655

Thr Asn Ser Pro Val Pro Glu Gln Ser Phe Pro Thr Pro Lys Thr
            660                 665                 670

Phe Cys Pro Ser Pro Gln Pro Pro Arg Gly Pro Gly Val Ser Thr Ile
            675                 680                 685

Ser Lys Pro Val Met Val His Gln Glu Pro Asn Phe Ile Tyr Arg Pro
            690                 695                 700

Ala Val Lys Ser Glu Val Leu Pro Gln Glu Met Leu Lys Arg Met Val
705                 710                 715                 720

Val Tyr Gln Thr Ala Phe Arg Gln Asp Phe Arg Lys Tyr Glu Glu Gly
                    725                 730                 735

Phe Asp Pro Tyr Ser Met Phe Thr Pro Glu Gln Ile Met Gly Lys Asp
                    740                 745                 750

Val Arg Leu Leu Arg Ile Lys Lys Glu Gly Ser Leu Asp Leu Ala Leu
                    755                 760                 765

Glu Gly Gly Val Asp Ser Pro Ile Gly Lys Val Val Ser Ala Val
            770                 775                 780

Tyr Glu Arg Gly Ala Ala Glu Arg His Gly Gly Ile Val Lys Gly Asp
785                 790                 795                 800

Glu Ile Met Ala Ile Asn Gly Lys Ile Val Thr Asp Tyr Thr Leu Ala
                    805                 810                 815

Glu Ala Glu Ala Ala Leu Gln Lys Ala Trp Asn Gln Gly Gly Asp Trp
                    820                 825                 830

Ile Asp Leu Val Val Ala Val Cys Pro Pro Lys Glu Tyr Asp Asp Glu
            835                 840                 845

Leu Ala Ser Leu Pro Ser Ser Val Ala Glu Ser Pro Gln Pro Val Arg
850                 855                 860

Lys Leu Leu Glu Asp Arg Ala Ala Val His Arg His Gly Phe Leu Leu
865                 870                 875                 880

Gln Leu Glu Pro Thr Asp Leu Leu Leu Lys Ser Lys Arg Gly Asn Gln
                    885                 890                 895

Ile His Arg

<210> SEQ ID NO 21
<211> LENGTH: 2180
<212> TYPE: DNA
<213> ORGANISM: Homo sapiens

<400> SEQUENCE: 21
agctccgagg gcggctggcc cggtcgcggt cgcggctctt tccagctcct ggcagccggg      60
```

```
cacccgaagg aacgggtcgt gcaacgacgc agctggacct ggcccagcca tggaccgaaa      120
agtggcccga gaattccggc ataaggtgga ttttctgatt gaaaatgatg cagagaagga      180
ctatctctat gatgtgctgc gaatgtacca ccagaccatg gacgtggccg tgctcgtggg      240
agacctgaag ctggtcatca atgaacccag ccgtctgcct ctgtttgatg ccattcggcc      300
gctgatccca ctgaagcacc aggtggaata tgatcagctg acccccggc gctccaggaa       360
gctgaaggag gtgcgtctgg accgtctgca ccccgaaggc ctcggcctga gtgtgcgtgg      420
tggcctggag tttggctgtg ggctcttcat ctcccacctc atcaaaggcg gtcaggcaga      480
cagcgtcggg ctccaggtag gggacgagat cgtccggatc aatggatatt ccatctcctc      540
ctgtacccat gaggaggtca tcaacctcat tcgaaccaag aaaactgtgt ccatcaaagt      600
gagacacatc ggcctgatcc ccgtgaaaag ctctcctgat gagcccctca cttggcagta      660
tgtggatcag tttgtgtcgg aatctggggg cgtgcgaggc agcctgggct cccctggaaa      720
tcgggaaaac aaggagaaga aggtcttcat cagcctggta ggctcccgag gccttggctg      780
cagcatttcc agcggcccca tccagaagcc tggcatcttt atcagccatg tgaaacctgg      840
ctccctgtct gctgaggtgg gattggagat aggggaccag attgtcgaag tcaatggcgt      900
cgacttctct aacctggatc acaaggaggg ccgggagctg ttcatgacag accgggagcg      960
gctggcagag gcgcggcagc gtgagctgca gcggcaggag cttctcatgc agaagcggct     1020
ggcgatggag tccaacaaga tcctccagga gcagcaggag atggagcggc aaaggagaaa     1080
agaaattgcc cagaaggcag cagaggaaaa tgagagatac cggaaggaga tggaacagat     1140
tgtagaggag gaagagaagt ttaagaagca atgggaagaa gactggggct caaaggaaca     1200
gctactcttg cctaaaaacca tcactgctga ggtacaccca gtaccccttc gcaagccaaa     1260
gtatgatcag ggagtggaac ctgagctcga gcccgcagat gacctggatg gaggcacgga     1320
ggagcaggga gagcaggatt ccggaaaata tgaggaaggc tttgacccct actctatgtt     1380
cacccccagag cagatcatgg ggaaggatgt ccggctccta cgcatcaaga aggagggatc     1440
cttagacctg gccctggaag gcggtgtgga ctcccccatt gggaaggtgg tcgtttctgc     1500
tgtgtatgag cggggagctg ctgagcggca tggtggcatt gtgaaagggg acgagatcat     1560
ggcaatcaac ggcaagattg tgacagacta caccctggct gaggctgagg ctgccctgca     1620
gaaggcctgg aatcagggcg gggactggat cgaccttgtg gttgccgtct gccccccaaa     1680
ggagtatgac gatgagctga ccttcttctg aagtccaaaa ggggaaacca aattcaccgt     1740
taggaaacag tgagctccgg ccccacctcg tgaacacaaa gcctcggatc agccttgaga     1800
gaggccacac tacacacacc agatggcatc cttgggacct gaatctatca cccaggaatc     1860
tcaaactccc tttggccctg aaccaggcc agataaggaa cagctcgggc cactcttctg      1920
aaggccaacg tggaggaaag ggagcagcca gccatttggg agaagatctc aaggatccag     1980
actctcattc ctttcctctg gcccagtgaa tttggtctct cccagctctg ggggactcct     2040
tccttgaacc ctaataagac cccactggag tctctctctc tccatccctc tcctctgccc     2100
tctgctctaa ttgctgccag gattgtcact ccaaaccttaa ctctgagctc attaataaaa     2160
tagatttatt ttccagctta                                                 2180

<210> SEQ ID NO 22
<211> LENGTH: 533
<212> TYPE: PRT
<213> ORGANISM: Homo sapiens
```

```
<400> SEQUENCE: 22

Met Asp Arg Lys Val Ala Arg Glu Phe Arg His Lys Val Asp Phe Leu
1               5                   10                  15

Ile Glu Asn Asp Ala Glu Lys Asp Tyr Leu Tyr Asp Val Leu Arg Met
            20                  25                  30

Tyr His Gln Thr Met Asp Val Ala Val Leu Val Gly Asp Leu Lys Leu
        35                  40                  45

Val Ile Asn Glu Pro Ser Arg Leu Pro Leu Phe Asp Ala Ile Arg Pro
    50                  55                  60

Leu Ile Pro Leu Lys His Gln Val Glu Tyr Asp Gln Leu Thr Pro Arg
65              70                  75                  80

Arg Ser Arg Lys Leu Lys Glu Val Arg Leu Asp Arg Leu His Pro Glu
                85                  90                  95

Gly Leu Gly Leu Ser Val Arg Gly Gly Leu Glu Phe Gly Cys Gly Leu
            100                 105                 110

Phe Ile Ser His Leu Ile Lys Gly Gly Gln Ala Asp Ser Val Gly Leu
        115                 120                 125

Gln Val Gly Asp Glu Ile Val Arg Ile Asn Gly Tyr Ser Ile Ser Ser
    130                 135                 140

Cys Thr His Glu Glu Val Ile Asn Leu Ile Arg Thr Lys Lys Thr Val
145                 150                 155                 160

Ser Ile Lys Val Arg His Ile Gly Leu Ile Pro Val Lys Ser Ser Pro
                165                 170                 175

Asp Glu Pro Leu Thr Trp Gln Tyr Val Asp Gln Phe Val Ser Glu Ser
            180                 185                 190

Gly Gly Val Arg Gly Ser Leu Gly Ser Pro Gly Asn Arg Glu Asn Lys
        195                 200                 205

Glu Lys Lys Val Phe Ile Ser Leu Val Gly Ser Arg Gly Leu Gly Cys
    210                 215                 220

Ser Ile Ser Ser Gly Pro Ile Gln Lys Pro Gly Ile Phe Ile Ser His
225                 230                 235                 240

Val Lys Pro Gly Ser Leu Ser Ala Glu Val Gly Leu Glu Ile Gly Asp
                245                 250                 255

Gln Ile Val Glu Val Asn Gly Val Asp Phe Ser Asn Leu Asp His Lys
            260                 265                 270

Glu Gly Arg Glu Leu Phe Met Thr Asp Arg Glu Arg Leu Ala Glu Ala
        275                 280                 285

Arg Gln Arg Glu Leu Gln Arg Gln Glu Leu Leu Met Gln Lys Arg Leu
    290                 295                 300

Ala Met Glu Ser Asn Lys Ile Leu Gln Glu Gln Glu Met Glu Arg
305                 310                 315                 320

Gln Arg Arg Lys Glu Ile Ala Gln Lys Ala Ala Glu Glu Asn Glu Arg
                325                 330                 335

Tyr Arg Lys Glu Met Glu Gln Ile Ser Glu Glu Glu Lys Phe Lys
            340                 345                 350

Lys Gln Trp Glu Glu Asp Trp Gly Ser Lys Glu Gln Leu Ile Leu Pro
        355                 360                 365

Lys Thr Ile Thr Ala Glu Val His Pro Val Pro Leu Arg Lys Pro Lys
    370                 375                 380

Tyr Asp Gln Gly Val Glu Pro Glu Leu Glu Pro Ala Asp Asp Leu Asp
385                 390                 395                 400

Gly Gly Thr Glu Glu Gln Gly Glu Gln Asp Phe Arg Lys Tyr Glu Glu
                405                 410                 415
```

```
Gly Phe Asp Pro Tyr Ser Met Phe Thr Pro Glu Gln Ile Met Gly Lys
            420                 425                 430

Asp Val Arg Leu Leu Arg Ile Lys Lys Glu Gly Ser Leu Asp Leu Ala
        435                 440                 445

Leu Glu Gly Gly Val Asp Ser Pro Ile Gly Lys Val Val Ser Ala
450                 455                 460

Val Tyr Glu Arg Gly Ala Ala Glu Arg His Gly Gly Ile Val Lys Gly
465                 470                 475                 480

Asp Glu Ile Met Ala Ile Asn Gly Lys Ile Val Thr Asp Tyr Thr Leu
            485                 490                 495

Ala Glu Ala Glu Ala Leu Gln Lys Ala Trp Asn Gln Gly Gly Asp
        500                 505                 510

Trp Ile Asp Leu Val Val Ala Val Cys Pro Pro Lys Glu Tyr Asp Asp
            515                 520                 525

Glu Leu Thr Phe Phe
    530
```

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gaggtaccat ggaccggaag gtggcccgag                                    30

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caggatccgg acaatttcat cccctac                                       27

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctcattgaaa atgacgcaga gaagg                                         25

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tctcactttg atggacacgg tctt                                          24

<210> SEQ ID NO 27

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaacccaacc gcctgccg                                                 18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgcagacggt ccaagcgt                                                 18

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtgaggccgg tgctgagtat g                                             21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gccaaagttg tcatggatga c                                             21

<210> SEQ ID NO 31
<211> LENGTH: 909
<212> TYPE: PRT
<213> ORGANISM: Mus sp.

<400> SEQUENCE: 31

Met Asp Arg Lys Val Ala Arg Glu Phe Arg His Lys Val Asp Phe Leu
1               5                   10                  15

Ile Glu Asn Asp Ala Glu Lys Asp Tyr Leu Tyr Asp Val Leu Arg Met
            20                  25                  30

Tyr His Gln Thr Met Asp Val Ala Val Leu Val Gly Asp Leu Lys Leu
        35                  40                  45

Val Ile Asn Glu Pro Asn Arg Leu Pro Leu Phe Asp Ala Ile Arg Pro
    50                  55                  60

Leu Ile Pro Leu Lys His Gln Glu Tyr Asp Gln Leu Thr Pro Arg Arg
65                  70                  75                  80

Ser Arg Lys Leu Lys Glu Val Arg Leu Asp Arg Leu His Pro Glu Gly
                85                  90                  95

Leu Gly Leu Ser Val Arg Gly Gly Leu Glu Phe Gly Cys Gly Leu Phe
            100                 105                 110
```

Ile Ser His Leu Ile Lys Gly Gly Gln Ala Asp Ser Val Gly Leu Gln
            115                 120                 125

Val Gly Asp Glu Ile Val Arg Ile Asn Gly Tyr Ser Ile Ser Ser Cys
    130                 135                 140

Thr His Glu Glu Val Ile Asn Leu Ile Arg Thr Lys Lys Thr Val Ser
145                 150                 155                 160

Ile Lys Val Arg His Ile Gly Leu Ile Pro Val Lys Ser Ser Pro Glu
                165                 170                 175

Glu Ser Leu Lys Trp Gln Tyr Val Asp Gln Phe Val Ser Glu Ser Gly
            180                 185                 190

Gly Val Arg Gly Gly Leu Gly Ser Pro Gly Asn Arg Thr Thr Lys Glu
    195                 200                 205

Lys Lys Val Phe Ile Ser Leu Val Gly Ser Arg Gly Leu Gly Cys Ser
210                 215                 220

Ile Ser Ser Gly Pro Ile Gln Lys Pro Gly Ile Phe Val Ser His Val
225                 230                 235                 240

Lys Pro Gly Ser Leu Ser Ala Glu Val Gly Leu Glu Thr Gly Asp Gln
                245                 250                 255

Ile Val Glu Val Asn Gly Ile Asp Phe Thr Asn Leu Asp His Lys Glu
            260                 265                 270

Ala Val Asn Val Leu Lys Ser Ser Arg Ser Leu Thr Ile Ser Ile Val
    275                 280                 285

Ala Gly Ala Gly Arg Glu Leu Phe Met Thr Asp Arg Glu Arg Leu Glu
    290                 295                 300

Glu Ala Arg Gln Arg Glu Leu Gln Arg Gln Glu Leu Leu Met Gln Lys
305                 310                 315                 320

Arg Leu Ala Met Glu Ser Asn Lys Ile Leu Gln Glu Gln Gln Glu Met
                325                 330                 335

Glu Arg Gln Arg Arg Lys Glu Ile Ala Gln Lys Ala Ala Glu Glu Asn
            340                 345                 350

Glu Arg Tyr Arg Lys Glu Met Glu Gln Ile Ser Glu Glu Glu Glu Lys
        355                 360                 365

Phe Lys Lys Gln Trp Glu Glu Asp Trp Gly Ser Lys Glu Gln Leu Ile
370                 375                 380

Leu Pro Lys Thr Ile Thr Ala Glu Val His Pro Val Pro Leu Arg Lys
385                 390                 395                 400

Pro Lys Ser Phe Gly Trp Phe Tyr Arg Tyr Asp Gly Lys Phe Pro Thr
                405                 410                 415

Ile Arg Lys Lys Ala Lys Glu Lys Lys Lys Ala Lys Tyr Asp Ser Leu
            420                 425                 430

Gln Asp Leu Arg Lys Asn Lys Lys Glu Leu Glu Phe Glu Gln Lys Leu
        435                 440                 445

Tyr Lys Glu Lys Glu Glu Met Leu Glu Lys Glu Lys Gln Leu Lys Ile
450                 455                 460

Asn Arg Leu Ala Gln Glu Val Ser Glu Thr Glu Arg Glu Asp Leu Glu
465                 470                 475                 480

Glu Ser Glu Lys Thr Gln Tyr Trp Val Glu Arg Leu Cys Gln Thr Arg
                485                 490                 495

Leu Glu Gln Ile Ser Ser Ala Glu Asn Glu Ile Pro Glu Met Thr Thr
            500                 505                 510

Gly Pro Pro Pro Pro Pro Ser Val Ser Pro Leu Ala Pro Pro Leu
        515                 520                 525

Arg Arg Phe Ala Gly Gly Ile His Leu His Thr Thr Asp Leu Asp Asp

```
            530                 535                 540
Ile Pro Leu Asp Met Phe Tyr Pro Pro Lys Thr Pro Ser Ala Leu
545                 550                 555                 560

Pro Val Met Pro His Pro Pro Ser Val Asn Ser Pro Ser Lys Val Pro
                565                 570                 575

Ala Pro Pro Val Leu Pro Ser Ser Gly His Val Ser Ser Ser Ser Ser
                580                 585                 590

Pro Trp Val Gln Arg Thr Pro Pro Ile Pro Ile Pro Pro Pro Pro
        595                 600                 605

Ser Ile Pro Thr Gln Asp Leu Thr Pro Thr Arg Pro Leu Pro Ser Ala
        610                 615                 620

Leu Glu Glu Ala Leu Gly Asn His Pro Phe Arg Thr Gly Asp Pro Gly
625                 630                 635                 640

His Pro Ala Asp Asp Trp Glu Ala Asn Thr His Ser Gly Lys Pro Ser
                645                 650                 655

Ser Ser Pro Thr Thr Glu Arg Ser Phe Pro Ala Pro Lys Thr Phe
                660                 665                 670

Cys Pro Ser Pro Gln Pro Pro Arg Gly Pro Gly Val Ser Thr Ile Ser
                675                 680                 685

Lys Pro Val Met Val His Gln Glu His Asn Phe Val Tyr Arg Pro Ala
        690                 695                 700

Val Lys Ser Glu Val Leu Pro Gln Glu Met Leu Lys Arg Met Val Val
705                 710                 715                 720

Tyr Gln Thr Ala Phe Arg Gln Asp Phe Arg Lys Tyr Glu Glu Gly Phe
                725                 730                 735

Asp Pro Tyr Ser Met Phe Ser Pro Glu Gln Ile Ala Gly Lys Asp Val
                740                 745                 750

Arg Leu Leu Arg Ile Lys Lys Glu Gly Ser Leu Asp Leu Ala Leu Glu
        755                 760                 765

Gly Gly Val Asp Ser Pro Val Gly Lys Val Val Val Ser Ala Val Tyr
770                 775                 780

Glu Gly Gly Ala Ala Glu Arg His Gly Val Val Lys Gly Asp Glu
785                 790                 795                 800

Ile Met Ala Ile Asn Gly Lys Ile Val Thr Asp Tyr Thr Leu Ala Glu
                805                 810                 815

Ala Glu Ala Ala Leu Gln Lys Ala Trp Asn Gln Gly Gly Asp Trp Ile
                820                 825                 830

Asp Leu Val Val Ala Val Cys Pro Pro Lys Glu Tyr Asp Asp Glu Leu
        835                 840                 845

Ser Ser Leu Pro Ser Ser Ala Ala Glu Ser Pro Gln Leu Ala Arg Lys
850                 855                 860

Gln Leu Glu Ala Tyr Glu Pro Val Cys Arg His Gly Phe Phe Leu Gln
865                 870                 875                 880

Leu Glu Pro Thr Asn Leu Leu Leu Lys Ser Arg Glu Arg Asn Gln Thr
                885                 890                 895

Asp Pro Ser Trp Arg Pro Ala Ser Ser Ala Pro Ser Pro
                900                 905

<210> SEQ ID NO 32
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 32

Met Asp Arg Lys Val Ala Arg Glu Phe Arg His Lys Val Asp Phe Leu
1               5                   10                  15

Ile Glu Asn Asp Ala Glu Lys Asp Tyr Leu Tyr Asp Val Leu Arg Met
            20                  25                  30

Tyr His Gln Thr Met Asp Val Ala Val Leu Val Gly Asp Leu Lys Leu
        35                  40                  45

Val Ile Asn Glu Pro Asn Arg Leu Pro Leu Phe Asp Ala Ile Arg Pro
    50                  55                  60

Leu Ile Pro Leu Lys His Gln Glu Thr Glu Gly Gly Thr Leu Gly Pro
65              70                  75                  80

Ser Ala Pro Arg Arg Ser Arg Pro Gln Arg Ala Trp Arg Pro Gly Ile
            85                  90                  95

Trp Leu Trp Thr Leu Tyr Leu Pro Pro His Gln Arg Trp Pro Gly Arg
            100                 105                 110

Gln Arg Trp Ala Ser Gly Arg Gly
            115                 120

<210> SEQ ID NO 33
<211> LENGTH: 533
<212> TYPE: PRT
<213> ORGANISM: Homo sapiens

<400> SEQUENCE: 33

Met Asp Arg Lys Val Ala Arg Glu Phe Arg His Lys Val Asp Phe Leu
1               5                   10                  15

Ile Glu Asn Asp Ala Glu Lys Asp Tyr Leu Tyr Asp Val Leu Arg Met
            20                  25                  30

Tyr His Gln Thr Met Asp Val Ala Val Leu Val Gly Asp Leu Lys Leu
        35                  40                  45

Val Ile Asn Glu Pro Ser Arg Leu Pro Leu Phe Asp Ala Ile Arg Pro
    50                  55                  60

Leu Ile Pro Leu Lys His Gln Val Glu Tyr Asp Gln Leu Thr Pro Arg
65              70                  75                  80

Arg Ser Arg Lys Leu Lys Glu Val Arg Leu Asp Arg Leu His Pro Glu
            85                  90                  95

Gly Leu Gly Leu Ser Val Arg Gly Gly Leu Glu Phe Gly Cys Gly Leu
            100                 105                 110

Phe Ile Ser His Leu Ile Lys Gly Gly Gln Ala Asp Ser Val Gly Leu
            115                 120                 125

Gln Val Gly Asp Glu Ile Val Arg Ile Asn Gly Tyr Ser Ile Ser Ser
        130                 135                 140

Cys Thr His Glu Glu Val Ile Asn Leu Ile Arg Thr Lys Lys Thr Val
145                 150                 155                 160

Ser Ile Lys Val Arg His Ile Gly Leu Ile Pro Val Lys Ser Ser Pro
                165                 170                 175

Asp Glu Pro Leu Thr Trp Gln Tyr Val Asp Gln Phe Val Ser Glu Ser
            180                 185                 190

Gly Gly Val Arg Gly Ser Leu Gly Ser Pro Gly Asn Arg Glu Asn Lys
            195                 200                 205

Glu Lys Lys Val Phe Ile Ser Leu Val Gly Ser Arg Gly Leu Gly Cys
        210                 215                 220

Ser Ile Ser Ser Gly Pro Ile Gln Lys Pro Gly Ile Phe Ile Ser His
225                 230                 235                 240
```

```
Val Lys Pro Gly Ser Leu Ser Ala Glu Val Gly Leu Glu Ile Gly Asp
            245                 250                 255

Gln Ile Val Glu Val Asn Gly Val Asp Phe Ser Asn Leu Asp His Lys
            260                 265                 270

Glu Gly Arg Glu Leu Phe Met Thr Asp Arg Glu Arg Leu Ala Glu Ala
            275                 280                 285

Arg Gln Arg Glu Leu Gln Arg Gln Glu Leu Leu Met Gln Lys Arg Leu
            290                 295                 300

Ala Met Glu Ser Asn Lys Ile Leu Gln Glu Gln Glu Met Glu Arg
305                 310                 315                 320

Gln Arg Arg Lys Glu Ile Ala Gln Lys Ala Ala Glu Glu Asn Glu Arg
            325                 330                 335

Tyr Arg Lys Glu Met Glu Gln Ile Val Glu Glu Glu Lys Phe Lys
            340                 345                 350

Lys Gln Trp Glu Glu Asp Trp Gly Ser Lys Glu Gln Leu Leu Leu Pro
            355                 360                 365

Lys Thr Ile Thr Ala Glu Val His Pro Val Pro Leu Arg Lys Pro Lys
            370                 375                 380

Tyr Asp Gln Gly Val Glu Pro Glu Leu Glu Pro Ala Asp Asp Leu Asp
385                 390                 395                 400

Gly Gly Thr Glu Glu Gln Gly Glu Gln Asp Phe Arg Lys Tyr Glu Glu
            405                 410                 415

Gly Phe Asp Pro Tyr Ser Met Phe Thr Pro Glu Gln Ile Met Gly Lys
            420                 425                 430

Asp Val Arg Leu Leu Arg Ile Lys Lys Glu Gly Ser Leu Asp Leu Ala
            435                 440                 445

Leu Glu Gly Gly Val Asp Ser Pro Ile Gly Lys Val Val Val Ser Ala
            450                 455                 460

Val Tyr Glu Arg Gly Ala Ala Glu Arg His Gly Gly Ile Val Lys Gly
465                 470                 475                 480

Asp Glu Ile Met Ala Ile Asn Gly Lys Ile Val Thr Asp Tyr Thr Leu
            485                 490                 495

Ala Glu Ala Glu Ala Leu Gln Lys Ala Trp Asn Gln Gly Gly Asp
            500                 505                 510

Trp Ile Asp Leu Val Val Ala Val Cys Pro Pro Lys Glu Tyr Asp Asp
            515                 520                 525

Glu Leu Thr Phe Phe
            530

<210> SEQ ID NO 34
<211> LENGTH: 909
<212> TYPE: PRT
<213> ORGANISM: Mus sp.

<400> SEQUENCE: 34

Met Asp Arg Lys Val Ala Arg Glu Phe Arg His Lys Val Asp Phe Leu
1               5                   10                  15

Ile Glu Asn Asp Ala Glu Lys Asp Tyr Leu Tyr Asp Val Leu Arg Met
            20                  25                  30

Tyr His Gln Thr Met Asp Val Ala Val Leu Val Gly Asp Leu Lys Leu
            35                  40                  45

Val Ile Asn Glu Pro Asn Arg Leu Pro Leu Phe Asp Ala Ile Arg Pro
            50                  55                  60

Leu Ile Pro Leu Lys His Gln Glu Tyr Asp Gln Leu Thr Pro Arg Arg
```

```
            65                  70                  75                  80
Ser Arg Lys Leu Lys Glu Val Arg Leu Asp Arg Leu His Pro Glu Gly
                    85                  90                  95

Leu Gly Leu Ser Val Arg Gly Gly Leu Glu Phe Gly Cys Gly Leu Phe
                100                 105                 110

Ile Ser His Leu Ile Lys Gly Gly Gln Ala Asp Ser Val Gly Leu Gln
                115                 120                 125

Val Gly Asp Glu Ile Val Arg Ile Asn Gly Tyr Ser Ile Ser Ser Cys
        130                 135                 140

Thr His Glu Glu Val Ile Asn Leu Ile Arg Thr Lys Lys Thr Val Ser
145                 150                 155                 160

Ile Lys Val Arg His Ile Gly Leu Ile Pro Val Lys Ser Ser Pro Glu
                165                 170                 175

Glu Ser Leu Lys Trp Gln Tyr Val Asp Gln Phe Val Ser Glu Ser Gly
                180                 185                 190

Gly Val Arg Gly Gly Leu Gly Ser Pro Gly Asn Arg Thr Thr Lys Glu
        195                 200                 205

Lys Lys Val Phe Ile Ser Leu Val Gly Ser Arg Gly Leu Gly Cys Ser
210                 215                 220

Ile Ser Ser Gly Pro Ile Gln Lys Pro Gly Ile Phe Val Ser His Val
225                 230                 235                 240

Lys Pro Gly Ser Leu Ser Ala Glu Val Gly Leu Glu Thr Gly Asp Gln
                245                 250                 255

Ile Val Glu Val Asn Gly Ile Asp Phe Thr Asn Leu Asp His Lys Glu
                260                 265                 270

Ala Val Asn Val Leu Lys Ser Ser Arg Ser Leu Thr Ile Ser Ile Val
        275                 280                 285

Ala Gly Ala Gly Arg Glu Leu Phe Met Thr Asp Arg Glu Arg Leu Glu
        290                 295                 300

Glu Ala Arg Gln Arg Glu Leu Gln Arg Gln Glu Leu Leu Met Gln Lys
305                 310                 315                 320

Arg Leu Ala Met Glu Ser Asn Lys Ile Leu Gln Glu Gln Gln Glu Met
                325                 330                 335

Glu Arg Gln Arg Arg Lys Glu Ile Ala Gln Lys Ala Ala Glu Glu Asn
                340                 345                 350

Glu Arg Tyr Arg Lys Glu Met Glu Gln Ile Ser Glu Glu Glu Glu Lys
                355                 360                 365

Phe Lys Lys Gln Trp Glu Glu Asp Trp Gly Ser Lys Glu Gln Leu Ile
        370                 375                 380

Leu Pro Lys Thr Ile Thr Ala Glu Val His Pro Val Pro Leu Arg Lys
385                 390                 395                 400

Pro Lys Ser Phe Gly Trp Phe Tyr Arg Tyr Asp Gly Lys Phe Pro Thr
                405                 410                 415

Ile Arg Lys Lys Ala Lys Glu Lys Lys Ala Lys Tyr Asp Ser Leu
                420                 425                 430

Gln Asp Leu Arg Lys Asn Lys Lys Glu Leu Glu Phe Glu Gln Lys Leu
        435                 440                 445

Tyr Lys Glu Lys Glu Glu Met Leu Glu Lys Glu Lys Gln Leu Lys Ile
        450                 455                 460

Asn Arg Leu Ala Gln Glu Val Ser Glu Thr Glu Arg Glu Asp Leu Glu
465                 470                 475                 480

Glu Ser Glu Lys Thr Gln Tyr Trp Val Glu Arg Leu Cys Gln Thr Arg
                485                 490                 495
```

```
Leu Glu Gln Ile Ser Ser Ala Glu Asn Glu Ile Pro Glu Met Thr Thr
            500                 505                 510
Gly Pro Pro Pro Pro Pro Ser Val Ser Pro Leu Ala Pro Pro Leu
        515                 520                 525
Arg Arg Phe Ala Gly Gly Ile His Leu His Thr Thr Asp Leu Asp Asp
530                 535                 540
Ile Pro Leu Asp Met Phe Tyr Tyr Pro Pro Lys Thr Pro Ser Ala Leu
545                 550                 555                 560
Pro Val Met Pro Met Pro Pro Ser Val Asn Ser Pro Ser Lys Val Pro
                565                 570                 575
Ala Pro Pro Val Leu Pro Ser Ser Gly His Val Ser Ser Ser Ser Ser
            580                 585                 590
Pro Trp Val Gln Arg Thr Pro Pro Ile Pro Ile Pro Pro Pro
            595                 600                 605
Ser Ile Pro Thr Gln Asp Leu Thr Pro Thr Arg Pro Leu Pro Ser Ala
        610                 615                 620
Leu Glu Glu Ala Leu Gly Asn His Pro Phe Arg Thr Gly Asp Pro Gly
625                 630                 635                 640
His Pro Ala Asp Asp Trp Glu Ala Asn Thr His Ser Gly Lys Pro Ser
                645                 650                 655
Ser Ser Pro Thr Thr Glu Arg Ser Phe Pro Ala Pro Lys Thr Phe
            660                 665                 670
Cys Pro Ser Pro Gln Pro Pro Arg Gly Pro Gly Val Ser Thr Ile Ser
                675                 680                 685
Lys Pro Val Met Val His Gln Glu His Asn Phe Val Tyr Arg Pro Ala
            690                 695                 700
Val Lys Ser Glu Val Leu Pro Gln Glu Met Leu Lys Arg Met Val Val
705                 710                 715                 720
Tyr Gln Thr Ala Phe Arg Gln Asp Phe Arg Lys Tyr Glu Gly Phe
                725                 730                 735
Asp Pro Tyr Ser Met Phe Ser Pro Glu Gln Ile Ala Gly Lys Asp Val
            740                 745                 750
Arg Leu Leu Arg Ile Lys Lys Glu Gly Ser Leu Asp Leu Ala Leu Glu
        755                 760                 765
Gly Gly Val Asp Ser Pro Val Gly Lys Val Val Val Ser Ala Val Tyr
770                 775                 780
Glu Gly Gly Ala Ala Glu Arg His Gly Gly Val Val Lys Gly Asp Glu
785                 790                 795                 800
Ile Met Ala Ile Asn Gly Lys Ile Val Thr Asp Tyr Thr Leu Ala Glu
                805                 810                 815
Ala Glu Ala Ala Leu Gln Lys Ala Trp Asn Gln Gly Gly Asp Trp Ile
            820                 825                 830
Asp Leu Val Val Ala Val Cys Pro Pro Lys Glu Tyr Asp Asp Glu Leu
            835                 840                 845
Ser Ser Leu Pro Ser Ser Ala Ala Glu Ser Pro Gln Leu Ala Arg Lys
        850                 855                 860
Gln Leu Glu Ala Tyr Glu Pro Val Cys Arg His Gly Phe Phe Leu Gln
865                 870                 875                 880
Leu Glu Pro Thr Asn Leu Leu Lys Ser Arg Glu Arg Asn Gln Thr
                885                 890                 895
Asp Pro Ser Trp Arg Pro Ala Ser Ser Ala Pro Ser Pro
            900                 905
```

MATERIALS AND METHODS FOR DELIVERING NUCLEIC ACIDS TO COCHLEAR AND VESTIBULAR CELLS

CROSS-REFERENCE TO RELATED APPLICATIONS

This application is the U.S. national phase, pursuant to 35 U.S.C. § 371, of International PCT Application No.: PCT/US2018/017104, filed on Feb. 6, 2018, designating the United States and published in English, which claims priority to and the benefit of U.S. Provisional Application No. 62/455,197, filed on Feb. 6, 2017, the disclosure of which is incorporated herein by reference in its entirety.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "167705-011002US_SEQ_LISTING.txt," created on Jun. 23, 2022, and is 144 kilobytes in size. The sequence listing contained in this .txt file is part of the specification and is incorporated herein by reference in its entirety.

BACKGROUND

Genetically-based hearing loss is a significant problem with few therapeutic options other than cochlear implants. Inherited hearing problems are often due to single gene defects. Prelingual deafness is diagnosed in 1/500 infants, of which about 50% have a genetic etiology. Usher syndrome, which is associated with a number of different clinical subtypes, each of which can be caused by a mutation in any of a number of different genes, is responsible for 3 to 6% of early childhood deafness. One of the more prevalent genetic defects, estimated to be 1-2% of all genetic deafness, occurs in the TMC1 gene. The most severe form of Usher Syndrome, USH1, is associated with defects in six genes: USH1, MYO7A (myosin 7a), USH1C (harmonin), CDH23 (cadherin 23), PCDH15 (protocadherin 15), SANS (sans; also known as USH1G) and CIB2 (calcium and integrin binding protein2).

The inner ear, e.g., cochlea, particularly the inner and outer hair cells (IHCs and OHCs) in the cochlea, is an attractive target for polynucleotide therapy approaches to intervene in hearing loss and deafness of various etiologies, most immediately monogenic forms of inherited deafness. However, it has been a challenge to efficiently target and transduce IHCs and OHCs as well as other inner ear cells that may be relevant to gene therapy approaches.

SUMMARY

The invention provides compositions and methods for targeting a cell of the inner ear of a subject (e.g., inner or outer hair cell) and expressing a transgene encoding a polypeptide of interest (e.g., TMC1, TMC2, MYO7A, USCH1C, CDH23, PCDH15, SANS, CIB2, USH2A, VLGR1, WHRN, CLRN1, PDZD7 USH1C (e.g., harmonin-a, b, or c)). In one embodiment, an Inner Ear Hair Cell Targeting AAV is administered to the inner ear of a subject having a genetic defect in auditory and/or vestibular mechanosensation.

As shown herein, an adeno-associated viruses (AAV) containing an ancestral scaffold capsid protein referred to as Anc80 or a specific Anc80 capsid protein (e.g., Anc80-0065) efficiently target various cells in the inner ear, such as IHCs and OHCs in vivo.

Gene transfer to inner ear cells in animal models has had limited efficacy due to limited transduction of one or more types of cells, e.g., the outer hair cells. However, the novel gene delivery modalities described herein, which include new compositions and methods based on an AAV containing an Anc80 capsid protein, provide highly efficient gene transfer to inner ear cells including both IHCs and OHCs.

In one aspect, the invention provides a synthetic inner ear hair cell targeting adeno-associated virus (AAV) vector, where the vector contains a polynucleotide encoding a human USH1 polypeptide, where the USH1 polypeptide is myosin 7a, harmonin (e.g., harmonin-a, harmonin-b, or harmonin-c), cadherin 23, protocadherin 15, SANS and calcium and integrin binding protein 2, or any other polypeptide described herein.

In another aspect, the invention provides a synthetic inner ear hair cell targeting adeno-associated virus (AAV) vector, where the vector encodes a capsid having at least about 85% sequence identity to Anc80L65, and contains a promoter that directs expression of a human TMC1 or TMC2 polynucleotide.

In another aspect, the invention provides a synthetic inner ear hair cell targeting adeno-associated virus (AAV) vector, where the vector contains a promoter that is an Espin promoter, a PCDH15 promoter, a PTPRQ promoter or a TMHS (LHFPL5) promoter that directs expression of a downstream polynucleotide.

In another aspect, the invention provides a cell containing the synthetic inner ear hair cell targeting adeno-associated virus (AAV) vector of previous aspect.

In another aspect, the invention provides a method of expressing a polypeptide in the inner ear of a subject, the method involving contacting a cell of the inner ear with a synthetic inner ear hair cell targeting adeno-associated virus (AAV) vector encoding a polypeptide of interest, where the AAV vector transfects at least about 70% of cells of the inner ear and contains ancestral AAV sequences.

In another aspect, the invention provides a method of expressing a polypeptide in the inner ear of a subject, the method involving contacting a cell of the inner ear with a synthetic adeno-associated virus (AAV) vector encoding a human polypeptide of interest, where the AAV vector encodes a capsid having at least about 85% sequence identity to Anc80L65.

In another aspect, the invention provides a method of treating a sensory transduction defect in a subject, the method involving contacting a cell of the subject with a synthetic inner ear hair cell targeting adeno-associated virus (AAV) vector, where the vector contains a polynucleotide encoding a human USH1 polypeptide, where the USH1 polypeptide is any one or more of myosin 7a, harmonin, cadherin 23, protocadherin 15, SANS and calcium and integrin binding protein 2.

In another aspect, the invention provides a method of treating a sensory transduction defect in a subject, the method involving contacting a cell of the subject with a synthetic inner ear hair cell targeting adeno-associated virus (AAV) vector, where the vector contains a promoter is any of an Espin promoter, a PCDH15 promoter, a PTPRQ promoter and a TMHS (LHFPL5) promoter.

In another aspect, the invention provides a method of treating a sensory transduction defect in a subject, the method involving contacting a cell of the subject with a synthetic inner ear hair cell targeting adeno-associated virus (AAV) vector, where the vector encodes a capsid having at least about 85% sequence identity to Anc80L65, and contains a promoter operably linked to a polynucleotide encoding an USH1 polypeptide that is myosin 7a, harmonin, cadherin 23, protocadherin 15, SANS and calcium or integrin binding protein 2.

In various embodiments of the above-aspects or any other aspect of the invention described herein, the sensory transduction defect is a genetic disorder associated with a genetic alteration in a polypeptide expressed in the inner ear. In other embodiments of the above aspects, the promoter is any one or more of an Espin promoter, a PCDH15 promoter, a PTPRQ promoter and a TMHS (LHFPL5) promoter. In other embodiments of the above aspects, the vector transduces inner and outer hair cells with at least about 70% or greater efficiency. In other embodiments of the above aspects, the harmonin polypeptide is harmonin-a, harmonin-b, or harmonin-c. In other embodiments of the above aspects, the cell is an outer or inner hair cell. In other embodiments of the above aspects, the vector contains a promoter directing expression of a downstream polynucleotide, and the promoter is an Espin promoter, a PCDH15 promoter, a PTPRQ promoter or a TMHS (LHFPL5) promoter. In other embodiments of the above aspects, the downstream polynucleotide is TMC1, TMC2 or an USH1 polypeptide that is myosin 7a, harmonin, cadherin 23, protocadherin 15, SANS and calcium or integrin binding protein 2. In particular embodiments of the above aspects, the harmonin polypeptide is harmonin-a, harmonin-b, or harmonin-c. In other embodiments of the above aspects, the synthetic inner ear hair cell targeting adeno-associated virus (AAV) vector targets inner and outer hair cells with at least about 70%, 80%, 90%, 95% or greater efficiency, even as high as 100% efficiency. In other embodiments of the above aspects, the human polypeptide is TMC1, TMC2, harmonin-a, harmonin-b, or harmonin-c. In other embodiments of the above aspects, the sensory transduction defect is a hearing disorder or vestibular disorder. In other embodiments of the above aspects, the sensory transduction defect is Usher Syndrome.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "Ancestral AAV sequence" is meant a designed sequence that is the product of genetic engineering arising from an analysis of naturally existing AAVs and prediction of an evolutionary ancestor.

By "Anc80 polypeptide" is meant a capsid polypeptide having at least about 85% amino acid identity to the following polypeptide sequence:

(SEQ ID NO:13)
MAADGYLPDWLEDNLSEGIREWWDLKPGAPKPKANQQKQDDGRGLVLPGY

KYLGPFNGLDKGEPVNAADAAALEHDKAYDQQLKAGDNPYLRYNHADAEF

QERLQEDTSFGGNLGRAVFQAKKRVLEPLGLVEEGAKTAPGKKRPVEQSP

QEPDSSSGIGKKGQQPARKRLNFGQTGDSESVPDPQPLGEPPAAPSGVGS

NTMAAGGGAPMADNNEGADGVGNASGNWHCDSTWLGDRVITTSTRT ALP

TYNNHLYKQISSQSGGSTNDNTYFGYSTPWGYFDFNRFHCHFSPRDWQRL

INNNWGFRPKKLNFKLFNIQVKEVTTNDGTTTIANNLTSTVQVFTDSEYQ

LPYVLGSAHQGCLPPFPADVFMI PQYGYLTLNNGSQAVGRSSFYCLEYF

PSQMLRTGNNFQFSYTFEDVPFHSSYAHSQSLDRLMNPLIDQYLYYLSRT

QTTSGTAGNRTLQFSQAGPSSMANQAKNWLPGPCYRQQRVSKTTNQNNNS

NFAWTGATKYHLNGRDSLVNPGPAMATHKDDEDKFFPMSGVLIFGKQGAG

NSNVDLDNVMITNEEEIKTTNPVATEEYGTVATNLQSANTAPATGTVNSQ

GALPGMVWQDRDVYLQGPIWAKIPHTDGHFHPSPLMGGFGLKHPPPQILI

KNTPVPANPPTTFSPAKFASFITQYSTGQVSVEIE ELQKENSKRWNPEI

QYTSNYNKSTNVDFAVDTNGVYSEPRPIGTRYLTRNL

By "Anc80 polynucleotide" is meant a nucleic acid molecule encoding a Anc80 polypeptide.

By "Seroprevalence" is meant the number of persons in a population who test positive for a specific disease based on serology (blood serum) specimens. In one embodiment, seroprevalence is characterized as a percentage of the total specimens tested or as a proportion per 100,000 persons tested.

By "Inner Ear Hair Cell Targeting AAV" is meant an adeno-associated virus that transfects at least 70% of inner hair cells and 70% of outer hair cells following administration to the inner ear of a subject or contact with a cell derived from an inner ear in vitro. Preferably, an Inner Ear Hair Cell targeting AAV is an AAV that transfects at least 90% of inner hair cells and 90% of outer hair cells after injecting to the cochlea in vivo. The transfection efficiency may be assessed using a gene encoding GFP in a mouse model.

By "mechanosensation" is meant a response to a mechanical stimulus. Touch, hearing, and balance of examples of the conversion of a mechanical stimulus into a neuronal signal. Mechanosensory input is converted into a response to a mechanical stimulus through a process termed "mechanotransduction."

By "TMC1 polypeptide" is meant a polypeptide having at least about 85% or greater amino acid sequence identity to NCBI Reference Sequence: NP_619636.2 or a fragment thereof having mechanotransduction channel activity. An exemplary amino acid sequence of TMC1 is provided below:

(SEQ ID NO:14)
 1  mspkkvqikv eekedetees sseeeeeved klprreslrp krkrtrdvin eddpepeped 61  eetrkareke rrrrlkrgae eeeideeele rlkaeldekr giiatvkckp wkmekkievl 121 keakkfvsen egalgkgkgk rwfafkmmma kkwakflrdf enfkaacvpw enkikaiesq -continued

```
181  fgssvasyfl  flrwmygvnm  vlfiltfsli  mlpeylwglp  ygslprktvp  raeeasaanf
241  gvlydfngla  qysvlfygyy  dnkrtigwmn  frlplsyflv  gimcigysfl  vvlkamtkni
301  gddgggddnt  fnfswkvfts  wdylignpet  adnkfnsitm  nfkeaiteek  aaqveenvhl
361  irflrflanf  fvfltlggsg  ylifwavkrs  gefaqqdpdt  lgwweknemn  mvmsllgmfc
421  ptlfdlfael  edyhplialk  wllgrifall  lgnlyvfila  lmdeinnkie  eeklvkanit
481  lweanmikay  nasfsenstg  ppffvhpadv  prgpcwetmv  gqefvrltvs  dvlttyvtil
541  igdflracfv  rfcnycwcwd  leygypsyte  fdisgnvlal  ifnqgmiwmg  sffapslpgi
601  nilrlhtsmy  fqcwavmccn  vpearvfkas  rsnnfylgml  llilflstmp  vlymivslpp
661  sfdcgpfsgk  nrmfeviget  lehdfpswma  kilrqlsnpg  lviavilvmv  laiyylnata
721  kgqkaanldl  kkkmkmqale  nkmrnkkmaa  araaaaagrq
```

By "TMC1 polynucleotide" is meant a polynucleotide encoding a TMC1 polypeptide. The sequence of an exemplary TMC1 polynucleotide is provided at NCBI Reference Sequence: NM_138691.2, which is reproduced below:

(SEQ ID NO:15)
```
   1  cagaaactat  gagggcagaa  cccagcaatc  tgtgctttct  ttcacaagcc  ctccaggagt
  61  tgctgaaatt  taggaatcat  tgccccaaaa  agtggccctc  ataatgatgc  cagatgggat
 121  cttactctgt  tgcccaggct  ggagtgcagt  ggtgcgatct  cggctctctg  caacctccgc
 181  ctcccaggtt  caagtgattc  tcctgcctcg  gcctcctgag  tagctgggat  ttcaggccat
 241  gaaagatcac  tgttttagtc  tgcgtggtgc  agtggaacag  atagacctcg  gtttgaatct
 301  cagctctact  gtttactaga  catgaaatgg  ggaaatctaa  aatgagatgc  agaagcctc
 361  aaaaatggaa  acccccctgt  gcttcacatc  tgaaaatctc  tgctggggc   agcaactttg
 421  agcctgtggg  gaaggaactg  tccacgtgga  gtggtctggt  gaatgcttaa  ggagctgcag
 481  aagggaagtc  cctctccaaa  ctagccagcc  actgagacct  tctgacagga  cacccccagg
 541  atgtcaccca  aaaagtaca   aatcaaagtg  gaggaaaaag  aagacgagac  tgaggaaagc
 601  tcaagtgaag  aggaagagga  ggtggaagat  aagctacctc  gaagagagag  cttgagacca
 661  aagaggaaac  ggaccagaga  tgttatcaat  gaggatgacc  cagaacctga  accagaggat
 721  gaagaaacaa  ggaaggcaag  agaaaaagag  aggaggagga  ggctaaagag  aggagcagaa
 781  gaagaagaaa  ttgatgaaga  ggaattggaa  agattgaagg  cagagttaga  tgagaaaaga
 841  caaataattg  ctactgtcaa  atgcaaacca  tggaagatgg  agaagaaaat  tgaagttctc
 901  aaggaggcaa  aaaaatttgt  gagtgaaaat  gaagggctc   ttgggaaagg  aaaaggaaaa
 961  cggtggtttg  catttaagat  gatgatggcc  aagaaatggg  caaaattcct  ccgtgatttt
1021  gagaacttca  aagctgcgtg  tgtcccatgg  gaaaataaaa  tcaaggctat  tgaaagtcag
1081  tttggctcct  cagtggcctc  atacttcctc  ttcttgagat  ggatgtatgg  agtcaatatg
1141  gttctcttta  tcctgacatt  tagcctcatc  atgttgccag  agtacctctg  gggtttgcca
1201  tatggcagtt  tacctaggaa  aaccgttccc  agagccgaag  aggcatcggc  agcaaacttt
1261  ggtgtgttgt  acgacttcaa  tggtttggca  caatattccg  ttctcttta   tggctattat
1321  gacaataaac  gaacaattgg  atggatgaat  ttcaggttgc  cgctctccta  ttttctagtg
1381  gggattatgt  gcattggata  cagcttctg   gttgtcctca  aagcaatgac  caaaaacatt
1441  ggtgatgatg  gaggtggaga  tgacaacact  ttcaatttca  gctggaaggt  ctttaccagc
1501  tgggactacc  tgatcggcaa  tcctgaaaca  gcagacaaca  aatttaattc  tatcacaatg
1561  aactttaagg  aagctatcac  agaagaaaaa  gcagcccaag  tagaagaaaa  cgtccacttg
```

-continued

```
1621  atcagattcc tgaggtttct ggctaacttc ttcgtgtttc taacacttgg agggagtgga
1681  tacctcatct tttgggctgt gaagcgatcc caggaatttg cacagcaaga tcctgacacc
1741  cttgggtggt gggaaaaaaa tgaaatgaac atggttatgt ccctcctagg gatgttctgt
1801  ccaacattgt ttgacttatt tgctgaatta gaagactacc atcctctcat cgctttgaaa
1861  tggctactgg gacgcatttt tgctcttctt ttaggcaatt tatacgtatt tattcttgca
1921  ttaatggatg agattaacaa caagattgaa gaggagaagc tagtaaaggc caatattacc
1981  ctttgggaag ccaatatgat caaggcctac aatgcatcat tctctgaaaa tagcactgga
2041  ccacccttt ttgttcaccc tgcagatgta cctcgaggac cttgctggga acaatggtg
2101  ggacaggagt ttgtgaggct gacagtctct gatgttctga ccacctacgt cacaatcctc
2161  attggggact ttctaagggc atgttttgtg aggttttgca attattgctg gtgctgggac
2221  ttggagtatg atatccttc atacaccgaa ttcgacatca gtggcaacgt cctcgctctg
2281  atcttcaacc aaggcatgat ctggatgggc tccttctttg ctcccagcct cccaggcatc
2341  aatatccttc gactccatac atccatgtac ttccagtgct gggccgttat gtgctgcaat
2401  gttcctgagg ccagggtctt caaagcttcc agatcaaata acttctacct gggcatgcta
2461  ctgctcatcc tcttcctgtc cacaatgcct gtcttgtaca tgatcgtgtc cctcccacca
2521  tcttttgatt gtggtccatt cagtggcaaa aatagaatgt ttgaagtcat tggagagacc
2581  ctggagcacg atttcccaag ctggatggcg aagatcttga cacagctttc aaaccctggg
2641  ctggtcattg ctgtcatttt ggtgatggtt ttggccatct attatctcaa tgctactgcc
2701  aagggccaga aggcagcgaa tctggatctc aaaaagaaga tgaaaatgca agctttggag
2761  aacaaaatgc gaaacaagaa aatggcagct gcacgagcag ctgcagctgc tggtcgccag
2821  taataagtat cctgagagcc cagaaaaggt acactttgcc ttgctgttta aaagtaatgc
2881  aatatgtgaa cgcccagaga acaagcactg tggaactgct attttcctgt tctacccttg
2941  atggattttc aaggtcatgc tggccaatta aggcatcatc agtcctacct gagcaacaag
3001  aatctaaact ttattccaag tcagaaactg tttctgcaga gccactctct cccctgctcc
3061  atttcgtgac tttttttttt ttttaacaa attgagttta gaagtgagtg taatccagca
3121  atacagttta ctggtttagt tggtgggtta attaaaaaaa atttgctcat atgaactttc
3181  attttatatg tttcttttgc c
```

By "TMC2 polypeptide" is meant a polypeptide having at least about 85% or greater amino acid sequence identity to NCBI Reference Sequence: NP_542789 or a fragment thereof that functions in mechanosensation. An exemplary amino acid sequence of TMC2 is provided below:

(SEQ ID NO:16)
```
  1  mshqvkglke earggvkgrv ksgsphtgdr lgrrssskra lkaegtpgrr gaqrsqkera
 61  ggspspgspr rkqtgrrrhr eelgeqerge aertcegrrk rderasfqer taapkrekei
121  prreekskrq kkprssslas sasggeslse eelaqileqv eekkkliatm rskpwpmakk
181  ltelreaqef vekyegalgk gkgkqlyayk mlmakkwvkf krdfdnfktq cipwemkikd
241  ieshfgssva syfiflrwmy gvnlvlfgli fglviipevl mgmpygsipr ktvpraeeek
301  amdfsvlwdf egyikysalf ygyynnqrti gwlryrlpma yfmvgsvfg ysliivirsm
361  asntqgstge gesdnftfsf kmftswdyli gnsetadnky asittsfkes ivdeqesnke
421  enihltrflr vlanfliicc lcgsgyliyf vvkrsqqfsk mqnvswyern eveivmsllg
```

```
481  mfcpplfeti aalenyhprt glkwqlgrif alflgnlytf llalmddvhl klaneetikn 541  ithwtlfnyy nssgwnesvp rpplhpadvp rgscwetavg iefmrltvsd mlvtyitill 601  gdflracfvr fmnycwcwdl eagfpsyaef disgnvlgli fnqgmiwmgs fyapglvgin 661  vlrlltsmyf qcwavmssnv phervfkasr snnfymglll lvlflsllpv aytimslpps 721  fdcgpfsgkn rmydvlqeti endfptflgk ifaflanpgl iipaillmfl aiyylnsvsk 781  slsranaqlr kkiqvlreve kshksvkgka tardsedtpk sssknatqlq ltkeettpps 841  asqsqamdkk aqgpgtsnsa srttlpasgh lpisrppgig pdsghapsqt hpwrsasgks 901  aqrpph
```

By "harmonin" polypeptide is meant a polypeptide having at least about 85% amino acid sequence identity to Q9Y6N9-1 (isoform 1), Q9Y6N9-2, Q9Y6N9-3, Q9Y6N9-4, Q9Y6N9-5 or a fragment thereof that functions in mechanosensation or that interacts with any one or more of USH1C, USH1G, CDH23 and MYO7A. The sequence of an exemplary harmonin-a polypeptide (isoform 1) is provided below:

(SEQ ID NO:17)
```
>sp|Q9Y6N9|USH1C_HUMAN Harmonin OS = Homo sapiens
GN = USH1C PE = 1 SV = 3
MDRKVAREFRHKVDFLIENDAEKDYLYDVLRMYHQTMDVAVLVGDLKLVI

NEPSRLPLFDAIRPLIPLKHQVEYDQLTPRRSRKLKEVRLDRLHPEGLGL

SVRGGLEFGCGLFISHLIKGGQADSVGLQVGDEIVRINGYSISSCTHEEV

INLIRTKKTVSIKVRHIGLIPVKSSPDEPLTWQYVDQFVSESGGVRGSLG

SPGNRENKEKKVFISLVGSRGLGCSISSGPIQKPGIFISHVKPGSLSAEV

GLEIGDQIVEVNGVDFSNLDHKEAVNVLKSSRSLTISIVAAAGRELFMTD

RERLAEARQRELQRQELLMQKRLAMESNKILQEQQEMERQRRKEIAQKAA

EENERYRKEMEQIVEEEEKFKKQWEEDWGSKEQLLLPKTITAEVHPVPLR

KPKYDQGVEPELEPADDLDGGTEEQGEQDFRKYEEGFDPYSMFTPEQIMG

KDVRLLRIKKEGSLDLALEGGVDSPIGKVVVSAVYERGAAERHGGIVKGD

EIMAINGKIVTDYTLAEAEAALQKAWNQGGDWIDLVVAVCPPKEYDDELT

FF
```

By "Ush1C polynucleotide" is meant a nucleic acid molecule encoding a harmonin polypeptide. The sequence of exemplary Ush1C polynucleotide NM_005709 is provided below:

(SEQ ID NO:18)
```
   1  agctccgagg gcggctggcc cggtcgcggt cgcggctctt tccagctcct ggcagccggg 61  cacccgaagg aacgggtcgt gcaacgacgc agctggacct ggcccagcca tggaccgaaa 121  agtggcccga gaattccggc ataaggtgga ttttctgatt gaaaatgatg cagagaagga 181  ctatctctat gatgtgctgc gaatgtacca ccagaccatg gacgtggccg tgctcgtggg 241  agacctgaag ctggtcatca tgaacccag ccgtctgcct ctgtttgatg ccattcggcc 301  gctgatccca ctgaagcacc aggtggaata tgatcagctg accccccggc gctccaggaa 361  gctgaaggag gtgcgtctgg accgtctgca ccccgaaggc ctcggcctga gtgtgcgtgg 421  tggcctggag tttggctgtg gctcttcat ctcccacctc atcaaaggcg gtcaggcaga 481  cagcgtcggg ctccaggtag gggacgagat cgtccggatc aatggatatt ccatctcctc 541  ctgtacccat gaggaggtca tcaacctcat tcgaaccaag aaaactgtgt ccatcaaagt 601  gagacacatc ggcctgatcc ccgtgaaaag ctctcctgat gagcccctca cttggcagta 661  tgtggatcag tttgtgtcgg aatctggggg cgtgcgaggc agcctgggct cccctggaaa 721  tcgggaaaac aaggagaaga aggtcttcat cagcctggta ggctcccgag gccttggctg 781  cagcatttcc agcggcccca tccagaagcc tggcatcttt atcagccatg tgaaacctgg 841  ctccctgtct gctgaggtgg gattggagat aggggaccag attgtcgaag tcaatggcgt 901  cgacttctct aacctggatc acaaggaggc tgtaaatgtg ctgaagagta gccgcagcct 961  gaccatctcc attgtagctg cagctggccg ggagctgttc atgacagacc gggagcggct 1021  ggcagaggcg cggcagcgtg agctgcagcg gcaggagctt ctcatgcaga gcggctggc 1081  gatggagtcc aacaagatcc tccaggagca gcaggagatg gagcggcaaa ggagaaaaga
```

-continued

```
1141  aattgcccag aaggcagcag aggaaaatga gagataccgg aaggagatgg aacagattgt
1201  agaggaggaa gagaagttta agaagcaatg ggaagaagac tggggctcaa aggaacagct
1261  actcttgcct aaaaccatca ctgctgaggt acacccagta cccctttcgca agccaaagta
1321  tgatcaggga gtggaacctg agctcgagcc cgcagatgac ctggatggag cacggagga
1381  gcagggagag caggatttcc ggaaatatga ggaaggcttt gacccctact ctatgttcac
1441  cccagagcag.atcatgggga aggatgtccg gctcctacgc atcaagaagg agggatcctt
1501  agacctggcc ctggaaggcg gtgtggactc ccccattggg aaggtggtcg tttctgctgt
1561  gtatgagcgg ggagctgctg agcggcatgg tggcattgtg aaggggacg agatcatggc
1621  aatcaacggc aagattgtga cagactacac cctggctgag gctgaggctg ccctgcagaa
1681  ggcctggaat cagggcgggg actggatcga ccttgtggtt gccgtctgcc ccccaaagga
1741  gtatgacgat gagctgacct tcttctgaag tccaaaaggg gaaaccaaat tcaccgttag
1801  gaaacagtga gctccgcccc cacctcgtga acacaaagcc tcggatcagc cttgagagag
1861  gccacactac acacaccaga tggcatcctt gggacctgaa tctatcaccc aggaatctca
1921  aactcccttt ggccctgaac cagggccaga taaggaacag ctcgggccac tcttctgaag
1981  gccaacgtgg aggaaaggga gcagccagcc atttgggaga agatctcaag gatccagact
2041  ctcattcctt tcctctggcc cagtgaattt ggtctctccc agctctgggg gactccttcc
2101  ttgaaccta ataagacccc actggagtct ctctctctcc atccctctcc tctgccctct
2161  gctctaattg ctgccaggat tgtcactcca aaccttactc tgagctcatt aataaaatag
2221  atttattttc cagctta
```

Other Exemplary harmonin sequences are provided below:

(SEQ ID NO:19)
Harmonin-B
>XM_011519832.2 PREDICTED: Homo sapiens USH1
protein network component harmonin (USH1C),
transcript variant X3, mRNA

AGCTCCGAGGGCGGCTGGCCCGGTCGCGGTCGCGGCTCTTTCCAGCTCCT

GGCAGCCGGGCACCCGAAGGAACGGGTCGTGCAACGACGCAGCTGGACCT

GGCCCAGCCATGGACCGAAAAGTGGCCCGAGAATTCCGGCATAAGGTGGA

TTTTCTGATTGAAAATGATGCAGAGAAGGACTATCTCTATGATGTGCTGC

GAATGTACCACCAGACCATGGACGTGGCCGTGCTCGTGGGAGACCTGAAG

CTGGTCATCAATGAACCCAGCCGTCTGCCTCTGTTTGATGCCATTCGGCC

GCTGATCCCACTGAAGCACCAGGTGGAATATGATCAGCTGACCCCCCGGC

GCTCCAGGAAGCTGAAGGAGGTGCGTCTGGACCGTCTGCACCCCGAAGGC

CTCGGCCTGAGTGTGCGTGGTGGCCTGGAGTTTGGCTGTGGGCTCTTCAT

CTCCCACCTCATCAAAGGCGGTCAGGCAGACAGCGTCGGGCTCCAGGTAG

GGGACGAGATCGTCCGGATCAATGGATATTCCATCTCCTCCTGTACCCAT

GAGGAGGTCATCAACCTCATTCGAACCAAGAAAACTGTGTCCATCAAAGT

GAGACACATCGGCCTGATCCCCGTGAAAAGCTCTCCTGATGAGCCCCTCA

CTTGGCAGTATGTGGATCAGTTTGTGTCGGAATCTGGGGCGTGCGAGGC

AGCCTGGGCTCCCCTGGAAATCGGGAAAACAAGGAGAAGAAGGTCTTCAT

CAGCCTGGTAGGCTCCCGAGGCCTTGGCTGCAGCATTTCCAGCGGCCCCA

TCCAGAAGCCTGGCATCTTTATCAGCCATGTGAAACCTGGCTCCCTGTCT

GCTGAGGTGGGATTGGAGATAGGGGACCAGATTGTCGAAGTCAATGGCGT

CGACTTCTCTAACCTGGATCACAAGGAGGCTGTAAATGCTGAAGAGTA

GCCGCAGCCTGACCATCTCCATTGTAGCTGCAGCTGGCCGGGAGCTGTTC

ATGACAGACCGGGAGCGGCTGGCAGAGGCGCGGCAGCGTGAGCTGCAGCG

GCAGGAGCTTCTCATGCAGAAGCGGCTGGCGATGGAGTCCAACAAGATCC

TCCAGGAGCAGCAGGAGATGGAGCGGCAAAGGAGAAAAGAAATTGCCCAG

AAGGCAGCAGAGGAAAATGAGAGATACCGGAAGGAGATGGAACAGATTGT

AGAGGAGGAAGAGAAGTTTAAGAAGCAATGGGAAGAAGACTGGGGCTCAA

AGGAACAGCTACTCTTGCCTAAAACCATCACTGCTGAGGTACACCCAGTA

CCCCTTCGCAAGCCAAAGTATGATCAGGGAGTGGAACCTGAGCTCGAGCC

CGCAGATGACCTGGATGGAGGCACGGAGGAGCAGGGAGAGCAGAAAGGAA

AAGATAAGAAGAAAGCCAAGTATGGCAGCCTGCAGGACTTGAGAAAGAAT

AAGAAAGAACTGGAGTTTGAGCAAAAGCTTTACAAAGAGAAAGAGGAAAT

GCTGGAGAAGGAAAAGCAGCTAAAGATCAACCGGCTGGCCCAGGAGGATT

TCCGGAAATATGAGGAAGGCTTTGACCCCTACTCTATGTTCACCCCAGAG

CAGATCATGGGGAAGGATGTCCGGCTCCTACGCATCAAGAAGGAGGGATC

CTTAGACCTGGCCCTGGAAGGCGGTGTGGACTCCCCCATTGGGAAGGTGG

TCGTTTCTGCTGTGTATGAGCGGGGAGCTGCTGAGCGGCATGGTGGCATT

GTGAAGGGGACGAGATCATGGCAATCAACGGCAAGATTGTGACAGACTA

```
CACCCTGGCTGAGGCTGAGGCTGCCCTGCAGAAGGCCTGGAATCAGGGCG

GGGACTGGATCGACCTTGTGGTTGCCGTCTGCCCCCCAAAGGAGTATGAC

GATGAGCTGACCTTCTTCTGAAGTCCAAAAGGGGAAACCAAATTCACCGT

TAGGAAACAGTGAGCTCCGGCCCCACCTCGTGAACACAAAGCCTCGGATC

AGCCTTGAGAGAGGCCACACTACACACACCAGATGGCATCCTTGGGACCT

GAATCTATCACCCAGGAATCTCAAACTCCCTTTGGCCCTGAACCAGGGCC

AGATAAGGAACAGCTCGGGCCACTCTTCTGAAGGCCAACGTGGAGGAAAG

GGACCAGCCAGCCATTTGGGAGAAGATCTCAAGGATCCAGACTCTCATTC

CTTTCCTCTGGCCCAGTGAATTTGGTCTCTCCCAGCTCTGGGGGACTCCT

TCCTTGAACCCTAATAACACCCCACTGGAGTCTCTCTCTCTCCATCCCTC

TCCTCTGCCCTCTGCTCTAATTGCTGCCAGGATTGTCACTCCAAACCTTA

CTCTGAGCTCATTAATAAAATAGATTTATTTTCCA (SEQ ID NO:20)
Harmonin-B Polypeptide
MDRKVAREFRHKVDFLIENDAEKDYLYDVLRMYHQTMDVAVLVG

DLKLVINEPSRLPLFDAIRPLIPLKHQVEYDQLTPRRSRKLKEVRLDRLH

PEGLGLSVRGGLEFGCGLFISHLIKGGQADSVGLQVGDEIVRINGYSISS

CTHEEVINLIRTKKTVSIKVRHIGLIPVKSSPDEPLTWQYVDQFVSESGG

VRGSLGSPGNRENKEKKVFISLVGSRGLGCSISSGPIQKPGIFISHVKPG

SLSAEVGLEIGDQIVEVNGVDFSNLDHKEAVNVLKSSRSLTISIVAAAGR

ELFMTDRERLAEARQRELQRQELLMQKRLAMESNKILQEQQEMERQRRKE

IAQKAAEENERYRKEMEQIVEEEEKFKKQWEEDWGSKEQLLLPKTITAEV

HPVPLRKPKSFGWFYRYDGKFPTIRKKGKDKKKAKYGSLQDLRKNKKELE

FEQKLYKEKEEMLEKEKQLKINRLAQEVSETEREDLEESEKIQYWVERLC

QTRLEQISSADNEISEMTTGPPPPPPSVSPLAPPLRRFAGGLHLHTTDLD

DIPLDMFYYPPKTPSALPVMPHPPPSNPPHKVPAPPVLPLSGHVSASSSP

WVQRTPPPIPIPPPPSVPTQDLTPTRPLPSALEEALSNHPFRTGDTGNPV

EDWEAKNHSGKPTNSPVPEQSFPPTPKTFCPSPQPPRGPGVSTISKPVMV

HQEPNFIYRPAVKSEVLPQEMLKRMVVYQTAFRQDFRKYEEGFDPYSMFT

PEQIMGKDVRLLRIKKEGSLDLALEGGVDSPIGKVVVSAVYERGAAERHG

GIVKGDEIMAINGKIVTDYTLAEAEAALQKAWNQGGDWIDLVVAVCPPKE

YDDELASLPSSVAESPQPVRKLLEDRAAVHRHGFLLQLEPTDLLLKSKRG

NQIHR (SEQ ID NO:21)
Harmonin-C
>NM_001297764.1 Homo sapiens USH1 protein network
component harmonin (USH1C), transcript variant 3,
mRNA
AGCTCCGAGGGCGGCTGGCCCGGTCGCGGTCGCGGCTCTTTCCAGCTCCT

GGCAGCCGGGCACCCGAAGGAACGGGTCGTGCAACGACGCAGCTGGACCT

GGCCCAGCCATGGACCGAAAAGTGGCCCGAGAATTCCGGCATAAGGTGGA

TTTTCTGATTGAAAATGATGCAGAGAAGGACTATCTCTATGATGTGCTGC

GAATGTACCACCAGACCATGGACGTGGCCGTGCTCGTGGGAGACCTGAAG

CTGGTCATCAATGAACCCAGCCGTCTGCCTCTGTTTGATGCCATTCGGCC

GCTGATCCCACTGAAGCACCAGGTGGAATATGATCAGCTGACCCCCCGGC

GCTCCAGGAAGCTGAAGGAGGTGCGTCTGGACCGTCTGCACCCCGAAGGC

CTCGGCCTGAGTGTGCGTGGTGGCCTGGAGTTTGGCTGTGGGCTCTTCAT

CTCCCACCTCATCAAAGGCGGTCAGGCAGACAGCGTCGGGCTCCAGGTAG

GGGACGAGATCGTCCGGATCAATGGATATTCCATCTCCTCCTGTACCCAT

GAGGAGGTCATCAACCTCATTCGAACCAAGAAAACTGTGTCCATCAAAGT

GAGACACATCGGCCTGATCCCCGTGAAAAGCTCTCCTGATGAGCCCCTCA

CTTGGCAGTATGTGGATCAGTTTGTGTCGGAATCTGGGGGCGTGCGAGGC

AGCCTGGGCTCCCCTGGAAATCGGGAAAACAAGGAGAAGAAGGTCTTCAT

CAGCCTGGTAGGCTCCCGAGGCCTTGGCTGCAGCATTTCCAGCGGCCCCA

TCCAGAAGCCTGGCATCTTTATCAGCCATGTGAAACCTGGCTCCCTGTCT

GCTGAGGTGGGATTGGAGATAGGGGACCAGATTGTCGAAGTCAATGGCGT

CGACTTCTCTAACCTGGATCACAAGGAGGGCCGGGAGCTGTTCATGACAG

ACCGGGAGCGGCTGGCAGAGGCGCGGCAGCGTGAGCTGCAGCGGCAGGAG

CTTCTCATGCAGAAGCGGCTGGCGATGGAGTCCAACAAGATCCTCCAGGA

GCAGCAGGAGATGGAGCGGCAAAGGAGAAAAGAAATTGCCCAGAAGGCAG

CAGAGGAAAATGAGAGATACCGGAAGGAGATGGAACAGATTGTAGAGGAG

GAAGAGAAGTTTAAGAAGCAATGGGAAGAAGACTGGGGCTCAAAGGAACA

GCTACTCTTGCCTAAAACCATCACTGCTGAGGTACACCCAGTACCCCTTC

GCAAGCCAAAGTATGATCAGGGAGTGGAACCTGAGCTCGAGCCCGCAGAT

GACCTGGATGGAGGCACGGAGGAGCAGGGAGAGCAGGATTTCCGGAAATA

TGAGGAAGGCTTTGACCCCTACTCTATGTTCACCCCAGAGCAGATCATGG

GGAAGGATGTCCGGCTCCTACGCATCAAGAAGGAGGGATCCTTAGACCTG

GCCCTGGAAGGCGGTGTGGACTCCCCCATTGGGAAGGTGGTCGTTTCTGC

TGTGTATGAGCGGGGAGCTGCTGAGCGGCATGGTGGCATTGTGAAAGGGG

ACGAGATCATGGCAATCAACGGCAAGATTGTGACAGACTACACCCTGGCT

GAGGCTGAGGCTGCCCTGCAGAAGGCCTGGAATCAGGGCGGGGACTGGAT

CGACCTTGTGGTTGCCGTCTGCCCCCCAAAGGAGTATGACGATGAGCTGA

CCTTCTTCTGAAGTCCAAAAGGGGAAACCAAATTCACCGTTAGGAAACAG

TGAGCTCCGGCCCCACCTCGTGAACACAAAGCCTCGGATCAGCCTTGAGA

GAGGCCACACTACACACACCAGATGGCATCCTTGGGACCTGAATCTATCA

CCCAGGAATCTCAAACTCCCTTTGGCCCTGAACCAGGGCCAGATAAGGAA

CAGCTCGGGCCACTCTTCTGAAGGCCAACGTGGAGGAAAGGGAGCAGCCA

GCCATTTGGGAGAAGATCTCAAGGATCCAGACTCTCATTCCTTTCCTCTG

GCCCAGTGAATTTGGTCTCTCCCAGCTCTGGGGGACTCCTTCCTTGAACC

CTAATAAGACCCCACTGGAGTCTCTCTCTCTCCATCCCTCTCCTCTGCCC

TCTGCTCTAATTGCTGCCAGGATTGTCACTCCAAACCTTACTCTGAGCTC

ATTAATAAAATAGATTTATTTTCCAGCTTA
```

-continued (SEQ ID NO:33)
Harmonin-C Polypeptide
MDRKVAREFRHKVDFLIENDAEKDYLYDVLRMYHQTMDVAVLVG

DLKLVINEPSRLPLFDAIRPLIPLKHQVEYDQLTPRRSRKLKEVRLDRLH

PEGLGLSVRGGLEFGCGLFISHLIKGGQADSVGLQVGDEIVRINGYSISS

CTHEEVINLIRTKKTVSIKVRHIGLIPVKSSPDEPLTWQYVDQFVSESGG

VRGSLGSPGNRENKEKKVFISLVGSRGLGCSISSGPIQKPGIFISHVKPG

SLSAEVGLETGDQIVEVNGVDFSNLDHKECRELFMTDRERLAEARQRELQ

RQELLMQKRLAMESNKILQEQQEMERQRRKEIAQKAAEENERYRKEMEQI

VEEEEKFKKQWEEDWGSKEQLLLPKTITAEVHPVPLRKPKYDQGVEPELE

PADDLDGGTEEQGEQDFRKYEEGFDPYSMFTPEQIMGKDVRLLRIKKEGS

LDLALEGGVDSPIGKVVVSAVYERGAAERHGGIVKGDEIMAINGKIVTDY

TLAEAEAALQKAWNQGGDWIDLVVAVCPPKEYDDELTFF

By "Espin promoter" is meant a regulatory polynucleotide sequence derived from NCBI Reference Sequence: NG_015866.1 that is sufficient to direct expression of a downstream polynucleotide in a cochlear cell. In one embodiment, the Espin promoter comprises at least about 350, 500, 1000, 2000, 3000, 4000, 5000, or more base pairs upstream of an Espin coding sequence.

By "protocadherin related 15 (PCDH15) promoter" is meant a regulatory polynucleotide sequence derived from NCBI Reference Sequence: NG_009191 that is sufficient to direct expression of a downstream polynucleotide in a cochlear cell. In one embodiment, the PCDH15 promoter comprises at least about 350, 500, 1000, 2000, 3000, 4000, 5000, or more base pairs upstream of an PCDH15 coding sequence.

By "protein tyrosine phosphatase, receptor type Q (PT-PRQ) promoter" is meant a regulatory polynucleotide sequence derived from GeneID: 374462 that is sufficient to direct expression of a downstream polynucleotide in a cochlear cell. In one embodiment, the PTPRQ promoter comprises at least about 350, 500, 1000, 2000, 3000, 4000, 5000, or more base pairs upstream of an PTPRQ coding sequence.

By "lipoma HMGIC fusion partner-like 5 (LHFPL5) promoter" also termed "TMHS promoter" is meant a regulatory polynucleotide sequence derived from NCBI Reference Sequence: GeneID: 222662 that is sufficient to direct expression of a downstream polynucleotide in a cochlear cell. In one embodiment, the TMHS promoter comprises at least about 350, 500, 1000, 2000, 3000, 4000, 5000, or more base pairs upstream of an PCDH15 coding sequence.

By "agent" is meant a polypeptide, polynucleotide, or small compound.

By "ameliorate" is meant decrease, suppress, attenuate, diminish, arrest, or stabilize the development or progression of a disease or disorder.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. Examples of diseases include genetic disorders characterized by a loss of function in a protein that functions in mechanosensory transduction that is expressed, for example, in the inner ear of a subject. In another embodiment, the disease is Usher Syndrome (e.g., USH1) or age-related hearing loss. In one embodiment, a disease is an auditory disorder associated with a genetic defect, such as a defect in TMC1, TMC2, MYO7A, USCH1C, CDH23, PCDH15, SANS, CIB2, USH2A, VLGR1, WHRN, CLRN1, PDZD7, USH1C (e.g., harmonin-a, b, or c).

By "effective amount" is meant the amount of an agent required to ameliorate the symptoms of a disease relative to an untreated patient. The effective amount of active agent(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

By "promoter" is meant a polynucleotide sufficient to direct transcription of a downstream polynucleotide.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule.

By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. Ina more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

By "transgene" is meant any piece of DNA that is inserted by artifice into a cell and becomes part of the genome of the organism that develops from that cell or, in the case of a nematode transgene, becomes part of a heritable extrachromosomal array. Such a transgene may include a gene which is partly or entirely heterologous (i.e., foreign) to the transgenic organism, or may represent a gene homologous to an endogenous gene of the organism.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Part 1: Highly Efficient Cochlear Gene Transfer

Part 3: Gene Therapy of Additional Mutations Involved in Hearing Loss

FIGS. 19A-19D are representative confocal images of a cochlea from an Ush1c mutant mouse injected through the RWM with 1 ml of Anc80-Harmonin::GFP (i.e., the GFP is fused to the Harmonin polypeptide) ($6\times10^{12}$ gc/ml) at P2, harvested at P9, and stained with actin (red; 19A), Myo7a (blue; 19B), and imaged for GFP (green; 19C). A merged image of (19A), (19B), and (19C) is shown in (19D).

Figure 20:
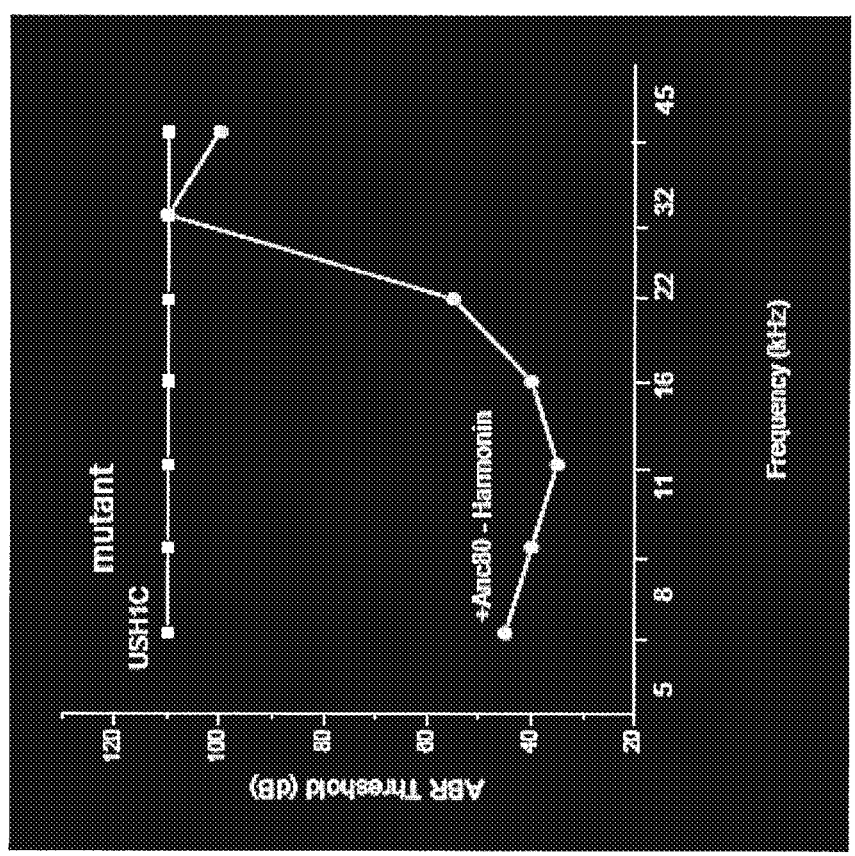

FIG. 20 is a graph showing ABR threshold plotted as a function of sound frequency for an Ush1c mutant mice (squares) and an Ush1c mutant mice injected with an Anc80-Harmonin::GFP vector (circles).

Figure 21:
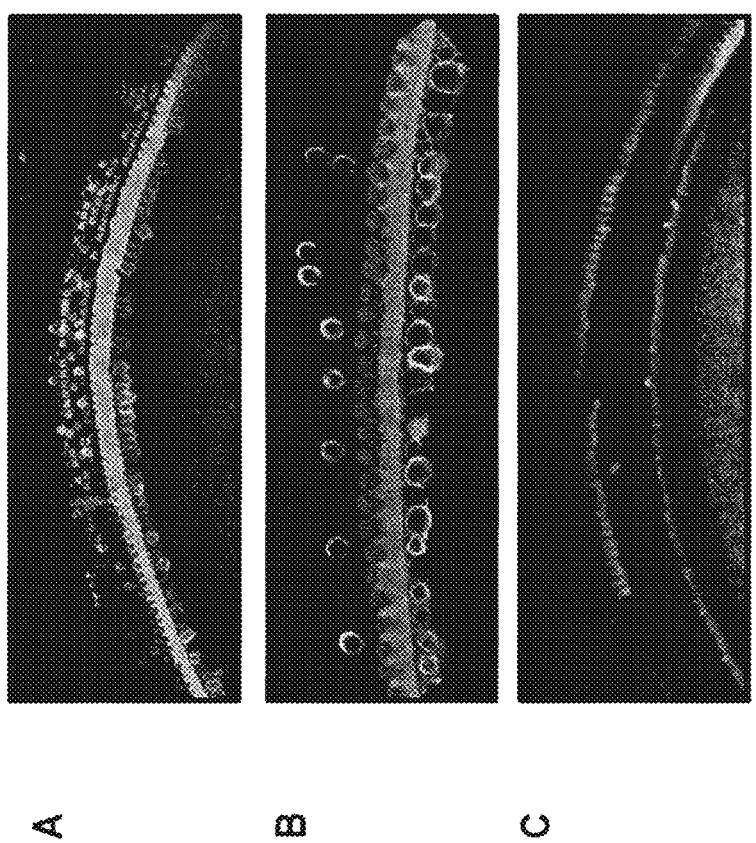

FIGS. 21A-21C show representative confocal images of a KCNQ4 –/– cochlea injected through the RWM with 1 µl of Anc80-KCNQ4 ($6\times10^{12}$ gc/ml) at P2, harvested at P9, and stained with Alexa 546—phalloidin (red) and an antibody against KCNQ4 (green) at low magnification (21A) or high magnification (21B) relative to uninjected cochlea at high magnification (21C).

Figure 22:
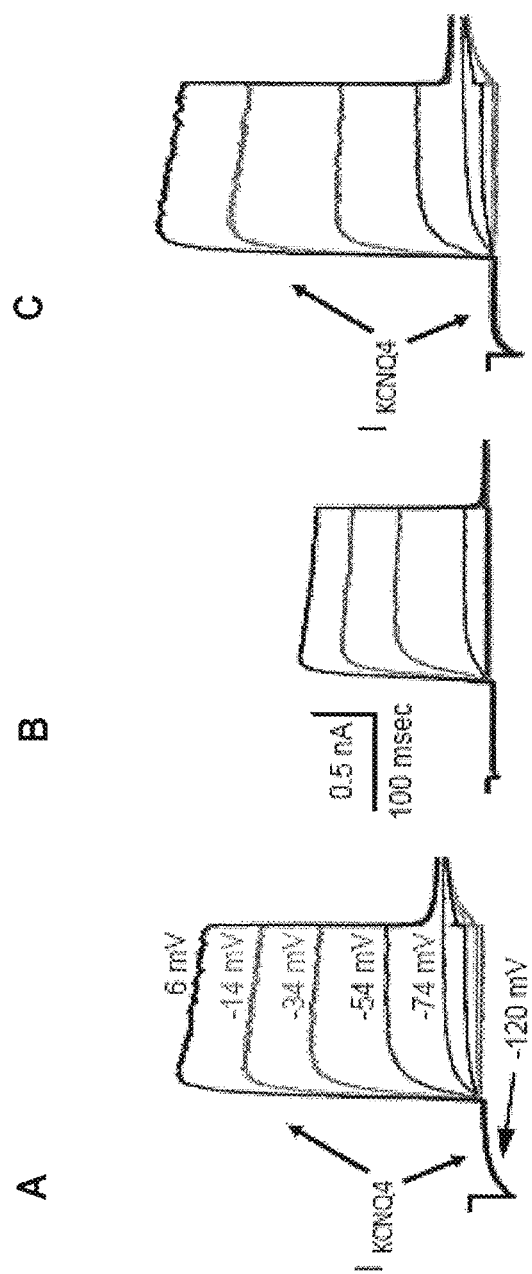

FIG. 22A-22C are a series of graphs that show the KCNQ4 current in a P10 wild type mouse (22A), a P10 KCNQ4 –/– mouse (22B), and a P10 KCNQ4 –/– mouse injected via the RWM ($2.4\times10^{13}$ gc/ml) with Anc80-KCNQ4 (22C). Cochleas were harvested 8 days after injection.

Figure 23:
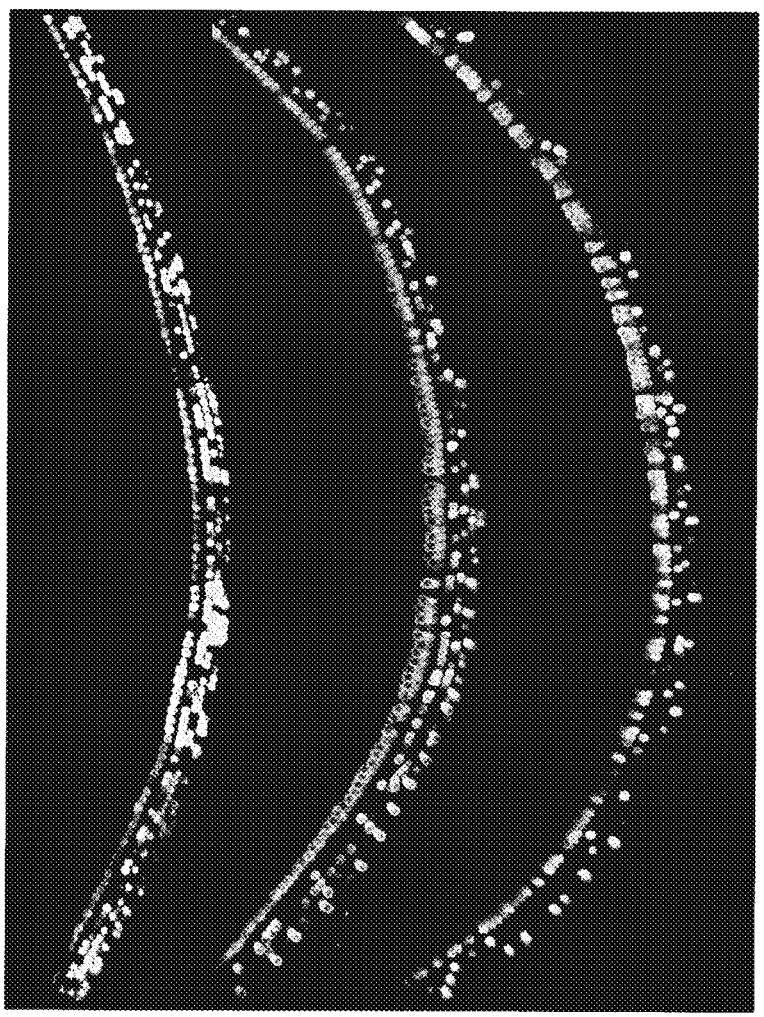

FIG. 23 is a series of three images of FM1-43 uptake (FM1-43 only permeates functional Tmc1 channels) in Tmc1 –/– tissue injected with the Anc80-CMV-Tmc1 vector. P2 Tmc1 –/– mice were injected via the RWM with the Anc80-CMV-Tmc1 vector ($2.4\times10^{13}$ gc/ml), and cochleas were harvested 6 to 7 days after injection.

Figure 24:
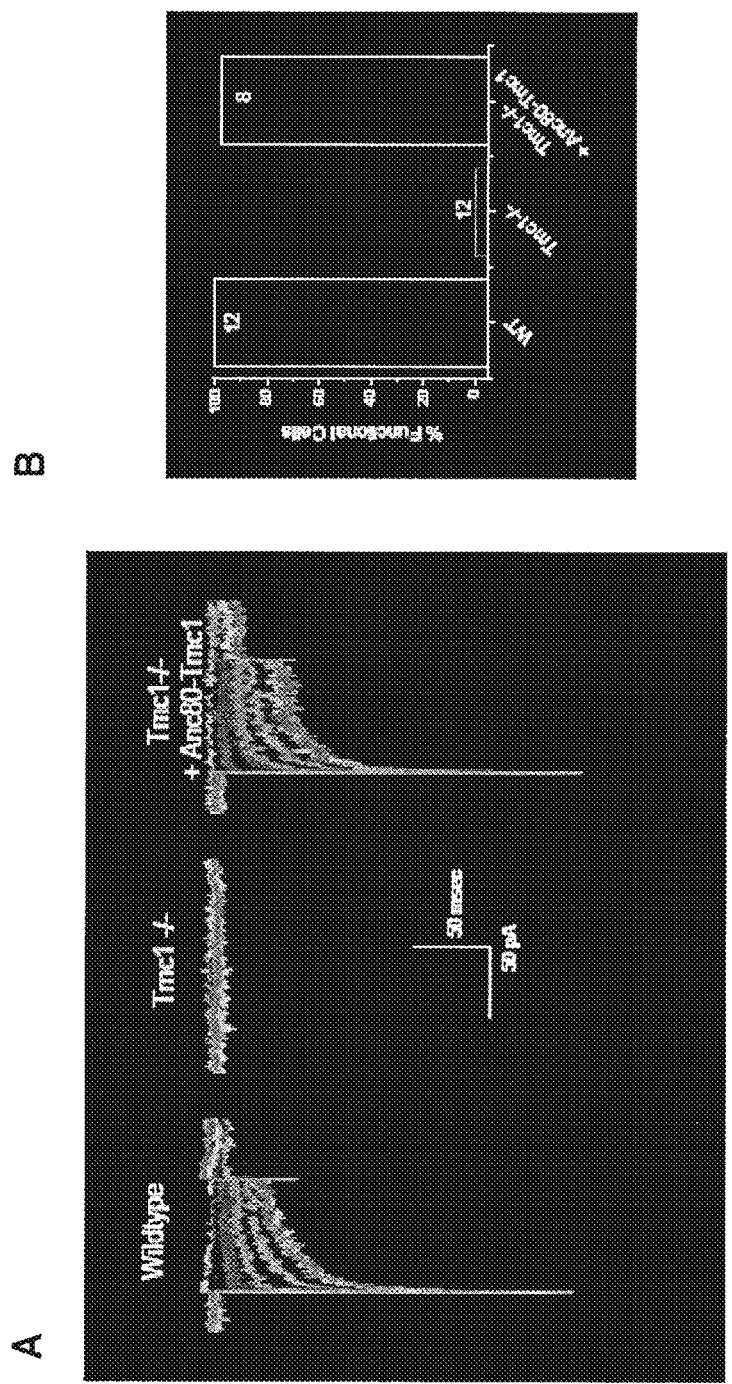

FIG. 24A shows representative families of sensory transduction currents recorded from IHCs of a P10 wild type mouse (left), a P10 Tmc1 –/– mouse (middle), and a P10 Tmc1 –/– mouse injected at P2 via the RWM ($2.4\times10^{13}$ gc/ml) with Anc80-CMV-Tmc1 (right). Cochleas were harvested 8 days after injection.

FIG. 24B is a graphical representation of the recovery rate of the mice shown in FIG. 24A. The graph in FIG. 24B indicates the percentage of functional cells in a wild type mouse (left), a Tmc1 –/– mouse (middle), and a Tmc1 –/– mouse injected with Anc80-CMV-Tmc1 (right).

Figure 25:
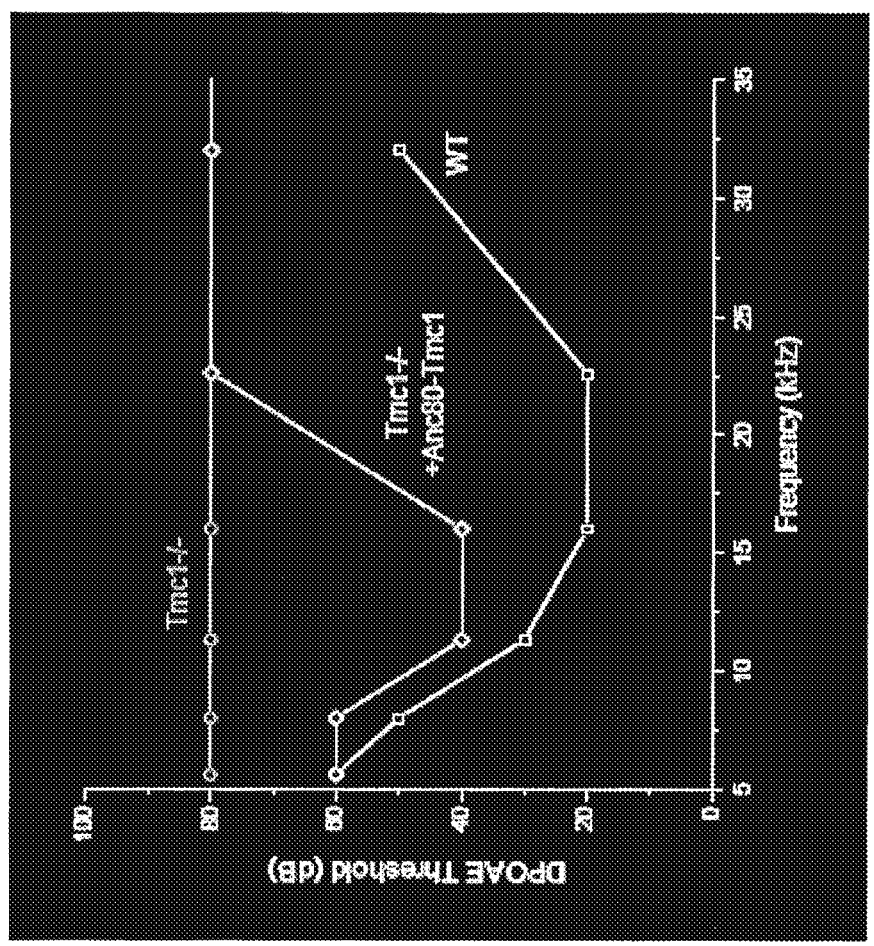

FIG. 25 is a graph showing the Distortion Product Otoacoustic Emissions (DPOAE) thresholds as a function of stimulus frequency for wild type, Tmc1 –/– mice, and Tmc1 –/– mice injected with Anc80-CMV-Tmc1.

FIGS. 26A-26C show the effect of various promoters on expression. FIG. 26A shows Anc80-Pcdh15-GFP expression in hair cells and supporting cells GFP and Myosin7a are shown in as indicated and hair cells are stained in red for Myosin7a, a hair cell marker. FIG. 26B shows Anc80-Myo6-GFP with inner and outer hair cells showing GFP expression. There was no counter stain for this experiment. FIG. 26C shows Anc80-KCNQ4-GFP with just outer hair cells showing GFP expression. The tissue was counter stained with phalloidin to illuminate hair cells.

DETAILED DESCRIPTION

The invention provides compositions and methods for delivering and expressing a protein (e.g., TMC1, TMC2, MYO7A, USCH1C, CDH23, PCDH15, SANS, CIB2, USH2A, VLGR1, WHRN, CLRN1, PDZD7 USH1C (e.g., harmonin-a, b, or c)) required for mechanosensation, including hearing, and/or vestibular function, in a cell of the inner ear of a subject, such as a cochlear cell (e.g., inner or outer hair cell), wherein the subject has a loss or reduction in the level or activity of that protein.

The invention is based, at least in part, on the discoveries that a rationally designed synthetic vector encoding an Anc80 capsid ("Anc80 vector") is useful for efficient transgene delivery to the cochlea; and that this vector could be used to deliver wild-type Ush1c into the inner ear of a murine model of Usher Syndrome. Round window membrane injection resulted in highly efficient transduction of inner and outer haircells in mice, a substantial improvement over conventional adeno-associated virus (AAV) vectors. Anc80 round window injection was well tolerated, as indicated by sensory cell function, hearing and vestibular function, and immunologic parameters. The ability of Anc80 to target outer hair cells at high rates, a requirement for restoration of complex auditory function, may enable future gene therapies for hearing and balance disorders. The mice injected with the Anc80 vector encoding Ush1c demonstrated recovery of gene and protein expression, restoration of sensory cell function, rescue of complex auditory function and recovery of hearing and balance behavior to near wild-type levels. The data represent unprecedented recovery of inner ear function and indicate that biological therapies to treat deafness may be suitable for translation to humans with genetic inner ear disorders.

Usher Syndrome

Human Usher syndrome (USH) is a rare genetic condition responsible for combined deafness and blindness. Inherited as an autosomal recessive trait, it affects 16,000 to 20,000 people in the United States and is responsible for 3 to 6% of early childhood deafness. Usher syndrome is classified under three clinical subtypes (USH-1, -2 and -3) according to the severity of the symptoms. USH1 is the most severe form. Patients who are affected by USH1 suffer congenital bilateral profound sensorineural hearing loss, vestibular areflexia and pre-pubertal retinitis pigmentosa (a progressive, bilateral, symmetric degeneration of rod and cone function of the retina). Unless fitted with a cochlear implant, individuals do not typically develop the ability to generate speech. While no biological treatments currently exist for Usher patients, early reintroduction of the wild-type form of the defective gene may allow for reversal of the disease.

Six Usher genes are associated with USH1: MYO7A (myosin 7a), USH1C (harmonin), CDH23 (cadherin 23), PCDH15 (protocadherin 15), SANS (sans) and CIB2 (calcium and integrin binding protein 2). These genes encode proteins that are involved in hair bundle morphogenesis in the inner ear and are part of an interactome (see, for example, Mathur & Yang, 2015, *Biochim. Biophys. Acta*, 1852:406-20). Harmonin resides at the center of the USH1 interactome where it binds to other Usher 1 proteins. Because of its PDZ (PSD-59 95/Dlg/ZO-1) interaction domains, harmonin has been proposed to function as a scaffolding protein. In vitro binding studies have shown that all other known USH1 proteins bind to PDZ domains of harmonin as do two of the USH2 proteins, usherin, and VLGR1. The USH1C gene consists of 28 exons, which code for 10 alternative splice forms of harmonin, grouped into three different subclasses (a, b and c) depending on the domain composition of the protein. The three isoforms differ in the number of PDZ protein-protein interaction domains, coiled-coiled (CC) domains, and proline-serine-threonine (PST) rich domains.

USH1 proteins are localized to the apex of hair cells in mechanosenosory hair bundles, which are composed of hundreds of stereocilia interconnected by numerous extracellular links. Cadherin 23 and Protocadherin 15, products of Usher genes (USH1D and USH1E, respectively) form tip-links located at the distal end of the stereocilia. Harmonin-b binds to CDH23, PCDH15, F-actin and itself. It is found at the tips of the stereocilia near the tip-link insertion point in hair cells where it is thought to play a functional role in transduction and adaptation in hair cells. Harmonin-b is expressed during early postnatal stages but its expression diminishes around postnatal day 30 (P30) in both the cochlea and vestibule. Harmonin-a also binds to cadherin 23 and is found in the stereocilia. Recent reports reveal an additional role for harmonin-a at the synapse where it associates with Cav1.3 Ca2+ channels to limit channel availability through an ubiquitin-dependent pathway.

Several mouse models for Usher syndrome have been identified or engineered over the past decade, seven of which affect harmonin. Of these, only one model, the Ush1c c.216G>A model, reproduces both auditory and retinal deficits that characterize human Usher Syndrome. Ush1c c.216G>A is a knock-in mouse model that affects expression of all conventional harmonin isoforms due a point mutation similar to the one found in a cohort of French-Acadian USH1C patients. The mutation introduces a cryptic splice site at the end of exon three of the Ush1c gene. Use of this cryptic splice site produces a frame-shifted transcript with a 35 bp deletion and results in translation of a severely truncated protein lacking PDZ, PST and CC domains. Homozygous c.216AA knock-in mice suffer from severe hearing loss at 1 month of age while heterozygous c.216GA mice do not present any abnormal phenotype. Cochlear histology in c.216AA mice shows disorganized hair bundles, abnormal cell rows and loss of both inner and outer hair cells in middle and basal turns at P30.

It is demonstrated herein that an AAV containing an ancestral AAV capsid protein successfully transduce hair cells and drive expression and correct localization of harmonin splice forms. Furthermore, it is demonstrated herein that early postnatal round window membrane injection of an AAV containing an ancestral AAV capsid protein as described herein successfully restore auditory and vestibular function in homozygous c.216AA mice. Recovery of auditory function in injected mice is associated with recovery of mRNA expression encoding for wild-type harmonin as well as preservation of hair bundle morphology and mechanotransduction. The results provided herein demonstrate that early re-introduction of wild-type harmonin using an AAV containing an ancestral AAV capsid protein as described herein may be useful for treating USH1C.

TMC1/TMC2

Over 40 distinct mutations have been identified in TMC1 that cause deafness. These are subdivided into 35 recessive mutations and 5 dominant mutations. Most of the recessive mutations cause profound, congenital hearing loss (e.g., DFNB7/11) though a few cause later onset, moderate to severe hearing loss. All of the dominant mutations cause progressive hearing loss (e.g., DFNA36), with onset in the mid-teen years. In particular, an AAV vector that includes an Anc80 capsid protein as described herein can be used to deliver a non-mutant (e.g., wild type) TMC1 sequence or TMC2 sequence, thereby preventing hearing loss (e.g., further hearing loss) and/or restoring hearing function.

Therapeutic Strategies for the Treatment of Hearing Loss

Since the sensory cells of the adult mammalian cochlea lack the capacity for self-repair, current therapeutic strategies (depending on the level and exact position of impairment) rely on amplification (hearing aids), better transmission of sound (middle ear prostheses/active implants), or direct neuronal stimulation (cochlear implants) to compensate for permanent damage to primary sensory hair cells or spiral ganglion neurons which form the auditory nerve and relay acoustic information to the brain. While these approaches have been transformative, they remain far from optimal in restoring complex human hearing function important for modern life. Specifically, major problems still include limited frequency sensitivity, unnatural sound perception, and limited speech discrimination in noisy environments.

Therapeutic gene transfer to the cochlea has been considered to further improve upon the current standard of care ranging from age-related and environmentally induced hearing loss to genetic forms of deafness. More than 300 genetic loci have been linked to hereditary hearing loss with over 70 causative genes described (Parker & Bitner-Glindzicz, 2015, Arch. Dis. Childhood, 100:271-8). Therapeutic success in these approaches relies significantly on the safe and efficient delivery of exogenous gene constructs to the relevant therapeutic cell targets in the organ of Corti (OC) in the cochlea.

The OC includes two classes of sensory hair cells: IHCs, which convert mechanical information carried by sound into electrical signals transmitted to neuronal structures and OHCs which serve to amplify and tune the cochlear response, a process required for complex hearing function. Other potential targets in the inner ear include spiral ganglion neurons, columnar cells of the spiral limbus, which are important for the maintenance of the adjacent tectorial membrane or supporting cells, which have protective functions and can be triggered to trans-differentiate into hair cells up to an early neonatal stage.

Injection to the cochlear duct, which is filled with high potassium endolymph fluid, could provide direct access to hair cells. However, alterations to this delicate fluid environment may disrupt the endocochlear potential, heightening the risk for injection-related toxicity. The perilymph-filled spaces surrounding the cochlear duct, scala tympani and scala vestibuli, can be accessed from the middle ear, either through the oval or round window membrane (RWM). The RWM, which is the only non-bony opening into the inner ear, is relatively easily accessible in many animal models and administration of viral vector using this route is well tolerated. In humans, cochlear implant placement routinely relies on surgical electrode insertion through the RWM.

Previous studies evaluating AAV serotypes in organotypic cochlear explant and in vivo inner ear injection have resulted in only partial rescue of hearing in mouse models of inherited deafness. Unexpectedly, an adeno-associated virus (AAV) containing an ancestral AAV capsid protein transduces OHCs with high efficiency. This finding overcomes the low transduction rates that have limited successful development of cochlear gene therapy using conventional AAV serotypes. An AAV containing an ancestral AAV capsid protein as described herein provides a valuable platform for inner ear gene delivery to IHCs and OHCs, as well as an array of other inner ear cell types that are compromised by genetic hearing and balance disorders. In addition to providing high transduction rates, an AAV containing an ancestral AAV capsid protein as described herein was shown to have an analogous safety profile in mouse and nonhuman primate upon systemic injection, and is antigenically distinct from circulating AAVs, providing a potential benefit in terms of pre-existing immunity that limits the efficacy of conventional AAV vectors.

Compositions and methods are described herein, however, that allow for highly efficient delivery of nucleic acids (e.g., AAV vectors, such as an ANC80 vector comprising a promoter (e.g., CMV, Espin, PCDH15, a PTPRQ, a TMHS (LHFPL5)) directing expression of a polynucleotide encoding one or more of TMC1, TMC2, MYO7A, USCH1C, CDH23, PCDH15, SANS, CIB2, USH2A, VLGR1, WHRN, CLRN1, PDZD7 USH1C (e.g., harmonin-a, b, or c) to cells, particularly cells within the inner ear, e.g., in the cochlea (or cells of the cochlea or cochlear cells). As used herein, inner ear cells refer to, without limitation, inner hair cells (IHCs), outer hair cells (OHCs), spiral ganglion neurons, stria vascularis, vestibular hair cells, vestibular ganglion neurons, and supporting cells. Supporting cells refer to cells in the ear that are not excitable, e.g., cells that are not hair cells or neurons. An example of a supporting cell is a Schwann cell.

Delivery of one or more of the nucleic acids described herein to inner ear cells can be used to treat any number of inherited or acquired hearing disorders, which are typically defined by partial hearing loss or complete deafness. The methods described herein can be used to treat a hearing disorder such as, without limitation, recessive deafness, dominant deafness, Usher syndrome, and other syndromic deafness, as well as hearing loss due to trauma or aging.

Methods of Making Viruses Carrying Specific Transgenes

As described herein, an adeno-associated virus (AAV) containing an ancestral AAV capsid protein are particularly efficient at delivering nucleic acids (e.g., transgenes, including but not limited to a polynucleotide encoding one or more of TMC1, TMC2, MYO7A, USCH1C, CDH23, PCDH15, SANS, CIB2, USH2A, VLGR1, WHRN, CLRN1, PDZD7 USH1C (e.g., harmonin-a, b, or c)) to inner ear cells, and a particularly effective class of ancestral AAV capsid proteins is designated by an ancestral scaffold capsid protein designated Anc80, which is shown in SEQ ID NO:1. The Anc80 vector is an example of an Inner Ear Hair Cell Targeting AAV that advantageously transduced greater than about 60%, 70%, 80%, 90%, 95%, or even 100% of inner or outer hair cells. One particular ancestral capsid protein that falls within the class of Anc80 ancestral capsid protein is Anc80-0065 (SEQ ID NO:2), however, WO 2015/054653, which is incorporated herein in its entirety, describes a number of additional ancestral capsid proteins that fall within the class of Anc80 ancestral capsid proteins.

In particular embodiments the adeno-associated virus (AAV) contains an ancestral AAV capsid protein that has a natural or engineered tropism for hair cells. In some embodiments, the virus is an Inner Ear Hair Cell Targeting AAV, which delivers a transgene (e.g., a polynucleotide encoding one or more of TMC1, TMC2, MYO7A, USCH1C, CDH23, PCDH15, SANS, CIB2, USH2A, VLGR1, WHRN, CLRN1, PDZD7 USH1C (e.g., harmonin-a, b, or c)) to the inner ear in a subject. In some embodiments, the virus is an AAV that comprises purified capsid polypeptides. In some embodiments, the virus is artificial. In some embodiments, the virus contains ancestral AAV sequences. In some embodiments, the virus is an AAV that has lower seroprevalence than AAV2. In some embodiments, the virus is an exome-associated AAV. In some embodiments, the virus is an exome-associated AAV1. In some embodiments, the virus comprises a capsid protein with at least 95% amino acid sequence identity or homology to Anc80 capsid proteins.

The viruses described herein that contain an Anc80 capsid protein can be used to deliver a variety of nucleic acids to inner ear cells. In one embodiment, an Inner Ear Hair Cell Targeting AAV (e.g., ANC80 vector) comprising a promoter (e.g., CMV, Espin, PCDH15, a PTPRQ, a TMHS (LHFPL5)) directing expression of a polynucleotide encoding one or more of TMC1, TMC2, MYO7A, USCH1C, CDH23, PCDH15, SANS, CIB2, USH2A, VLGR1, WHRN, CLRN1, PDZD7 USH1C (e.g., harmonin-a, b, or c). A nucleic acid sequence delivered to a cell for the purpose of expression oftentimes is referred to as a transgene. Representative transgenes that can be delivered to, and expressed in, inner ear cells include, without limitation, a transgene encoding a polypeptide that functions in auditory and/or vestibular mechanosensation (e.g., TMC1, TMC2, MYO7A, USCH1C, CDH23, PCDH15, SANS, CIB2, USH2A, VLGR1, WHRN, CLRN1, PDZD7 (e.g., harmonin-a, b, or c)), a transgene that encodes a neurotrophic factor (e.g., GDNV, BDNF, or HSP70), an immunomodulatory protein or an anti-oncogenic transcript. In addition, representative transgenes that can be delivered to, and expressed in, inner ear cells also include, without limitation, a transgene that encodes an antibody or fragment thereof, an antisense, silencing or long non-coding RNA species, or a genome editing system (e.g., a genetically-modified zine finger nuclease, transcription activator-like effector nucleases (TALENs), or clustered regularly interspaced short palindromic repeats (CRISPRs)). Further, representative transgenes that can be delivered to, and expressed in, inner ear cells include nucleic acids designated ACTG1, ADCY1, ATOHI, ATP6V1B1, BDNF, BDP1, BSND, DATSPER2, CABP2, CD164, CDC14A, CDH23, CEACAM16, CHD7, CCDC50, CIB2, CLDN14, CLICS, CLPP, CLRN1, COCH, COL2A1, COL4A3, COL4A4, COL4A5, COL9A1, COL9A2, COL11A1, COL11A2, CRYM, DCDC2, DFNA5, DFNB31, DFNB59, DIAPH1, EDN3, EDNRB, ELMOD3, EMOD3, EPS8, EPS8L2, ESPN, ESRRB, EYA1, EYA4, FAM65B, FOXI1, GIPC3, GJB2, GJB3, GJB6, GPR98, GRHL2, GPSM2, GRXCR1, GRXCR2, HARS2, HGF, HOMER2, HSD17B4, ILDR1, KARS, KCNE1, KCNJ10, KCNQ1, KCNQ4, KITLG, LARS2, LHFPL5, LOXHD1, LRTOMT, MARVELD2, MCM2, MET, MIR183, MIRN96, MITF, MSRB3, MT-RNR1, MT-TS1, MYH14, MYH9, MYO15A, MYO1A, MYO3A, MYO6, MYO7A, NARS2, NDP, NF2, NT3, OSBPL2, OTOA, OTOF, OTOG, OTOGL, P2RX2, PAX3, PCDH15, PDZD7, PJVK, PNPT1, POLR1D, POLR1C, POU3F4, POU4F3, PRPS1, PTPRQ, RDX, S1PR2, SANS, SEMA3E, SERPINB6, SLC17A8, SLC22A4, SLC26A4, SLC26A5, SIX1, SIX5, SMAC/DIABLO, SNAI2, SOX10, STRC, SYNE4, TBC1D24, TCOF1, TECTA, TIMM8A, TJP2, TNC, TMC1, TMC2, TMIE, TMEM132E, TMPRSS3, TRPN, TRIOBP, TSPEAR, USH1C, USH1G, USH2A, USH2D, VLGR1, WFS1, WHRN, and XIA. In particular embodiments, the transgene is one or more of MYO7A, CDH23, PCDH15, SANS, CIB2, USH2A, VLGR1, WHRN, CLRN1, PDZD7, USH1C (e.g., harmonin-a, b, or c).

Expression of a transgene may be directed by the transgene's natural promoter (i.e., the promoter found naturally with the transgenic coding sequence) or expression of a transgene may be directed by a heterologous promoter (e.g., CMV promoter, Espin promoter, a PCDH15 promoter, a PTPRQ promoter and a TMHS (LHFPL5) promoter). For example, any of the transgenes described herein can be used with its natural promoter. Alternatively, any of the transgenes described herein can be used with a heterologous promoter. As used herein, a heterologous promoter refers to a promoter that does not naturally direct expression of that sequence (i.e., is not found with that sequence in nature). Representative heterologous promoters that can be used to direct expression of any of the transgenes indicated herein include, for example, a CMV promoter, a CBA promoter, a CASI promoter, a P promoter, and a EF-1 promoter, an alpha9 nicotinic receptor promoter, a prestin promoter, a Gfi1 promoter, and a Vglut3 promoter. In addition, a promoter that naturally directs expression of one of the above-referenced transgenes (e.g., a KCNQ4 promoter, a Myo7a promoter, a Myo6 promoter or an Atoh1 promoter) can be used as a heterologous promoter to direct expression of a transgene. In other embodiments, the promoter is an Espin promoter, a PCDH15 promoter, a PTPRQ promoter and a TMHS (LHFPL5) promoter.

Methods of making a transgene (e.g., TMC1, TMC2, USH1C (e.g., harmonin-a, b, or c), MYO7A, USCH1C, CDH23, PCDH15, SANS, CIB2, USH2A, VLGR1, WHRN, CLRN1, PDZD7) for packaging into a virus that contains an Anc80 capsid protein are known in the art, and utilize conventional molecular biology and recombinant nucleic acid techniques. In one embodiment, a construct that includes a nucleic acid sequence encoding an Anc80 capsid protein and a construct carrying the transgene flanked by suitable Inverted Terminal Repeats (ITRs) are provided, which allows for the transgene to be packaged within the Anc80 capsid protein.

The transgene can be packaged into an AAV containing an Anc80 capsid protein using, for example, a packaging host cell. The components of a virus particle (e.g., rep sequences, cap sequences, inverted terminal repeat (ITR) sequences) can be introduced, transiently or stably, into a packaging host cell using one or more constructs as described herein. The viruses described herein contain at least an Anc80 capsid protein; the other components of a virus particle (e.g., rep sequences, ITR sequences) can be based on an ancestral sequence or a contemporary sequence. In some instances, for example, the entire virus particle can be based on ancestral sequences. Such viruses can be purified using routine methods.

In general, as used herein, "nucleic acids," can include DNA and RNA, and also can include nucleic acids that contain one or more nucleotide analogs or backbone modifications. Nucleic acids can be single-stranded or double-stranded, which usually depends upon its intended use. Nucleic acids that can be used in the methods described herein can be identical to a known nucleic acid sequence, or nucleic acids that can be used in the methods described herein can differ in sequence from such known sequences. Simply by way of example, nucleic acids (or the encoded polypeptides) can have at least 75% sequence identity (e.g., at least 80%, 81%, 82%, 83%, 84%, 85%, 86%, 87%, 88%, 89%, 90%, 91%, 92%, 93%, 94%, 95%, 96%, 97%, 98%, or 99% sequence identity) to a known sequence.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity is performed using the computer program ClustalW and default parameters, which allows alignments of nucleic acid or polypeptide sequences to be carried out across their entire length (global alignment). Chenna et al., 2003, Nucleic Acids Res., 31(13):3497-500. ClustalW calculates the best match between a query and one or more subject sequences, and aligns them so that identities, similarities and differences are determined. Gaps of one or more residues can be inserted into a query sequence, a subject sequence, or both, to maximize sequence alignments. For pairwise alignment of nucleic acid sequences, the default parameters are used (i.e., word size: 2; window size: 4; scoring method: percentage; number of top diagonals: 4; and gap penalty: 5); for an alignment of multiple nucleic acid sequences, the following parameters are used: gap opening penalty: 10.0; gap extension penalty: 5.0; and weight transitions: yes. For pairwise alignment of polypeptide sequences, the following parameters are used: word size: 1; window size: 5; scoring method: percentage; number of top diagonals: 5; and gap penalty: 3. For multiple alignment of polypeptide sequences, the following parameters are used: weight matrix: BLOSUM (blocks substitution matrix); gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher web site or at the European Bioinformatics Institute website on the World Wide Web.

Changes can be introduced into a nucleic acid sequence, which can lead to changes in the amino acid sequence of the encoded polypeptide if the nucleic acid sequence is a coding sequence. For example, changes can be introduced into nucleic acid coding sequences using mutagenesis (e.g., site-directed mutagenesis, PCR-mediated mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al. (1978, in Atlas of Protein Sequence and Structure, 5 (Suppl. 3):345-352), which provides frequency tables for amino acid substitutions), and a non-conservative substitution is one in which an amino acid residue is replaced with an amino acid residue that does not have a similar side chain.

A nucleic acid can be contained within a construct, which also can be referred to as a vector or a plasmid. Constructs are commercially available or can be produced by recombinant techniques routine in the art. A construct containing a nucleic acid can have expression elements that direct and/or regulate expression of such a nucleic acid, and also can include sequences such as those for maintaining the construct (e.g., origin of replication, a selectable marker). Expression elements are known in the art and include, for example, promoters, introns, enhancer sequences, response elements, or inducible elements.

Pharmaceutical Compositions

An Inner Ear Hair Cell Targeting AAV (e.g., Anc805 vector) comprising a promoter (e.g., CMV, Espin, PCDH15, a PTPRQ, a TMHS (LHFPL5)) and a polynucleotide that is one or more of USH1, MYO7A, USH1C (harmonin-a, b, c), CDH23, PCDH15, SANS and CIB2, usually suspended in a physiologically compatible excipient, can be administered to a subject (e.g., a human or non-human mammal) by injection to the inner ear of a subject through the round window. Suitable carriers include saline, which may be formulated with a variety of buffering solutions (e.g., phosphate buffered saline), lactose, sucrose, calcium phosphate, gelatin, dextran, agar, pectin, and water. The Inner Ear Hair Cell Targeting AAV is administered in sufficient amounts to transduce or infect the cells and to provide sufficient levels of gene transfer and expression to provide a therapeutic benefit without undue adverse effects.

The dose of the Inner Ear Hair Cell Targeting AAV administered to a subject will depend primarily on factors such as the condition being treated, and the age, weight, and health of the subject. For example, a therapeutically effective dosage of an Inner Ear Hair Cell Targeting AAV to be administered to a human subject generally is in the range of from about 0.1 ml to about 10 ml of a solution containing concentrations of from about $1 \times 10^1$ to $1 \times 10^{12}$ genome copies (GCs) of AAVs (e.g., about $1 \times 10^3$ to $1 \times 10^9$ GCs).

Methods of Delivering Nucleic Acids to Inner Ear Cells

Methods of delivering nucleic acids to cells generally are known in the art, and methods of delivering viruses (which also can be referred to as viral particles) containing a transgene to inner ear cells in vivo are described herein. As described herein, about $10^8$ to about $10^{12}$ viral particles can be administered to a subject, and the virus can be suspended within a suitable volume (e.g., 10 μL, 50 μL, 100 μL, 500 μL, or 1000 μL) of, for example, artificial perilymph solution.

A virus containing a promoter (e.g., CMV, Espin, PCDH15, a PTPRQ, a TMHS (LHFPL5)) and a transgene (e.g., TMC1, TMC2, USH1C (e.g., harmonin-a, b, or c), MYO7A, USCH1C, CDH23, PCDH15, SANS, CIB2, USH2A, VLGR1, WHRN, CLRN1, PDZD7) as described herein can be delivered to inner ear cells (e.g., cells in the cochlea) using any number of means. For example, a therapeutically effective amount of a composition including virus particles containing one or more different types of transgenes as described herein can be injected through the round window or the oval window, typically in a relatively simple (e.g., outpatient) procedure. In some embodiments, a composition comprising a therapeutically effective number of virus particles containing a transgene, or containing one or more sets of different virus particles, wherein each particle in a set can contain the same type of transgene, but wherein each set of particles contains a different type of transgene than in the other sets, as described herein can be delivered to the appropriate position within the ear during surgery (e.g., a cochleostomy or a canalostomy).

In one embodiment, an Inner Ear Hair Cell Targeting AAV (e.g., Anc80 vector) comprising a promoter (e.g., CMV, Espin, PCDH15, a PTPRQ, a TMHS (LHFPL5)) and a polynucleotide that is one or more of USH1, MYO7A, USH1C (harmonin-a, b, c), CDH23, PCDH15, SANS and CIB2 is injected through the round window of a subject in need thereof.

In addition, delivery vehicles (e.g., polymers) are available that facilitate the transfer of agents across the tympanic membrane and/or through the round window, and any such delivery vehicles can be used to deliver the viruses described herein. See, for example, Arnold et al., 2005, *Audiol. Neurootol.*, 10:53-63.

The compositions and methods described herein enable the highly efficient delivery of nucleic acids to inner ear cells, e.g., cochlear cells. For example, the compositions and methods described herein enable the delivery to, and expression of, a transgene in at least 80% (e.g., at least 85, 90, 91, 92, 93, 94, 95, 96, 97, 98, or 99%) of inner hair cells or delivery to, and expression in, at least 80% (e.g., at least 85, 90, 91, 92, 93, 94, 95, 96, 97, 98, or 99) of outer hair cells.

As demonstrated herein, expression of a transgene delivered using an AAV containing an Anc80 capsid protein can result in regeneration of inner hair cells (IHCs), outer hair cells (OHCs), spiral ganglion neurons, stria vascularis, vestibular hair cells, and/or vestibular ganglion neurons (e.g. Atoh1, NF2) such that hearing or vestibular function is restored for an extended period of time (e.g., months, years, decades, a life time).

As discussed in WO 2015/054653, an AAV containing an Anc80 capsid protein can be characterized by its seroprevelance and/or the extent it is neutralized relative to conventional AAVs (i.e., an AAV not containing an Anc80 capsid protein). Seroprevalence is understood in the art to refer to the proportion of subjects in a population that is seropositive (i.e., has been exposed to a particular pathogen or immunogen), and is calculated as the number of subjects in a population who produce an antibody against a particular pathogen or immunogen divided by the total number of individuals in the population examined. Determining the seroprevalence of a virus is routinely performed in the art and typically includes using an immunoassay to determine the prevalence of one or more antibodies in samples (e.g., blood samples) from a particular population of individuals. In addition, several methods to determine the extent of neutralizing antibodies in a serum sample are available. For example, a neutralizing antibody assay measures the titer at which an experimental sample contains an antibody concentration that neutralizes infection by 50% or more as compared to a control sample without antibody. See, also, Fisher et al. (1997, Nature Med., 3:306-12) and Manning et al. (1998, Human Gene Ther, 9:477-85). Representative conventional AAVs include, without limitation, AAV8 (or a virus comprising an AAV8 capsid protein) and/or AAV2 (or a virus comprising an AAV2 capsid protein).

Kits

The invention also provides a pharmaceutical pack or kit comprising one or more containers filled with one or more of the ingredients of the pharmaceutical compositions of the invention (e.g., Inner Ear Hair Cell Targeting AAV (e.g., Anc80 vector) comprising a promoter (e.g., CMV, Espin, PCDH15, a PTPRQ, a TMHS (LHFPL5)) and a polynucleotide that is one or more of USH1, MYO7A, USH1C (harmonin-a, b, c), CDH23, PCDH15, SANS and CIB2). Associated with such container(s) can be a notice in the form prescribed by a governmental agency regulating the manufacture, use or sale of pharmaceuticals or biological products, which notice reflects approval by the agency of manufacture, use or sale for human administration.

The invention also provides kits for treatment or prevention of a disease or disorder (or symptoms) thereof associated with a defect in auditory and/or vestibular mechanosensation. In one embodiment, the kit includes an effective amount of an Inner Ear Hair Cell Targeting AAV (e.g., Anc80 vector) comprising a promoter (e.g., CMV, Espin, PCDH15, a PTPRQ, a TMHS (LHFPL5)) and a polynucleotide that is one or more of USH1, MYO7A, USH1C (harmonin-a, b, c), CDH23, PCDH15, SANS and CIB2 in unit dosage form, together with instructions for administering the angiogenesis-inhibiting compound to a subject suffering from or susceptible to a disease or disorder or symptoms thereof associated with angiogenesis, wherein the effective amount of an angiogenesis-inhibiting compound is less than 500 mg of the compound. In preferred embodiments, the kit comprises a sterile container which contains the angiogenesis-inhibiting compound; such containers can be boxes, ampules, bottles, vials, tubes, bags, pouches, blister-packs, or other suitable container form known in the art. Such containers can be made of plastic, glass, laminated paper, metal foil, or other materials suitable for holding medicaments. The instructions will generally include information about the use of the angiogenesis-inhibiting compound for treatment of a disease or disorder or symptoms thereof associated with angiogenesis; in preferred embodiments, the instructions include at least one of the following: description of the angiogenesis-inhibiting compound; dosage schedule and administration for treatment of a disease or disorder or symptoms thereof associated with angiogenesis; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Conventional molecular biology, microbiology, biochemical, and recombinant DNA techniques within the skill of the art can be used in accordance with the present disclosure. Such techniques are explained fully in the literature. The invention will be further described in the following examples, which do not limit the scope of the methods and compositions of matter described in the claims.

EXAMPLES

Example 1—an Adeno-Associated Virus (AAV) Containing an Ancestral AAV Capsid Protein Results in Safe and Efficient Cochlear Gene Transfer The following methods and materials were used in Example 1.

Viral Vectors

AAV2/1, 2/2, 2/6, 2/8, 2/9 and AAV2/Anc80 with a CMV-driven eGFP transgene and the Woodchuck hepatitis virus Post-transcriptional Regulatory Element (WPRE) cassette were prepared at Gene Transfer Vector Core (vector.meei.harvard.edu) at Massachusetts Eye and Ear as previously described. AAV2/Anc80 plasmid reagents are available through addgene.com.

Animal Models and General Methods

All experiments were approved by Boston Children's Hospital (protocol #12-02-2146) as well as the Institutional Biosafety Committee (protocol #IBC-P00000447). Wild-type C57BL/6J and CBA/CaJ mice were obtained from the Jackson Laboratory (Bar Harbor, Me.) and animals of either sex were used for experimentation in an estimated 50/50 ratio. Group sizes per experiment for the in vitro and in vivo transduction assays and subsequent endpoints were determined by access to specimen and technical feasibility. Reported observations on Anc80 transduction were qualitatively validated in subsequent experiments with various vector lots (except for the human vestibular tissue transduction due to the unique and limited nature of access to specimen). No statistical analysis between serotype transduction efficiencies was performed due to the limited access to specimen and qualitative nature of the reported findings.

Example 1A—In Vivo Injections

Mouse pups (P0 to P2) were injected via the round window membrane (RWM) using beveled glass microinjection pipettes. Pipettes were pulled from capillary glass (WPI) on a P-2000 pipette puller (Sutter Instrument, Novato, Calif.) and were beveled (~20 µm tip diameter at a 28° angle) using a micropipette beveler (Sutter Instrument, Novato, Calif.). EMLA cream (lidocaine 2.5% and prilocaine 2.5%) was applied externally for analgesia using sterile swabs to cover the surgical site (left mastoid prominence). Body temperature was maintained on a 38° C. warming pad prior to surgery. Pups were anesthetized by rapid induction of hypothermia into ice/water for 2-3 minutes until loss of consciousness, and this state was maintained on a cooling platform for 5-10 minutes during the surgery. The surgical site was disinfected by scrubbing with Betadine and wiping with 70% Ethanol in repetition three times. A post-auricular incision was made to expose the transparent otic bulla, a micropipette was advanced manually through the bulla and overlying fascia, and the RWM was penetrated by the tip of the micropipette. Approximately 1 µL of virus was injected unilaterally within 1 min into the left ear manually in 5 (AAV1), 4 (AAV2), 2 (AAV8), 1 (AAV6), 3 (Anc80) C57BL/6 animals. In order to control for factors related to the specific vector preparation such as quality and purity, Anc80 results were confirmed in subsequent studies with different vector lots from independent preparation which were confirmatory of our qualitative findings presented here (data not shown). Injections were performed per group in a non-blinded fashion. Occasionally, the injection needle was inserted too deep, too shallow or at the wrong angle. If there was visible damage to the middle or inner ear structures, the samples were excluded from further analysis. Success rates of injection ranged between ~50% to ~80% depending on the experience level of the injector. After the injection, the skin incision was closed using a 6-0 black monofilament suture (Surgical Specialties, Wyomissing, Pa.). Pups were subsequently returned to the 38° C. warming pad for 5-10 min and then put back to their mother for breeding.

Figure 1:
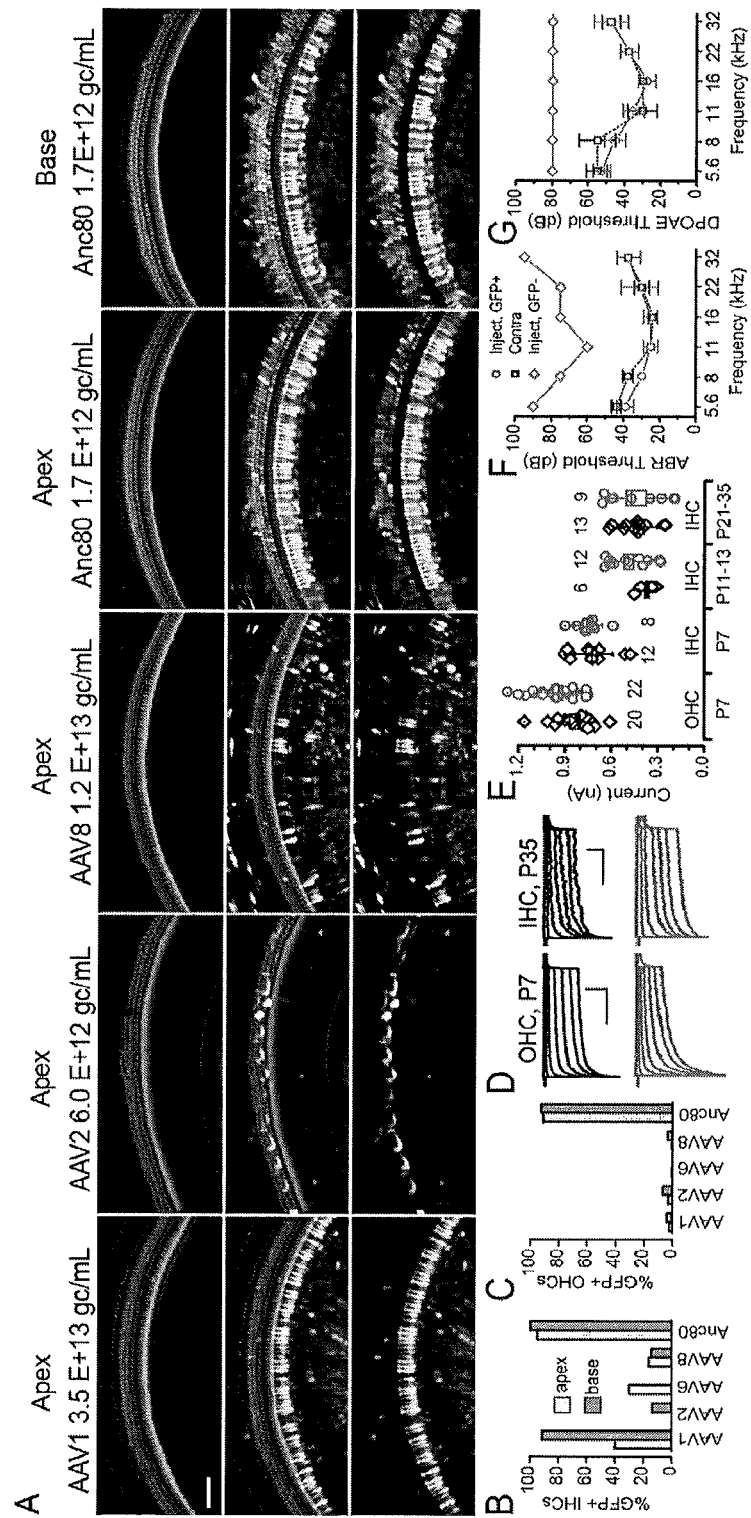
FIG. 1A-1G provides a series of micrographs (A) and six panels of graphs (B-G). In vivo cochlear transduction of natural AAV serotypes and Anc80. (A) Confocal images of mouse organs of Corti, counterstained with Alexa-546-phalloidin (red) and imaged for eGFP (green—shown throughout this document as bright staining in middle and bottom panels). Mice were injected with 1 μL of AAV stock solution at the titer indicated above each panel. Scale bar=50 μm. (B) Quantification of eGFP-positive IHCs in the base and apex of AAV-eGFP injected cochleae. (C) Quantification of eGFP-positive OHCs in the base and apex of AAV-eGFP injected cochleae. One ear per C57BL/6 mouse was injected in 5 (AAV1), 4 (AAV2), 2 (AAV8), 1 (AAV6), 3 (Anc80) animals. (D) Families of sensory transduction currents recorded at P7 (left) from eGFP-negative OHCs (black) and eGFP-positive OHCs (green). Hair bundles were deflected between −0.1 and 1 μm in 0.1 μm increments. Vertical scale bar indicates 200 pA; horizontal indicates 20 msec. Currents from eGFP negative (black) and eGFP-positive (green) P35 IHCs are shown on the right. Vertical scale bar indicates 100 pA; horizontal indicates 20 msec. (E) Sensory transduction current amplitudes plotted for 103 IHCs and OHCs at the ages indicated at the bottom. Data from eGFP-negative (black) and eGFP-positive (green) are shown. The numbers of cells in each group are shown on the graph. All mice were injected at P1. (F) Mean±standard deviation (SD). ABR thresholds plotted for four Anc80-injected ears (green) and four uninjected ears (black) together with data from one injected ear that had no eGFP fluorescence due to injection-related damage (red). (G) Mean±SD. DPOAE thresholds are plotted for four Anc80-injected ears (green) and four uninjected ears (black) and one negative control ear with injection damage without eGFP fluorescence (red). Injection titers for data points in B-G are as in A.

Consistent with prior reports, AAV1 transduced IHCs with moderate to high efficiency (FIG. 1A, 1B). These studies indicate AAV2, 6, and 8 targeted low numbers of IHCs, with only AAV8 demonstrating roughly equivalent transduction in apex and base (FIG. 1B). Also, consistent with prior reports, there was minimal OHC transduction (<5%) for all conventional AAV serotypes tested. However, Anc80 transduced nearly 100% of IHCs and ~90% of OHCs (FIG. 2A-2C) at a 20- (for AAV1) to 3-fold (for AAV2) lower dose. Transduction at equal dose of $1.36 \times 10^{12}$ GC for all serotypes resulted in substantial IHC and OHC transduction for Anc80, but minimal IHC targeting for AAV1, 2, and 8, and none noted in OHCs as observed by live-cell imaging by epifluorescent microscopy (FIG. 8C, 8D).

Figure 3:
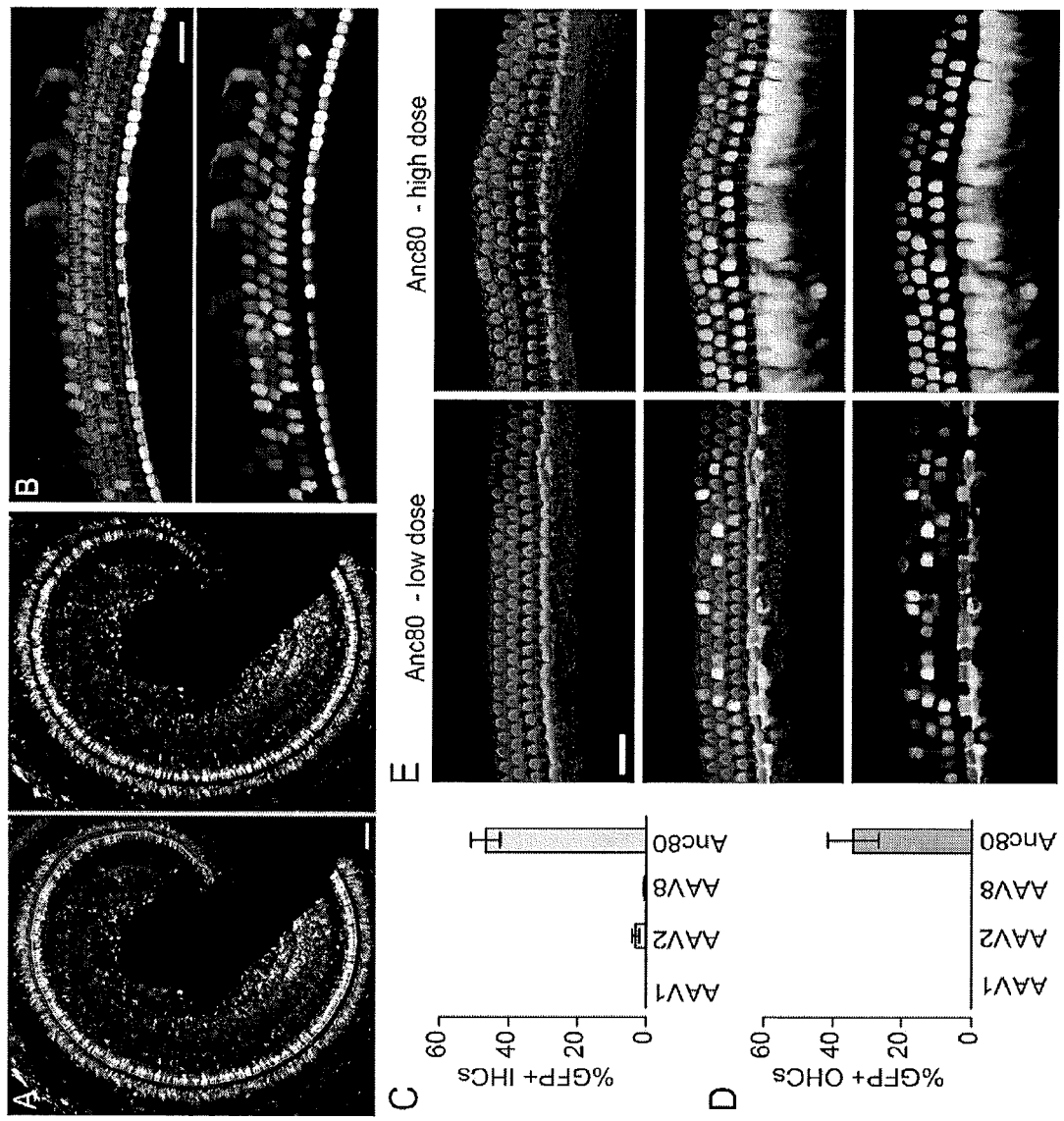
FIG. 3A-3E are images showing extensive Inner and Outer Hair Cell transduction in murine cochleae with Anc80. (A) Low-magnification image of the entire apical portion of a mouse cochlea injected at P1 with 1 µL of Anc80-eGFP at $1.7 \times 10^{12}$ GC/mL. The cochlea was harvested at P10 and stained with Alexa546-phalloidin (red) and imaged for eGFP (green). Scale bar=100 (B) High magnification view of a basal portion from a different mouse cochlea injected at P1 with 1 µL of Anc80-493 eGFP at $1.7 \times 10^{12}$ GC/mL. The cochlea was harvested at P10 and stained with Alexa546-phalloidin (red) and imaged for eGFP (green). Scale bar=20 (C, D) Quantitative comparison of inner and outer hair cell transduction efficiency at an equal dose for all serotypes following round window injection of P1-2 C57BL/6 mice. Mice cochleae in C,D were injected with $1.36 \times 10^{12}$ of AAV1, AAV2, AAV8, and Anc80 and harvested at 7-9 days for live-cell imaging and quantitation by epifluorescent microscopy (n=8 per group). (E) Dose-dependency of Anc80 hair cell transduction. Cochleae exposed to two different Anc80-eGFP titers ($1.8 \times 10^{12}$ versus $1.36 \times 10^{12}$ GC) were fixed and stained with Alexa546-phalloidin (red) and imaged for eGFP (green). Scale bar=20 µm

The Anc80-transduced samples were subsequently fixed, stained and imaged by confocal microscopy, revealing a dose-dependency of hair cell transduction (FIG. 1E). The unparalleled OHC targeting (FIG. 1C, FIG. 3) illustrates qualitatively distinct transduction biology of Anc80 compared to other AAVs. Similar levels of Anc80 transduction were found throughout the cochlea from base to apex in a total of three Anc80-injected mice (FIG. 1A, B, C). Low magnification views of the cochlear apex (FIG. 3A) showed strong eGFP expression far from the injection site. High magnification images of the base reveal 100% IHC and 95% OHC transduction (FIG. 3B).

Since some forms of genetic deafness also cause vestibular dysfunction, Anc80 may be a useful vector for gene delivery into human vestibular organs. To investigate this possibility, human vestibular epithelia were harvested from four adult patients undergoing resection of vestibular schwannoma tumors; the sensory epithelium was placed in culture as previously described. For AAV transduced samples, FIG. 3C reveal strong eGFP fluorescence throughout the human vestibular epithelium in both hair cells and supporting cells. A high-magnification view in an epithelium counterstained with Myo7A in FIG. 3D revealed that 83% (19/23) of Myo7A-positive hair cells were also eGFP-positive, suggesting that Anc80 can transduce both mouse and human hair cells efficiently.

Example 1B—Hair Cell Electrophysiology

Cochleae were excised, mounted on glass coverslips and viewed on an Axio Examiner.A1 upright microscope (Carl Zeiss, Oberkochen, Germany) equipped with a 63× water-immersion objective and differential interference contrast optics. Electrophysiological recordings were performed at room temperature (22° C.-24° C.) in standard solutions containing (in mM): 137 NaCl, 5.8 KCl, 10 HEPES, 0.7 NaH2PO4, 1.3 CaCl2, 0.9 MgCl2, and 5.6 D-glucose, vitamins (1:100), and amino acids (1:50) as in MEM (Life Technologies, Carlsbad, Calif.) (pH 7.4; ~310 mOsm/kg). Recording electrodes (3-4 MΩ) were pulled from R-6 glass (King Precision Glass, Claremont, Calif.) and filled with intracellular solution containing (in mM): 140 CsCl, 5 EGTA-KOH, 5 HEPES, 2.5 Na2ATP, 3.5 MgCl2, and 0.1 CaCl2 (pH 7.4; ~280 mOsm/kg). The whole-cell, tight-seal technique was used to record mechanotransduction currents using an Axopatch 200B (Molecular Devices, Sunnyvale, Calif.). Hair cells were held at −84 mV. Currents were filtered at 5 kHz with a low-pass Bessel filter, digitized at ≥20 kHz with a 12-bit acquisition board (Digidata 1440A, Molecular Devices, Sunnyvale, Calif.), and recorded using pCLAMP 10 software (Molecular Devices, Sunnyvale, Calif.). Hair bundles from IHCs and OHCs were deflected using stiff glass probes mounted on a PICMA chip piezo actuator (Physik Instrumente, Karlsruhe, Germany) driven by an LVPZT amplifier (E-500.00, Physik Instrumente, Karlsruhe, Germany) and filtered with an 8-pole Bessel filter (Model 3384 filter, Krohn-Hite Corporation, Brockton, Mass.) at 40 kHz to eliminate residual pipette resonance. Stiff glass probes were designed to fit into the concave aspect of the array of hair cell stereocilia for whole-bundle recordings (3-4 µm diameter for OHCs and 4-5 µm diameter for IHCs). For the whole cell electrophysiology recording at >P10, cochlea tissues were dissected at P5-7 and incubated in MEM(1×)+GlutaMAXTM-I medium with 1% FBS at 37° C., 5% CO2 for up to 30 days.

Representative currents evoked by hair bundle deflections from P7 OHCs and P35 IHCs revealed no differences in amplitude, sensitivity or kinetics, between eGFP positive and eGFP-negative control cells (FIG. 1D). 51 eGFP positive and 52 eGFP-negative hair cells were recorded from all regions of the cochlea and from ages between one and five weeks after exposure to Anc80. Responses were indistinguishable from wild-type in all cases (FIG. 1E), which confirmed that Anc80 transduction had no detrimental effects on sensory cell function.

Example 1E—Hearing Tests

Auditory brainstem response (ABR) and distortion product otoacoustic emissions (DPOAE) data were collected as described previously. DPOAE is an assay for proper cochlear amplification and tuning and is a sensitive measure of outer hair cell viability. Stimuli tested in anesthetized mice varied between 10 and 90 dB sound pressure level at frequencies of 5.6, 8, 11.3, 16, 22.6, and 32 kHz. Four Anc80-injected ears and four uninjected ears and one negative control ear with injection damage without eGFP fluorescence were analyzed at P28-P30.

Minimal sound thresholds required to evoke ABRs were plotted (FIG. 1F) and revealed no difference in threshold between injected and uninjected ears. Histological analysis revealed strong eGFP fluorescence in all four injected ears (data not shown). In one case, there were no eGFP-positive cells and ABR thresholds were elevated (FIG. 1F), suggesting the injection failed and that the needle may have breached the cochlear duct and caused permanent damage. Despite robust outer hair cell transduction by Anc80-eGFP, no difference was found in DPOAE thresholds relative to uninjected control ears (FIG. 1G). Thus, data from ABRs and DPOAEs indicate that RWM injection, Anc80 transduction and transgene expression in IHCs and OHCs are all safe for auditory function.

Example 1F—Rotarod Test

Five C57BL/6 mice were tested for balance behavior on the rotarod device. Mice with impaired vestibular function are known to perform poorly on the rotarod device. Previous studies highlighted the ability of this rotarod test to detect balance dysfunction when only one ear is affected. Three mice injected at P1 and tested at P36 and two uninjected control mice at P79. All mice were tested using the following rotarod protocol. On day one, mice were trained to balance on a rod that was rotating at four RPM for five minutes. On day two, the mice were tested in five trials with each trial separated by five minutes. For each trial, the rod accelerated one RPM from a starting rate of two RPM. The time (in seconds) was recorded until the mice fell off the device.

Figure 2:
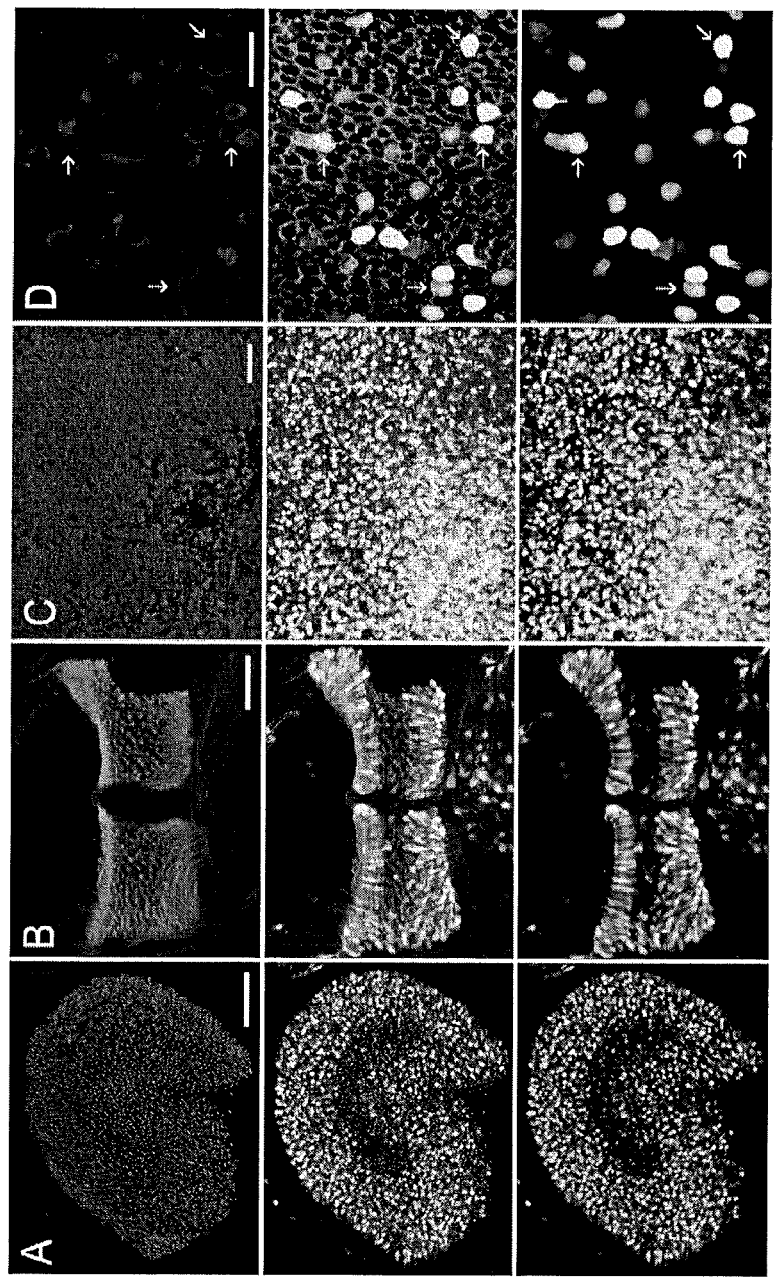
FIG. 2A-2D are images showing Anc80-eGFP transduction in vestibular sensory epithelia. (A) Mouse utricle from a P1 mouse injected with 1 μL Anc80-eGFP ($1.7 \times 10^{12}$ GC/mL). The tissue was harvested at P10 fixed and stained with Alexa546-phalloidin (red) and imaged for eGFP (green). Morphological assessment across multiple focal planes of eGFP-positive cells demonstrated transduction of stereotypical flask-shaped morphology of type I cells and the cylinder morphology of type II cells in every sample examined (not shown). Scale bar=100 µm. (B) The crista of the posterior semicircular canal from the same mouse described for panel A. Scale bar=50 µm. (C) The sensory epithelium of a human utricle. The tissue was exposed to $10^{10}$ GC Anc80.CMV.eGFP.WPRE for 24 hours, cultured for 10 days, fixed, stained with Alexa546-phalloidin (red) and imaged for eGFP fluorescence (green). Scale bar=100 µm. (D) High magnification view of a human epithelium in the utricle stained with Alexa546-phalloidin (red) and Myo7A (blue) and imaged for eGFP (green) transduced in identical conditions as in C. White arrows in the overlay panel indicate selected eGFP-positive/Myo7A-positive cells. Scale bar=20 µm.
Figure 4:
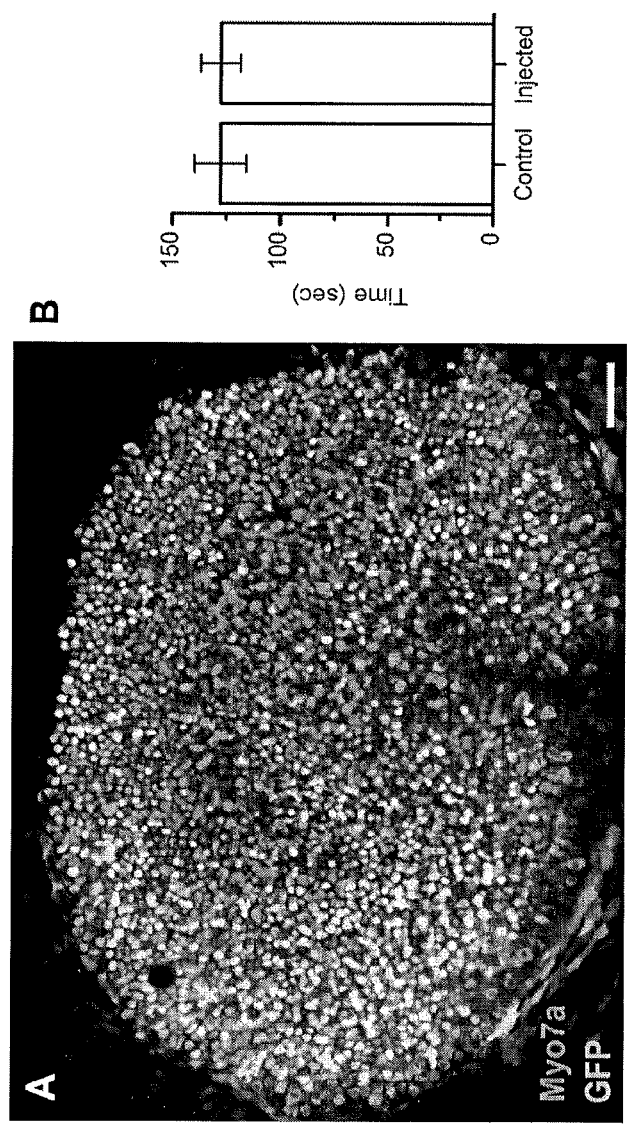
FIGS. 4A and 4B are an image and a graph, respectively, showing vestibular function following Anc80 cochlear transduction. Mice were injected at P1 with Anc80.CMV.eGFP via the RWM and evaluated for expression and balance function on the rotarod device. Expression of eGFP (green) in the vestibular tissue is via confocal microscopy with immunofluorescent staining for Myo7A (red) (A). Rotarod data revealed no difference between injected and uninjected controls. The mean time until the mice fell off the device+/−SEM is plotted. N=3 animals, 5 trials each (injected) and 2 animals 5 trials each (control) (B). Scale bar=50 µm Part 2: Gene Therapy Restores Auditory and Vestibular Function in a Mouse Model of Usher Syndrome, Type 1c

Since the perilymphatic solutions of the cochlea are continuous with those of the vestibular labyrinth, it was evaluated whether Anc80-eGFP injected via the cochlear RWM would transduce vestibular sensory organs. Indeed, whole-mounts of vestibular epithelia revealed robust eGFP expression in both type I and type II hair cells of the utricle, a vestibular organ sensitive to gravity and linear head movements and in the semicircular canals, which are sensitive to rotational head movements (FIG. 2A, 2B). Thus, to address the safety concern that Anc80 transduction may affect balance, injected mice with confirmed vestibular expression performed the rotarod test for vestibular function similarly to uninjected controls (FIG. 4).

Part 2: Gene Therapy Restores Auditory and Vestibular Function in a Mouse Model of Usher Syndrome, Type 1c Example 2—Mouse Model of Usher Syndrome The following methods and materials were used in Example 2.

Tissue Preparation

Utricle and organ of Corti from Ush1c c.216G>A heterozygous or homozygous mutant mice were harvested from postnatal day 0 to 8 (P0 to P8) for electrophysiological studies. Postnatal mouse pups were killed by rapid decapitation. The temporal bones were excised and bathed in MEM (Invitrogen, Carlsbad, Calif.) supplemented with 10 mM HEPES (pH 7.4). The organ of Corti was dissected away without the use of enzyme as described previously (53). Utricles were removed after 10 min protease treatment (Protease XXIV, Sigma) at 0.1 mg/ml. The excised organs were mounted on round glass coverslips. A pair of thin glass fibers previously glued to the coverslip was placed on the edge of the tissue to stabilize it in a flat position. Tissues were either used acutely or kept in culture in presence of 1% Fetal Bovine Serum. Cultures were maintained for 7 to 8 days and the media was replaced every 2 to 3 days for experiments that involved viral vectors infection in vitro.

Animals

Ush1c c.216G>A knock-in mice were obtained from Louisiana State University Health Science Center. The imported strain while on a C57BL6 background were previously bred out of the Cdh23 (Ahl) mutation causing age related hearing loss (48, 49). All procedures used for this work met the NIH guidelines for the care and use of laboratory animals and were approved by the Institutional Animal Care and Use Committees at Boston Children's Hospital (Protocols #12-02-2146, #14-03-2659R and #15-01-2878R). Mice were genotyped using toe clip (before P8) or ear punch (after P8) and PCR was performed as described previously (32). For all studies, both male and female mice were used in approximately equal proportions. No randomization paradigm was otherwise applied.

Viral Vector Generation

Total RNA was isolated from cochleae of c.216AA mutant mice (RNAqueous micro kit, Ambion) and reverse transcribed with QuantiTect Reverse Transcription kit (Qiagen). The cDNA of trunc-harmonin was amplified by PCR with Platinum Taq DNA polymerase High Fidelity (Invitrogen) and primers: Trunc-harmonin.F(KpnI) GAG GTA CCA TGG ACC GGA AGG TGG CCC GAG; Trunc-harmomin.RV(BamHI) CAG GAT CCG GAC AAT TTC ATC CCC TAC. The 387 bp PCR product was cloned with TA cloning kit (Invitrogen), and confirmed by sequencing. To generate a GFP fusion construct, the truncated harmonin fragment was subcloned into pEGFP-C1 with KpnI and BamHI. The NheI-XbaI EGFP::trunc-harmonin cDNA was transferred into an AAV shuttle vector. Custom vectors were packaged with AAV2 inverted terminal repeats (ITRs) into the AAV1 capsid where the transgene cassette was driven by a CMV promoter (AAV2/1.CMV.EGFP::trunc-harmomin.hGH, 1.92 E14 gc/m, BCH).

Harmonin-a1 and harmonin-b1 plasmid were prepared in our laboratory from EGFP tagged labeled constructs graciously provided by Lily Zheng and James Bartles (52) (Department of Cell and Molecular Biology, Northwestern University, Feinberg School of medicine, Chicago, Ill.). Harmonin-a1 was originally obtained from mouse kidney and harmonin-b1 from isolated mouse cochlea sensory epithelium. We further modified the harmonin-a1 construct to replace the EGFP tag with tdTomato at its N terminal end. Fluorescently labeled and unlabeled constructs were packaged into AAV vectors. Viral vectors were generated by the viral core facility at Boston Children's Hospital and the Gene Transfer Vector Core at the Massachusetts Eye and Ear Infirmary. The following vectors were generated: AAV2/1.CMV.tdTomato::harmonin-a1 4.33 10^13 gc/ml (BCH); AAV2/1.CMV.EGFP::harmonin-b1 2.73 564 10^14 gc/ml (BCH); AAV2/1.CMV.EGFP-harmonin-a1: 2.81 10^12 gc/ml (MEEI); AAV2/1.CMV.EGFP-trunc-harmonin; 1.92 10^14 gc/ml (BCH); AAV2/Anc80.CMV.harmonin-a1: 1.93 10^12 gc/ml (MEEI); AAV2/Anc80.CMV.harmonin-b1: 1.74 10^12 gc/ml (MEEI); AAV2/Anc80.CMV.truncharm.WPRE: 9.02 567 10^12 gc/ml (MEEI); For in vitro experiments, 10 µl of concentrated vector was applied to 1 ml MEM supplemented media on acutely dissected tissue in presence of 1% Fetal Bovine Serum for 24 h. Cultures were subsequently maintained for up to 10 days.

Round Window Membrane (RWM) Injection

RWM injections were performed as approved by the Institutional Animal Care and Use Committees at Boston Children's Hospital animal protocol #15-01-2878R. 0.8 µl-1 ul of AAV vectors were injected in neonatal mice P0-P1 and P10-P12. P0-P1 mice were first anesthetized using hypothermia exposure while P10-P12 mice were anesthetized with isoflurane. Upon anesthesia, post-auricular incision was made to expose the otic bulla and visualize the cochlea. Injections were done through the RWM with a glass micropipette controlled by a micromanipulator (Askew et al. 2015). The volume of the injected materials was controlled at an approximately 0.02 µl/min for 10 min. Standard post-operative care was applied. Sample size for in vivo studies were determined on a continuing basis to optimize the sample size and decrease the variance.

Electrophysiological Recording

Recordings were performed in standard artificial perilymph solution containing (in mM): 144 NaCl, 0.7 NaH2PO4, 5.8 KCl, 1.3 CaCl2, 0.9 MgCl2, 5.6 D-glucose, and 10 HEPES-NaOH, adjusted to pH 7.4 and 320 mOsmol/kg. Vitamins (1:50) and amino acids (1:100) were added from concentrates (Invitrogen, Carlsbad, Calif.). Hair cells were viewed from the apical surface using an upright Axioskop FS microscope (Zeiss, Oberkochen, Germany) equipped with a 63× water immersion objective with differential interference contrast optics. Recording pipettes (3-5 MΩ) were pulled from borosilicate capillary glass (Garner Glass, Claremont, Calif.) and filled with intracellular solution containing (in mM): 135 KCl, 5 EGTA-KOH, 10 HEPES, 2.5 K2ATP, 3.5 MgCl2, 0.1 CaCl2, pH 7.4. Currents were recorded under whole-cell voltage-clamp at a holding potential of −64 mV at room temperature. Data were acquired using an Axopatch Multiclamp 700A or Axopatch 200A (Molecular devices, Palo Alto, Calif.) filtered at 10 kHz with a low pass Bessel filter, digitized at ≥20 kHz with a 12-bit acquisition board (Digidata 1322) and pClamp 8.2 and 10.5 (Molecular Devices, Palo Alto, Calif.). Data were analyzed offline with OriginLab software and are presented as means±standard deviations unless otherwise noted.

Statistical Analyses

Test and control vectors were evaluated in at least three mice per group at each time point to ensure reproducibility. Sample sizes are noted in figure legends. All animals with successful RWM injection were included in the study analysis. Those animals with unsuccessful injection were excluded from the mean but included in the legend for full disclosure. Injection success was determined according to ABR recovery with thresholds>90 dB SPL. Statistical analyses were performed with Origin 2016 (OriginLab Corporation). Data are presented as means±standard deviations (S.D) or standard error of the mean (S.E.M) as noted in the text and figure legend. One-way analysis of variance (ANOVA) was used to determine significant differences between the means.

Example 2A—Scanning Electron Microscopy (SEM)

SEM was performed at P7, P18 and ~P42 (6 weeks) along the organ of Corti of control and mutant mice. P18 SEM was performed in collaboration with Dr. Edwin Rubel at the University of Washington. Inner ears were fixed in 4% glutaraldehyde in 0.1 M sodium phosphate at 4° C. overnight. The next day specimens were rinsed three times in 0.1 M sodium phosphate buffer (PB) and post-fixed in 1% osmium tetroxide in 0.1 M PB for 30 min in an ice bath. Specimens were then rinsed in 0.1 M PB and dehydrated through a graded ethanol series: 35%, 70%, 95%, and 100% (×2). Samples were critical point dried, mounted on SEM stubs, and sputter coated with Au/Pd. SEM was performed using a JEOL JSM-840A scanning electron microscope. A similar preparation was performed for P8 and 6 weeks stages by Dr. Géléoc and Dr. Indzhykulian. Organ of Corti explants were fixed in 2.5% glutaraldehyde in 0.1 M cacodylate buffer (Electron Microscopy Sciences) supplemented with 2 mM $CaCl_2$ for 1 h at room temperature. Specimens were dehydrated in a graded series of acetone, critical-point dried from liquid $CO_2$, sputter-coated with 4-5 nm of platinum (Q150T, Quorum Technologies, United Kingdom), and observed with a field emission scanning electron microscope (S-4800, Hitachi, Japan).

Figure 12:
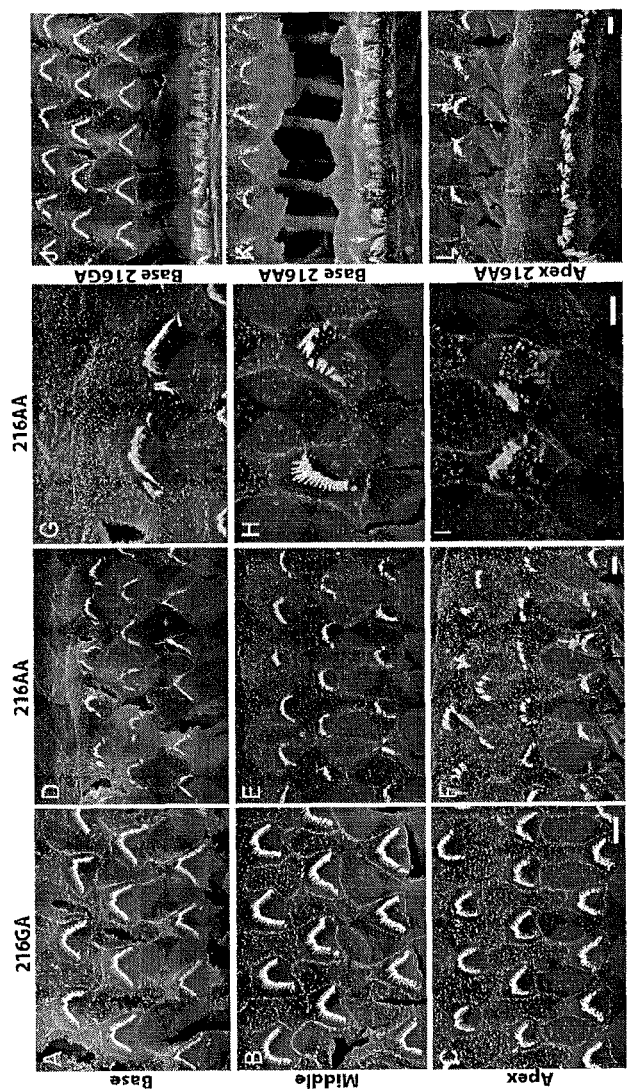
FIGS. 12A-12L are images showing an analysis of hair bundle morphology in Ush1c c.216G>A mice at P18 by SEM. (A-C) Heterozygous c.216GA mice displayed normal hair bundle morphology at P18. (D-I) Disorganized hair bundles were observed along the organ of P18 Homozygous c.216AA mutant mice. (J-L) IHCs hair bundle were mildly disrupted in c.216AA mice. Distance measured from apex tip: Base 3.5-4 mm; Mid 1.8-2.2 mm; Apex 0.6-0.8 mm. Scale bar low magnification: 5 µm; high magnification: 1 µm.

Homozygous c.216AA mutant mice are deaf and show circling and head tossing behaviors characteristics of vestibular dysfunction. Previous work from Lentz et al. (34) described pronounced inner and outer hair cell degeneration at the base of the cochlea at P30. Degeneration and hair cell death was also observed in the middle turn, while the apical portion of the organ was better preserved at 1 month of age. It was hypothesized that hair cell degeneration occurs progressively during development of the inner ear organs and, to assess hair cell survival at earlier stages, SEM analysis was performed along the organ of Corti at P8 and P18. Outer hair cells (OHCs) and inner hair cells (IHCs) of heterozygous c.216GA mice were preserved and their bundles were properly oriented at these ages (FIG. 5A-5C, 5G, 5I and FIG. 12A-12C, 12K). However, disorganized hair bundles were evident along the entire length of the organ of Corti in homozygous c.216AA mice at both ages analyzed (FIG. 12D-12F, 12H, 12J-12L and FIG. 19D-19J, 19L). At P8, IHC bundles were mildly disorganized at the base, mid and apical regions (FIG. 12D-12F, 12J). Numerous IHC bundles displayed a wavy pattern and mild disorganization of the stereocilia rows (FIG. 12J). While many OHCs of c.216AA mutant mice possessed well-preserved hair bundles (FIG. 12H, 12K), fragmented and disorganized hair bundles were evident sporadically along the organ (FIG. 12D-12F, 12L). Disruption was more pronounced at P18, though the majority of hair cells were still present as previously reported (35) (FIG. 12D-12F).

Figure 11:
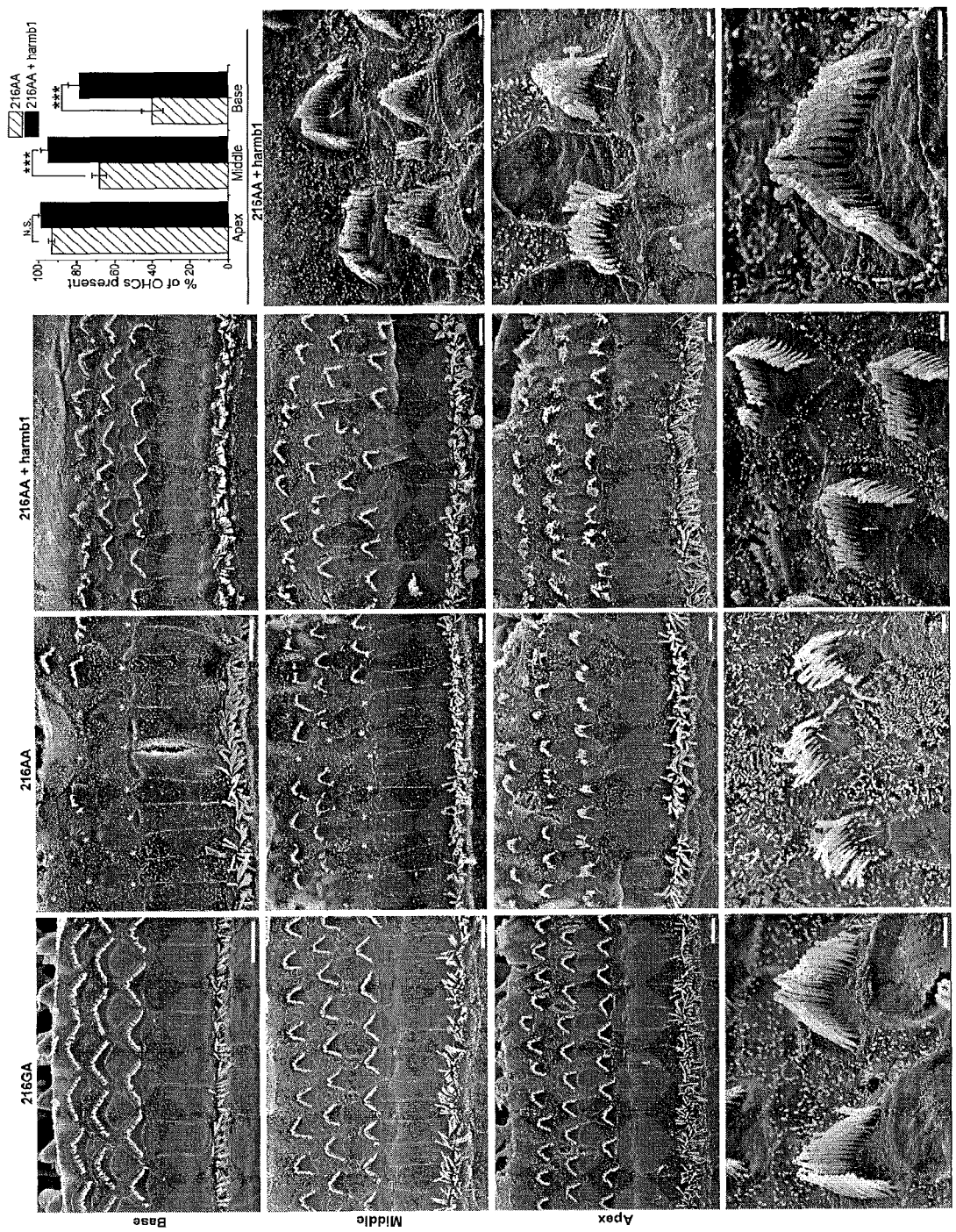
FIG. 11 are scanning electron microscopy images of the organ of Corti in mice injected with AAV2/Anc80.CMV.harmonin-b1. Basal, Middle and Apical regions of the organ of Corti were imaged at six weeks in c.216GA, c.216AA and c.216AA mice injected at P1 (RMW injection 0.8 µl AAV2/Anc80.CMV.harmonin-b1). OHC and IHC hair bundles were preserved in c.216GA mice but appeared disorganized along the organ of Corti in c.216AA mice. Noticeable hair cell loss (asterisk) and hair bundle disorganization was observed in c.216AA mice with more pronounced degeneration in the basal end of the organ. Hair bundles of c.216AA mice lacked normal stereocilia rows. The shorter rows appeared to be retracted while the tallest rows were maintained in c.216AA mice (arrow). While hair cell loss and bundle disorganization were still evident in rescued c.216AA mice, hair cell survival was noticeably higher in the basal and middle regions of the Organ. Hair cell counts are summarized in the bar graph. A total of 1824 cells were counted in c.216AA mice (4 ears) and 792 in rescued c.216AA mice (2 ears). Mean±S.E. High magnification imaging reveals rescue of the staircase array in injected c.216AA mice (arrow) in many but not all cells (arrowhead). Scale bar low magnification: 5 µm; high magnification: 1 µm.

To assess hair bundle morphology in mice that have undergone gene therapy with harmonin-b1, temporal bones of 6-week old untreated (or uninjected) and treated (or injected) mice were prepared for SEM analysis. Untreated c.216AA mice displayed severe hair cells loss at the basal and middle regions of the organ (FIG. 11). In the basal region, OHCs were mostly absent in the first row and present sporadically in the second and third rows. In the middle region of the organ, the first row of OHCs was also largely absent. Milder phenotypes were observed in the apical end. High magnification SEM also revealed severely disorganized hair bundles along the entire length of the organ of c.216AA mutant mice. Remarkably, in 6 weeks old c.216AA mice, no hair bundles were observed that retained the typical staircase structure with all three rows of stereocilia. Instead, hair cells from c.216AA mice displayed disorganized hair bundles with retracted stereocilia along the first row, abnormal second row and fairly preserved tallest row. In contrast, reduced hair cell loss and normal hair bundles were observed in c.216AA mice after treatment with harmonin-b1. Hair cells counts were estimated from the presence or absence of hair bundles in representative fields of view. The data revealed pronounced preservation of hair cell number in injected mice from the base to the apex of the organ, from 40 to 79% in the base, 68 to 95% in the middle and 93 to 99% in the apex (n=1824 cells from n=4 c.216AA mice ears and n=792 from n=2 rescued c.216AA ears). Although abnormal hair bundles were still evident in harmonin-b1 injected mice, most hair bundles possessed three rows of stereocilia and had morphology almost indistinguishable from their heterozygous controls (FIG. 11).

Example 2B—FM1-43 Imaging 5 micromolar FM1-43 (Invitrogen) was diluted in extracellular recording solution and applied to tissues for 10 seconds and then washed 3 times in extracellular recording solution to remove excess dye and prevent uptake via endocytosis. After 5 minutes the intracellular FM1-43 was imaged using an epifluorescence light source, differential interference contrast optics, and an FM1-43 filter set (Chroma Technologies) on a Zeiss Axioscope FS plus with water immersion 20×, 40×, and 63× objectives. Images were captured at 16-bit with a CCD camera and Argus-20 image processor (Hamamatsu) using background fluorescence subtraction. The same gain and contrast settings were maintained for the acquisition of all images and analyzed offline with Adobe Photoshop or Image-J software.

To assess hair cell function at earlier stages, FM1-43 uptake in acutely dissected inner ear organs was analyzed at P4. Upon brief applications (<10 s), FM1-43 permeates hair cells that possess functional mechanosensitive channels (36, 37, 38). Uniform FM1-43 uptake was observed in hair cells of c.216GA mice (FIG. 6A), but the level of uptake varied among OHCs of c.216AA mice, suggesting that some, but not all, cells retained functional transduction channels (FIG. 6B). Similar observations were made along the entire length of the cochlea. No tonotopic differences were noted. FM1-43 uptake also decreased in IHCs of c.216AA mice during the first postnatal week (data not shown). FM1-43 uptake also was assessed in utricle hair cells of mutant mice. Interestingly, in c.216AA mutant mice, uptake was restricted to the extra-striola region at P6, suggesting that hair cells of the striola region lack mechanosensitive channels open at rest (FIG. 6C, 6D).

Example 2C—Mechanical Stimulation

OHCs and IHCs: Mechanical stimuli were transmitted via a stiff glass probe mounted on a one-524 dimensional PICMA chip piezo actuator (Physik Instruments, Waldbronn, Germany) driven by a 400 mA ENV400 Amplifier (Piezosystem Jena Germany, 54). The tip of the probe was fired polished (Fire polisher, H602, World Precision Instruments Inc., Sarasota, Fla.) to fit stereociliary bundle (51). Deflections were evoked by applying voltage steps filtered with an 8-pole Bessel filter (Khron-Hite, 528 Brockton, Mass.) at 50 kHz to eliminate residual pipette resonance. Hair bundle deflections were monitored using a C2400 CCD camera (Hamamatsu, Japan). Voltage steps were used to calibrate the motion of the stimulus probe around ±2 µm of its rest position. Video images of the probe were recorded to confirm absence of off-axis motion and calibrate the probe motion (spatial resolution of ~4 nm). The 10-90% rise-time of the probe was ~20 µsec.

VHCs: Mechanical stimuli were transmitted via a stiff glass probe mounted on a piezoelectric bimorph element. Coupling was performed by gentle suction of the kinocilium into the stimulus pipette. Deflections were evoked by applying voltage steps to the piezoelectrical device which consisted of two bimorphs mounted in series and directly coupled to the stimulus probe. Voltage steps were controlled by pClamp 8.0 software and filtered with a 8 pole Bessel filter at 1 kHz (Khron-Hite, Brockton, Mass.). Hair bundle deflections were monitored using a C2400 CCD camera (Hamamatsu, Japan). The motion of the stimulus probe was calibrated around (±2 µm) its rest position prior to the experiments.

Figure 5:
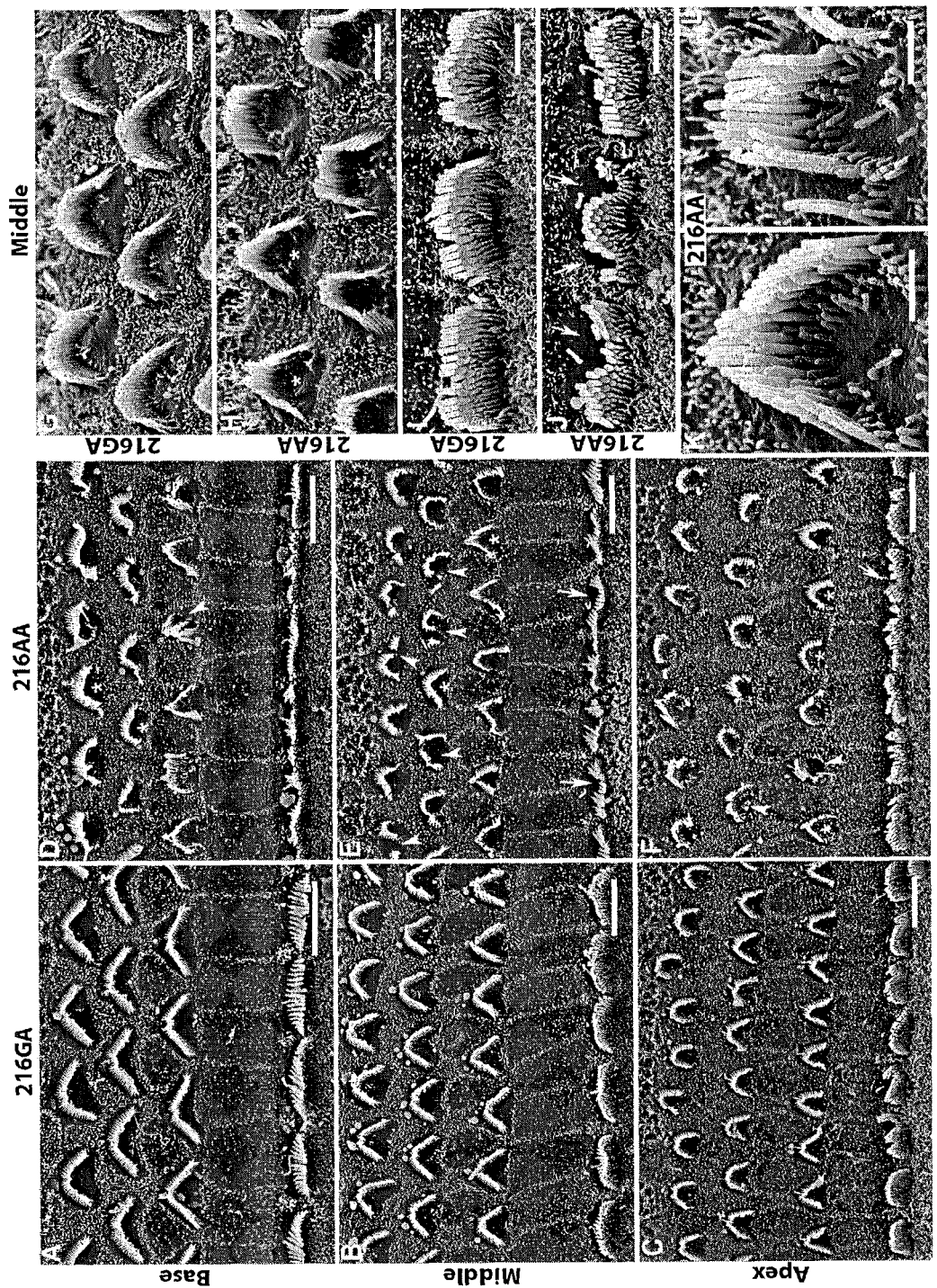
FIGS. 5A-5L are images showing scanning electron microscopy of the organ of Corti in Ush1c c.216G>A mutant mice at P8. (A-F) Basal, middle and apical regions of the organ of Corti were imaged in P8 c.216GA (n=3 mice) and c.216AA (n=4 mice) mutant mice. OHC and IHC hair bundles were preserved in heterozygous mice but some hair bundles appeared disorganized along the organ of Corti in homozygous 216AA mice. (G-L) High magnification images revealed fragmented and disorganized bundles with disruptions in the staircase array in many but not all OHC (G-H) and IHCs (I-J). Examples of OHC hair bundles imaged in the middle region of the organ at P8 illustrate a preserved (K) and a disorganized hair bundle (L) present in the same preparation. Stars indicate preserved hair bundles; arrowhead, disorganized hair bundles; and arrows, wavy IHC bundles. Scale bars low mag.: 5 µm (A-F); high mag.: 2 µm (G), 3 µm (H), 1-863 J) and 1 µm (K,L).

During the first postnatal week, auditory and vestibular epithelia retain mechanosensitive hair cells, including some with relatively normal morphology (FIG. 5). In the organ of Corti, recordings were obtained from the middle and apical turns of the cochlea from P3 to P6 c.216AA mice from hair cells with bundles that appeared normal and those with more severely disrupted hair bundles. In c.216AA mutants, OHCs retained mechanosensitivity, although the amplitudes of the responses were significantly reduced by ~63% to 170±80 pA (n=24; p<0.001, FIG. 6E, 6F, 6G). A wide range of response amplitudes was observed in OHCs, between 31 and 292 pA in c.216AA mice. Significant difference (p<0.01) was observed when data were grouped according to hair bundle morphology: currents evoked in mutant hair cells that possessed severely disorganized bundles were smaller than those evoked in mutant cells that had more preserved hair bundles, 120±65 pA (n=9) and 201±74 pA (n=15), respectively. Despite the reduction in current amplitude, hair cell responses to mechanical displacements retained similar properties to those of heterozygous c.216GA mice. Stimulus response [I(X)] curves were fitted using a second-order Boltzmann equation (FIG. 6F) and the fit was used to determine the 10-90% operating range (FIG. 13B). No significant difference (p=0.054) in operating range was observed between OHCs recorded from c.216GA and c.216AA. Similarly, while hair bundles from IHCs of c.216AA mutant mice appeared mildly disrupted under the DIC microscope, transduction currents were significantly reduced at P6 (FIG. 13E, 13F, 13G). At a holding potential of −64 mV, maximum transduction currents in heterozygous c.216GA IHCs (P6-P7) averaged 587±96 pA (n=21) but were reduced by 46% to 316±127 pA (n=19; p<0.001) in c.216AA IHCs. A significant (p<0.01) reduction in the operating range was measured in IHCs of c.216AA mutant mice (FIG. 13G).

Adaptation, defined as a decline in the transduction current in the presence of a constant bundle deflection, was also present in the c.216AA mutant mice. Adaptation kinetics were analyzed using double exponential fits to determine fast and slow components. While both components were slower in IHCs and OHCs from c.216AA mutant mice the difference was only significant for the slow component (p<0.05 in OHCs, and p<0.001 in IHCs; FIG. 13C, 13D, 13H, 13I). On the other hand, the extent of adaptation measured at Popen=0.5 was significantly less in OHCs and IHCs of c.216AA than c.216GA hair cells (FIG. 20E, 20J; p<0.001). Together, these results demonstrate that mechanosensitivity is mildly compromised in inner and outer hair cells of c.216AA mice and importantly that both cell types survive throughout the first postnatal week, a prerequisite for gene therapy and restoration of cellular function.

In vestibular hair cells, a reduction in mechanotransduction currents also was observed in c.216AA mice. In the extra-striola region, c.216AA currents were significantly (p<0.001) reduced to 109±30 pA (n=9, P5-P7) versus 231±53 pA (n=8, P6-P7) for c.216GA currents (FIG. 6E, 6F, 6H). Very small or no currents were recorded from hair cell of the striola region (6±13 pA, n=6, P5-P7), in agreement with the absence of FM1-43 uptake in that region (see below; FIG. 6C, 6D). While utricle hair bundles appeared grossly well-preserved by DIC microscopy, transduction currents were significantly reduced or absent from hair cells in the extra-striola and striola, respectively. Thus, with the exception of the striola region, these results suggest that the transduction apparatus is correctly assembled and targeted in mutant mice but that the number of functional complexes is reduced in neonatal mice.

Figure 8:
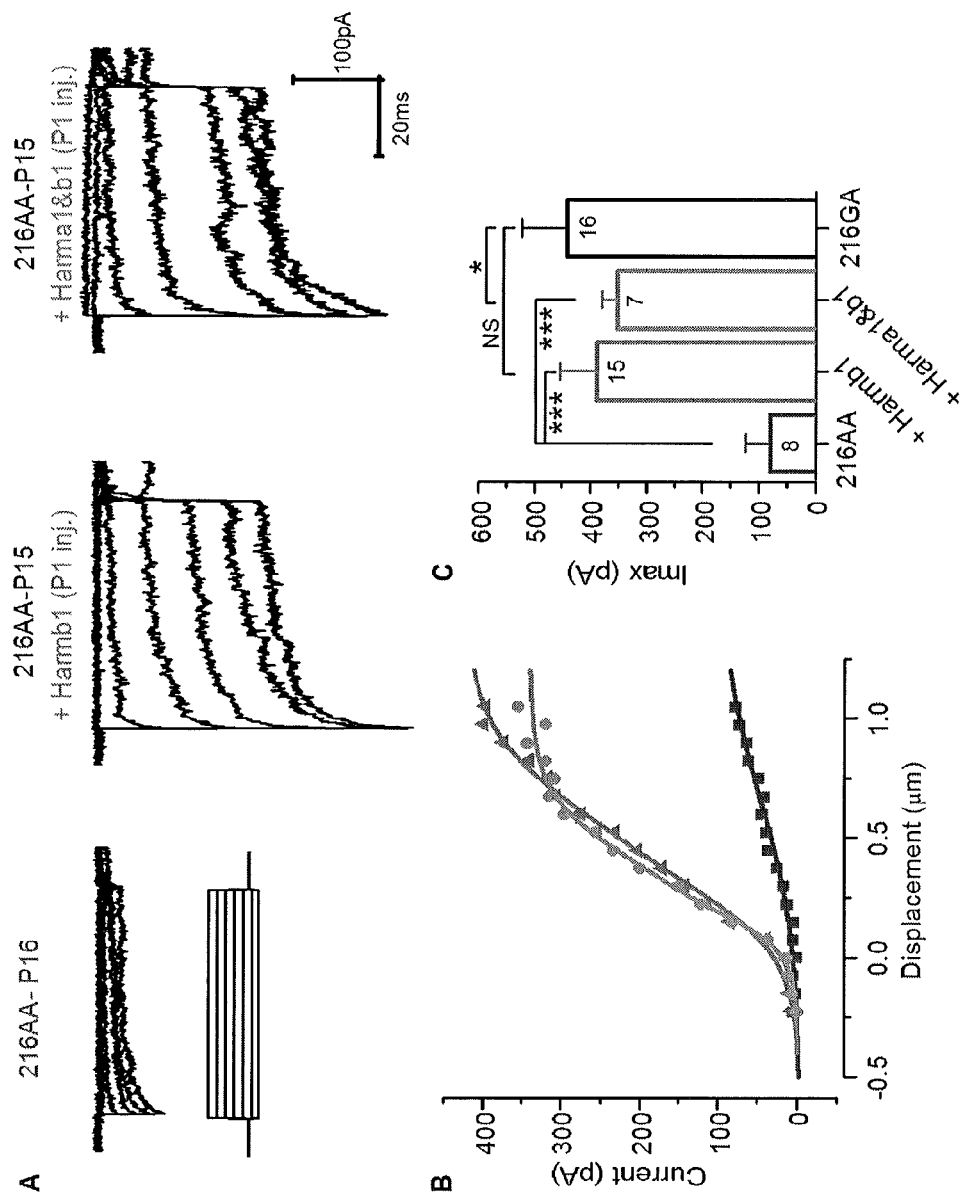
FIGS. 8A-8C are images showing recovery of mechanotransduction in hair cells of mice injected with Anc80 harmonin vectors. (A-C) Mechanotransduction currents were recorded in IHCs of c.216AA uninjected control mice (n=8 cells, one mouse) and c.216AA mice injected at P1 with AAV2/Anc80.CMV.harmonin-b1 (0.8 µl, n=15 cells, one mouse) or a combined injection of the AAV2/Anc80.CMV.harmonin-b1 and AAV2/Anc80.CMV.harmonin-a1 (0.5 µl+0.5 µl, n=7 cells, one mouse). Organotypic cultures were prepared at P6 and recordings were performed between P15 and P16 (9 to 10 DIV). While small mechanotransduction currents could be induced by hair bundle stimulations of c.216AA mice, larger currents were evoked in c.216AA mice injected with vectors driving harmonin-b1 or dual harmonin-a1 and -b1 expression (A). Corresponding I/X curve for each dataset and double Boltzmann fitting function. Respective maximal mechanotransduction current Imax=102.1 pA (c.216AA); 424.3 pA (c.216AA+harmonin-b1) and 341.1 pA (c.216AA+harmonin-a1&-b1) (B). Average responses (Mean±S.D.) show significant recovery of transduction (***P<0.001) for harmonin-b1 and harmonin-a1+-b1 injected relative to unjected mice. Average transduction currents were not significantly different in harmonin-b1 injected mice and c.216GA control mice (N.S. P>0.5). Recovery of mechanotransduction was also not significantly improved when harmonin-a and harmonin-b were combined. (C), one-way ANOVA.

Next, function in c.216AA hair cells exposed to AAV vectors driving harmonin expression was assessed. To enhance the likelihood of functional rescue with exogenous harmonin, untagged harmonin-a1 or harmonin-b1 coding sequences driven by a CMV promoter were packaged into an AAV capsid known as Anc80 (39). The Anc80 capsid has recently been shown to transduce 100% of IHCs and 80-90% of OHCs in vivo (40). We hypothesize that harmonin-b is required for mechanotransduction in both IHCs and OHCs and is necessary for auditory function in both cell types. RWM injections of AAV2/Anc80.CMV.harmonin-b1 (0.8 µl, $1.9 \times 10^{12}$ gc/ml) and separately a mixture of AAV2/Anc80.CMV.harmonin-a1 ($1.7 \times 10^{12}$ gc/ml)+ AAV2/Anc80.CMV.harmonin-b1 (0.5 µl+0.5 µl) were performed and mechanotransduction responses assessed 2 weeks after treatment. Tissue was extracted at P5-P6, before the cochlea became ossified and was maintained in culture for 10 days. Although mature OHCs (>P10) do not survive ex-vivo recording paradigms, robust electrophysiological recordings were obtained from IHCs at the equivalent of P14-P16. Results are presented in FIG. 8. While IHCs from uninjected mice displayed severely reduced transduction currents at P16 (79±43 pA, n=8), recovery of sensory transduction was evident in mice that received the AAV treatment. Significant recovery (*$P<0.001$) was observed in mice injected at P1 with harmonin-b1 or a combination of both b1 and a1 with respective average maximal transduction currents of 388±66 pA (n=15) and 352±28 pA (n=7; FIG. 8C**). Transduction current amplitudes in IHCs after treatment with harmonin-b1 were not significantly different from control c.216GA mice. The level of recovery was not significantly altered by co-injection of harmonin-b1 and harmonin-a1. These results suggest that delivery of exogenous harmonin-b1 via RWM injection at early stages can restore mechanotransduction in IHCs.

Example 2D—Confocal Imaging

To prepare the tissue for confocal imaging from postnatal mice P0-P8, fixation was performed for 15 min with 4% Paraformaldehyde (PFA). Permeabilization with 0.01% triton and counterstaining with Alexa Fluor phalloidin (Invitrogen, 1/200) was used to labeled actin filaments. Images were obtained on a LSM700 Zeiss confocal microscope. In older mice (4 to 8 weeks), temporal bones were removed after euthanasia and placed in 4% PFA for 1 hour, followed by decalcification for 24 to 36 hours with 120 mM EDTA. The sensory epithelium was then dissected out and injected as above for immunostaining. Mouse anti-CTBP2 (BD bioscience #612044, 1/200) was applied for 48 hours and counterstained with Alexa Fluor goat anti-mouse (1/200) overnight at 4° C. to label ribbon synapses. Images were acquired on a Zeiss LSM 710 laser confocal microscope (IDDRC Imaging Core grant P30 HD18655) and processed with Zeiss LSM image viewer 4.2.

Figure 7:
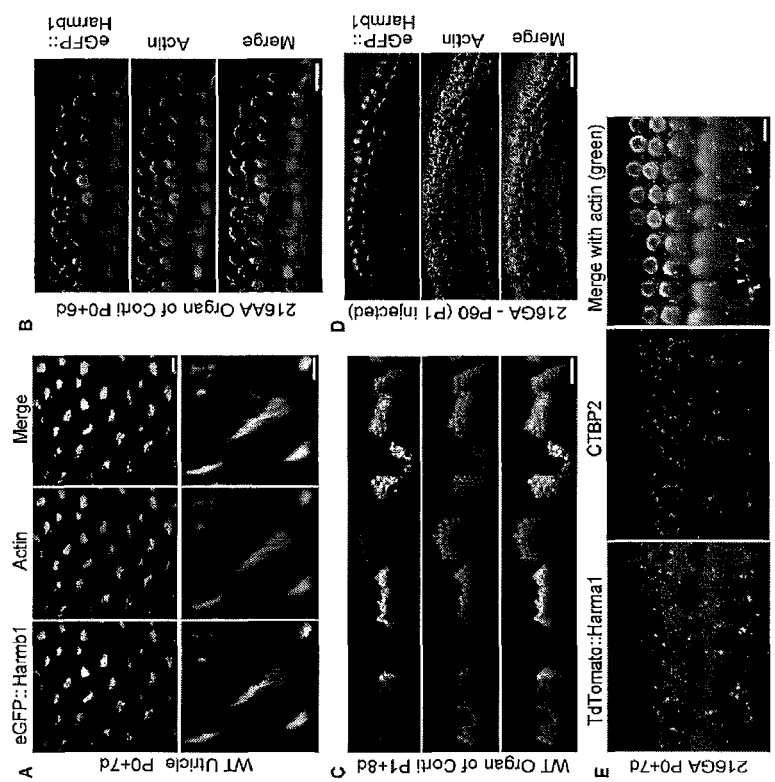
FIGS. 7A-7E are images showing expression and localization of fluorescently labeled harmonin in tissues exposed to adeno-associated viral vectors in vitro and in vivo. (A-C) Acutely dissected P0-P1 inner ear tissue were exposed to AAV2/1 vectors for 24 h, kept in culture for 7 to 8 days before being fixed, counterstained (Alexa Fluor phalloidin, Invitrogen) and imaged with a Zeiss LSM confocal microscope. A large number of sensory hair cells were infected in wild-type utricle and expression of harmonin-b1 fused to EGFP was evident in most hair cells with specific localization at the apex of the sensory hair bundle (A, scale bar: 10 µm—upper panels; 5 µm—lower panels). Similarly expression of EGFP::harmonin-b1 was evident at the tip of the stereocilia in OHCs and IHCs of c.216AA and wild-type mice (B, scale bar: 10 µm; C, scale bar: 3 µm). When AAV2/1.CMV.EGFP::harmonin-b1 vectors were injected at P1, EGFP signal was detected in some IHCs and OHCs at P60 in the left injected ear (D, scale bar: 30 µm). Exogenous tdTomato::harmonin-a1 was detected in the cell body of IHCs and OHCs in P7 organotypic cultures exposed to AAV2/1.CMV.tdTomato::harmonin-a1 for 24 h at P0 (E, scale bar: 5 µm). Some harmonin-a1 puncta were colocalized with CTBP2 (blue; mouse anti-CTBP2 1/200, BD bioscience) in particular at the base of the sensory cells presumably near the ribbon synapse. No expression was observed in the stereociliary bundle.

Previous work revealed expression of two alternative splice forms of harmonin in sensory hair cells. To assess the ability of AAV vectors to drive expression of exogenous harmonin splice forms, utricles and organs of Corti from neonatal c.216AA and wild-type (C57BL/6J) mice were exposed to AAV2/1 vectors coding for eGFP fused to the N-terminus of harmonin-b1 (eGFP::harmonin-b1) or tdTomato fused to the 181 N-terminus of harmonin-a1 (tdTomato::harmonin-a1). The vectors were applied either in vitro or in vivo through RWM injection (1 µl) at P1. When applied in vitro, P0-P1 tissues were incubated in the presence of the vectors for 24 hours and maintained in culture for one week. Confocal images show that hair cells of wild-type, c.216GA and c.216AA mice were successfully transduced (FIG. 7A-7C, 7E). EGFP::harmonin-b1 signal was evident at the tips of the stereocilia in VHCs (FIG. 7A), IHCs and OHCs (FIG. 7B, 7C). EGFP signal was also detected at P60 in OHCs and IHCs in the basal portion of the cochlea of mice injected at P1 (FIG. 14D). TdTomato::harmonin-a1 was detected at the base of auditory hair cells (FIG. 14E). Co-staining with a ribbon synapse marker CTBP2 frequently revealed colocalization in P7 IHCs (FIG. 14E) but not in P7 utricles (data not shown). Localization of exogenous fusion constructs was consistent with previous work that localized harmonin-b to the distal end of stereocilia, near the tip-link insertions (26, 27, 28) and harmonin-a to the synapse (30, 31).

Example 2E—Auditory Brainstem Responses (ABRs) and Distortion Products (DPOAEs)

ABRs and DPOAEs were recorded from mice anesthetized with xylazine (5-10 mg/kg i.p.) and ketamine (60-100 mg/kg i.p.). Subcutaneous needle electrodes were inserted into the skin a) dorsally between the two ears (reference electrode); b) behind the left pinna (recording electrode); and c) dorsally at the rump of the animal (ground electrode). The meatus at the base of the pinna was trimmed away to expose the ear canal. For ABR recordings the ear canal and hearing apparatus (EPL Acoustic system, MEEI, Boston) were presented with 5-millisec tone pips. The responses were amplified (10,000 times), filtered (0.1-3 kHz), and averaged with an analog-to-digital board in a PC based data-acquisition system (EPL, Cochlear function test suite, MEEI, Boston). Sound level was raised in 5 to 10 dB steps from 0 to 110 dB sound pressure level (decibels SPL). At each level, 512 to 1024 responses were averaged (with stimulus polarity alternated) after "artifact rejection". Threshold was determined by visual inspection. Data were analyzed and plotted using Origin-2015 (OriginLab Corporation, MA). Thresholds averages±standard deviations are presented unless otherwise stated. For DPOAEs, f1 and f2 primary tones (f2/f1=1.2) were presented with f2 varied between 5.6 and 45.2 kHz in half-octave steps and L1-L2=10 dB SPL. At each f2, L2 was varied between 10 and 80 dB SPL in 10 dB SPL increments. DPOAE threshold was defined from the average spectra as the L2-level eliciting a DPOAE of magnitude 5 dB SPL above the noise floor. The mean noise floor level was under 0 dB SPL across all frequencies. Stimuli were generated with 24-bit digital I-O cards (National Instruments PXI-4461) in a PXI-1042Q chassis, amplified by an SA-1 speaker driver (Tucker-Davis Technologies, Inc.), and delivered from two electrostatic drivers (CUI CDMG15008-03A) in our custom acoustic system. An electret microphone (Knowles FG-23329-P07) at the end of a small probe tube was used to monitor ear-canal sound pressure. The majority of these experiments were not performed under blind conditions.

To determine if truncated harmonin interfered with normal auditory function, Anc80.CMV.trunc-harm vectors were generated to over-express the truncated protein. The vectors were injected via RWM into the inner ears of c.216GA mice. ABR and DPOAES were measured at 4, 6 and 12 weeks and found no difference in thresholds between injected and uninjected c.216GA mice (recordings from 6 weeks old mice shown in FIG. 16C-16D). The data serve as a control for the injection technique, the vector and importantly, argue that exogenous truncated harmonin does not compete with endogenous full-length harmonin, implying that the endogenous truncated form in c.216AA hair cells is unlikely to interfere with exogenous full-length harmonin expressed via gene therapy vectors.

Figure 16:
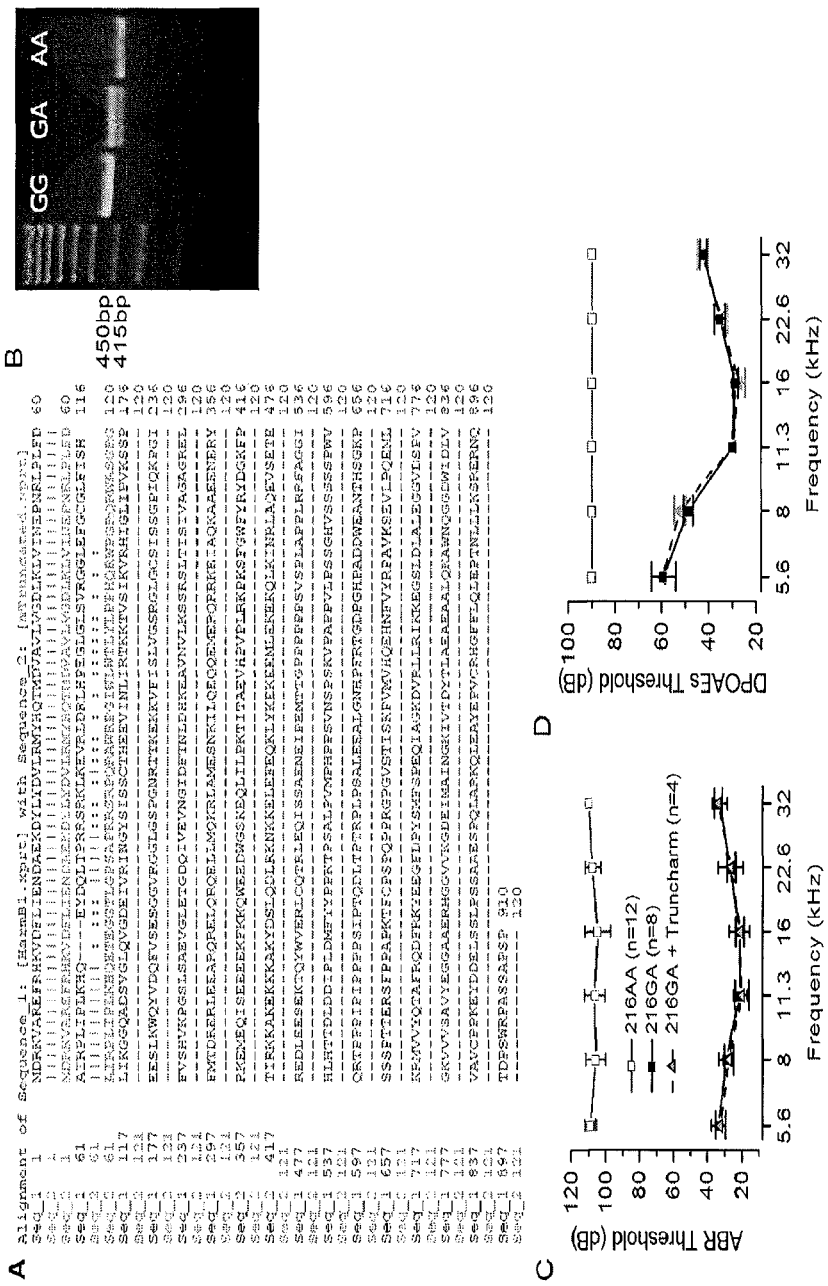
FIGS. 16A-16D show the mutant form of harmonin expressed in Ush1c c.216G>A mice does not alter hair cell or auditory function. (A) Sequence alignment between the wild-type harmonin-b1 protein (Seq_1: SEQ ID NO:34) and the truncated harmonin (Seq_2: SEQ ID NO:32) that is secreted as a result of the cryptic splicing and frame shift associated with the acadian G>A mutation in exon 3 of the Ush1c gene. (B) Semi-quantitative RT-PCR from auditory organs of P2-P3 wild-type mice, c.216GA and c.216AA mutant mice confirms expression of the wild-type (450 bp) and truncated (~35 bp) harmonin in c.216GA and c.216AA mice. (C-D) Auditory brainstem responses (ABR, C) and Distortion products (DPOAEs, D) were measured at 6 weeks old c.216GA injected mice and control c.216GA and c.216AA mice. Plots are shown as averages ±S.E. No threshold shift was observed in injected versus control 216GA mice.

To determine if harmonin gene augmentation can rescue auditory and balance function in Ush1c mice, P0-P1 RWM injections of AAV2/Anc80.CMV.harmonin-a1 (0.8 1.7× 10^12 gc/ml) or AAV2/Anc80.CMV.harmonin-b1 (0.8 µl, 1.9×10^12 gc/ml) were performed and auditory brainstem responses (ABRs), distortion product otoacoustic emissions (DPOAEs), acoustic startle reflexes, open field and rotarod behavior assessed. Mice were assessed at six weeks, a stage at which c.216AA mice suffer from profound hearing loss and vestibular dysfunction. Some of the mice were further tested at 3 and 6 months. None of the 12 mice injected with AAV2/Anc80.CMV.harmonin-a1 recovered auditory function at 6 weeks (FIG. 9A-9C), suggesting exogenous expression of harmonin-a1 was insufficient for auditory rescue. However, 19 of 25 mice injected with AAV2/Anc80.CMV.harmonin-b1 recovered significant auditory function at 6 weeks. At low frequencies (5.6 to 16 kHz), best ABR thresholds in AAV2/Anc80.CMV.harmonin-b1 injected ears were at 25-30 dB SPL, remarkably similar to thresholds of wild-type mice (FIG. 16A-16B). Partial rescue was observed at 22.6 kHz and little to none at 32 kHz. Rescue of DPOAE thresholds was also evident, consistent with rescue of function in OHCs (FIG. 16C). Eight of the mice that possessed auditory thresholds<45 dB SPL for stimuli 8-11.3 kHz were tested at later stages to assess the longevity of the rescue. From 6 weeks to 3 months, ~10 dB SPL ABR threshold shifts were observed in the low frequency range and ~30 dB SPL in the high frequency range (FIG. 16D). A similar shift was also observed in the DPOAEs thresholds (FIG. 16E). After this time point, ABR thresholds and DPOAEs remained stabled up to 6 months of age (FIG. 16D-16E), the latest time point tested.

Figure 9:
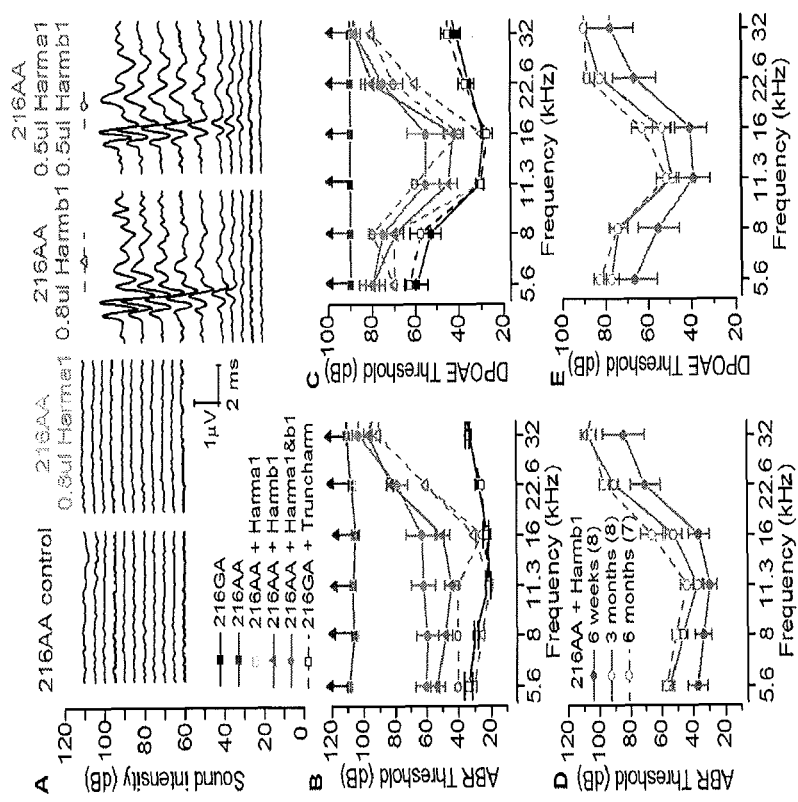
FIG. 9A-9E are images showing ABR and DPOAE threshold recovery in mice injected at P1 with AAV2/Anc80.CMV.harmonin-b1. (A) Representative ABR responses for 16 kHz tones in 6 weeks old c.216AA control mice and c.216AA mice injected at P1 via RWM injection of vectors encoding harmonin-a1, harmonin-b1 or a combination of the two. Recovered ABR thresholds near 30 dB SPL were measured in mice injected with harmonin-b1 alone or harmonin-a1 and b1 together. (B) Mean ABR responses obtained for: c.216 AA (n=13); c.216GA (n=12); c.216AA+harmonin-a1 (n=12); c.216AA+harmonin-b1 (n=19 rescued/25 tested); c.216AA+harmonin-a1&-b1 (n=6 rescued/11 tested). Mean±S.E, continuous lines. Dotted lines: ABR thresholds for the entire frequency range in mice whose 16 kHz recordings are shown in panel A. (C) Mean DPOAEs responses obtained for: c.216AA (n=13); c.216GA (n=12); c.216AA+harmonin-a1 (n=12); c.216AA+harmonin-b1 (n=15 rescued-DPOAEs<70 dB SPL/25 tested); c.216AA+harmonin-a1&-b1 (n=4 rescued DPOAEs<70 dB SPL/11 tested). Mean±S.E, continuous lines. Dotted lines: DPOAEs thresholds for the four mice whose recordings are illustrated in panel A. Arrows indicate that the thresholds are higher than the maximal stimulus level tested. (D-E) ABRs and DPOAEs responses obtained at 6 weeks and 3 months in eight mice that showed initial ABR thresholds under or equal to 45 dB. Six of the eight mice were kept for 6 months and had ABRs and DPOAEs assessed (dotted line). Mean±S.E. While ABRs and DPOAEs thresholds shifts were evident over the first three month, hearing rescue was still prominent at 6 months of age in the lower frequency range.
Figure 14:
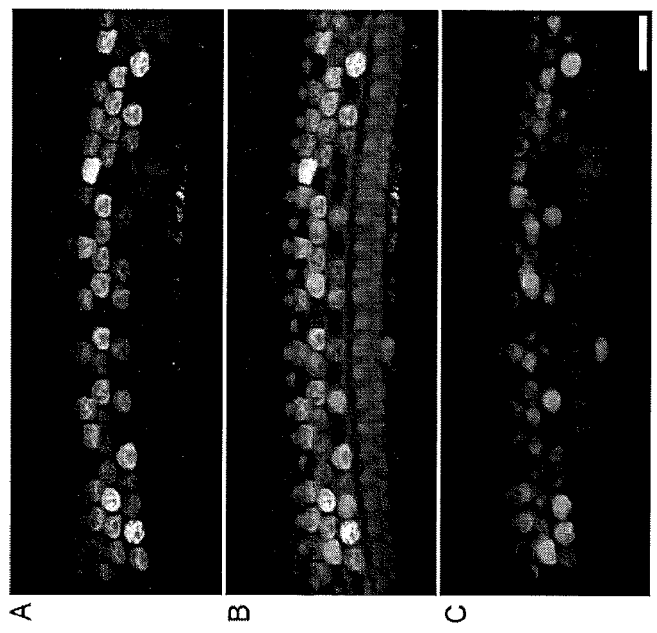
FIGS. 14A-14C are images showing expression of fluorescently labeled harmonin-a and harmonin-b Anc80 vectors at 6 weeks in c.216AA organ of Corti after P1 dual vector injection. (A-C) Confocal images of the basal turn in 6 weeks old c.216AA mice after P1 co-injection of AAV2/Anc80.CMV.tdTomato::harmonin-a1 (0.5 µl; $4.11E^{12}$ gc/ml) and AAV2/Anc80.CMV.eGFP::harmonin-b1 (0.5 µl; 2.99E^12 gc/ml). 69% and 74% of the total number of cells respectively expressed eGFP (A) and tdTomato (C) and 65% expressed both markers demonstrating successful co-transduction. Scale bar: 20 µm.

To assess whether both harmonin-a1 and harmonin-b1 are required for more complete auditory rescue, particularly at the high frequency end, AAV2/Anc80.CMV.tdTomato::harmonin-a1 (0.5 µl; 238 4.1E^12 gc/ml) and AAV2/Anc80.CMV.eGFP::harmonin-b1 (0.5 µl; 3.0E^12 gc/ml) were co-injected. 65% of the hair cells expressed both harmonin-a1 and harmonin-b1, as evident from cells positive for both fluorescent tags (FIG. 14). Fluorescently labeled harmonin-a1 was occasionally observed in the stereocilia of mice exposed to AAV2/Anc80.CMV.tdTomato::harmonin-a1, perhaps due to over expression. ABR and DPOAE thresholds in mice co-injected with unlabeled harmonin-a1 and harmonin-b1 vectors (FIG. 9) were similar to those injected with harmonin-b1 alone and did not provide further improvement, suggesting that harmonin-a1 may be dispensable for auditory function. Importantly, the data demonstrate that harmonin-b1 alone is sufficient for significant restoration of auditory thresholds at low frequencies (FIG. 9).

Figure 15:
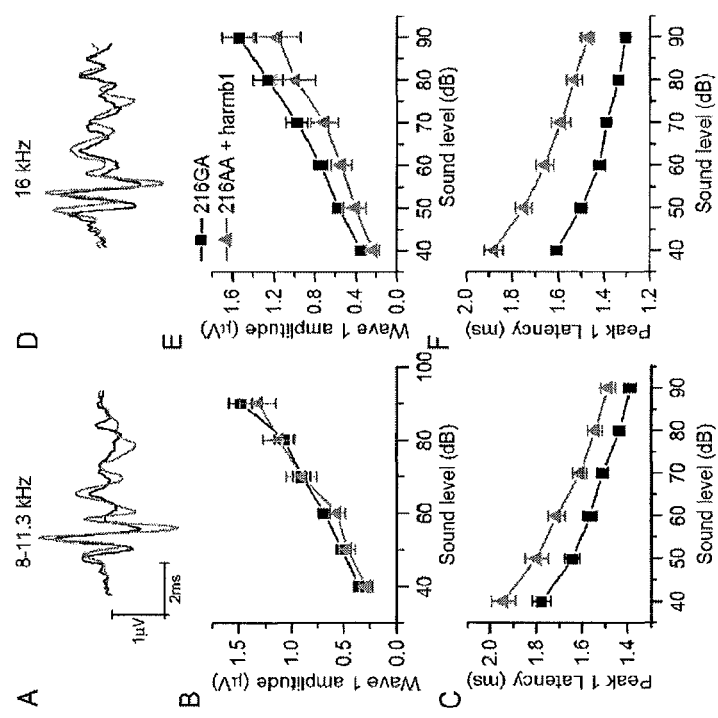
FIGS. 15A-15F are data showing an analysis of ABR response in 6 weeks old control c.216GA and injected rescued c.216AA mice. (A, D) Example of ABR responses at 8 and 16 kHz for control c.216GA and rescued c.216AA mice. (B-C, E-F) Average peak 1 amplitude (B-D) and latency (C-D) at 8-11.3 and 16 kHz in 6 weeks old mice with comparable thresholds (n=8 c.216GA, n=5 c.216AA+Harmonin-b1 RWM P1). Mean±S.E.: One-way ANOVA.

To further evaluate the extent of the rescue, ABR waveforms, from mice with thresholds≤45 dB SPL, were analyzed and compared between eight control c.216GA mice and five c.216AA mice injected with AAV2/Anc80.CMV.harmonin-b1. The analysis for responses at 8-11.3 kHz and 16 kHz revealed normal wave 1 amplitudes (non-significant differences, P>0.2, Student t-test) and longer peak 1 latencies (P>0.001) (FIG. 15), suggesting a possible lag in neurotransmission at the synapse. In many animals, auditory rescue was also observed in the contralateral ear, with ABR thresholds as low as 20 dB SPL at 11.3 kHz (harmonin-b1: average 59.7±5.3 dB SPL, n=15/25; harmonin-a1+-b1: 255 average 76.2±10.3 dB SPL, n=4-6). Diffusion of AAV vectors to the contralateral ear has been previously observed (37) and likely occurs via the perilymphatic duct that remains continuous with the subarachnoid space in newborn mice.

We also wondered whether injections at later developmental stages might lead to partial auditory rescue. RWM injections of AAV2/Anc80.CMV.harmonin-b1 (0.8 µl) at P10-P12 were performed and auditory thresholds assessed at 6 weeks. None of the P10-P12 injected mice had detectable DPOAEs and their ABR thresholds did not differ from the uninjected c.216AA control mice (n=10; data not shown), suggesting the window of opportunity for intervention may be limited to early postnatal stages, possibly due to low viral transduction efficiency in older tissue or degeneration of the organ of Corti at later development stages.

Example 2F—RT-PCR in the Usher Mouse Model cDNA was prepared from 6 auditory organs of P2-P3 wild-type, heterozygous and homozygous Ush1c c.216G>A mice using QuantiTect Revese Transcription Kit (Qiagen). cDNA encoding full length (450 bp) or truncated harmonin (−35 bp) was amplified using the following primers: Forward primer mUsh1c_Ex2F: 5' CTC ATT GAA AAT GAC GCA GAG AAG G 3', Reverse mUsh1c_Ex5R: 5' TCT CAC TTT GAT GGA CAC GGT CTT 3'. These primers are specific for mouse Ush1c sequences and will amplify both endogenous and AAV2-derived Ush1c as the target sequence is outside the region of the human knocked in portion of the Ush1c c.216A allele. DNA and RNA levels were also assessed from mouse tissue collected at six weeks posttreatment. DNA and RNA were isolated from the cochlea using TRIzol reagent (Life Technologies, Carlsbad, Calif.) according to the manufacturer's protocol. RNA was reverse transcribed using GoScript reverse transcription system (Promega, Madison, Wis.). Radiolabeled PCR was carried out using GoTaq Green Master Mix (Promega, Madison, Wis.). For viral DNA amplification, primers specific for mouse Ush1c: mUsh1c_Ex3F (5'-GAA CCC AAC CGC CTG CCG) and mUsh1c_Ex4WTR (5'-TGC AGA CGG TCC AAG CGT-3') were used. These primers will only amplify the viral Ush1c DNA because the homozygous Ush1c.216AA mice have the human USH1C c.216A gene knocked in to exon 3 and 4, replacing the mouse sequence (32). For cDNA amplification of full-length (450 bp) and aberrantly spliced/truncated harmonin (415 bp), the same primers as above were used (mUsh1c_Ex2F and mUsh1c_Ex5R). Gapdh primers were: mGapdh_Ex3F (5'-611 GTG AGG CCG GTG CTG AGT ATG-3') and mGapdh_Ex4R (5'-GCC AAA GTT GTC ATG GAT GAC-3'). Products were separated on a 6% nondenaturing polyacrylamide gel and quantified using a Typhoon 9400 phosphorimager (GE Healthcare).

Since previous studies raised the possibility that truncated harmonin may disrupt function by competing with full-length harmonin for endogenous binding partners (34, 35), we wondered whether persistent expression of the truncated protein may limit recovery in c.216AA mice injected with vectors that express exogenous full-length harmonin (FIG. 16A). To address this concern, expression of Ush1c transcripts in c.216GA and c.216AA mice was examined using an RT-PCR assay. Consistent with previous reports, Ush1c transcripts that encoded full-length and truncated harmonin were detected in c.216GA cochleas and only transcripts that encoded truncated harmonin were detected in c.216AA cochleas (FIG. 16B).

Figure 17:
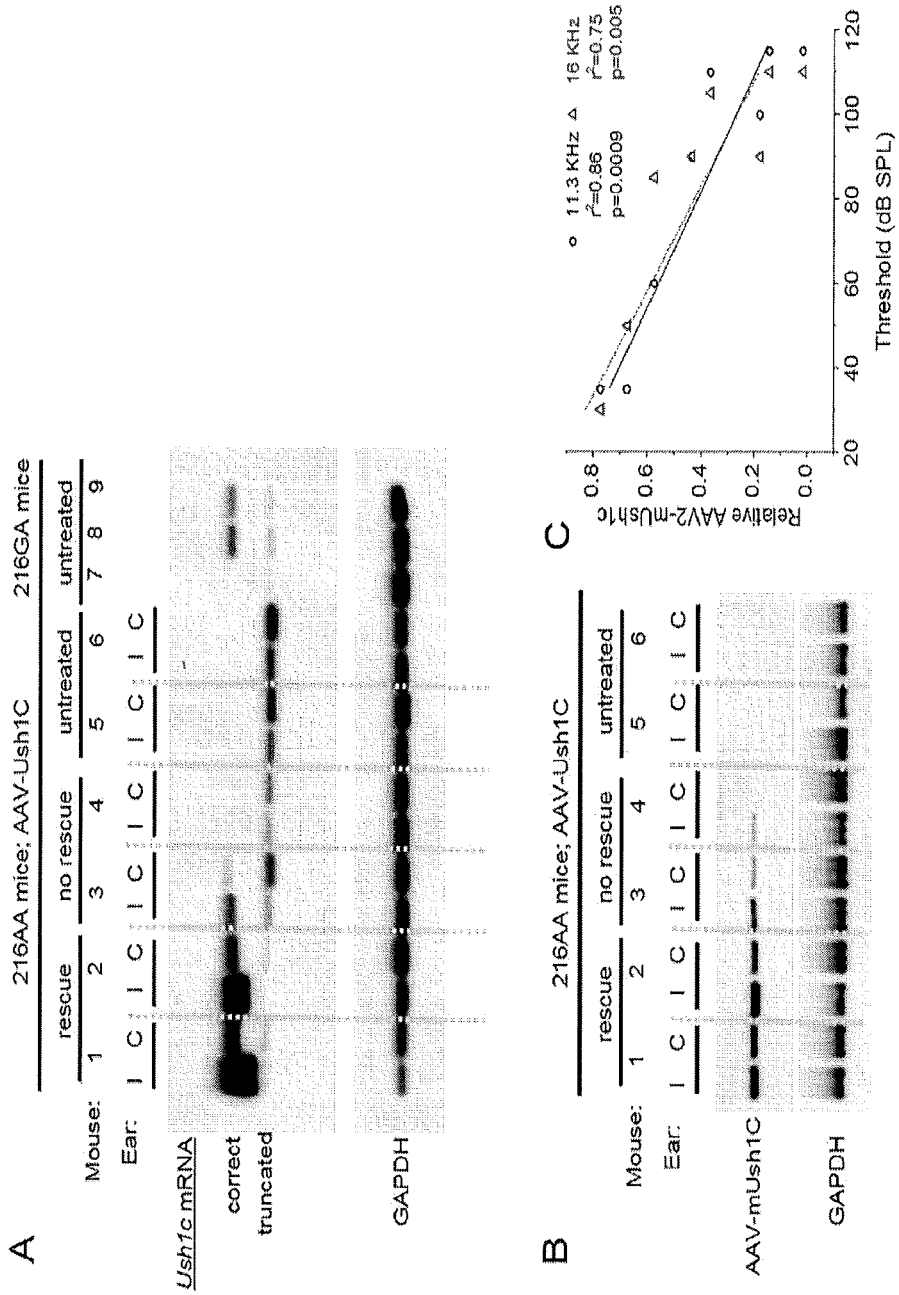
FIGS. 17A-17C are images showing recovery of correct Ush1c splicing in the inner ear of 6 weeks old mice injected with AAV2/Anc80.CMV.harmonin-b1. (A) Semi-quantitative RT-PCR quantification of correctly spliced (450 bp) and aberrant (415 bp) mRNA from the Ush1c.216A allele shows recovery of correct Ush1c splicing in injected (I) and contralateral ears (C) of c.216AA rescued mice #1 and #2 (35 dB SPL response at 11.3 kHz from injected ears). Mouse #3 with poor ABR response (90 dB SPL at 11.3 kHz) shows modest recovery of correct mRNA expression and mouse #4 (100 dB SPL at 11.3 kHz) shows none. While the correct splice form is not detected in uninjected c.216AA mice (mice #5,6), both the correct and truncated splice forms are detected in c.216GA mice (mice #7,8,9). Corresponding mouse Gapdh shown in the bottom panel was amplified to confirm the relative amount of material. (B) Semi-quantitative radiolabeled PCR analysis confirms the presence AAV-mUsh1c in injected and contralateral ears of Ush1c.216AA mice. Relative levels of AAV-mUsh1c DNA were present but reduced in mice #3 and #4. (C) Relative amount of AAV-mUsh1c correlates with ABR thresholds. Analysis for 11.3 and 16 kHz are illustrated. Linear regressions show high correlations between the two.
Figure 17D:
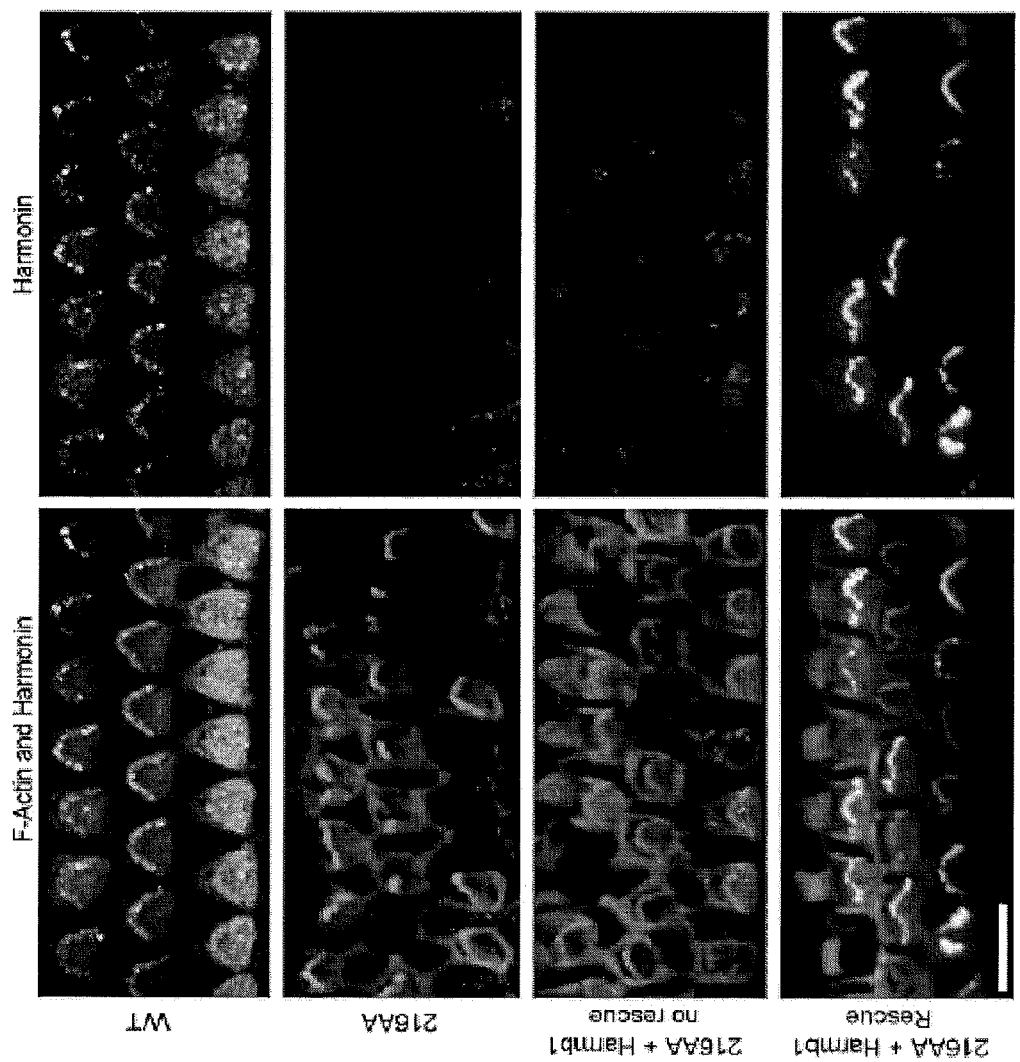
Figure 18:
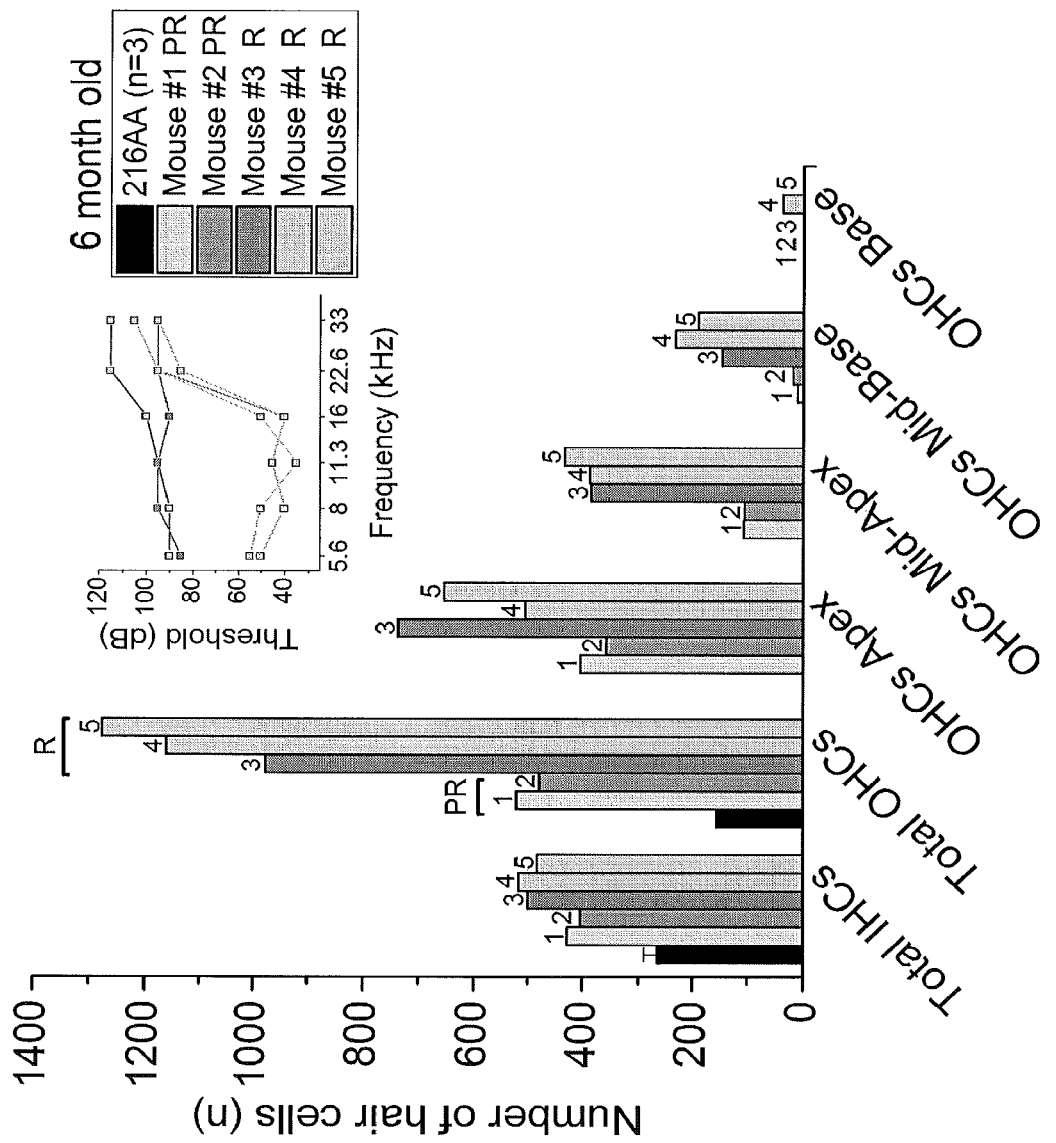
FIG. 18 is a graph showing long term ABR threshold recovery correlates with OHCs survival in the mid to apical region of the auditory organ. Hair cell count across the entire Organ of Corti was performed post-mortem in left ears of three uninjected c.216AA and five injected c.216AA (P1 RWM injection, 0.8 µl AAV2/Anc80.CMV.harmonin-b1) at 6 months of age. Insert: While two of the mice (#1 and #2) showed poor ABR response thresholds across the entire range tested (≥95 dB SPL), three (#3-5) responded with thresholds ranging 35 and 55 dB SPL for sound stimuli between 5.6 and 16 kHz. The total number of IHC and OHCs hair cells was increased in injected mice. Comparison of rescued injected mice with those injected that had poor rescue shows that the number of IHCs was not different but a significant number of OHCs were noted in the rescued mice. Analysis across the entire length of the organ showed the difference can be accounted for as an increase in hair cell survival from the mid to apical regions of the organ.
Figure 19:
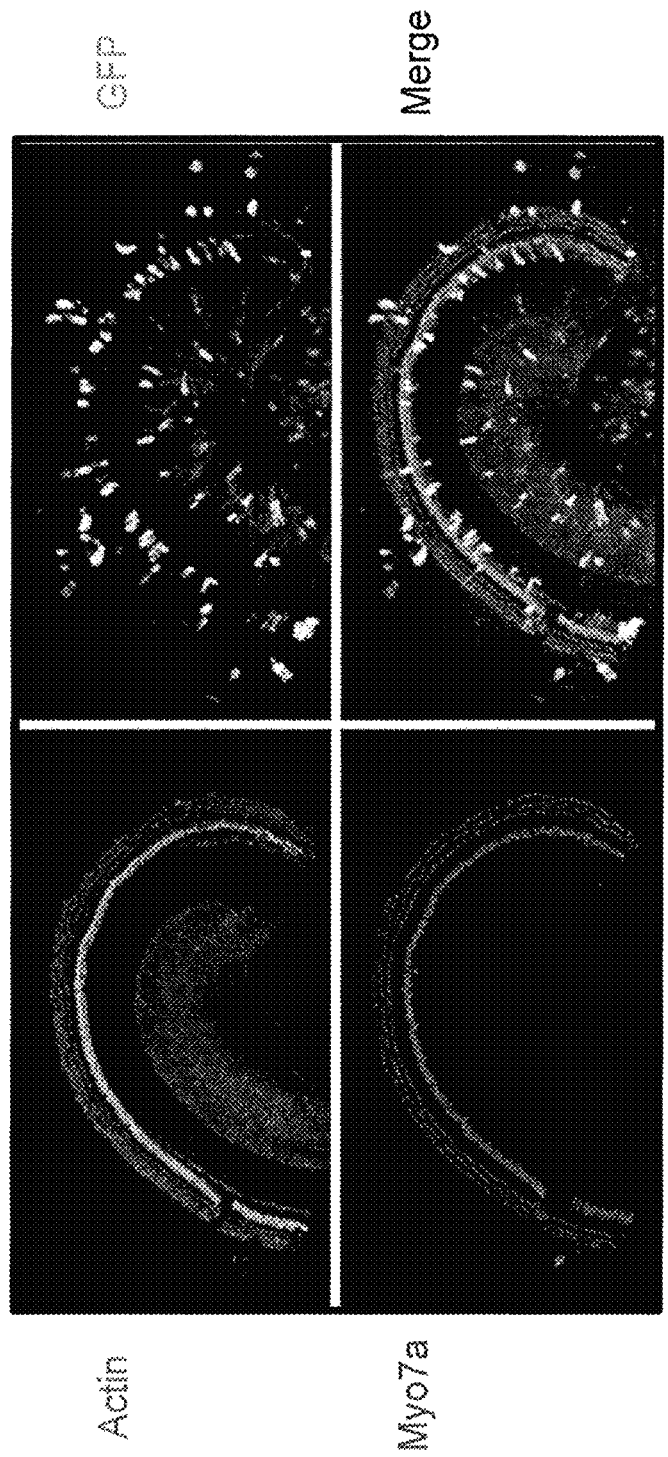

To confirm expression of AAV2/Anc80.CMV.harmonin-b1 and explore the relationship between viral expression level and ABR thresholds, DNA and RNA were isolated from injected and contralateral cochleae and quantified by PCR and RT-PCR, respectively. Expression was assessed in six-week old c.216GA and AAV2/Anc80.CMV.harmonin-b1 (0.8 µl; 1.93 10^12 gc/ml)-injected and non-injected c.216AA mice. Samples included two injected mice with good ABR rescue (thresholds≤35 dB SPL at 11.3 kHz) and two with poor ABR rescue (thresholds≥90 dB SPL at 11.3 kHz). RNA encoding the correct splice form of harmonin (FIG. 18A) and AAV2/Anc80.CMV.harmonin-b1 DNA (FIG. 18B) were detected in all of the injected cochleae and, to a lesser extent, in the contralateral cochleae of all animals tested. There was variability between animals in ABR thresholds and amount of DNA and RNA expressed (FIG. 18C). However, a strong correlation was found between AAV2/Anc80.CMV.harmonin-b1 DNA levels, the amount of RNA encoding for the correct splice form of harmonin and ABR threshold levels, which suggests that the variability in ABR data may be a direct result of AAV expression. To assess long term hair cell survival in mice that had successful recovery of ABR thresholds, tissue was prepared and the number of IHCs and OHCs counted at 6 months of age from 5 mice (FIG. 17). While the number of IHCs did not vary in the two cohorts, 50% or more OHCs remained in the three mice that showed long term ABR rescue. OHC survival was observed along the entire organ with the exception of the basal turn (FIG. 17).

Example 2G—Acoustic Startle Responses

The acoustic startle responses (ASR) were measured using the Startle Monitor (Kinder Scientific). Mice were placed in a small-sized, nonrestrictive, cubical Plexiglas recording chamber (27 cm×10 cm×652 12.5 cm) fixed on a piezo/plexiglass sensing assembly and allowed to acclimate for 5 min with a 60 dB SPL background white noise. Each session consisted of 35 trials, during which a single noise pulse ranging in 10 dB SPL intensities from 60-120 db SPL was delivered with an inter-trial interval averaging 30 s (25-35 s range). Pulses were arranged in a pseudorandom order, on a constant 60 dB SPL background noise to limit external noise interference. The Startle Monitor system reduced the response to each pulse into measurements of first N, max N, and max time of the response (ms), for calculations of peak startle response (ASR amplitude) and time from stimulus to peak startle response (ASR latency). ASR were all conducted blind.

To assess whether the ABR/DPOAE recovery yielded behaviorally relevant recovery of auditory function, acoustic startle responses was measured in mice injected with AAV2/Anc80.CMV.harmonin-a1, AAV2/Anc80.CMV.harmonin-b1 and those injected with both vectors. Analysis of the startle response to white noise showed partial rescue of the response in 6 weeks old mice injected with AAV2/Anc80.CMV.harmonin-b1 and in mice that were co-injected with both vectors (FIG. 10A). Mice that received harmonin-a1 alone were similar to uninjected c.216AA mice and did not recover startle responses.

Example 2H—Vestibular Assessment

Vestibular function was assessed using open field and rotarod balance test. The open field test was conducted using a circular frame measuring 42 cm in diameter, placed inside a sound chamber with overhead LED lighting, set to 30 lux at the center, inside a dimmed room. Mice were placed one at a time inside the circular open field, and allowed to explore for 5 min. Behavior was recorded and tracked using Ethovision XT, enabling measures of distance traveled and velocity. Open field assessments were all conducted blind. The rotarod performance involved placement of mice on a rod in an enclosed housing that began rotating at 4 rpm and accelerated at a rate of 0.1 rpm s-1. The mice were placed on the rods on day one for 5 min to get familiarized with the equipment. The next day, the animals were placed on the rods for a total of 5 trials. A 5 min resting period was imposed between trials. The length of time the animals were able to remain on the device before dropping onto the instrumented floor of the housing was displayed on a timer and recorded after each test run.

Since the perilymphatic space is continuous between the cochlea and vestibular labyrinth, AAV vectors injected via RWM may transduce vestibular sensory organs as well. To assess vestibular behavior, mice were tested for their performance on a rotarod. While poor rotarod performance was observed in c.216AA and c.216AA mice injected with AAV2/Anc80.CMV.harmonin-a1 mice (latency to fall <22 sec on average), c.216AA mice injected with AAV2/Anc80.CMV.harmonin-b1 and those co-injected with harmonin-a1 and -b1 vectors maintained balance function on the rotarod for 60-120 seconds, consistent with control c.216GA mice (FIG. 10B).

Recovery in open field behavior was also observed in harmonin-b1 and dual harmonina1 and b1 injected c.216AA mice. Representative open-field exploration traces are plotted in FIG. 17C. c.216GA mice explored the border of the field and displayed minimal full body rotations, whereas c.216AA mice displayed more activity throughout the entire chamber with increased full body rotations quantified as rotations/min (FIG. 10D-10E). Surprisingly, while no ABR rescue was observed in mice injected with AAV2/Anc80.CMV.harmonin-a1, open field data demonstrated recovery of vestibular function to the level of the control mice. Behavior of c.216GA mice injected with AAV2/Anc80.CMV.trunc-harmonin did not differ from the control c.216GA mice, again indicating a lack of interference between truncated and wild-type harmonin (FIG. 10C-10E).

Figure 6:
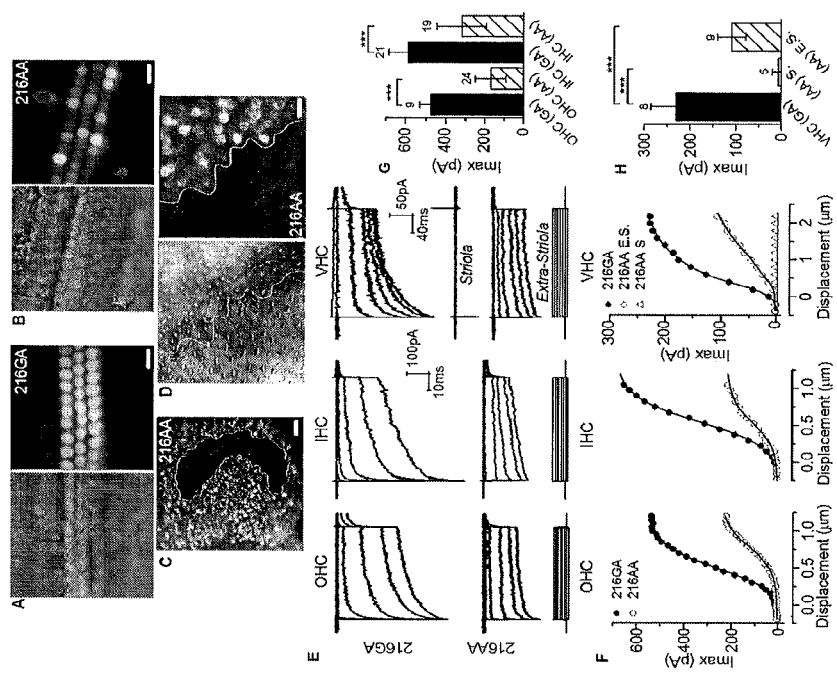
FIGS. 6A-6H are images showing mechanotransduction in hair cells of Ush1c c.216G>A neonatal mutant mice. (A-D) The permeable styryl dye FM1-43 was used to assess the presence of open transduction channels in hair cells of c.216GA and c.216AA mice. In the organ of Corti, FM uptake was reduced in sensory hair cells of c.216AA mice at P4 (A-B, mid base). Note that IHC FM1-43 fluorescence appears dimmer as IHCs are in a different focal plan. Left: DIC, Right: FM1-43; Scale bar 10 µm. In the utricle, FM1-43 uptake was restricted to the extra-striola region in c.216AA mutants at P6 (C; scale bar 50 µm) while utricular hair cells retained gross normal bundle morphology as assessed by DIC (D; scale bar 10 µm). The white line on panel D delineate the striola (no uptake) and extra-striola regions (uptake). Experiment was repeated three times. (E-H) Mechanotransduction was assessed in OHCs, IHCs and VHCs in neonatal c.216GA and c.216AA mice (number of mice recorded from respectively are: n=7, 6 for OHCs, n=2, 4 for IHCs and n=2, 6 for VHCs, number of cells are indicated above the bar graph). Representative transduction currents (E), their associated current/displacement plots fitted with a second order Boltzmann function (F) and average peak transduction current are plotted (G-H). In the cochlea, recordings were obtained in the middle and mid-apical turn of the organ at P3-P6. In the utricle transduction currents were recorded from VHCs of the extra-striola and striola region between P5 and P7 (E-F). While hair bundles appeared well preserved under DIC, smaller average transduction currents were evoked in c.216AA mutants (H). Average peak transduction was significantly different between the two genotypes in OHCs, IHCs and VHCs (***$P<0.01$, One-way ANOVA).
Figure 10:
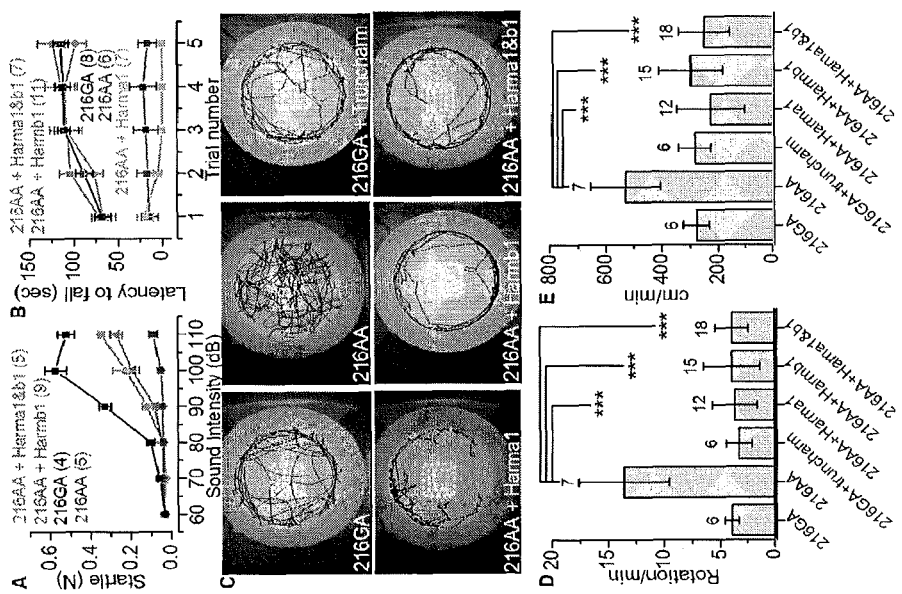
FIG. 10A-10E are images showing startle response, rotarod performance and open field behavior recovery in mice injected at P1 with AAV2/Anc80.CMV.harmonin-a1 and AAV2/Anc80.CMV.harmonin-b1. (A) Startle response to white noise stimuli was recorded in 6 weeks old control c.216GA, c.216AA and c.216AA injected mice. Partial startle rescue was evident in mice injected with harmonin-b1 but not harmonin-a1 (data overlapping with control c.216AA mice). Averages are shown ±S.E. (B) Rotarod performance was recorded between 4 and 6 weeks in control c.216GA, c.216AA and c.216AA injected mice. Full recovery was observed in mice injected with harmonin-b1 and harmonin-a1/b1. No recovery was observed with harmonin-a1 alone. Averages are shown ±S.E. (C-E) Open field observations were performed for 5 min in 6 weeks old control c.216GA, c.216AA and c.216AA and c.216GA injected mice. Representative tracks over 2.5 min are shown (B). While c.216AA mutant mice explore the entire field and perform repetitive full body rotations, c.216AA mice injected at Pb with harmonin-a1, harmonin-b1 or the combination of the two vectors demonstrate normal behavior similar to their heterozygous c.216GA counterparts or c.216GA mice injected with the truncated vector. (C). Graphs illustrate the mean±S.D. for the number of rotations and distance covered per minute. Significant recovery ***P<0.001 was observed between the uninjected and injected mice. Statistical analysis by one-way ANOVA.

Example 3—Polynucleotide Therapy of Additional Mutations Involved in Hearing Loss Example 3A—In Vivo Experiments Behavioral assays demonstrated partial vestibular rescue with harmonin-a1, as circling behavior was abolished but harmonin-a1 injected mice failed the rotarod test. Mice injected with harmonin-b1, on the other hand, had functional recovery in both tests (FIG. 10). The absence of transduction and FM1-43 uptake in the striola regions indicates that hair cells of the striola region and perhaps type I cell function depends on proper harmonin expression (FIG. 6).

While auditory rescue was prominent at low but not high frequencies (FIG. 9), preservation of hair bundle morphology at 6 weeks was observed along the entire organ (FIG. 11). The absence of rescue at high frequencies is unlikely due to damage caused by the injection. High frequency hearing loss was not observed in any of the c.216GA injected with AAV vectors (FIG. 16C-16D). AAV targeting along the entire length of the cochlea argues against a lack of transduction efficiency at the base as an explanation. One possibility is that other harmonin isoforms, such as the short harmonin-c, may be necessary for rescue of function in the basal high frequency end of the cochlea. Alternatively, since cochlear development begins at the basal end, it is possible that by P0, hair cells from the basal high frequency end have matured beyond the point of repair. If this is the case embryonic intervention may allow better rescue in the high frequency region.

Anc80 vectors carrying the coding sequence for mouse TMC1 driven by a modified CMV promoter were generated using a helper virus free system and a double transfection method as described previously (Grimm et al., 2003, Mol. Ther., 7:839:50). A triple flag-tag (FLAG) sequence was fused to the C-terminal end of the TMC coding sequence to enable visualization of the expressed protein. Anc80-CMV-Tmc vector was purified using an iodixanol step gradient followed by ion exchange chromatography. Titers ranged from $1\times10^{12}$ to $1\times10^{13}$ gc/ml as measured by quantitative PCR using primer sets specific for the human beta-globin intronic element. Virus aliquots were stored at $-80°$ C. and thawed just prior to use.

Mice, age P0-P2, were used for in vivo delivery of viral vectors as described below according to protocols approved by the Institutional Animal Care and Use Committee (protocols #2659, #2146) at Boston Children's Hospital. C57BL/6J (Jackson Laboratories) or Swiss Webster mouse lines (Taconic) were used for wild-type control mice, and mice that carried TMC1 mutant alleles (TMC1Δ/Δ or Tmc1 −/−) were on a C57BL/6J background as described previously (Kawashima et al., 2011, J. Clin. Invest., 121:4796-809).

To prepare tissue for evaluation, temporal bones were harvested from mouse pups at P0-P10. Pups were euthanized by rapid decapitation and temporal bones were dissected in MEM (Invitrogen) supplemented with 10 mM HEPES, 0.05 mg/ml ampicillin, and 0.01 mg/ml ciprofloxacin at pH 7.40. The membranous labyrinth was isolated under a dissection scope, Reissner's membrane was peeled back, and the tectorial membrane and stria vascularis were mechanically removed. Organ of *Corti* cultures were pinned flatly beneath a pair of thin glass fibers adhered at one end with Sylgard to an 18-mm round glass coverslip. The tissue was used acutely for electrophysiological studies. For mice older than P10, temporal bones were harvested after euthanizing the animal with inhaled $CO_2$, and cochlear whole mounts were generated.

All mean values and error bars presented in the figures represent mean±SD. Comparisons for statistical significance between injected ears and uninjected ears were performed using a two-tailed paired t test. $P<0.05$ was considered significant.

Example 3B—In Vivo Injection of Viral Vectors

Mouse pups (P0-P2) were injected via the round window membrane (RWM) using beveled glass microinjection pipettes. Pipettes were pulled from capillary glass on a P-2000 pipette puller (Sutter Instruments) and were beveled (~20 μm tip diameter at a 28° angle) using a micropipette beveler (Sutter Instruments). EMLA cream (lidocaine 2.5% and prilocaine 2.5%) was applied externally for analgesia using sterile swabs to cover the surgical site (left mastoid prominence). Body temperature was maintained on a 37° C. warming pad for 30-60 minutes prior to surgery.

Pups were anesthetized by rapid induction of hypothermia for 2-3 minutes until loss of consciousness, and this state was maintained on a cooling platform for 10-15 minutes during the surgery. The surgical site was disinfected by scrubbing with Betadine and wiping with 70% Ethanol in repetition three times. A post-auricular incision was made to expose the transparent otic bulla, a micropipette was advanced by micromanipulator (MP-30, Sutter Instrument Company) through the bulla and overlying fascia, and the RWM was penetrated by the tip of the micropipette.

Approximately 1 μl of virus at titers between $10^{12}$ and $10^{14}$ gc/mL ($10^9$ and $10^{11}$ total viral particles) was injected unilaterally at 0.1 μl/min into the left ear using a pneumatic microinjector (WPI Nanoliter 2010). The skin incision was closed using a 6-0 monofilament suture (Ethicon). Pups were then returned to the warming pad for recovery.

Example 3C—Immunofluorescence

Immunostaining was performed to determine the distribution of expression of a transgene delivered by a viral vector. To do so, immunostaining was performed on freshly dissected organs of Corti, immersion fixed for 1 h at room temperature with 4% paraformaldehyde diluted in PBS. The tissue was then rinsed in PBS, permeabilized in 0.01-0.1% Triton X-100 for 30 minutes, and counterstained for 1 h with AlexaFluor546-phalloidin (Molecular Probes, 1:200 dilution) to label filamentous actin.

For localization of exogenously expressed TMC::FLAG fusion proteins, the tissue was blocked for 1 hour using 2% BSA and 5% Normal Goat Serum, and was incubated overnight at 4° C. with an antibody to the FLAG motif (BD Biosciences, 1:200 dilution). For hair cell counts, tissue was blocked in Normal Goat Serum for 1 hour, stained with a rabbit anti-Myosin VIIa primary antibody (Proteus Biosciences, 1:1000 dilution) at 4° C. overnight, and labeled with goat anti-rabbit antibody conjugated to AlexaFluor488 (Life Technologies, 1:200 dilution) for 1 h. Samples were mounted on glass coverslips with Vectashield mounting medium (Vector Laboratories), and imaged at 10×-63× magnification using a Zeiss LSM700 confocal microscope.

Figure 13:
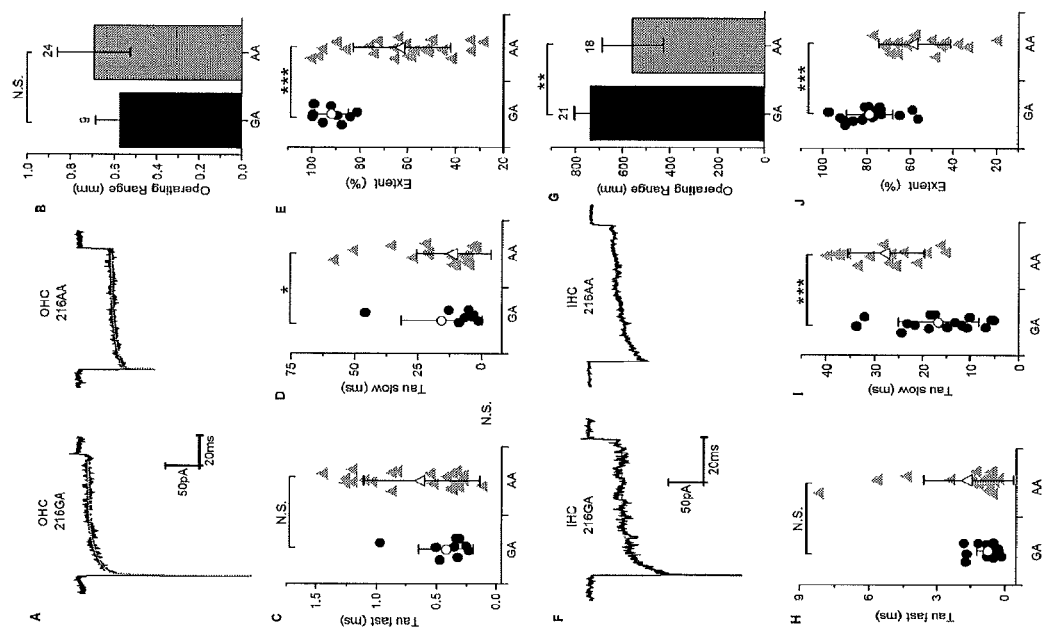
FIGS. 13A-13J are images showing mechanotranduction properties in c.216AA mutant mice. (A-E) Analysis of mechanotransduction in neonatal OHCs from middle and mid-apical turns of the cochlea, P3-P6. Representative current traces from ~Po=0.5 were fit with a double exponential decay function to assess adaptation in c.216GA and c.216AA mutant (A). Fits were used to generate fast (C) and slow (D) time constants as well as the extent of adaptation (E). The 10-90% operating range was not significantly altered (B). Extent of adaptation in c.216AA mice was significantly less than or heterozygous OHCs as shown in this scatter plot (E). (F-J) Analysis of mechanotransduction in neonatal IHCs. 10-90% operating range values were smaller in c.216GA versus c.216AA IHCs (G). Adaptation was always present albeit slightly slower and with a significant lesser extent in c.216AA IHCs (H-J). Statistical analysis is indicated in each plot: *P<0.05, P<0.01 and *P<0.001, one-way ANOVA.

FIG. 13 shows immunofluorescence that demonstrates uniform Anc80 delivery of Harmonin to Ush1c mutant mice, and FIG. 28 shows immunofluorescence that demonstrates Anc80 delivery of KCNQ4 to cells in KCNQ4 mutant mice.

Example 3D—Hair Cell Electrophysiology

Organotypic cochlear cultures were bathed in standard artificial perilymph containing 137 mM NaCl, 0.7 mM $NaH_2PO_4$, 5.8 mM KCl, 1.3 mM $CaCl_2$, 0.9 mM $MgCl_2$, 10 mM Hepes, and 5.6 mM D-glucose. Vitamins (1:50) and amino acids (1:100) were added to the solution from concentrates (Invitrogen), and NaOH was used to adjust the final pH to 7.40 (310 mosmol/kg). Recording pipettes (3 to 5 megohms) were pulled from R6 capillary glass (King Precision Glass) and filled with intracellular solution containing 135 mM CsCl, 5 mM Hepes, 5 mM EGTA, 2.5 mM $MgCl_2$, 2.5 mM Na2— adenosine triphosphate, and 0.1 mM $CaCl_2$, where CsOH was used to adjust the final pH to 7.40 (285 mosmol/kg). Whole-cell, tight-seal voltage-clamp recordings were done at −84 mV at room temperature (22° to 24° C.) using an Axopatch 200B amplifier (Molecular Devices). Sensory transduction currents were filtered at 10 kHz with a low-pass Bessel filter and digitized at ≥20 kHz with a 16-bit acquisition board (Digidata 1440A) and pCLAMP 10 software (Molecular Devices). Data were stored for offline analysis using OriginPro 8 (OriginLab).

FIG. 23 shows recovery of potassium currents to near wild type levels (FIG. 23A) in KCNQ4 −/− cells transfected with Anc80-KCNQ4 relative to the mutant mice (FIG. 23B).

Example 3E—Auditory Brainstem Responses (ABR)

ABR recordings were conducted as described previously (Maison et al., 2010, J. Neurosci., 30:6751-62). Briefly, P25-P30 mice were anesthetized via IP injection (0.1 ml/10 g-body weight) with 50 mg of ketamine and 5 mg of xylazine diluted into 5 ml of 0.9% saline. ABR experiments were performed at 32° C. in a sound-proof chamber. To test hearing function, mice were presented pure tone stimuli of 5.6 kHz, 8 kHz, 11.3k Hz, 16 kHz, 22.6 kHz, or 32 kHz at sound pressure levels between 10 and 115 dB in 5 dB steps until a threshold intensity that evoked a reproducible ABR waveform (peaks I-IV) was detected. Using an alternating polarity stimulus, 512 to 1024 responses were collected and averaged for each sound pressure level. Waveforms with amplitude larger than 15 µV (peak-to-trough) were discarded by an "artifact reject" function. Prior to the onset of ABR testing, the flap of skin and cartilage that typically obscures the entrance of the external auditory meatus was trimmed away with dissecting scissors, and sound pressure at the entrance of the ear canal was calibrated for each individual test subject at all stimulus frequencies. Acoustic stimuli were delivered directly to the studied ear through a custom probe tube speaker/microphone assembly (EPL PXI Systems) consisting of two electrostatic earphones (CUI Miniature Dynamics) to generate primary tones and a Knowles miniature microphone (Electret Condenser) to record ear-canal sound pressure. Sound stimuli consisted of 5-ms tone bursts (0.5 ms rise-fall with a $\cos^2$ onset, delivered at 40/s). ABR signals were collected using subcutaneous needle electrodes inserted at the pinna (active electrode), vertex (reference electrode), and rump (ground electrode). ABR potentials were amplified (10,000×), pass-filtered (0.3-10 kHz), and digitized using custom data acquisition software (LabVIEW). Sound stimuli and electrode voltage were sampled at 40-µs intervals using a digital I-O board (National Instruments) and stored for offline analysis. Threshold was defined visually as the lowest decibel level at which any wave (I-IV) could be detected and reproduced with increasing sound intensities. ABR thresholds were averaged within each experimental group and used for statistical analysis.

FIG. 20 graphically demonstrates that delivery of an Anc80 viral vector encoding and expressing Harmonin can provide nearly complete recovery of auditory function, particularly at lower frequencies (e.g., about 5 to about 22 kHz).

Example 3F—Quantitative RT-PCR Analysis

Experiments were performed to evaluate the amount of virus present in the cochlea following in vivo administration. Two TMC1 −/− mice were injected in the left ear at P1. Cochlea were excised from left and right ears and maintained in culture for 3 days, the equivalent of P10. RNA was extracted and quality was confirmed using an Agilent Bioanalyzer (Agilent Technologies), and reverse transcribed into cDNA for quantitative RT-PCR analysis with efficient primer sets specific to TMC1 with SYBR GreenER qPCR reagent (Invitrogen) as previously described (Kawashima et al., 2011, J. Clin. Invest., 121:4796-809).

To amplify a fragment of TMC1, the following primers were used: 5'-CAT CTG CAG CCA ACT TTG GTG TGT-3' (SEQ ID NO:9) and 5'-AGA GGT AGC CGG AAA TTC AGC CAT-3' (SEQ ID NO:10). Expression levels were normalized to those of Actb (encoding β-actin) amplified with 5'-TGA GCG CAA GTA CTC TGT GTG GAT-3' (SEQ ID NO:11) and 5'-ACT CAT CGT ACT CCT GCT TGC TGA-3' (SEQ ID NO:12). All primers were designed to span introns, and validated using melt curve analysis and negative controls. Data were analyzed using the ΔΔCT method, relative to Actb and the difference between injected and uninjected ears. In injected ears, TMC1 mRNA expression was 12-fold higher than in uninjected ears.

Example 3G—FM1-43 Labeling

FM1-43 dye loading experiments were performed as described previously (Gale et al., 2001, J. Neurosci., 21:7013-25; Meyers et al., 2003, J. Neurosci., 23:4054-65; and Géléoc & Holt, 2003, Nat. Neurosci., 10:1019-20). Coverslips with adherent cochlear cultures were placed under an upright microscope (Zeiss Axioscope FS Plus) on a glass-bottomed chamber. Five-µM FM1-43FX (Invitrogen) diluted in artificial perilymph was applied for 10 sec and the tissue was washed three times in artificial perilymph to remove dye from the outer leaflet of the cell membrane. After 5 minutes, intracellular FM1-43 was imaged using an FM1-43 filter set and an epifluorescence light source with a 63× water immersion objective. The tissue was fixed and processed for immunofluorescence as described above.

FIG. 23 are the immunostaining images showing uptake of FM1-43 dye by cells exposed to an Anc80 viral vector as described herein, and FIG. 28 graphically demonstrates that TMC1 delivered by an Anc80 viral vector as described herein restores sensory transduction in Tmc1-deficient hair cells in vivo.

Example 3H—Distortion Product Otoacoustic Emissions (DPOAE)

DPOAE data were collected under the same conditions, and during the same recording sessions as ABR data. Primary tones were produced at a frequency ratio of 1.2 (f2/f1) for the generation of DPOAEs at 2f1-f2, where the f2 level was 10 dB sound pressure level below f1 level for each f2/f1 pair. The f2 levels were swept in 5-dB steps from 20 to 80 dB. Waveform and spectral averaging were used at each level to increase the signal-to-noise ratio of the recorded ear-canal sound pressure. The amplitude of the DPOAE at 2f1-f2 was extracted from the averaged spectra, along with the noise floor at nearby points in the spectrum. Iso-response curves were interpolated from plots of DPOAE amplitude versus sound level. Threshold was defined as the f2 level required to produce DPOAEs at 0 dB.

FIG. 25 graphically demonstrates that TMC1 delivered using an Anc80 viral vector as described herein rescues outer hair cell function in TMC1 −/− mice, particularly at lower frequencies (e.g., about 5 to about 16 kHz).

Figure 26:
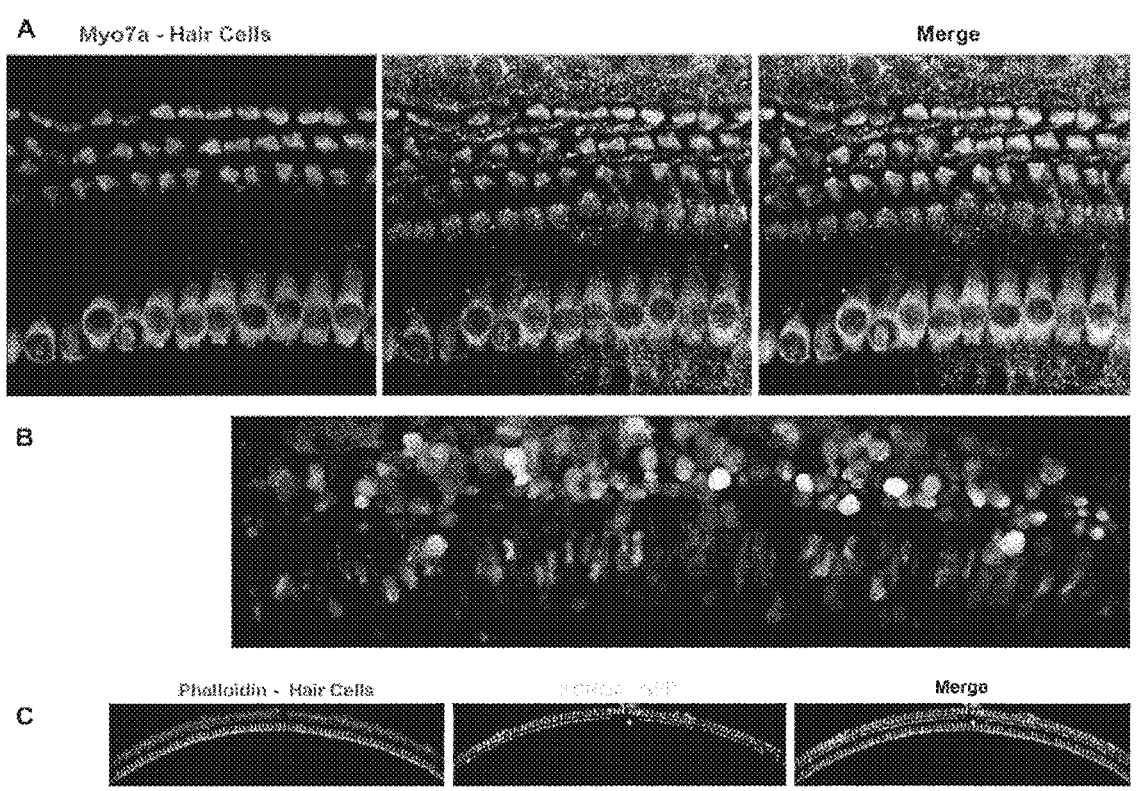

FIG. 26 demonstrates the effect of promoters Pcdh15, Myo6 and KCNQ4 on GFP expression in hair cells.

OTHER EMBODIMENTS

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

```
                          Sequence Listing

Anc80 capsid protein (SEQ ID NO: 1)
MAADGYLPDWLEDNLSEGIREWWDLKPGAPKPKANQQKQDDGRGLVLPGYKYLGPFNGLDKGEPV
NAADAAALEHDKAYDQQLKAGDNPYLRYNHADAEFQERLQEDTSFGGNLGRAVFQAKKRVLEPLG
LVEEGAKTAPGKKRPVEQSPQEPDSSSGIGKKGQQPAX₁KRLNFGQTGDSESVPDPQPLGEPPAAP
SGVGSNTMX₂AGGGAPMADNNEGADGVGNASGNWHCDSTWLGDRVITTSTRTWALPTYNNHLYKQI
SSQSGX₃STNDNTYFGYSTPWGYFDFNRFHCHFSPRDWQRLINNNWGFRPKX₄LNFKLFNIQVKEV
TTNDGTTTIANNLTSTVQVFTDSEYQLPYVLGSAHQGCLPPFPADVFMIPQYGYLTLNNGSQAVG
RSSFYCLEYFPSQMLRTGNNFX₅FSYTFEDVPFHSSYAHSQSLDRLMNPLIDQYLYYLSRTOTTSG
TAGNRX₆LQFSQAGPSSMANQAKNWLPGPCYRQQRVSKTX₇NQNNNSNFAWTGATKYHLNGRDSLV
NPGPAMATHKDDEDKFFPMSGVLIFGKQGAGNSNVDLDNVMITX₈EEEIKTTNPVATEX₉YGTVAT
NLQSX₁₀NTAPATGTVNSQGALIDGMVWQX₁₁RDVYLQGPIWAKIPHTDGMFHPSPLMGGFGLKHPPP
QILIKNTPVPANPPTTESPAKFASFITQYSTGQVSVEIEWELQKENSKRWNPEIQYTSNYNKSTN
VDFAVDTNGVYSEPRPIGTRYLTRNL
where X₁ = K/R; X₂ = A/S; X₃ = A/G; X₄ = R/K; X₅ = E/Q; X₆ = T/E; X₇
= A/T; X₈ = S/N; X₉ = Q/E; X₁₀ = S/A; X₁₁ = N/D Anc80-L0065 eapsid protein (SEQ ID NO: 2)
MAADGYLPDWLEDNLSEGIREWWDLKPGAPKPKANQQKQDDGRGLVLPGYKYLGPFNGLDKGEPV
NAADAAALEHDKAYDQQLKAGDNPYLRYNHADAEFQERLQEDTSFGGNLGRAVFQAKKRVLEPLG
LVEEGAKTAPGKKRPVEQSPQEPDSSSGIGKKGQQPARKRLNFGQTGDSESVPDPQPLGEPPAAP
SGVGSNTMAAGGGAPMADNNEGADGVGNASGNWHCDSTWLGDRVITTSTRTWALPTYNNHLYKQI
SSQSGGSTNDNTYFGYSTPWGYFDFNRFHCHFSPRDWQRLINNNWGFRPKKLNFKLFNIQVKEVT
TNDGTTTIANNLTSTVQVFTDSEYQLPYVLGSAHQGCLPPFPADVFMIPQYGYLTLNNGSQAVGR
SSFYCLEYFPSQMLRTGNNFQFSYTFEDVPFHSSYAHSQSLDRLMNPLIDQYLYYLSRTQTTSGT
AGNRTLQFSQAGPSSMANQAKNWLPGPCYRQQRVSKTTNQNNNSNFAWTGATKYHLNGRDSLVNP
GPAMATHKDDEDKFFPMSGVLIFGRQGAGNSNVDLDNVMITNEEEIKTTNPVATEEYGTVATNLQ
SANTAPATGTVNSQGALPGMVWQDRDVYLQGPIWAKIPHTDGHFHPSPLMGGFGLKHPPPQILIK
NTPVPANPPTTFSPAKFASFITQYSTGQVSVEIEWELQKENSKRWNPEIQYTSNYNKSTNVDFAV
DTNGVYSEPRPIGTRYLTRNL pAAV-TMC2 (SEQ ID NO: 3)
Left-inverted terminal repeat (L-ITR): 1-130 nt
Cytomegalovirus (CMV) promoter: 206-799 nt
Simian virus 40 (SV40) misc intron: 831-963 nt
Transmembrane channel-like 1 (TMC1ex1): 982-3,267 nt
Post-transcriptional regulatory element from Woodchuck hepatitis
virus (WPRE): 3,268-3,821 nt
Bovine growth hormone (bGH) polyA signal: 3,822-4,086 nt
Right-inverted terminal repeat (R-ITR): 4,124-4,253 nt
ctgcgcgctcgctcgctcactgaggccgcccgggcaaagcccgggcgtcgggcgacctttggtcg
cccggcctcagtgagcgagcgagcgcgcagagagggagtggccaactccatcactaggggttcct
tgtagttaatgattaacccgccatgctacttatctacgtagccatgctctaggaagatcggaatt
cgcccttaagctagctagttattaatagtaatcaattacggggtcattagttcatagcccatata
tggagttccgcgttacataacttacggtaaatggcccgcctggctgaccgcccaacgaccccgc
ccattgacgtcaataatgacgtatgttcccatagtaacgccaatagggactttccattgacgtca
atgggtggagtatttacggtaaactgcccacttggcagtacatcaagtgtatcatatgccaagta
cgcccctattgacgtcaatgacggtaaatggcccgcctggcattatgcccagtacatgaccttta
tgggactttcctacttggcagtacatctacgtattagtcatcgctattaccatggtgatgcggtt
ttggcagtacatcaatgggcgtggatagcggttttgactcacggggatttccaagtctccaccca
ttgacgtcaatgggagtttgttttggcaccaaaatcaacgggactttccaaaatgtcgtaacaac
tccgccccattgacgcaaatgggcggtaggcgtgtacggtggggaggtctatataagcagagctgg
tttagtgaaccgtcagatcctgcagaagttggtcgtgaggcactgggcaggtaagtatccaaggtt
acaagacaggtttaaggagaccaatagaaactgggcttgtcgagacagagaagactcttgcgttt
ctgataggcacctattggtcttactgacatccactttgcctttctCtccaCaggtgtccaggcgg
ccgcggATGCCACCCAAAAAAGTGCAAATCCAAGTGGAGGAGAAAGAAGAGGATACAGAGGAAAG
CTCAAGTGAAGAAGAAGAAGATAAGCTACCCAGAAGAGAGAGCTTGAGACCAAAGAGGAAACGGA
CCAGAGATGTCATCAATGAGGATGACCCAGAACCGGAGCCGGAGGATGAAGAAACAAGAAAGGCA
AGAGAAAAGAAAGGCGGAGGAGGCTGCGGAGAGGAGCGGAAGAAGAAGAAGAAATTGATGAAGA
```

```
GGAATTAGAACGGTTAAAAGCACTGCTCGATGAGAATAGACAAATGATCGCTACTGTCAAATGTA
AACCTTGGAAAATGGAGAAGAAAATTGAAGTTCTCAAGGAAGCAAAGAAATTTGTGAGTGAGAAT
GAAGGCGCTCTTGGGAAAGGAAAGGGAAAGAAGTGGTTTGCATTTAAGATGATGATGGCCAAGAA
ATGGGCAAAATTCCTCCGAGATTTTGAGAACTTCAAAGCGGCTTGCGTCCCATGGGAAAACAAAA
TCAAGGCAATTGAAAGTCAGTTTGGTTCCTCAGTGGCCTCGTACTTCCTGTTCCTCAGGTGGATG
TACGGCGTCAACATGGTTCTCTTTGTGTTGACCTTCAGCCTCATCATGTTACCGGAGTACCTCTG
GGGTTTACCGTACGGCAGCTTACCTAGGAAAACAGTCCCAAGAGCTGAAGAAGCATCTGCAGCCA
ACTTTGGTGTGTTGTATGACTTCAATGGCCTGGCGCAGTACTCTGTCCTCTTTTATGGCTATTAC
GACAATAAACGCACGATCGGATGGCTGAATTTCCGGCTACCTCTTTCCTACTTCCTGGTGGGGAT
TATGTGCATTGGATACAGCTTCCTGGTTGTCCTCAAAGCGATGACCAAAAATATTGGTGACGATG
GTGGTGGCGATGACAACACTTTCAACTTCAGCTGGAAGGTGTTCTGTAGCTGGGACTATCTGATT
GGTAACCCTGAAACAGCCGACAACAAGTTTAACTCTATCACGATGAACTTTAAGGAAGCCATCAT
AGAAGAGAGCCGCACAGGTGGAGGAGAACATCCACCTCATCAGATTTCTGAGGTTTCTCGCTA
ACTTCTTCGTGTTCCTCACACTTGGTGCAAGTGGATACCTCATCTTTTGGGCTGTGAAGCGATCC
CAGGAGTTCGCCCAGCAAGATCCTGACACCCTTGGGTGGTGGGAAAAAAATGAAATGAACATGGT
AATGTCCCTCCTGGGGATGTTCTGTCCCACCCTGTTTGACTTATTTGCTGAACTGGAAGATTACC
ATCCTCTCATTGCTCTGAAGTGGCTCCTGGGGCGCATTTTTGCTCTTCTTCTAGGCAACTTGTAT
GTATTCATTCTCGCCTTGATGGATGAGATTAACAACAAGATTGAAGAGGAGAAGCTTGTGAAGGC
CAATATTACCCTGTGGGAAGCCAACATGATTAAGGCTTACAATGAATCTCTCTGGGCTCTCTG
GGAACACCACAGGAGCACCCTTTTTCGTTCATCCTGCAGATGTCCCTCGCGGTCCCTGCTGGGAA
ACAATGGTGGGCAGGAATTCGTGCGTCTCACCGTTTCTGACGTCCTGACCACTTACGTCACGAT
CCTCATTGGCGACTTCCTCAGAGCATGTTTCGTGAGGTTCTGCAATTACTGCTGGTGCTGGGACT
TAGAATATGGATATCCTTCATACACAGAATTCGACATCAGTGGCAACGTCCTCGCTCTGATCTTC
AACCAAGGCATGATCTGGATGGGCTCCTTCTTCGCTCCTAGCCTCCCGGGCATCAACATCCTCCG
TCTCCACACATCCATGTATTTCCAGTGCTGGGCTGTGATGTGCTGCAATGTTCCCGAGGCCAGGG
TGTTCAAAGCTTCCAGATCCAACAACTTCTACCTCGGCATGCTGCTACTCATCCTCTTCCTGTCC
ACCATGCCGGTCCTGTACATGATCGTCTCCCTCCCGCCATCTTTTGATTGTGGGCCCTTCAGTGG
TAAAAACAGGATGTTTGAAGTCATCGGTGAGACCCTGGAACATGACTTCCCAAGCTGGATGGCGA
AGATCCTGAGGCAGCTTTCTAACCCCGGCCTTGTCATTGCTGTCATTCTGGTGATGGTTCTGACC
ATCTATTATCTCAATGCTACTGCCAAGGGCCAGAAAGCAGCGAATCTGGACCTCAAAAGAAGAT
GAAACAGCAAGCTTTGGAGAACAAAATGCGAAACAAGAAAATGGCAGCGGCTCGAGCAGCTGCAG
CTGCTGGTGGCCAGTAAggatccaatcaacctctggattacaaaatttgtgaaagattgactggt
attcttaactatgttgctccttttacgctatgtggatacgctgctttaatgcctttgtatcatgc
tattgcttcccgtatggctttcatttctcctccttgtataaatcctggttgctgtctctttatg
aggagttgtggcCogttgtcaggcaacgtggcgtggtgtgcactgtgtttgctgacgcaacccc
actggttggggcattgccaccacctgtcagctccttccgggacttttcgctttcccctccctat
tgccacggcggaactcatcgccgcctgccttgccgctgctggacagggcgctcggctgttgggca
ctgacaattccgtggtgttgtcggggaaatcatcgtcctttccttggctgctcgcctgtgttgcc
acctggattctgcgcgggacgtccttctgctacgtccctttcggccctcaatccagcggaccttcc
ttcccgcggcctgctgccggctctgcggcctcttccgcgtcttcgagatctgcctcgactgtgcc
ttctagttgccagccatctgttgtttgcccctccccgtgccttccttgaccctggaaggtgcca
ctcccactgtccttctaataaaatgaggaaattgcatcgcattgtctgagtaggtgtcattct
attctgggggtggggtggggcaggacagcaaggggaggattgggaagacaatagcaggcatgc
tggggactcgagttaagggcgaattcccgataaggatcttcctagagcatggctacgtagataag
tagcatggcgggttaatcattaactacaaggaaccccctagtgatggagttggccactccctctct
gcgcgctcgctcgctcactgaggccgggcgaccaaaggtcgcccgacgcccgggctttgcccggg
cggcctcagtgagcgagcgagcgcgcagccttaattaacctaattcactggccgtcgttttacaa
cgtcgtgactgggaaaccctggcgttacccaacttaatcgccttgcagcacatcccccttcgc
cagctggcgtaatagcgaagagcccgcaccgatcgcccttcccaacagttgcgcagcctgaatg
gcgaatgggacgcgccctgtagcggcgcattaagcgcggcgggtgtggtggttacgcgcagcgtg
accgctacacttgccagcgccctagcgcccgctcctttcgctttcttcccttcctttctcgccac
gttcgccggctttccccgtcaagctctaaatcggggggctcccctttagggttccgatttagtgctt
tacggcacctcgaccccaaaaaacttgattagggtgatggttcacgtagtgggccatcgccctga
tagacggtttEtcgccctttgacgttggagtccacgttctttaatagtggactcttgttccaaac
tggaacaacactcaaccctatctcggtctattcttttgatttataagggattttgccgatttcgg
cctattggttaaaaaatgagctgatttaacaaaaatttaacgcgaattttaacaaaatattaacg
tttataatttcaggtggcatcttttcggggaaatgtgcgcggaacccctatttgttattttttcta
aatacattcaaatatgtatccgctcatgagacaataaccctgataaatgcttcaataatattgaa
aaaggaagagtatgagtattcaacatttccgtgtcgcccttattccctttttgcggcattttgc
cttcctgtttttgctcacccagaaacgctggtgaaagtaaaagatgctgaagatcagttgggtgc
acgagtgggttacatcgaactggatctcaatagtggtaagatccttgagagttttcgccccgaag
aacgttttccaatgatgagcactttttaaagttctgctatgtggcgcggtattatcccgtattgac
gccgggcaagagcaactcggtcgccgcatacactattctcagaatgacttggttgagtactcacc
agtcacagaaaagcatcttacggatggcatgacagtaagagaattatgcagtgctgccataacca
tgagtgataacactgcggccaacttacttctgacaacgatcggaggaccgaaggagctaaccgct
tttttgcacaacatgggggatcatgtaactcgccttgatcgttgggaaccggagctgaatgaagc
cataccaaacgacgagcgtgacaccacgatgcctgtagtaatggtaacaacgttgcgcaaactat
taactggcgaactacttactctagcttcccggcaacaattaatagactggatggaggcggataaa
gttgcaggaccacttctgcgctcggcccttccggctggctggtttattgctgataaatctggagc
cggtgagcgtgggtctcgcggtatcattgcagcactggggccagatggtaagccctcccgtatcg
tagttatctacacgacggggagtcaggcaactatggatgaacgaaatagacagatcgctgagata
ggtgcctcactgattaagcattggtaactgtcagaccaagtttactcatatatactttagattga
tttaaaacttcattttttaatttaaaaggatctaggtgaagatcctttttgataatctcatgacca
aaatcccttaacgtgagttttcgttccactgagcgtcagaccccgtagaaaagatcaaaggatct
tcttgagatcctttttttctgcgcgtaatctgctgcttgcaaacaaaaaaaccaccgctaccagc
ggtggtttgtttgccggatcaagagctaccaactctttttccgaaggtaactggcttcagcagag
cgcagataccaaatactgtccttctagtgtagccgtagttaggccaccacttcaagaactctgta
```

Sequence Listing

```
gcaccgcctacatacctcgctctgctaatcctgttaccagtggctgctgccagtggcgataagtc
gtgtcttaccgggttggactcaagacgatagttaccggataaggcgcagcggtcgggctgaacgg
ggggttcgtgcacacagcccagcttggagcgaacgacctacaccgaactgagatacctacagcgt
gagctatgagaaagcgccacgcttcccgaagggagaaaggcggacaggtatccggtaagcggcag
ggtcggaacaggagagcgcacgagggagcttccaggggggaaacgcctggtatctttatagtcctg
tcgggtttcgccacctctgacttgagcgtcgatttttgtgatgctcgtcagggggggcggagccta
tggaaaaacgccagcaacgcggcctttttacggttcctggcctttttgctgcggttttgctcacat
gttctttcctgcgttatccctgattctgtggataaccgtattaccgcctttgagtgagctgata
ccgctcgccgcagccgaacgaccgagcgcagcgagtcagtgagcgaggaagcggaagagcgccca
atacgcaaaccgcctctccccgcgcgttggccgattcattaatgcagctggcacgacaggtttcc
cgactggaaagcgggcagtgagcgcaacgcaattaatgtgagttagctcactcattaggcacccc
aggctttacactttatgcttccggctcgtatgttgtgtggaattgtgagcggataacaatttcac
acaggaaacagctatgaccatgattacgccagatttaattaagg pAAV-TMC1ex2 (SEQ ID NO: 4)
L-ITR: 1-130
CMV promoter: 206-799
SV40 misc intron: 831-963
TMC1ex2: 982-3,255
WPRE: 3,256-3,809
bGH polyA signal: 3,810-4,074
R-ITR: 4,112-4,241
ctgcgcgctcgctcgctcactgaggccgcccgggcaaagcccgggcgtcgggcgacctttggtcg
cccggcctcagtgagcgagcgagcgcgcagagagggagtggccaactccatcactaggggtcct
tgtagttaatgattaacccgccatgctacttatctacgtagccatgctctaggaagatcggaatt
cgcccttaagctagctagttattaatagtaatcaattacggggtcattagttcatagcccatata
tggagttccgcgttacataacttacggtaaatggcccgcctggctgaccgcccaacgacccccgc
ccattgacgtcaataatgacgtatgttcccatagtaacgccaatagggactttccattgacgtca
atgggtggagtatttacggtaaactgcccacttggcagtacatcaagtgtatcatatgccaagta
cgccccctattgacgtcaatgacggtaaatggcccgcctggcattatgcccagtacatgacctta
tgggactttcctacttggcagtacatctacgtattagtcatcgctattaccatggtgatgcggtt
ttggcagtacatcaatgggcgtggatagcggtttgactcacggggatttccaagtctccaccca
ttgacgtcaatgggagtttgttttggcaccaaaatcaacgggactttccaaaatgtcgtaacaac
tccgccccattgacgcaaatgggcggtaggcgtgtacggtgggaggtctatataagcagagctgg
tttagtgaaccgtcagatcctgcagaagttggtcgtgaggcactgggcaggtaagtatcaaggtt
acaagacaggtttaaggagaccaatagaaactgggcttgtcgagacagagaagactcttgcgttt
ctgataggcacctattggtcttactgacatccactttgccttctctccacaggtgtccaggcgg
ccgcggATGTTGCAAATCCAAGTGGAGGAGAAAGAAGAGGATACAGAGGAAAGCTCAAGTGAAGA
AGAAGAAGATAAGCTACCCAGAAGAGAGAGCTTGAGACCAAAGAGGAAACGGACCAGAGATGTCA
TCAATGAGGATGACCCAGAACCGGAGCCGGAGGATGAAGAACAAGAAAGGCAAGAGAAAAAGAA
AGGCGGAGGAGGCTGCGGAGAGGAGCGGAAGAAGAAGAAGAAATTGATGAAGAGGAATTAGAACG
GTTAAAAGCACTGCTCGATGAGAATAGACAAATGATCGCTACTGTCAAATGTAAACCTTGGAAAA
TGGAAGAAAATTGAAGTTCTCAAGGAAGCAAAGAAATTTGTGAGTGAGAATGAAGGCGCTCTT
GGGAAAGGAAAGGGAAAGAAGTGGTTTGCATTTAAGATGATGATGGCCAAGAAATGGGCAAAATT
CCTCCGAGATTTTGAGAACTTCAAAGCGGCTTGCGTCCCATGGAGAAACAAAATCAAGGCAATTG
AAAGTCAGTTTGGTTCCTCAGTGGCCTCGTACTTCCTGTTCCTCAGGTGGATGTACGGCGTCAAC
ATGGTTCTCTTTGTGTTGACCTTCAGCCTCATCATGTTACCGGAGTACCTCTGGGGTTTACCGTA
CGGCAGCTTACCTAGGAAAACAGTCCCAAGAGCTGAAGAAGCATCTGCAGCCAACTTTGGTGTGT
TGTATGACTTCAATGGCCTGGCGCAGTACTCTGTCCTCTTTTTATGGCTATTACGACAATAAACGC
ACGATCGGATGGCTGAATTTCCGGCTACCTCTTTCCTACTTCCTGGTGGGGATTATGTGCATTGG
ATACAGCTTCCTGGTTGTCCTCAAAGCGATGACCAAAATATTGGTGACGATGGTGGTGGCGATG
ACAACACTTTCAACTTCAGCTGGAAGGTGTTCTGTAGCTGGGACTATCTGATTGGTAACCCTGAA
ACAGCCGACAACAAGTTTAACTCTATCACGATGAACTTTAAGGAAGCCATCATAGAAGAGAGAGC
CGCACAGGTGGAGGAGAACATCCACCTCATCAGATTTCTGAGGTTTCTCGCTAACTTCTTCGTGT
TCCTCACACTTGGTGCAAGTGGATACCTCATCTTTTGGGCTGTGAAGCGATCCCAGGAGTTCGCC
CAGCAAGATCCTGACACCCTTGGGTGGTGGGAAAAAAATGAAATGAACATGGTAATGTCCCTCCT
GGGGATGTTCTGTCCCACCCTGTTTGACTTATTTGCTGAACTGGAAGATTACCATCCTCTCATTG
CTCTGAAGTGGCTCCTGGGGCGCATTTTTGCTCTTCTTCTAGGCAACTTGTATGTATTCATTCTC
GCCTTGATGGATGAGATTAACAACAAGATTGAAGAGGAGAAGCTTGTGAAGGCCAATATTACCCT
GTGGGAAGCCAACATGATTAAGGCTTACAATGAATCTCTCTCTGGGCTCTCTGGGAACACCACAG
GAGCACCCTTTTCGTTCATCCTGCAGATGTCCCTCGCGGTCCCTGCTGGGAAACAATGGTGGG
CAGGAATTCGTGCGTCTCACCGTTTCTGACGTCCTGACCACTTACGTCACGATCCTCATTGGCGA
CTTCCTCAGAGCATGTTTCGTGAGGTTCTGCAATTACTGCTGGTGCTGGGACTTAGAATATGGAT
ATCCTTCATACACAGAATTCGACATCAGTGGCAACGTCCTCGCTCTGATCTTCAACCAAGGCATG
ATCTGGATGGGCTCCTTCTTCGCTCCTAGCCTCCCGGGCATCAACATCCTCCGTCTCCACACATC
CATGTATTTCCAGTGCTGGGCTGTGATGTGCTGCAATGTTCCCGAGGCCAGGGTGTTCAAAGCTT
CCAGATCCAACAACTTCTACCTCGGCATGCTGCTACTCATCCTCTTCCTGTCCACCATGCCGGTC
CTGTACATGATCGTCTCCCTCCCGCCATCTTTTGATTGTGGGCCCTTCAGTGGTAAAAACAGGAT
GTTTGAAGTCATCGGTGAGACCCTGGAACATGACTTCCCAAGCTGGATGGCGAAGATCCTGAGGC
AGCTTTCTAACCCCGGCCTTGTCATTGCTGTCATTCTGGTGATGGTTCTGACCATCTATTATCTC
AATGCTACTGCCAAGGGCCAGAAAGCAGCGAATCTGGACCTCAAAAAGAAGATGAAACAGCAAGC
TTTGGAGAACAAAATGCGAAACAAGAAAATGGCAGCGGCTCGAGCAGCTGCAGCTGCTGGTGGCC
AGTAAggatccaatcaacctctggattacaaaatttgtgaaagattgactggtattcttaactat
gttgctccttttacgctatgtggatacgctgctttaatgcctttgtatcatgctattgcttccg
tatggctttcatttctcctccttgtataaatcctggttgctgtctctttatgaggagttgtggc
ccgttgtcaggcaacgtggcgtggtgtgcactgtgtttgctgacgcaaccccactggttggggc
attgccaccacctgtcagctccttcggggactttcgctttccccctcccctattgccacggcgga
``` actcatcgccgcctgccttgcccgctgctggacaggggctcggctgttgggcactgacaattccg
tggtgttgtcggggaaatcatcgtcctttccttggctgctcgcctgtgttgccacctggattctg
cgcgggacgtccttctgctacgtccctcggccctcaatccagcggaccttccttcccgcggcct
gctgccggctctgcggcctcttccgcgtcttcgagatctgcctcgactgtgcttctagttgcca
gccatctgttgtttgccctccccccgtgccttccttgaccctggaaggtgccactcccactgtcc
tttcctaataaaatgaggaaattgcatcgcattgtctgagtaggtgtcattctattctgggggt
ggggtggggcaggacagcaaggggggaggattgggaagacaatagcaggcatgctggggactcgag
ttaagggcgaattcccgataaggatcttcctagagcatggctacgtagataagtagcatggcggg
ttaatcattaactacaaggaaccccctagtgatggagttggccactccctctctgcgcgctcgctc
gctcactgaggccgggcgaccaaaggtcgcccgacgcccgggctttgcccggcggcctcagtga
gcgagcgagcgcgcagccttaattaacctaattcactggccgtcgttttacaacgtcgtgactgg
gaaaaccctggcgttacccaacttaatcgccttgcagcacatcccccttcgccagctggcgtaa
tagcgaagaggcccgcaccgatcgcccttcccaacagttgcgcagcctgaatggcgaatgggacg
cgccctgtagcggcgcattaagcgcggcgggtgtggtggttacgcgcagcgtgaccgctacactt
gccagcgccctagcgcccgctcctttcgctttcttcccttcctttctcgccacgttcgcggcgtt
tccccgtcaagctctaaatcgggggctcccttttagggttccgatttagtgctttacggcacctcg
accccaaaaaacttgattagggtgatggttcacgtagtgggccatcgccctgatagacggttttt
cgccctttgacgttggagtccacgttctttaatagtggactcttgttccaaactggaacaacact
caaccctatctcggtctattctttttgatttataagggattttgccgatttcggcctattggttaa
aaaatgagctgatttaacaaaaatttaacgcgaattttaacaaaatattaacgtttataatttca
ggtggcatctttcggggaaatgtgcgcggaacccctatttgtttatttttctaaatacattcaaa
tatgtatccgctcatgagacaataaccctgataaatgcttcaataatattgaaaaaggaagagta
tgagtattcaacatttccgtgtcgcccttattcccttttttgcggcattttgccttcctgtttttt
gctcacccagaaacgctggtgaaagtaaaagatgctgaagatcagttgggtgcacgagtgggtta
catcgaactggatctcaatagtggtaagatccttgagagttttcgccccgaagaacgttttccaa
tgatgagcacttttaaagttctgctatgtggcgcggtattatcccgtattgacgccgggcaagag
caactcggtcgccgcatacactattctcagaatgacttggttgagtactcaccagtcacagaaaa
gcatcttacggatggcatgacagtaagagaattatgcagtgctgccataaccatgagtgataaca
ctgcggccaacttacttctgacaacgatcggaggaccgaaggagctaaccgcttttttgcacaac
atggggatcatgtaactcgccttgatcgttgggaaccggagctgaatgaagccataccaaacga
cgagcgtgacaccacgatgcctgtagtaatggtaacaacgttgcgcaaactattaactggcgaac
tacttactctagcttcccggcaacaattaatagactggatggaggcggataaagttgcaggacca
cttctgcgctcggcccttccggctggctggtttattgctgataaatctggagccggtgagcgtgg
gtctcgcggtatcattgcagcactggggccagatggtaagccctcccgtatcgtagttatctaca
cgacggggagtcaggcaactatggatgaacgaaatagacagatcgctgagataggtgcctcactg
attaagcattggtaactgtcagaccaagtttactcatatatactttagattgatttaaaacttca
tttttaatttaaaaggatctaggtgaagatcctttttgataatctcatgaccaaaatcccttaac
gtgagttttcgttccactgagcgtcagaccccgtagaaaagatcaaaggatcttcttgagatcct
ttttttctgcgcgtaatctgctgcttgcaaacaaaaaaaccaccgctaccagcggtggtttgttt
gccggatcaagagctaccaactctttttccgaaggtaactggcttcagcagagcgcagataccaa
atactgtccttctagtgtagccgtagttaggccaccacttcaagaactctgtagcaccgcctaca
tacctcgctctgctaatcctgttaccagtggctgctgccagtggcgataagtcgtgtcttaccgg
gttggactcaagacgatagttaccggataaggcgcagcggtcgggctgaacggggggttcgtgca
cacagcccagcttggagcgaacgacctacaccgaactgagatacctacagcgtgagctatgagaa
agcgccacgcttcccgaagggagaaaggcggacaggtatccggtaagcggcagggtcggaacagg
agagcgcacgagggagcttccaggggaaacgcctggtatctttatagtcctgtcgggtttcgcc
acctctgacttgagcgtcgatttttgtgatgctcgtcaggggggcggagcctatggaaaaacgcc
agcaacgcggcctttttacggttcctggccttttgctgcggttttgctcacatgttctttcctgc
gttatcccctgattctgtggataaccgtattaccgcctttgagtgagctgataccgctcgccgca
gccgaacgaccgagcgcagcgagtcagtgagcgaggaagcggaagagcgcccaatacgcaaaccg
cctctuuccgcgcgttggccgattcattaatgcagctggcacgacaggtttcccgactggaaagc
gggcagtgagcgcaacgcaattaatgtgagttagctcactcattaggcaccccaggctttacact
ttatgcttccggctcgtatgttgtgtggaattgtgagcggataacaatttcacacaggaaacagc
tatgaccatgattacgccagatttaattaagg pAAV-TMC2 (SEQ ID NO: 5)
L-ITR: 1-130
CMV promotes: 206-799
SV40 misc intron: 831-963
TMC2: 981-3,647
WPRE: 3,655-4,208
bGH polyA signal: 4,209-4,473
R-ITR: 4,511-4,640
ctgcgcgctcgctcgctcactgaggccgcccgggcaaagcccgggcgtcgggcgacctttggtcg
cccgcctcagtgagcgagcgagcgcgcagagagggagtggccaactccatcactaggggttcct
tgtagttaatgattaacccgccatgctacttatctacgtagccatgctctaggaagatcggaatt
cgcccttaagctagctagttattaatagtaatcaattacgggtcattagttcatagcccatata
tggagttccgcgttacataacttacggtaaatggcccgcctggctgaccgcccaacgacccccgc
ccattgacgtcaataatgacgtatgttcccatagtaacgccaatagggactttccattgacgtca
atgggtggagtatttacggtaaactgcccacttggcagtacatcaagtgtatcatatgccaagta
cgccccctattgacgtcaatgacggtaaatggcccgcctggcattatgcccagtacatgaccta
tgggactttcctacttggcagtacatctacgtattagtcatcgctattaccatggtgatgcggtt
ttggcagtacatcaatgggcgtggatagcggtttgactcacggggatttccaagtctccaccca
ttgacgtcaatgggagtttgttttggcaccaaaatcaacgggactttccaaaatgtcgtaacaac
tccgccccattgacgcaaatgggcggtaggcgtgtacggtgggaggtctatataagcagagctgg
tttagtgaaccgtcagatcctgcagaagttggtcgtgaggcactgggcaggtaagtatcaaggtt
acaagacaggtttaaggagaccaatagaaactgggcttgtcgagacagagaagactcttgcgttt -continued Sequence Listing

```
ctgataggcacctattggtcttactgacatccactttgcctttctctccacaggtgtccaggcgg
ccgccATGAGCCCCAGTTAAAGAGCTTGGACGAGGAAGGTGACAAGTCAGCAAGAAGACCCACA
AGGAAACAAACCTCCAGAGCTGCATGTCCCCAAGACGGGCACCGAGCCCAATCTAGCCGGAAGGA
TCCTGCTAAGGGTAGCCCAAGACCAGGGTCTTCCCGGAAGAAACAGATGGAACATGGAAGCTATC
ACAAGGGGTTGCAGGGACAGAAACCACGAAAGGTGGAGAGGTCTCTACAAGGGAGGAAGAAGGAT
CGGAGAACTTCCCTTAAGGAGCAGAGAGCATCTCCAAAGAAGGAGAGGGAGGCTCTGAGGAAGGA
GGCAGGCAAGCAGCTGAGAAAACCCAGGTCCACTTCCTTGGGCTCCAGTGTCTCTACTGGAGACT
CCCTGTCTGAGGAGGAGCTGGCTCAGATCCTGGAACAGGTAGAAGAAAAAAAGAAGCTCATCACT
ACCGTGAGGAACAAACCCTGGCCCATGGCAAAGAAGCTGAGGGAACTCAGGGAAGCCCAAGCCTT
TGTGGAGAAGTATGAAGGAGCCTTGGGGAAAGGCAAGGGCAAACACCTCTACGCCTACAGGATGA
TGATGGCTAAGAAATGGGTCAAGTTTAAGAGGGACTTTGATAATTTCAAGACTCAATGTATTCCC
TGGGAAATGAAGATCAAGGACATTGAAAGTCACTTCGGTTCTTCTGTGGCATCTTACTTCATCTT
TCTCCGATGGATGTATGGAGTTAACCTTGTCCTTTTTGGCTTaATATTTGGTCTAGTCATCATCC
CAGAGGTGCTGATGGGCATGCCCTATGGAAGTATACCCAGAAAGACGGTGCCTCGGGCTGAGGAA
GAGCGAGCCATGGACTTCTCTGTCCTTTGGGATTTTGAGGGCTACATCAAATATTCTGCTCTCTT
CTATGGCTACTACAACAACCAGCGGACCATTGGATGGCTGAGGTACAGGCTGCCCATGGCTTACT
TTATGGTGGGGGTCAGCGTGTTTGGCTACAGCTTGATGATCGTCATTAGGTCGATGGCCAGCAAT
ACCCAGGGTAGCACCAGTGAGGGGGACAGTGACAGCTTCACGTTCAGCTTCAAGATGTTCACCAG
CTGGGACTACCTCATCGGGAATTCAGAGACAGCAGACAACAAATATGTCTCCATCACTACCAGCT
TCAAGGAGTCTATAGTGGACGAACAAGAGAGTAACAAAGAAGGGAATATCCACCTGACAAGATTC
CTCCGCGTCCTGGCCAACTTTCTCATTCTCTGCTGTCTGTGTGGAAGCGGGTACCTCATTTACTT
TGTGGTGAAACGGTCCCAGGAGTTCTCCAAAATGCAAAATGTCAGCTGGTATGAAAGGAATGAGG
TGGACATCGTGATGTCTCTGCTAGGGATGTTTTGTCCCCCTCTGTTTGAAACCATCGCTGCCTTG
GAGAATTATCACCCACGAACTGGGCTGAAGTGGCAGCTGGGCCGCATCTTTGCCCTTTTCCTGGG
AAACCTCTACACGTTTCTCCTGGCCCTCATGGACGATGTCCACCTTAAGCTTTCTAATGAGGAAA
AAATCAAGAACATCACTCACTGGACCCTGTTTAACTATTACAATTCCTCAGGTGGGAATGAGAGT
GTGCCCCGGCCACCACCACACCCTGCAGATGTGCCCAGAGGTTCTTGCTGGGAGACAGCTGTGGG
CATTGAGTTTATGAGGCTCACCGTGTCTGACATGCTGGTAACATACCTCACCATCTTGGTCGGAG
ATTTCCTCCGAGCTTGTTTTGTCCGGTTCATGAATCACTGCTGGTGTTGGGACCTCGAGGCTGGT
TTTCCCTCATATGCCGAGTTTGATATTAGTGGAAATGTGTTGGGTTTGATCTTCAACCAAGGAAT
GATCTGGATGGGCTCCTTCTATGCTCCAGGACTGGTGGGCATCAATGTCCTGCGCCTGTTGACCT
CCATGTACTTCCAGTGCTGGGCAGTGATGAGCAGCAACGTTCCCCATGAGCGTGTGTTTAAAGCC
TCCCGATCCAACAACTTCTACATGGGCCTCCTGCTGTTGGTGCTCTTCCTCAGCCTCCTGCCTGT
GGCCTACACTGTCATGTCTCTCCACCCTCGTTTGACTGTGGCCCCTTCAGTGGGAAAAACAGAA
TGTACGATGTCCTCCATGAGACCATCGAGAACGATTTCCCTAAGTTCCTGGGCAAGATCTTTGCG
TTCCTTGCCAACCCAGGCCTGATCATTCCAGCCATCCTGCTAATGTTTCTGGCCATTTACTACCT
GAACTCAGTTTCAAAAAGTCTTTCCAGAGCTAATGCCCAGCTGCGAAAGAAGATCCAAGCGCTCC
GTGAAGTTGAGAAGAACCATAAATCCATCAAGGGAAAAGCCATAGTCACATATTCAGAGGACACA
ATCAAGAACAGCTCCAAAAATGCCACCCAGATACATCTTACTAAAGAAGAGCCCACATCTCACTC
TTCCAGCCAAATCCAGACCCTGGACAAGAAAGCGCAGGGCCCCCACACCTCCAGTACTGAGGGTG
GGGCCTCGCCGTCTACCTCCTGGCACCATGTTGGGTCTCAACCACCGAGAGGCAGACGAGATTCT
GGCCAACCCCAGTCTCAGACTTATACAGGCAGGTCACCTTCTGGAAAGAGAACCCAGAGGCCTCA
CAACTGAtaagcttggatccaatcaacctctggattacaaaatttgtgaaagattgactggtatt
cttaactatgttgctccttttacgctatgtggatacgctgctttaatgcctttgtatcatgctat
tgcttcccgtatggctttcattttctcctccttgtataaatccttggctgctgtctttatgagg
agttgtggcccgttgtcaggcaacgtggcgtggtgtgcactgtgtttgctgacgcaaccccact
ggttgggcattgccaccacctgtcagctcctttccgggactttcgctttcccctcctattgc
cacggcggaactcatcgccgcctgccttgccgctgctggacaggggctcggctgttgggcactg
acaattccgtggtgttgtcggggaaatcatcgtccttcttggctgctgcctgttgccacc
tggattctgcgcgggacgtccttctgctacgtccctcggccctcaatccagcggaccttccttc
ccgcggcctgctgccggctctgcggcctcttccgcgtcttcgagatctgcctcgactgtgccttc
tagttgccagccatctgttgtttgcccctccccgtgccttccttgaccctggaaggtgccactc
ccactgtccttcctaataaaatgaggaaattgcatcgcattgtctgagtaggtgtcattctatt
ctggggggtggggtggggcaggacaagggggaggattgggaagacaatagcaggcatgctgg
ggactcgagttaagggcgaattcccgataaggatcttcctagagcatggctacgtagataagtag
catggcgggttaatcattaactacaaggaaccccctagtgatggagttggccactccctctgcg
cgctcgctcgctcactgaggccgggcgaccaaaggtcgcccgacgcccgggctttgcccgggcgg
cctcagtgagcgagcgagcgcgcagccttaattaacctaattcactggccgtcgttttacaacgt
cgtgactgggaaaaccctggcgttacccaacttaatcgccttgcagcacatccccctttcgccag
ctggcgtaatagcgaagaggcccgcaccgatcgcccttcccaacagttgcgcagcctgaatggcg
aatgggacgcgccctgtagcggcgcattaagcgcggcgggtgtggtggttacgcgcagcgtgacc
gctacacttgccagcgccctagcgcccgctcctttcgctttcttcccttcctttctcgccacgtt
cgccggctttccccgtcaagctctaaatcgggggctccctttagggttccgatttagtgctttac
ggcacctcgaccccaaaaaacttgattagggtgatggttcacgtagtgggccatcgccctgatag
acggttttcgccctttgacgttggagtccacgttctttaatagtggactcttgttccaaactgg
aacaacactcaaccctatctcggtctattcttttgatttataagggattttgccgatttcggcct
attggttaaaaaatgagctgatttaacaaaaatttaacgcgaattttaacaaaataatcgttt
ataatttcaggtggcatctttcggggaaatgtgcgcggaaccccatatttgttatttttctaaat
acattcaaatatgtatccgctcatgagacaataaccctgataaatgcttcaataatattgaaaaa
ggaagagtatgagtattcaacatttccgtgtcgcccttattcccttttttgcggcattttgcctt
cctgtttttgctcacccagaaacgCtggtgaaagtaaaagatgctgaagatcagttgggtgcacg
agtgggttacatcgaactggatctcaatagtggtaagatcctcgagagttttcgccccgaagaac
gttttccaatgatgagcacttttaaagttctgctatgtggcgcggtattatcccgtattgacgcc
gggcaagagcaactcggtcgccgcatacactattctcagaatgacttggttgagtactcaccagt
cacagaaaagcatcttacggatggcatgacagtaagagaattatgcagtgctgccataaccatga
gtgataacactgcggccaacttacttctgacaacgatcggaggaccgaaggagctaaccgctttt
ttgcacaacatgggggatcatgtaactcgccttgatcgttgggaaccggagctgaatgaagccat
```

```
accaaacgacgagcgtgacaccacgatgcctgtagtaatggtaacaacgttgcgcaaactattaa
ctggcgaactacttactctagcttcccggcaacaattaatagactggatggaggcggataaagtt
gcaggaccacttctgcgctcggccctccggctggctggttattgctgataaatctggagccgg
tgagcgtgggtctcgcggtatcattgcagcactggggccagatggtaagccctcccgtatcgtag
ttatctacacgacggggagtcaggcaactatggatgaacgaaatagacagatcgctgagataggt
gcctcactgattaagcattggtaactgtcagaccaagtttactcatatatactttagattgattt
aaaacttcattttaatttaaaaggatactaggtgaagatccttttttgataatctcatgaccaaaa
tcccttaacgtgagttttcgttccactgagcgtcagaccccgtagaaaagatcaaaggatcttct
tgagatcctttttttctgcgcgtaatctgctgcttgcaaacaaaaaaaccaccgctaccagcggt
ggtttgtttgccggatcaagagctaccaactcttttccgaaggtaactggcttcagcagagcgc
agataccaaatactgtccttctagtgtagccgtagttaggccaccacttcaagaactctgtagca
ccgcctacatacctcgctctgctaatcctgttaccagtggctgctgccagtggcgataagtcgtg
tcttaccgggttggactcaagacgatagttaccggataaggcgcagcggtcgggctgaacggggg
gttcgtgcacacagcccagcttggagcgaacgacctacaccgaactgagatacctacagcgtgag
ctatgagaaagcgccacgcttcccgaagggagaaaggcggacaggtatccggtaagcggcagggt
cggaacaggagagcgcacgagggagcttccaggggggaaacgcctggtatctttatagtcctgtcg
ggtttcgccacctctgacttgagcgtcgatttttgtgatgctcgtcaggggggcggagcctatgg
aaaaacgccagcaacgcggcctttttacggttcctggccttttgctgcggttttgctcacatgtt
ctttcctgcgttatcccctgattctgtggataaccgtattaccgcctttgagtgagctgataccg
ctcgccgcagcgaacgaccgagcgcagcgagtcagtgagcgaggaagcggaagagcgcccaata
cgcaaaccgcctctccccgcgcgttggccgattcattaatgcagCtggcacgacaggtttcccga
ctggaaagcgggcagtgagcgcaacgcaattaatgtgagttagctcactcattaggcacccagg
ctttacactttatgcttccggctCgtatgttgtgtggaattgtgagcggataacaatttcacaca
ggaaacagctatgaccatgattacgccagatttaattaagg
``` pAAV-Pmyo6-TMC1ex1 (SEQ ID NO: 6)
L-ITR: 1-141
Myosin 6 (myo6) promoter: 155-1,356
TMC1ex1: 1,425-3,710
hGH polyA signal: 3,745-4,225
R-ITR: 4,262-4,402

```
cctgcaggcagctgcgcgctcgctcgctcactgaggccgccgggcaaagcccgggcgtcgggcg
acctttggtcgcccggcctcagtgagcgagcgagcgcgcagagagggagtggccaactccatcac
tagggggttcctgcggccgcacgcgTGCAAGAACCCTCACTGGCTGAACTATCTTGCCAGCCCCTT
ATTTTGTTTTCATATTAACCTCTTTTTTCTAGTAAAGGAGATGTTTGCTCTCAAATTTGCATAGG
AATGTAATATTTAATTTAAAAAGATGACCCACATATGACCTTATAAGGACAGTAAAATTAAACAA
CCGGAAAGATAAAGCGGGCCAGTTGGCTCAGTTCTATAAAACCAGCCCACAAGGATTGTCACTAT
TCTTAGGCTTGCGCGGGCTACATGATGAGTTCCAGGACTGCCTGGTTACAGACCGAGACTCTCTC
AAGAGTCCAGATAAACAACAACAAAGGGGGCGAGGTGGAAATACAGGGGCTGTAAGAAGTAAATA
TGATATCTGCATGGGAGGCTAGCCAGAGAAGAAAAAATTTTCTTCGTGGTTCAATCCTCCAAGG
GCTGAACAGGAAGTTGACGCAGGCAGGTGAGGAGCACGAGCCTAGATGGGCTGCGGTGCCACCCT
TAATCCCCACAAGCGAGTTCCTCCGCAATTCGCCTGTCCCACTCTCAACTTTTCTTCAACTGACT
CTTTGCTGTGGTCCCTCGCTGTGGCAGTGGAAACAACTACCACTGCGAGGTAGGGAATGTCATGA
GGGGCTACCTGCAGCCCTTGGCTTGCAGGGATGCAGGGATGCGGTCGGAACCTGAGGCCCCGCCC
TTCTCTTGCCCCACGCCATTAGGCCACGCCCCTACCCAGCACTCCTTCAACCACCCCCTTCCCCG
GCGCCTCATGAGGTCCCGCCCCTCTCAACCCTAGCTCTTGAGGCCTCCCCTTCACAGCCGCCCCG
GCGTTCCTTGACTTGAGGCCACGTCCCTCTGCTCCTTCATTCCCAAGACCCTACGCTTTGCGAGT
CCTCCCTGTCCTGCTGCCTAGGACCCCGCCCCTCTCAGCCCTTCTGCCCCAAGACCCCGCCCCTT
AGGCTGTTCCCCCCCACTGGCCAATGAAGACCCGCCCTTTCTTTAGCCGCCCCGCCCCGGTCCCA
CAAAATCCCGCCTCCGGCCCCGCCTCCCGCCCCCTTGGGCGCTCCGTAGCAGTGACGTGCGCAGG
CTGGGCACTCTGCAGGGCTCTCTGGCCGGCGGGTGGAGACCGATCCGGGATCTGTCCCAGCAGGA
AGCGTATCCCGGCCGCCGTCGTGCTGTCGTCTCCGGTGCTCGCTCTCGGCCGCGGTGTCGCGCTT
GCCCTTCGCGCCCGCAGCCCGGCAGCCTCTCgagcTCAAGCTTCGAATTCgtcgacaggATGCCA
CCCAAAAAAGTGCAAATCCAAGTGGAGGAGAAAGAAGAGGATACAGAGGAAAGCTCAAGTGAAGA
AGAAGAAGATAAGCTACCCAGAAGAGAGAGCTTGAGACCAAAGAGGAAACGGACCAGAGATGTCA
TCAATGAGGATGACCCAGAACCGGAGCCGGAGGATGAAGAAACAAGAAAGGCAAGAGAAAAAGAA
AGGCGGAGGAGGCTGCGGAGAGGAGCGGAAGAAGAAGAAGAAATTGATGAAGAGGAATTAGAACG
GTTAAAAGCACTGCTCGATGAGAATAGACAAATGATCGCTACTGTCAAATGTAAACCTTGGAAAA
TGGAGAAGAAAATTGAAGTTCTCAAGGAAGCAAAGAAATTTGTGAGTGAGAATGAAGGCGCTCTT
GGGAAAGGAAAGGGAAAGAAGTGGTTTGCATTTAAGATGATGATGGCCAAGAAATGGGCAAAATT
CCTCCGAGATTTTGAGAACTTCAAAGCGGCTTGCGTCCCATGGGAAAACAAAATCAAGGCAATTG
AAAGTCAGTTTGGTTCCTCAGTGGCCTCGTACTTCCTGTTCCTCAGGTGGATGTACGGCGTCAAC
ATGGTTCTCTTTGTGTTGACCTTCAGCCTCATCATGTTACCGGAGTACCTCTGGGGTTTACCGTA
CGGCAGCTTACCTAGGAAAACAGTCCCAAGAGCTGAAGAAGCATCTGCAGCCAACTTTGGTGTGT
TGTATGACTTCAATGGCCTGGCGCAGTACTCTGTCCTCTTTTATGGCTATTACGACAATAAACGC
ACGATCGGATGGCTGAATTTCCGGCTACCTCTTTCCTACTTCCTGGTGGGGATTATGTGCATTGG
ATACAGCTTCCTGGTTGTCCTCAAAGCGATGACCAAAAATATTGGTGACGATGGTGGTGGCGATG
ACAACACTTTCAACTTCAGCTGGAAGGTGTTCTGTAGCTGGGACTATCTGATTGGTAACCCTGAA
ACAGCCGACAACAAGTTTAACTCTATCACGATGAACTTTAAGGAAGCCATCATAGAAGAGAGAGC
CGCACAGGTGGAGGAGAACATCCACCTCATCAGATTTCTGAGGTTTCTCGCTAACTTCTTCGTGT
TCCTCACACTTGGTGCAAGTGGATACCTCATCTTTTGGGCTGTGAAGCGATCCCAGGAGTTCCCT
CAGCAAGATCCTGACACCCTTGGGTGGTGGGAAAAAAATGAAATGAACATGGTAATGTCCCTCCT
GGGGATGTTCTGTCCCACCCTGTTTGACTTATTTGCTGAACTGGAAGATTACCATCCTCTCATTG
CTCTGAAGTGGCTCCTGGGGCGCATTTTGCTCTTCTTCTAGGCAACTTGTATGTATTCATTCTC
GCCTTGATGGATGAGATTAACAACAAGATTGAAGAGGAGAAGCTTGTGAAGGCCAATATTACCCT
GTGGGAAGCCAACATGATTAAGGCTTACAATGAATCTCTCTCTGGGCTCTCTGGGAACACCACAG
GAGCACCCTTTTTCGTTCATCCTGCAGATGTCCCTCGCGGTCCCTGCTGGGAAACAATGGTGGGG
```

CAGGAATTCGTGCGTCTCACCGTTTCTGACGTCCTGACCACTTACGTCACGATCCTCATTGGCGA
CTTCCTCAGAGCATGTTTCGTGAGGTTCTGCAATTACTGCTGGTGCTGGGACTTAGAATATGGAT
ATCCTTCATACACAGAATTCGACATCAGTGGCAACGTCCTCGCTCTTGATCTTCAACCAAGGCATG
ATCTGGATGGGCTCCTTCTTCGCTCCTAGCCTCCCGGGCATCAACATCCTCCGTCTCCACACATC
CATGTATTTCCAGTGCTGGGCTGTGATGTGCTGCAATGTTCCCGAGGCCAGGGTGTTCAAAGCTT
CCAGATCCAACAACTTCTACCTCGGCATGCTGCTACTCATCCTCTTCCTGTCCACCATGCCGGTC
CTGTACATGATCGTCTCCCTCCCGCCATCTTTTGATTGTGGGCCCTTCAGTGGTAAAAACAGGAT
GTTTGAAGTCATCGGTGAGACCCTGGAACATGACTTCCCAAGCTGGATGGCGAAGATCCTGAGGC
AGCTTTCTAACCCCGGCCTTGTCATTGCTGTCATTCTGGTGATGGTTCTGACCATCTATTATCTC
AATGCTACTGCCAAGGGCCAGAAAGCAGCGAATCTGGACCTCAAAAAGAAGATGAAACAGCAAGC
TTTGGAGAACAAAATGCGAAACAAGAAAATGGCAGCGGCTCGAGCAGCTGCAGCTGCTGGTGGCC
AGTAAGCGGCCGCTCGAGCCTAAGCTTCTAGAagatctacgggtggcatccctgtgaccctccc
cagtgcctctcctggccctggaagttgccactccagtgcccaccagccttgtcctaataaaatta
agttgcatcatttttgtctgactaggtgtccttctataatattatggggtggaggggggtggtatg
gagcaaggggcaagttgggaagacaacctgtagggcctgcggggtctattgggaaccaagctgga
gtgcagtggcacaatcttggctcactgcaatctccgcctcctgggttcaagcgattctcctgcct
cagcctcccgagttgttgggattccaggcatgcatgaccaggctcagctaatttttgttttttg
gtagagacggggtttcaccatattggccaggctggtctccaactcctaatctcaggtgatctacc
caccttggcctcccaaattgctgggattacaggcgtgaaccactgctcccttccctgtccttctg
attttgtaggtaaccacgtgcggaccgagcggccgcaggaaccctagtgatggagttggccact
ccctctctgcgcgctcgctcgctcactgaggccgggcgaccaaaggtcgcccgacgcccgggctt
tgcccgggcggcctcagtgagcgagcgagcgcgcagctgcctgcaggggcgcctgatgcggtatt
ttctccttacgcatctgtgcggtatttcacaccgcatacgtcaaagcaaccatagtacgcgccct
gtagcggcgcattaagcgcggcgggtgtggtggttacgcgcagcgtgaccgctacacttgccagc
gccctagcgcccgctccttcgctttcttcccttcctttctcgccacgttcgccggctttccccg
tcaagctctaaatcgggggctccctttagggttccgatttagtgctttacggcacctcgacccca
aaaaacttgatttgggtgatggttcacgtagtgggccatcgccctgatagacgqttttttcgccct
ttgacgttggagtccacgttctttaatagtggactcttgttccaaactggaacaacactcaaccc
tatctcgggctattcttttgatttataaggggattttgccgatttcggcctattggttaaaaaatg
agctgatttaacaaaaatttaacgcgaattttaacaaaatattaacgtttacaatttttatggtgc
actctcagtacaatctgctctgatgccgcatagttaagccagccccgacacccgccaacacccgc
tgacgcgccctgacgggcttgtctgctcccggcatccgcttacagacaagctgtgaccgtctccg
ggagctgcatgtgtcagaggttttcaccgtcatcaccgaaacgcgcgagacgaaagggcctcgtg
atacgcctatttttataggttaatgtcatgataataatggtttcttagacgtcaggtggcacttt
tcggggaaatgtgcgcggaaccccttatttgttttatttttctaaatacattcaaatatgtatccgc
tcatgagacaataaccctgataaatgcttcaataatattgaaaaaggaagagtatgagtattcaa
catttccgtgtcgcccttattccttttttgcggcattttgccttcctgtttttgctcacccaga
aacgctggtgaaagtaaaagatgctgaagatcagttgggtgcatgagtgggttacatcgaactgg
atctcaacagcggtaagatccttgagagttttcgccccgaagaacgttttccaatgatgagcact
tttaaagttctgctatgtggcgcggtattatcccgtattgacgccgggcaagagcaactcggtcg
ccgcatacactattctcagaatgacttggttgagtactcaccagtcacagaaaagcatcttacgg
atggcatgacagtaagagaattatgcagtgctgccataaccatgagtgataacactgcggccaac
ttacttctgacaacgatcggaggaccgaaggagctaaccgcttttttgcacaacatgggggatca
tgtaactcgccttgatcgttgggaaccggagctgaatgaagccataccaaacgacgagcgtgaca
ccacgatgcctgtagcaatggcaacaacgttgcgcaaactattaactggcgaactacttactcta
gcttcccggcaacaattaatagactggatggaggcggataaagttgcaggaccacttctgcgctc
ggcccttccggctggctggtttattgctgataaatctggagccggtgagcgtgggtctcgcggta
tcattgcagcactggggccagatggtaagccctcccgtatcgtagttatctacacgacggggagt
caggcaactatggatgaacgaaatagacagatcgctgagataggtgcctcactgattaagcattg
gtaactgtcagaccaagtttactcatatactttagattgatttaaaacttcattttttaattta
aaaggatctaggtgaagatcctttttgataatctcatgaccaaaatcccttaacgtgagttttcg
ttccactgagcgtcagacccgtagaaaagatcaaaggatcttcttgagatcctttttttctgcg
cgtaatctgctgcttgcaaacaaaaaaaccaccgctaccagcggtggtttgtttgccggatcaag
agctaccaactctttttccgaaggtaactggcttcagcagagcgcagataccaaatactgtcctt
ctagtgtagccgtagttaggccaccacttcaagaactctgtagcaccgcctacatacctcgctct
gctaatcctgttaccagtggctgctgccagtggcgataagtcgtgtcttaccgggttggactcaa
gacgatagttaccggataaggcgcagcggtcgggctgaacggggggttcgtgcacacagcccagc
ttggagcgaacgacctacaccgaactgagatacctacagcgtgatgagaaagcgccacgct
tcccgaagggagaaaggcggacaggtatccggtaagcggcagggtcggaacaggagagcgcacga
gggagcttccaggggggaaacgcctggtatctttatagtcctgtcgggtttcgccacctctgactt
gagcgtcgatttttgtgatgctcgtcagggggcggagcctatgaaaaacgccagcaacgcggc
ctttttacggttcctggccttttgctggccttttgctcacatgt pAAV-Pmyo6-TMC1ex1 (SEQ ID NO: 7)
L-ITR: 1-141
myo6 promoter: 155-1,396
TMC1ex2: 1,425-4,439
hGH polyA signal: 4,474-4,954
R-ITR: 4,991-5,131
cctgcaggcagctgcgcgctcgctcgctcactgaggccgcccgggcaaagcccgggcgtcgggcg
acctttggtcgcccggcctcagtgagcgagcgagcgcgcagagagggagtggccaactccatcac
taggggttcctgcggccgcacgcgTGCAAGAACCCTCACTGGCTGAACTATCTTGCCAGCCCCTT
ATTTTGTTTTCATATTAACCTCTTTTTTCTAGTAAAGGAGATGTTTGCTCTCAAATTTGCATAGG
AATGTAATATTTAATTTAAAAAGATGACCCACATATGACCTTATAAGGACAGTAAAATTAAACAA
CCGGAAAGATAAAGCGGGCCAGTTGGCTCAGTTCTATAAAACCAGCCCACAAGGATTGTCACTAT
TCTTAGGCTTGCGCGGGCTACATGATGAGTTCCAGGACTGCCTGGTTACAGACCGAGACTCTCTC
AAGAGTCCAGATAAACAACAACAAAGGGGGCGAGGTGGAAATACAGGGGCTGTAAGAAGTAAATA

```
TGATATCTGCATGGGAGGCTAGCCAGAGAAGAAAAAATTTTCTTCCGTGGTTCAATCCTCCAAGG
GCTGAACAGGAAGTTGACGCAGGCAGGTGAGGAGCACGAGCCTAGATGGGCTGCGGTGCCACCCT
TAATCCCCACAAGCGAGTTCCTCCGCAATTCGCCTGTCCCACTCTCAACTTTTCTTCAACTGACT
CTTTGCTGTGGTCCCTCGCTGTGGCAGTGGAAACAACTACCACTGCGAGGTAGGGAATGTCATGA
GGGGCTACCTGCAGCCCTTGGCTTGCAGGGATGCAGGGATGCGGTCGGAACCTGAGGCCCCGCCC
TTCTCTTGCCCCACGCCATTAGGCCACGCCCCTACCCAGCACTCCTTCAACCACCCCCTTCCCCG
GCGCCTCATGAGGTCCCGCCCCTCTCAACCCTAGCTCTTGAGGCCTCCCCTTCACAGCCGCCCCG
GCGTTCCTTGACTTGAGGCCACGTCCCTCTGCTCCTTCATTCCCAAGACCCTACGCTTTGCGAGT
CCTCCCTGTCCTGCTGCCTAGGACCCCGCCCCTCTCAGCCCTTCTGCCCCAAGACCCCGCCCCTT
AGGCTGTTCCCGCCCACTGGCCAATGAAGACCCGCCCTTTCTTTAGCCGCCCCGCCCCGGTCCCA
CAAAATCCCGCCTCCGGCCCCGCCTCCCGCCCCCTTGGGCGCTCCGTAGCAGTGACGTGCGCAGG
CTGGGCACTCTGCAGGGCTCTCTGGCCGGCGGGTGGAGACCGATCCGGGATCTGTCCCAGCAGGA
AGCGTATCCCGGCCGCCGTCGTGCTGTCGTCTCCGGTGCTCGCTCTCGGCCGCGGTGTCGCGCTT
GCCCTTCGCGCCCGCAGCCCGGCAGCCTCTCgagCTCAAGCTTCGAATTCgtcgacaggATGTTG
CAAATCCAAGTGGAGGAGAAAGAAGAGGATACAGAGGAAAGCTCAAGTGAAGAAGAAGAAGATAA
GCTACCCAGAAGAGAGAGCTTGAGACCAAAGAGGAAACGGACCAGAGATGTCATCAATGAGGATG
ACCCAGAACCGGAGCCGGAGGATGAAGAAACAAGAAAGGCAAGAGAAAAGAAAGGCGGAGGAGG
CTGCGGAGAGGAGCGGAAGAAGAAGAAGAAATTGATGAAGAGGAATTAGAACGGTTAAAAGCACT
GCTCGATGAGAATAGACAAATGATCGCTACTGTCAAATGTAAACCTTGGAAAATGGAGAAGAAAA
TTGAAGTTCTCAAGGAAGCAAAGAAATTTGTGAGTGAGAATGAAGCGCTCTTGGGAAAGGAAAG
GGAAAGAAGTGGTTTGCATTTAAGATGATGATGGCCAAGAAATGGGCAAAATTCCTCCGAGATTT
TGAGAACTTCAAAGCGGCTTGCGTCCCATGGGAAAACAAAATCAAGGCAATTGAAAGTCAGTTTG
GTTCCTCAGTGGCCTCGTACTTCCTGTTCCTCAGGTGGATGTACGGCGTCAACATGGTTCTCTTT
GTGTTGACCTTCAGCCTCATCATGTTACCGGAGTACCTCTGGGGTTTACCGTACGGCAGCTTACC
TAGGAAAACAGTCCCAAGAGCTGAAGAAGCATCTGCAGCCAACTTTGGTGTGTTGTATGACTTCA
ATGGCCTGGCGCAGTACTCTGTCCTCTTTTATGGCTATTACGACAATAAACGCACGATCGGATGG
CTGAATTTCCGGCTACCTCTTTCCTACTTCCTGGTGGGGATTATGTGCATTGGATACAGCTTCCT
GGTTGTCCTCAAAGCGATGACCAAAAATATTGGTGACGATGGTGGCGATGACAACACTTTCA
ACTTCAGCTGGAAGGTGTTCTGTAGCTGGGACTATCTGATTGGTAACCCTGAAACAGCCGACAAC
AAGTTTAACTCTATCACGATGAACTTTAAGGAAGCCATCATAGAAGAGAGAGCCGCACAGGTGGA
GGAGAACATCCACCTCATCAGATTTCTGAGGTTTCTCGCTAACTTCTTCGTGTTCCTCACACTTG
GTGCAAGTGGATACCTCATCTTTTGGGCTGTGAAGCGATCCCAGGAGTTCGCCCAGCAAGATCCT
GACACCCTTGGGTGGTGGGAAAAAAATGAAATGAACATGGTAATGTCCCTCCTGGGGATGTTCTG
TCCCACCCTGTTTGACTTATTTGCTGAACTGGAAGATTACCATCCTCTCATTGCTCTGAAGTGGC
TCCTGGGGCGCATTTTTGCTCTTCTTCTAGGCAACTTGTATGTATTCATTCTCGCCTTGATGGAT
GAGATTAACAACAAGATTGAAGAGGAGAAGCTTGTGAAGGCCAATATTACCCTGTGGGAAGCCAA
CATGATTAAGGCTTACAATGAATCTCTCTCTGGGCTCTCTGGGAACACCACAGGAGCACCCTTTT
TCGTTCATCCTGCAGATGTCCCTCGCGGTCCCTGCTGGGAAACAATGGTGGGCAGGAATTCGTG
CGTCTCACCGTTTCTGACGTCCTGACCACTTACGTCACGATCCTCATTGGCGACTTCCTCAGAGC
ATGTTTCGTGAGGTTCTGCAATTACTGCTGGTGCTGGGACTTAGAATATGGATATCCTTCATACA
CAGAATTCGACATCAGTGGCAACGTCCTGCTCTGATCTTCAACCAAGGCATGATCTGGATGGGC
TCCTTCTTCGCTCCTAGCCTCCCGGGCATCAACATCCTCCGTCTCCACACATCCATGTATTTCCA
GTGCTGGGCTGTGATGCTGCAATGTTCCCGAGGCCAGGGTGTTCAAAGCTTCCAGATCCAACA
ACTTCTACCTCGGCATGCTGCTACTCATCCTCTTCCTGTCCACCATGCCGGTTCCTGTACATGATC
GTCTCCCTCCCGCCATCTTTTGATTGTGGGCCCTTCAGTGGTAAAAACAGGATGTTTGAAGTCAT
CGGTGAGACCCTGGAACATGACTTCCCAAGCTGGATGGCGAAGATCCTGAGGCAGCTTTCTAACC
CCGGCCTTGTCATTGCTGTCATTCTGGTGATGGTTCTGACCATCTATTATCTCAATGCTACTGCC
AAGGGCCAGAAAGCAGCGAATCTGGACCTCAAAAAGAAGATGAAACAGCAAGCTTTGGAGAACAA
AATGCGAAACAAGAAAATGGCAGCGGCTCGAGCAGCTGCAGCTGCTGGTGGCCAGTGGATCCAC
GGCCGGTCGCCACCATGGTGAGCAAGGGCGAGGAGCTGTTCACCGGGGTGGTGCCCATCCTGGTC
GAGCTGGACGGCGACGTAAACGGCCACAAGTTCAGCGTGTCCGGCGAGGGCGAGGGCGATGCCAC
CTACGGCAAGCTGACCCTGAAGTTCATCTGCACCACCGGCAAGCTGCCCGTGCCCTGGCCCACCC
TCGTGACCACCCTGACCTACGGCGTGCAGTGCTTCAGCCGCTACCCCGACCACATGAAGCAGCAC
GACTTCTTCAAGTCCGCCATGCCCGAAGGCTACGTCCAGGAGCGCACCATCTTCTTCAAGGACGA
CGGCAACTACAAGACCCGCGCCGAGGTGAAGTTCGAGGGCGACACCCTGGTGAACCGCATCGAGC
TGAAGGGCATCGACTTCAAGGAGGACGGCAACATCCTGGGGCACAAGCTGGAGTACAACTACAAC
AGCCACAACGTCTATATCATGGCCGACAAGCAGAAGAACGGCATCAAGGTGAACTTCAAGATCCG
CCACAACATCGAGGACGGCAGCGTGCAGCTCGCCGACCACTACCAGCAGAACACCCCCATCGGCG
ACGGCCCCGTGCTGCTGCCCGACAACCACTACCTGAGCACCCAGTCCGCCCTGAGCAAAGACCCC
AACGAGAAGCGCGATCACATGGTCCTGCTGGAGTTCGTGACCGCCGCCGGGATCACTCTCGGCAT
GGACGAGCTGTACAAGTAAGCGGCCGCTCGAGCCTAAGCTTCTAGAagatctacgggtggcatcc
ctgtgacccctccccagtgCctctcctggccctggaagttgccactccagtgcccaccagccttg
tcctaataaaattaagttgcatcattttgtctgactaggtgtccttctataatattatggggtgg
aggggggtggtatggagcaaggggcaagttgggaagacaacctgtagggcctgcggggtctattg
ggaaccaagctggagtgcagtggcacaatcttggctcactgcaatctccgcctcctgggttcaag
cgattctcctgcctcagcctcccgagttgttgggattccaggcatgcatgaccaggctcagctaa
ttttgttttttggtagagacggggtttcaccatattggccaggctggtctcgaactcctaatc
tcaggtgatctacccaccttggcctcccaaattgctgggattacaggcgtgaaccactgctccct
tccctgtccttctgattttgtaggtaaccacgtgcggaccgagcggccgcaggaaccctagtga
tggagttggccactccctctgcgcgctcgctcgctcactgaggccgggcgaccaaaggtcgcc
cgacgcccgggctttgcccgggcggcctcagtgagcgagcgagcgcgcagctgcctgcaggggcg
cctgatgcggtattttctccttacgcatctgtgcggtatttcacaccgcatacgtcaaagcaacc
atagtacgcgccctgtagcggcgcattaagcgcggcgggtgtggtggttacgcgcagcgtgaccg
ctacacttgccagcgccctagcgcccgctcctttcgctttcttcccttcctttctcgccacgttc
gccggctttccccgtcaagctctaaatcgggggctccctttagggttccgatttagtgctttacg
gcacctcgaccccaaaaaacttgatttgggtgatggttcacgtagtgggccatcgccctgataga
cggttttcgccctttgacgttggagtccacgttctttaatagtggactcttgttccaaactgga
```

```
acaacactcaaccctatctcgggctattcttttgatttataagggattttgccgatttcggccta
ttggttaaaaaatgagctgatttaacaaaaatttaacgcgaattttaacaaaatattaacgttta
caattttatggtgcactctcagtacaatctgctctgatgccgcatagttaagccagccccgacac
ccgccaacacccgctgacgcgccctgacgggcttgtctgctcccggcatccgcttacagacaagc
tgtgaccgtctccgggagctgcatgtgtcagaggttttcaccgtcatcaccgaaacgcgcgagac
gaaagggcctcgtgatacgcctattttttataggttaatgtcatgataataatggtttcttagacg
tcaggtggcacttttcggggaaatgtgcgcggaacccctatttgtttatttttctaaatacattc
aaatatgtatccgctcatgagacaataaccctgataaatgcttcaataatattgaaaaaggaaga
gtatgagtattcaacatttccgtgtcgcccttattcccttttttgcggcattttgccttcctgtt
tttgctcacccagaaacgctggtgaaagtaaaagatgctgaagatcagttgggtgcacgagtggg
ttacatcgaactggatctcaacagcggtaagatccttgagagttttcgccccgaagaacgttttc
caatgatgagcacttttaaagttctgctatgtggcgcggtattatcccgtattgacgccgggcaa
gagcaactcggtcgccgcatacactattctcagaatgacttggttgagtactcaccagtcacaga
aaagcatcttacggatggcatgacagtaagagaattatgcagtgctgccataaccatgagtgata
acactgcggccaacttacttctgacaacgatcggaggaccgaaggagctaaccgcttttttgcac
aacatggggggatcatgtaactcgccttgatcgttgggaaccggagctgaatgaagccataccaaa
cgacgagcgtgacaccacgatgccLgtagcaatggcaacaacgttgcgcaaactattaactggcg
aactacttactctagcttcccggcaacaattaatagactggatggaggcggataaagttgcagga
ccacttctgcgctcggcccttccggctggctggtttattgctgataaatctggagccggtgagcg
tgggtctcgcggtatcattgcagcactggggccagatggtaagccctcccgtatcgtagttatct
acacgacggggagtcaggcaactatggatgaacgaaatagacagatcgctgagataggtgcctca
ctgattaagcattggtaactgtcagaccaagtttactcatatatactttagattgatttaaaact
tcatttttaatttaaaaggatctaggtgaagatcctttttgataatctcatgaccaaaatccctt
aacgtgagttttcgttccactgagcgtcagacccccgtagaaaagatcaaaggatcttcttgagat
cctttttttctgcgcgtaatctgctgcttgcaaacaaaaaaaccaccgctaccagcggtggtttg
tttgccggatcaagagctaccaactctttttccgaaggtaactggcttcagcagagcgcagatac
caaatactgtccttctagtgtagccgtagttaggccaccacttcaagaactctgtagcaccgcct
acatcctcgctctgctaatcctgttaccagtggctgctgccagtggcgataagtcgtgtcttac
cgggttggactcaagacgatagttaccggataaggcgcagcggtcgggctgaacggggggttcgt
gcacacagcccagcttggagcgaacgacctacaccgaactgagatacctacagcgtgagctatga
gaaagcgccacgcttcccgaagggagaaaggcggacaggtatccggtaagcggcagggtcggaac
aggagagcgcacgagggagcttccaggggaaacgcctggtatctttatagtcctgtcgggtttc
gccacctctgacttgagcgtcgatttttgtgatgctcgtcaggggggcggagcctatggaaaaac
gccagcaacgcggcctttttacggttcctggccttttgctggccttttgctcacatgt pAAV-10myo6-TMC2 (SEQ ID NO: 8)
L-ITR: 1-141
myo6 promoter: 155-1,396
TMC2: 1,425-4,091
hGH polyA signal: 4,126-4,606
R-ITR: 4,643-4,783
cctgcaggcagctgcgcgctcgctcgctcactgaggccgcccgggcaaagcccgggcgtcgggcg
acctttggtcgcccggcctcagtgagcgagcgagcgcgcagagagggagtggccaactccatcac
tagggggttcctgcggccgcacgcgTGCAAGAACCCTCACTGGCTGAACTATCTTGCCAGCCCCTT
ATTTTGTTTTCATATTAACCTCTTTTTTCTAGTAAAGGAGATGTTTGCTCTCAAATTTGCATAGG
AATGTAATATTTAATTTAAAAAGATGACCCACATATGACCTTATAAGGACAGTAAAATTAAACAA
CCGGAAAGATAAAGCGGGCCAGTTGGCTCAGTTCTATAAAACCAGCCCACAAGGATTGTCACTAT
TCTTAGGCTTGCGCGGGCTACATGATGAGTTCCAGGACTGCCTGGTTACAGACCGAGACTCTCTC
AAGAGTCCAGATAAACAACAACAAAGGGGGCGAGGTGGAAATACAGGGGCGTGAAGAAGTAAATA
TGATATCTGCATGGGAGGCTAGCCAGAGAAGAAAAAATTTTCTTCCGTGGTTCAATCCTCCAAGG
GCTGAACAGGAAGTTGACGCAGGCAGGTGAGGAGCACGAGCCTAGATGGGCTGCGGTGCCACCCT
TAATCCCCACAAGCGAGTTCCTCCGCAATTCGCCTGTCCCACTCTCAACTTTTCTTCAACTGACT
CTTTGCTGTGGTCCCTCGCTGTGGCAGTGGAAACAACTACCACTGCGGTAGGTAGGGAATGTCATGA
GGGGCTACCTGCAGCCCTTGGCTTGCAGGGATGCAGGGATGCGGTCGGAACCTGAGGCCCCGCCC
TTCTCTTGCCCCACGCCATTAGGCCACGCCCCTACCCAGCACTCCTTCAACCACCCCCTTCCCCG
GCGCCTCATGAGGTCCCGCCCCTCTCAACCCTAGCTCTTGAGGCCTCCCCTTCACAGCCGCCCCG
GCGTTCCTTGACTTGAGGCCACGTCCCTCTGCTCCTTCATTCCCAAGACCCTACGCTTTGCGAGT
CCTCCCTGTCCTGCTGCCTAGGACCCCGCCCCTCTCAGCCCTTCTGCCCCAAGACCCCGCCCCTT
AGGCTGTTCCCGCCCACTGGCCAATGAAGACCCGCCCTTTCTTTAGCCGCCCCGCCCCGGTCCCA
CAAAATCCCGCCTCCGGCCCCGCCTCCCGCCCCCTTGGGCGCTCCGTAGCAGTGACGTGCGCAGG
CTGGGCACTCTGCAGGGCTCTCTGGCCGGCGGGTGGAGACCGATCTGGGATCTGTCCCAGCAGGA
AGCGTATCCCGGCCGCCGTCGTGCTGTCGTCTCCGGTGCTCGCTCTCGGCCGCGGTGTCGCGCTT
GCCCTTCGCGCCCGCAGCCCGGCAGCCTCTCgagCTCAAGCTTCGAATTCgtcgacaggATGAGC
CCCCAGTTAAAGAGCTTGGACGAGGAAGGTGACAAGTCAGCAAGAAGACCCACAAGGAAACAAAC
CTCCAGAGCTGCATGTCCCCAAGACGGGCACCGAGCCCAATCTAGCCGGAAGGATCCTGCTAAGG
GTAGCCCAAGACCAGGGTCTTCCCGGAAGAAACAGATGGAACATGGAAGCTATCACAAGGGGTTG
CAGGGACAGAAACCACGAAAGGTGGAGAGGTCTCTACAAGGGAGGAAGAAGGATCGGAGAACTTC
CCTTAAGGAGCAGAGAGCATCTCCAAAGAAGGAGAGGGAGGCTCTGAGGAAGGAGGCAGGCAAGC
AGCTGAGAAACCCAGGTCCACTTCCTTGGGCTCCAGTGTCTCTACTGGAGACTCCCTGTCTGAG
GAGGAGCTGGCTCAGATCCTGGAACAGGTAGAAGAAAAAAGAAGCTCATCACTACCGTGAGGAA
CAAACCCTGGCCCATGGCAAAGAAGCTGAGGGAACTCAGGGAAGCCCAAGCCTTTGTGGAGAAGT
ATGAAGGAGCCTTGGGGAAAGGCAAGGGCAAACACCTCTACGCCTACAGGATGATGATGGCTAAG
AAATGGGTCAAGTTTAAGAGGGACTTTGATAATTTCAAGACTCAATGTATTCCCTGGGAAATGAA
GATCAAGGACATTGAAAGTCACTTCGGTTCTTCTGTGGCATCTTACTTCATCTTTCTCCGATGGA
TGTATGGAGTTAACCTTGTCCTTTTTGGCTTaATATTTGGTCTAGTCATCATCCCAGAGGTGCTG
ATGGGCATGCCCTATGAAGTATACCCAGAAAGCGGTGCCTCGGGCTGAGGAAGAGCGAGCCAT
GGACTTCTCTGTCCTTTGGGATTTTGAGGGCTACATCAAATATTCTGCTCTCTTCTATGGCTACT
```

```
Sequence Listing

ACAACAACCAGCGGACCATTGGATGGCTGAGGTACAGGCTGCCCATGGCTTACTTTATGGTGGGG
GTCAGCGTGTTTGGCTACAGCTTGATGATCGTCATTAGGTCGATGGCCAGCAATACCCAGGGTAG
CACCAGTGAGGGGGACAGTGACAGCTTCACGTTCAGCTTCAAGATGTTCACCAGCTGGGACTACC
TCATCGGGAATTCAGAGACAGCAGACAACAAATATGTCTCCATCACTACCAGCTTCAAGGAGTCT
ATAGTGGACGAACAAGAGAGTAACAAAGAAGGGAATATCCACCTGACAAGATTCCTCCGCGTCCT
GGCCAACTTTCTCATTCTCTGCTGTCTGTGTGGAAGCGGGTACCTCATTTACTTTGTGGTGAAAC
GGTCCCAGGAGTTCTCCAAAATGCAAAATGTCAGCTGGTATGAAAGGAATGAGGTGGAGATCGTG
ATGTCTCTGCTAGGGATGTTTTGTCCCCCTCTGTTTGAAACCATCGCTGCCTTGGAGAATTATCA
CCCACGAACTGGGCTGAAGTGGCAGCTGGGCCGCATCTTTGCCCTTTTCCTGGGAAACCTCTACA
CGTTTCTCCTGGCCCTCATGGACGATGTCCACCTTAAGCTTTCTAATGAGGAAAAAATCAAGAAC
ATCACTCACTGGACCCTGTTTAACTATTACAATTCCTCAGGTGGGAATGAGAGTGTGCCCCGGCC
ACCACCACACCCTGCAGATGTGCCCAGAGGTTCTTGCTGGGAGACAGCTGTGGGCATTGAGTTTA
TGAGGCTCACCGTGTCTGACATGCTGGTAACATACCTCACCATCTTGGTCGGAGATTTCCTCCGA
GCTTGTTTTGTCCGGTTCATGAATCACTGCTGGTGTTGGGACCTCGAGGCTGGTTTTCCCTCATA
TGCCGAGTTTGATATTAGTGGAAATGTGTTGGGTTTGATCTTCAACCAAGGAATGATCTGGATGG
GCTCCTTCTATGCTCCAGGACTGGTGGGCATCAATGTCCTGCGCCTGTTGACCTCCATGTACTTC
CAGTGCTGGGCAGTGATGAGCAGCAACGTTCCCCATGAGCGTGTGTTTAAAGCCTCCCGATCCAA
CAACTTCTACATGGGCTGCTGCTGTTGGTGCTCTTCCTCAGCCTCCTGCCTGTGGCCTACACTG
TCATGTCTCTCCCACCCTCGTTTGACTGTGGCCCCTTCAGTGGGAAAAACAGAATGTACGATGTC
CTCCATGAGACCATCGAGAACGATTTCCCTAAGTTCCTGGGCAAGATCTTTGCGTTCCTTGCCAA
CCCAGGCCTGATCATTCCAGCCATCCTGCTAATGTTTCTGGCCATTTACTACCTGAACTCAGTTT
CAAAAAGTCTTTCCAGAGCTAATGCCCAGCTGCGAAAGAAGATCCAAGCGCTCCGTGAAGTTGAG
AAGAACCATAAATCCATCAAGGGAAAAGCCATAGTCACATATTCAGAGGACACAATCAAGAACAG
ctccaaaaatgccacccagatacatcttactaaagaacagcccacatctcactcttccagcgaaa
TCCAGACCCTGGACAAGAAAGCGCAGGGCCCCCACACCTCCAGTACTGAGGGTGGGGCCTCGCCG
TCTACCTCCTGGCACCATGTTGGGTCTCAACCACCGAGAGGCAGACGAGATTCTGGCCAACCCCA
GTCTCAGACTTATACAGGCAGGTCACCTTCTGGAAAGAGAACCCAGAGGCCTCACAACTGAGCGG
CCGCTCGAGCCTAAGCTTCTAGAagatctacgggtggcatccctgtgacccctcccagtgcctc
tcctggccctggaagttgccactccagtgcccaccagccttgtcctaataaaattaagttgcatc
attttgtctgactaggtgtccttctataatattatgggtggagggggtggtatggagcaaggg
gcaagttgggaagacaacctgtagggcctgcggggtctattgggaaccaagctggagtgcagtgg
cacaatcttggctcactgcaatctccgcctcctgggttcaagcgattctcctgcctcagcctccc
gagttgttgggattccaggcatgcatgaccaggctcagctaattttttgtttttttggtagagacg
gggtttcaccatattggccaggctggtctccaactcctaatctcaggtgatctacccaccttggc
ctcccaaattgctgggattacaggcgtgaaccactgctcccttccctgtccttctgattttgtag
gtaaccacgtgcggaccgagcggccgcaggaacccctagtgatggagttggccactccctctctg
cgcgctcgctcgctcactgaggccgggcgaccaaaggtcgcccgacgcccgggctttgcccgggc
ggcctcagtgagcgagcgagcgcagctgcctgcaggggcgcctgatgcggtattttctcctta
cgcatctgtgcggtatttcacaccgcatacgtcaaagcaaccatagtacgcgccctgtagcggcg
cattaagcgcggcgggtgtggtggttacgcgcagcgtgaccgctacacttgccagcgccctagcg
cccgctcctttcgctttcttcccttcctttctcgccacgttcgccggctttccccgtcaagctct
aaatcggggctcccctttagggttccgatttagtgctttacggcacctcgaccccaaaaaacttg
atttgggtgatggttcacgtagtgggccatcgccctgatagacggtttttcgccctttgacgttg
gagtccacgttctttaatagtggactcttgttccaaactggaacaacactcaaccctatctcggg
ctattcttttgatttataagggattttgccgatttcggcctattggttaaaaaatgagctgattt
aacaaaaatttaacgcgaattttaacaaaatattaacgtttacaattttatggtgcactctcagt
acaatctgctctgatgccgcatagttaagccagccccgacacccgccaacacccgctgacgcgcc
ctgacgggcttgtctgctcccggcatccgcttacagacaagctgtgaccgtctccgggagctgca
tgtgtcagaggttttcaccgtcatccaccgaaacgcgcgagacgaaagggcctcgtgatacgccta
ttttataggttaatgtcatgataataatggtttcttagacgtcaggtggcacttttcggggaaa
tgtgcgcggaacccctatttgtttatttttctaaatacattcaaatatgtatccgctcatgagac
aataaccctgataaatgcttcaataatattgaaaaaggaagagtatgagtattcaacatttccgt
gtcgcccttattccctttttttgcggcattttgccttcctgtttttgctcacccagaaacgctggt
gaaagtaaaagatgctgaagatcagttgggtgcacgagtgggttacatcgaactggatctcaaca
gcggtaagatccttgagagttttcgccccgaagaacgttttccaatgatgagcacttttaaagtt
ctgctatgtggcgcggtattatcccgtattgacgccgggcaagagcaactcggtcgccgcataca
ctattctcagaatgacttggttgagtactcaccagtcacagaaaagcatcttacggatggcatga
cagtaagagaattatgcagtgctgccataaccatgagtgataacactgcggccaacttacttctg
acaacgatcggaggaccgaaggagctaaccgcttttttgcacaacatgggggatcatgtaactcg
ccttgatcgttgggaaccggagctgaatgaagccataccaaacgacgagcgtgacaccacgatgc
ctgtagcaatggcaacaacgttgcgcaaactattaactggcgaactacttactctagcttcccgg
caacaattaatagactggatggaggcggataaagttgcaggaccacttctgcgctcggcccttcc
ggctggctggtttattgctgataaatctggagccggtgagcgtgggtctcgcggtatcattgcag
cactggggccagatggtaagccctcccgtatcgtagttatctacacgacggggagtcaggcaact
atggatgaacgaaatagacagatcgctgagataggtgcctcactgattaagcattggtaactgtc
agaccaagtttactcatatatactttagattgatttaaaacttcatttttaatttaaaaggatct
aggtgaagatcctttttgataatctcatgaccaaaatcccttaacgtgagttttcgttccactga
gcgtcagaccccgtagaaaagatcaaaggatcttcttgagatcctttttttctgcgcgtaatctg
ctgcttgcaaacaaaaaaaccaccgctaccagcggtggtttgtttgccggatcaagagctaccaa
ctctttttccgaagataactggcttcagcagagcgcagataccaaatactgtccttctagtgtag
ccgtagttaggccaccacttcaagaactctgtagcaccgcctacatacctcgctctgctaatcct
gttaccagtggctgctgccagtggcgataagtcgtgtcttaccgggttggactcaagacgatagt
taccggataaggcgcagcggtcgggctgaacggggggttcgtgcacacagcccagcttggagcga
acgacctacaccgaactgagatacctacagcgtgagctatgagaaagcgccacgcttcccgaagg
```

```
gagaaaggcggacaggtatccggtaagcggcagggtcggaacaggagagcgcacgagggagcttc
caggggggaaacgcctggtatctttatagtcctgtcgggtttcgccacctctgacttgagcgtcga
tttttgtgatgctcgtcagggggcggagcctatggaaaaacgccagcaacgcggcctttttacg
gttcctggccttttgctggccttttgctcacatgt
```

What is claimed is:

1. A method of restoring hearing function and vestibular function in a subject with a hearing disorder or vestibular disorder, the method comprising:
    injecting to inner ear cells of the subject, a synthetic inner ear hair cell targeting adeno-associated virus (AAV) vector,
    wherein the vector:
        encodes a capsid having at least 85% sequence identity to Anc80 of SEQ ID NO:1,
        comprises a promoter selected from the group consisting of an Espin promoter, a protocadherin 15 (PCDH15) promoter, a protein tyrosine phosphatase receptor type Q (PTPRQ) promoter, and a tetraspan membrane protein of hair cell stereocilia (TMHS) (lipoma HMGIC fusion partner-like 5, LHFPL5) promoter, and
        comprises a polynucleotide,
            wherein the promoter directs expression of the polynucleotide encoding transmembrane channel-like 1 (TMC1),
    thereby restoring hearing function and vestibular function in the subject.

2. The method of claim 1, wherein the administering reverses hearing loss.

3. The method of claim 2, wherein the hearing loss is partial hearing loss or complete deafness.

4. The method of claim 2, wherein recovery of hearing function is associated with preservation of hair bundle morphology and/or restoration of mechanotransduction.

5. The method of claim 1, wherein the subject with the hearing disorder or vestibular disorder suffers from Usher syndrome.

6. The method of claim 1, wherein the injecting occurs through a round window membrane.

7. The method of claim 1, wherein the AAV vector is AAV1 or AAV2.

8. The method of claim 1, wherein the AAV vector is AAV1.

9. The method of claim 1, wherein the AAV vector encodes the Anc80 capsid of SEQ ID NO:1.

* * * * *